United States Patent
Deacon et al.

[11] Patent Number: 6,015,661
[45] Date of Patent: Jan. 18, 2000

[54] METHODS FOR THE DETECTION OF NON-PATHOGENIC HIV-1 STRAINS CONTAINING DELETIONS IN THE NEF CODING REGION AND U3 REGION OF THE LTR

[75] Inventors: Nicholas John Deacon, Balwyn; Dale Alan McPhee, Fitzroy; Suzanne Crowe, South Yarra, all of Australia

[73] Assignee: The Macfarlane Burnet Centre for Medical Research Limited, Fairfield, Australia

[21] Appl. No.: 08/488,551

[22] Filed: Jun. 7, 1995

Related U.S. Application Data

[63] Continuation-in-part of application No. 08/388,353, Feb. 14, 1995.

[30] Foreign Application Priority Data

May 17, 1995 [AU] Australia .......................... PN3021/95

[51] Int. Cl.[7] .............................. C12Q 1/70; C12Q 1/68; G01N 33/53
[52] U.S. Cl. .................................... 435/5; 435/7.1; 435/6
[58] Field of Search .................... 435/5, 7.1; 424/188.1, 424/187.1

[56] References Cited

U.S. PATENT DOCUMENTS 5,221,610  6/1993  Montagnier et al. ..................... 435/7.1

FOREIGN PATENT DOCUMENTS

| 05078386 | 3/1993 | Japan . |
|---|---|---|
| WO 87/06259 | 10/1987 | WIPO . |
| WO 90/13641 | 11/1990 | WIPO . |
| WO 91/05864 | 5/1991 | WIPO . |
| WO 91/19795 | 12/1991 | WIPO . |
| WO 92/00987 | 1/1992 | WIPO . |
| WO 94/17825 | 8/1994 | WIPO . |
| WO 94/29437 | 12/1994 | WIPO . |

OTHER PUBLICATIONS

Kirchoff et al., 1995, New Engl. J. Med. 332: 228–232.
Huang et al., 1995, J. Virol. 69:93–100.
Terwilliger et al., 1991, Proc. Natl. Acad. Sci. USA 88:10971–10975.
Michael et al., 1995, J. Virol. 69: 6758–6769.
Goodenow et al., 1989, J. Acquir. Immune Defic. Syndr. 2:344–352.
Shioda et al., 1994, J. Virol. 68:7689–7696.
Ruprecht et al., 1995, The Lancet 346:177–178.
Daniel et al (1992) "Protective Effects of a Live Attenuated SIV Vaccine with a Deletion in the nef Gene," *Science* 258:1938–1941.

(List continued on next page.)

*Primary Examiner*—Donald E. Adams
*Assistant Examiner*—Jeffrey S. Parkin
*Attorney, Agent, or Firm*—Scully, Scott, Murphy and Presser

[57] ABSTRACT

The present invention is directed toward immunologic- and nucleic acid-based methodologies for the detection of non-pathogenic human immunodeficiency virus type 1 (HIV-1) strains in the body fluids of HIV-infected individuals. A blood donor infected with HIV-1 and a cohort of six blood or blood product recipients infected from this donor were studied. These patients, who remained free of HIV-1-related disease and displayed stable and normal CD4 lymphocyte counts 10 to 14 years after infection, were termed long-term nonprogressors (LTNPs). The molecular characterization of HIV-1 sequences obtained from either virus isolates or patient peripheral blood mononuclear cells (PBMCs) of LTNPs identified similar deletions in the nef gene and in the region of overlap of nef and the U3 region of the long terminal repeat (LTR). These deletions corresponded to amino acids 166–206, or nucleotides 9281 to 9437, of the HIV-1$_{NL43}$ nef/LTR region. Methods were developed to detect the presence of nonpathogenic HIV-1 strains carrying these deletions in HIV-infected patients.

5 Claims, 104 Drawing Sheets

OTHER PUBLICATIONS

Kestler III et al (1991) "Importance of the nef Gene for Maintenance of High Virus Loads and for Development of AIDS," *Cell 65*:651–662.

Learmont et al (1992) "Long–Term Symptomless HIV–1 Infection in Recipients of Blood Products from a Single Donor," *The Lancet 340 (8824)*:863–867.

Ojwang et al (1992) "Inhibition of Human Immunodeficiency Virus Type I Expression by a Hairpin Ribozyme," *Proc. Natl. Acad. Sci. USA 89*:10802–10806.

FIGURE 1

| i |
|---|
| ii |
| iii |
| iv |
| v |
| vi |
| vii |
| viii |
| ix |
| x |
| xi |
| xii |
| xiii |
| xiv |
| xv |
| xvi |
| xvii |
| xviii |

FIGURE 1 (i)

```
        8072                                                  8121        8171
NL43    GAACAGAGATTTGGGAATAACATGACCTGGATGGAGTGGGACAGAGAGAAATTAA        CAATTACACACAAGCTTAATACACTCCTTAATTGAAGAATCGCAAAACCAGC
        *** ******* * ************************ * ***********            **** *********** * *** ************ * ***** ***********
D36P    GAAGAGAGATTTGGGAGAACATGACCTGGATGCAGTGGGACAGAGAAATTCA            CAATCACACACAAAATACATATACTCCTTAATTGAAGAATCGCAGAACCAAC
        *** ******* * ************************ * ***********            **** ************ *** ************** ***** ***********
C18S    GAAACAATTTGGGATAACATGACCTGGATGCAGTGGGACAGAGAAATTGA              CAATTACACACAAATACATAATATACACTCCTTAATTGAAGAATCGCAGAACCAAC
        *** ******* * ************************* ***********            **** ********** *** ** * *********** ***** ***********
C18M    GAAACAATTTGGGATAACATGACCTGGATGCAGTGGGACAGAGAAATTGA              CAATTACACACAAATACATAATATACACTCCTTAATTGAAGAATCGCAGAACCAAC
                                              *********** *            **** *********** **** *************** ***** ***********
C98H                                       GAAATTAA                   CAATTACACAAGATTAATATACAACTTAATTGAAGAATCGCAGAACCAAC
```

FIGURE 1 (ii)

```
NL43  AAGAAAAGAATGAACAAGAATTATTGGAATTAGATAAATGGGCAAGTTTG  8221
D36P  AAGAAAAGAATGAACAAGAACTATTGGAATTGGATCAATGGGCAAGTTTG
      *********  **** *** ************ *** *************
C18S  AAGAAAAAATGAACTAGAATTATTGGAATTGGATAAATGGGCAAATTTG
      ******** ***** *** ************* **** *******
C18M  AAGAAAAAATGAACTAGAATTATTGGAATTGGATAAATGGGCAAATTTG
      ******** ***** *** ************* **** *******
C98H  AAGAAAAGAATGAACAAGACTTATTGGAATTAGATAAATGGGCAAGTTTG

NL43  TGGAATTGGTTTAACATAACAAATTGGCTGTGTGGTATATAAAATTATTCAT  8271
D36P  TGGAATTGGTTTGACATAACAAATTGGCTGTGTGGTATATAAAATATTCAT
      ************ ***************************** *******
C18S  TGGAATTGGTTTAGTATATATCAAACTGGCTATGGTGGCTATGGTGGCTATGGTATATAAAATTATTCAT
C18M  TGGAATTGGTTTAGTATATATCAAACTGGCTATGGTATATAAAATTATTCAT
      ************ * ***** *****  ******** **************
C98H  TGGAATTGGTTTGACATAACAAGTGGGCTGTGGTATATAAAATTATTCAT
```

FIGURE 1 (iii)

```
NL43  AATGATAGTAGGAGGCTTGGTAGGTTTAAGAATAGTTTTTGCTGTACTTT   8321
D36P  AATGGTAGTAGGAGGCTTGATAGGTTTAAGAATAGTTTTTGCTGTACTTT   ****
C18S  AATGGTAGTAGGAGGCTTGGTAGGTTTAAGAATAGTTTTTACTGTACTTT   ****
C18M  AATGGTAGTAGGAGGCTTGGTAGGTTTAAGAATAGTTTTACTGTACTTT    ****
C98H  AATGATAGTAGGAGGCTTGGTAGGTTTAAGAATAGTTTTAGCTGTACTTT   ****
```

```
                  SA8    SA9                          SA10
NL43  CTATAGTGAATAGAGTTAGGCAGGGATATTCACCATTATCGTTTCAGACC   8371
D36P  CTATAGTGAATAGAGTTAGGCAGGGATACTCACCATTGTCGTTTCAGACC   ****
C18S  CTATAGTTAATAGAGTTAGGCAGGGATACTCACCATTATCGTTTCAGACC   ****
C18M  CTATAGTTAATAGAGTTAGGCAGGGATACTCACCATTATCGTTTCAGACC   ****
C98H  CTATAGTGAATAGAGTTAGGCAGGGATACTCACCATTATCGTTTCAGACC   ****
```

FIGURE 1 (iv)

```
                                                                 Tat termination NL43
NL43    CACCTCCCAATCCCGAGGGGACCCGACAGGCCCGAAGGAATAGAAGAAGA   8421
        *      ***** ** ********************************
D36P    CTCCTCCCAACCCCGAGGGGACCCGACAGGCCCGAAGGAATCGAAGAAGA
        *      ****** **********************************
C18S    CACCTCCCAACCCCGAGGGGACCCGACAGGCCCGAAGGAATCGAAGAAGA
        *      ***** *  ********************************
C18M    CACCTCCCAACCCCGAGGGGACCCGACAGGCCCGAAGGAATCGAAGAAGA
        *      ****** **********************************
C98H    CACCTCCCAACCCCGAGGGGACCCGACAGGCCCGAAGGAATCGAAGAAGA NL43    AGGTGGAGAGAGAGACAGAGACAGATCCATTCGATTAGTGAACGGATCCT   8471
        *******************                *     *** 
D36P    AGGTGGAGAGAGAGACAGAGACAGATCCACTCGATTAGTACACGGATTCT
        *******************     ***        *     ****** **
C18S    AGGTGGAGAGAGAGACAGAGGCAGCTCCACTCGATTAGTGCACGGATTCT
        *******************      **        *     ****** **
C18M    AGGTGGAGAGAGAGACAGAGGCAGCTCCACTCGATTAGTGCACGGATTCT
        *******************                *     ****** **
C98H    AGGTGGAGAGAGAGACAGAGACAGATCCAGTCGATTAGTGCACGGATTCT
                           D36P, C18S, C18M & C98H Tat termination
```

FIGURE 1 (v)

```
NL43   TAGCACTTATCTGGGACGATCTGCGGAGCCCTGTGCCTCTTCAGCTACCAC  8521
D36P   TAGCACTTTTCTGGGACGACCTGAGGAGCCCTGTGCCTCTTCCTCTACCAC  ****  *** ************
C18S   TAGCACTTTTCTGGGACGACCTGAGGAGTCCTGTGCCTCTTCAGCTACCAC  ****  *** *************
C18M   TAGCACTTTTCTGGGTCGACCTCGAGGAGTCCTGTGCCTCTTCAGCTACCAC  ****  *** *************
C98H   TAGCACTTTTCTGGGTCGACCTGCGAGGAGCCCTGTCCCTCTTCAGCTACCAC  ****  *****************

NL43   CGCTTGAGAGACTTACTCTTGATTGTAACGAGGATTGTGGAACTTCTGGG  8571
D36P   CACTTGAGAGACTTACTCTTGATTGTAACAAGGATTGTGGAACTTCTGGG  *  ***********************************************
C18S   CACTTGAGAGACTTACTCTTGATTGTAACGAGGATTGTGGAACTTCTGGG  * *************************************************
C18M   CGCTTGAGAGACTTACTCTTGATTGTAACGAGGATTGTGGAACTTCTGGG  ***************************************************
C98H   CGCTTGAGAGACTTACTCTTGATTGTAACGAGGATTGTGGAACTTCTGGG  ***************************************************
```

FIGURE 1 (vi)

```
NL43  ACGCAGGGGGTGGGAAGCCCCTCAAATATTGGTGGAATCTCCTACAGTATT  8621
D36P  ACGCAGGGGATGGGAAGCCCCTCAAATATTGGTGGAACCTCCTAAAGTATT
C18S  ACGCAGGGGATGGGAAGCCCCTCAAATACTGGTGGAATCTCCTGCAGTATT
C18M  ACGCGGGGGATGGGAAGCCCCTCAAATACTGGTGGAATCTCCTGCAGTATT
C98H  ACGCAGGGGTGGGAAGCCCCTCAAATATTGGTGGAATCTCCTACAATATT
                                 NL43 Rev termination NL43  GGAGTCAGGAACTAAAGAATAGTGCTGTTAACTTGCTCAATGCCACAGCC  8671
D36P  GGAGCCAGGAACTGCAGAAGAGTGCTGTGTTATCTTGCTCAATGCCACCGCC
C18S  GGAGGCAGGAACTACAGAAGAGTGCTGTTGTTAGCTTGTTCAATGGCACGCC
C18M  GGAGACAGGAACTACAGAAGAGTGCAGTTAGCTTGTTCAATGCCATAGCC
C98H  GGAGTCAGGAACTCAAGAAGAGTGCTATTAGCTTGTTCAATGCCACCGCC
                               C18S, C18M & C98H Rev termination
```

FIGURE 1(vii)

```
NL43  ATAGCAGTAGCTGAGGGGACAGATAGGGGTTATAGAAGTATTACAAGCAGC  8721
      **************************************************
D36P  ATAGCAGTAGCTGAGGGGACAGATAGAGTTTAGAAGTATTACAAAGAGC
      *************************  *  ****  ************
C18S  ATAGCAGTAGCTGAGGGGACAGATAGAGTTATAGAAGCTTTACGAAGGC
      *************************  ***********  **  *  ***
C18M  ATAGCAGTAGCTGAGGGGACAGATAGAGCTATAGAAGGATTACAAAGAGC
      ***************************  ********  *********
C98H  ATAGCAGTAGCTGAGGGGACAGATAGAGTTATAGAAGTATTACAAAGAGC
                   D36P Rev termination NL43  TTATAGAGCTATTCGCCACATACCTAGAAGAATAAGACAGGGCTTGGAAA  8771
      **************  *****************   **
D36P  TTATAGAGCTATCCTCCACATACCTAGAAGAATAAGACAGGGCCTCGAAA
      ************  *  *********************************
C18S  TTATAGAGCTATTCTCCACATACCTAGAAGAATAAGACAGGGCTTAGAAA
      ***  *******  **********************************
C18M  TTATAGAGCTATTCTCCACATACCTAGAAGAATAAGACAGGGCTTAGAAA
      **  **********************************************
C98H  TTGTAGAGCTGTTCTCCACATACCTAGAAGAATAAGACAGGGCTTCGAAA
```

FIGURE 1 (viii)

```
                Env termination      Nef start
NL43   GGATTTTGCTATAAGATGGGTGGCAAGTGGTCAAAAAGTAGTGTGATTGG  8821
       *     ************************ ******************
D36P   TGGCTTTGCTATAAAATGGGTGGCAAGTGGTGAGCAAAAGTAGTGTAGTCAG
       **    *********** **************  **************** *
C18S   GGGCTTTGCTATAAAATGGGTGGCAAGTGGTCAGAAAGTAGTGTGGTTAG
       **   ************ ****** ******  *******  *******
C18M   GGGCTTTGCTGTGTAAATGGG-------------------------------
       **   ****** *   ****
C98H   GGGCTATGCTATAAAATGGGTGGCAAGTGGTTAAAAAGTAGTATGGTTAG
                                      D36P Nef termination nef duplication region
NL43   ATGGCCTGCTGTAAGGGAAAGAATGAGAGCTGAGCCAGCAGCAGATG  8871
                                    ** ** *  *
D36P   ATAGCATG--------------------------------CATCATAAG
       *  * **
C18S   AAGGCATG-----------------------------------------
         * **
C18M   -------------------------------------------------
C98H   ATGGCCTGCTGTAAGGGAAAAAATGAAACAAGCTGAGCCAGCAGCAGAAG
       ****************    ** *   * ********* ********
```

FIGURE 1 (ix)

```
NL43  GGGTGGGGAGCAGTATCTCGAGACCTAGAAAAACATGGAGCAATCACAAGT  8921
D36P  ********** **
      GGGTGGGGGC----------------------------------------
C18S  --------------------------------------------------
C18M  ************ ************************** ******
      ------------------------------------------------**
C98H  GGGTGGGAGCAATATCTCGAGACCTAGGAAAACATGGAGCAATCCCAAGT

NL43  AGCAATATACAGCAGCTAACAATGCTGCTTGTGCCTGGCTAGAAGCACAAGA  8971
D36P  ** ** ******************* * **********************
      ----CAACAACTAACAATGCTGATCGTGCCTGGCTAGAAGCACAAGA
C18S  ---------------------------------------------
C18M  ***** ** ********************  *****************
      ----------------------------**
C98H  AGCAATACAACAACTAACAATGCTAATTGTGCCTGGCTAGAAGCACAAGA
```

SIVmac239 IPTC

FIGURE 1(x)

```
NL43  GGAGGAAGAGGTGGGTTTTCCAGTCACACCTCAGGTACCTTTAAGACCAA              9021
      * ********** ***** *********** *********
D36P  GAAGGAAGAAGCGGGTTTTCCAGTCAAACCTCAGGTA-------------TACCTTTAAGAC--
                                      *              *************
C18S  ----------------------------------------------------------------
C18M  ----------------------------------------------------------------
      ******* ** *****   ** ***************************
C98H  GGAGGAGGAAGTGGGTTTTCCAGTCAAACCTCAGGTACCTTTAAGACCAA

Poly purine tract

NL43  TGACTTACAAGGCAGCTGTAGATCTTAGCCACTTTTTAAAAGAAAAGGGGG             9071
                                ******************************
D36P  -----------GCTGTAGATCTTAGCCACTTTTTAAAAGAAAAGGGGG
              ****** *************************
C18S  ------AAGGCAGCTATAGATCTTAGCCGCTTTTTAAAAGAAAAGGGGG
            ***************** *********************
C18M  ---------------GATCTTAGCCACTTTTTAAAAGAAAAGGGGG
                    ****** ************************
C98H                                GCCACTTTTAAAAGAAAGGGGG
                                    *****    *****   ********
C54P  TGACTTACAAG-----AGCCACTTTTAAAAGAAAAGGGGG

C18S & C18F nef termination
                 C18M and C98H nef Termination
```

FIGURE 1 (xi)

```
              [  U3
NL43   GGACTGGAAGGGCTAATTCACTCCCAAAGAAGACAAGATATCCTTGATCT     9121
D36P   ********************************************
       GGACTGGAAGGGCTAATTCACTCCCAAAGAAGACAAGATA----------
C18S   ********************************* ** *******
       GGACTGGAAGGGCTAATTCACTCCCAAAGAAGACAGAGAAGA--------
C18M   ********************* ** ** **  ** ******
       GGACTGGAAGGGCTAATTCACTCACAGAGAAGA-----------------
C98H   ****************** ****** *****
       GGACTGGAAGGGCTAATTCACTCCTAAAGAAGACAAGATATCCTTGATCT
C54P   ** *****  ********   ******  *******  **********
       GGACTGGAAGGGCTAATTCGCTCCCAAAGAAGACAAGATATCCTTGATCT

SA12
NL43   GTGGATCTACCACACACAAGGCTACTTCCCTGATTGGCAGAACTACACAC     9171
D36P   --------------------------------------------------
C18S   --------------------------------------------------
C18M   --------------------------------------------------
C98H   -------*********************-------  ************
       ---TTGGATCTACCACACACAAGGCTACT---------------------
C54P   *** ************************************ ********
       GTGGGTCTACCACACACAAGGCTACTTCCCTGAGTGGCAGAACTACACAC
```

FIGURE 1 (xii)

```
              [    NRE   --->
NL43   CAGGGCCAGGGGGTCAGATATCCCACTGACCTTTGGATGGTGCTACAAGCTA   9221
            * ****** *** 
D36P   ------------------------------------CACAGTGCTGCAAACTA

C18S   --------------------------------------------------

C18M   --------------------------------------------------
                     ***** ****** ****  *  *** 
C98H   -----------------------ATCCACTGACTTTTGG,TGGTGCTTCAAATTA
       ************ ***** ***** ******************* *** 
C54P   CAGGGCCAGGGACCAGATATCCCACTGACCCTTTGGATGGTGCTGCAAACGA myb             NF-AT
NL43   GTACCAGTTTGAGCCAGATAAGGTAGAAGAGGCCAATAAAGGAGAGAACAC   9271
       ******** *** **** ******************************* *
D36P   TTACCAGTGGAGTCAGCGAAGATAGAAGAGGCCAATGGAGGAGAAAACCA
       ******* ** * *  *                   **  *  **** ****
C18S   ---TCAGTTGAACCAGAACCAGAAGAAGATAGAAGAGGCCATGAAGAAGAACAA
       ******* ** ** *  *                  ****  *  **** ****
C18M   ---TCAGTTGAACCAGAACCAGAAGAAGAATGAAGAGGCCATGAAGAAGAACAA
       ******** * ***  *  *                *** *  *  **** ****
C98H   GTACCAGTGGGANCCAGA--AGAGAGAAGATAGAAGAGGCCAATGGAGGAGAACAA-
       ****  ****  *                        ***
C54P   GTGCCAGTGTGGAAACAGAGAAGATAGAAGAGGCCAATGGAGGAGAAAACAA
            (myb)
```

FIGURE 1 (xiii)

```
                                                                        NF-AT
NL43   CAGCTTGTTACACCCTGTGAGCCTGCATGGAATGGATGACCCTGAGAGAG   9321
D36P   CAGATTGTT-------------------------------------------
       *** ******
C18S   CAGATTGTT-------------------------------------------
       *** ******
C18M   CAGATTGTT-------------------------------------------
       *** ******
C98H   ---------------------------------------------------
       *** ****
C54P   CAGACTGTT-------------------------------------------
          **

<-- NRE ]                       USF
NL43   AAGTGTTAGAGTGGAGGTTTGACAGCCGCCTAGCATTTCATCACGTGGCC   9371
D36P   --------------------------------------*---*--*----
                                              CCGTTTGTT
C18S   ---------------------------------------*----**---
                                                 CTGCT
C18M   -------------------------------------------------
C98H   ---------------------------------------------A---
C54P   -------------------------------------------------
```

FIGURE 1 (xiv)

```
                            TCF-1α                           Nef termination
NL43   CGAGAGCTGCATCCGGAGTACTTCAAGAACTGCTGACATCGAGCTTGCTA 9421
        *           **   ** **    **      *  **    *   **
D36P   CTGTTGGGGACTTTCCATCCGTTGGGGACTTTCCAAGGGGCGTGGCCTG
        *           **   **    *       **              **
C18S   CCGTTGGGGACTTTCCA,,,,,,GGAGACGTGGCCTGAGTGATAAGCCG
        *                                              *
C18M   TGCTCAGCTGGGGACTTTCCAGAAGGCGCGGCCTGAGTGACTAAGCCCCG
        *                  **   **  **     **
C98H   CAGAGTGTGGGGACTCTCCACAACAGAGTGTGGGGACTTTCCAAGGAGGC
        **                 **   **     **   *** *
C54P   ----CCGTTGGGGACTTTCCAAGGAGGGCGTGGCCTGAGTGACTAAGTTCC D36P, C18S, C18M, & C98H extra NFKB
          D36P & C98H   extra NFKB
```

FIGURE 1 (xv)

```
       NFKB                                          NFKB              Sp1
                                                                                        9461
NL43   CAAGGGACTTTCCG,,,,,,,,,,,CTGGGGACTTTCCAG,GGAGGCGTGGC
       *****                    ***************  ***********
D36P   GGTGACTAGTTCCG,,,,,,,,,,,GTGGGGACTTTCCAA,GAAGGCGCGGC
       *  **********            ***************  ** ********
C18S   CTGGGGACTTTCCGAAGAGGCGTGACGGGGACTTTCCAA,GGCGACGTGGC
       ** **********            *** **********  ** ********
C18M   TTGGGACTTTCCGAAGAGGCATGAAGGGACTTTCCAAG,GCAGGCGTGGC
          *  *********         *   ***********   *** ******
C98H   GTGGCCTGAGTGACTAAGTTCCGTTGGGACTTTCCAA,AAAGGCGAGGC
       **  ***********          ***************  *** ******
C54P   GTTGGGACTTTCCAAGGAGGC,,GCGGGACTTTCCAA,GGAGGCGCGGC
          ***********          ** **********   **********

C18S & C18M NFkB                            NFkB              Sp1
            D36P and C98H 3'-half NFκB
```

FIGURE 1 (xvi)

```
                Sp1            Sp1                              TATA box
NL43  CTGGGCGGGACTGGGGAGTGGGCGAGCCC,TCAGATGCTGCATATAAGCAG         9510
D36P  CTGGGCGGGACTGGGGAGTGGGCGAGCCC,****************************
C18S  CTGGGCGGGACTGGGGAGTGGGCGAGCCC,****************************
C18M  CTGGGCGGGACTGGGGAGTGGGCGAGCCC,***************T************
C98H  CTGGGCCGGA-CTGGGGAGTGC-GAGCC-,***************T************
C54P  CTGGGCGGGACTGGGGAGGGGCGAGCCC,***************T*****G*******
         Sp1
                U3                                    R
                                          TAR
NL43  CTGCTTTTTGCCTGTACTGGGTCTCTCTGGTTAGACCAGATCTGAGCCTG          9560
D36P  ************************************************
C18S  CTGCTTTCTGCCTGTACTGGGTCTCTCTGGTTAGACCAGATCTGAGCCTG
C18M  CTGCTTTCTGCCTGTACTGGGTCTCTCTGGTTAGACCAGATCTGAGCCTG
C98H  CTGCTTTCTGCCTGTACTGGGTCTCTCTGGTTAGACCAGATCTGAGCCTG
C54P  CTGCTTTCTGCCTGTACTGGGTCTCTCTGGTTAGACCAGATCTGAGCCTG
```

FIGURE 1 (xvii)

Polyadenylation

```
        9610
NL43  GGAGCTCTCTGGCTAACTAGGGAACCCACTGCTTAAGCCTCAATAAAGCT
D36P  **************************************************
C18S  **************************************************
C18M  **************************************************
C98H  **************************************************
C54P  **
      G  incomplete
```

```
         R         ][    U5                            9660
NL43  TGCCTTGAGTGCTTCAAGTAGTGTGTGCCCGTCTGTTGTGTGACTCTGGT
D36P  **************************************************
C18S  **************************************************
C18M  **************************************************
C98H  **************************************************
```

FIGURE 1 (xviii)

```
NL43  AACTAGAGATCCCTCAGACCCTTTTAGTCAGTGTGGAAAATCTCTAGCA  9709
      * *****                                     *****
D36P  ATCTAGA                                      1305
      * *****                                     *****
C18S  ATCTAGA                                      1209
      * ***************************************************
C18M  ATCTAGAGATCCCTCAGACCATTTTAGTCCGTGTGGAAAATCTCTAGCA  END
      * *****                                     *****
C98H  ATCTAGA                                      1399
```

FIGURE 2A

| | | |
|---|---|---|
| NL43 | 73 | PTSQSRGDPTGPKE# 86 |
| D36PBMC | | PSSQPRGDPTGPKESKKKVERETETDPLD# |
| C18 HIV$_{StV}$ | | PTSQPRRDPTGQKESKKKVERETEAAPLD# |
| C18 HIV$_{MBC}$ | | PTSQPRRDPTGQKESKKKVERETEAAPLD# |
| C98 HIV | | PTSQPRRDPTGQKESKKKVERETETDPVD# |

FIGURE 2B (i)

| | | |
|---|---|---|
| NL43 | 26 | DPPPNPEGTRQARRNRRRRWRERQRQIHSISERILSTYLG 65 |
| D36PBMC | | DPPPNPEGTRQARRNRRRRWRERQRQIHSISTRILSTFLG |
| C18 HIV$_{StV}$ | | DPPPNPEGTRQARRNRRRRWRERQRQLHSISARILSTFLG |
| C18 HIV$_{MBC}$ | | DPPPNPEGTRQARRNRRRRWRERQRQLHSISARILSTFLG |
| C98 HIV | | DPPPNPEGTRQARRNRRRRWRERQRQIQSISARILSTFLG |

FIGURE 2B (ii)

```
NL43        RSAEPVPLQLPPLPPLERLTLDCNEDCGTSGTQGVGSPQILVE   105
D36 PBMC    RPEEPVPLPLPPLERLTLDCNKDCGTSGTQGMGSPQILVE
C18 HIV_stv RPEESVPLQLPPLERLTLDCNEDCGTSGTQGMGSPQILVE
C18 HIV_MBC RPEESVPLQLPPLERLTLDCNEDCGTSGTQGMGSPQILVE
C98 HIV     RPEEPVPLQLPPLERLTLDCNEDCGTSGTQGVGSPQILVE NL43        SPTVLESGTKE#                                  116
D36PBMC     PPKVLEPGTAEECCYLAQCHRHSSS#
C18 HIV_stv SPAVLEAGTTEECC#
C18 HIV_MBC SPAVLEAGTTEECC#
C98 HIV     SPTILESGTQEECY#
```

FIGURE 3 (i)

| | | |
|---|---|---|
| NL43 | EQIWNNMTWMEWDREINNYTSLIHSLIEESQNQQEKNEQELLELDKWASL | |
| D36PBMC | EEIWENMTWMQWEKEIHNHTKYIYSLLEKSQNQQEKNEQELLELDQWASL | |
| C18 HIV$_{StV}$ | ETIWDNMTWMQWEREIDNYTNIIYTLIEESQNQQEKNELELLELDKWANL | |
| C18 HIV$_{MBC}$ | | |
| C98 HIV | EINNYTRTIYNLIEESQNQQEKNEQDLLELDKWASL | 639 |

| | | |
|---|---|---|
| NL43 | WNWFNITNWLWYIKLFIMIVGGLVGLRIVFAVLSIVNRVRQGYSPLSFQT | |
| D36 PBMC | WNWFDITKWLWYIKIFIMVVGGLIGLRIVFAVLSIVNRVRQGYSPLSFQT | |
| C18 HIV$_{StV}$ | WNWFSISNWLWYIKLFIMVVGGLVGLRIVFTVLSIVNRVRQGYSPLSFQT | |
| C18 HIV$_{MBC}$ | | |
| C98 HIV | WNWFDITSGLWYIKLFIMIVGGLVGLRIVLAVLSIVNRVRQGYSPLSFQT | 689 |

FIGURE 3 (ii)

```
NL43       HLPIPRGPDRPEGIEEEGGERDRSIRLVNGSLALIWDDLRSLCLFSYH   739
D36 PBMC   LLPTPRGPDRPEGIEEEGGERDRSTRLVHGFLALFWDDLRSLCLFLYH
C18 HIVStv HLPTPKGPDRPEGIEEEGGERDRGSSTRLVHGFLALFWDDLRSLCLFSYH
C18 HIVMBC
C98 HIV    HLPTPRGPDRPEGIEEEGGERDRSSRLVHGFLALFWDLRSLCLFSYH

NL43       RLRDLLLIVTRIVELLGRRGWEALKYWWNLLQYWSQELKNSAVNLLNATA   789
D36 PBMC   HLRDLLLIVTRIVELLGRRGWEALKYWWNLLKYWSQELQKSAVILLNATA
C18 HIVStv HLRDLLLIVTRIVELLGRRGWEALKYWWNLLQYWRQELQKSAVSLFNGTA
C18 HIVMBC
C98 HIV    RLRDLLLIVTRIVELLGRRGWEALKYWWNLLQYWSQELKKSAISLFNATA

NL43       IAVAEGTDRVIEVLQAAYRAIRHIPRRIRQGLERILL#              839
D36 PBMC   IAVAEGTDRVLEVLQRAYRAILHIPRRIRQGLEMALL#
C18 HIVStv IAVAEGTDRVIEALRRAYRAILHIPRRIRQGLERALL#
C18 HIVMBC
C98 HIV    IAVAEGTDRVIEVLQRACRAVLHIPRRIRQGFERAML#
```

FIGURE 4

```
NL43       MGGKWSKSSSVIGWPAVRERMRRAEPAADGVGAVSRDLEKHGAITSSNTAA         50
           ****
D36 PBMC   MGGK#                                                       4
           ******  ***
C18.HIVstv MGGKWSESSVVRRHVPLRQGSYRS#                                   24
           *
C18 HIVMBC MRILATF#                                                    7
           ****  *       ******  *   ******  ****   ******  ****
C98 HIV    MGGKWLKSSMVRWPAVREKMKQAEPAAEGVGAISRDLGKHGAIPSSNTT            50

NL43       NNAACAWLEAQEEEEVGFPVTPQVPLRPMTYKAAVDLSHFLKEKGGLEGL          100
           ***  ************************************  *******
C98 HIV    NNANCAWLEAQEEEEVGFPVKPQVPLRPMTYKATF#                         85

NL43       IHSQRRQDILDLWIYHTQGYFPDWQNYTPGPGVRYPLTFGWCYKLVPVEP          150

NL43       DKVEEANKGENTSLLHPVSLHGMDDPEREVLEWRFDSRLAFHHVARELHP          200

NL43       EYFKNC*                                                     206
```

FIGURE 5

| | | | |
|---|---|---|---|
| | NFkB | | NFkkB |

9419
NL43        CGAGCTTGCTACAAGGGACTTTCC....GCTGGGGACTTTCCAGGGA
             ******************* * ********************
D36 PBMC    ΔCTGTTGGGGACTTTCCATCCGTTGGGGACTTTCCAAGGC
                  ******************* *
C18 HIVstv  ΔCCGTTTGTTCCGTTGGGACTTTCCA-GGA
                   *  * *********************
C18 HIVMBC  ΔCTGCTTGCTCAGCTGGGACTTTCCA-GAA
                    ******************* *
C98 HIV     ΔACAGAGTGTGGGGACTCTCCACAACAGAGTGTGGGACTTTCCAAGGA
                *
C54 PBMC    ΔCCGTTGGGACTTTCCAAGGA NFkB                    Sp1             Sp1            Sp1
NL43      GGCGTGGCCTGGGCGGGACTGGGGAGTGGGCG-AGCCCTCA        9492
          ***************                * **
DC36 PBMC GGCGTGGCCTGGGGCGGGACTAGTTCCGGTGGGG-ACTTTCCA
          *  **************                * **
C18 HIVstv GACGTGGCCTGAGTGACTAAG-CCGCTGGGG-ACTTTCCG
           *                                * **
C18 HIVMBC GGCGCGGCCTGAGTGACTAAGCCCCGTTGGG-ACTTTCCG
           **************                   * **
C98 HIV    GGCGTGGCCTGAGTGACTAAGTTCCGTTGGGGACTTTCCA
           **************                   * *
C54 PBMC   GGCGTGGCCTGAGTGACTAAGTTCCGTTGGGACTTTCCAA
           Sp1                                3' half NFkB   NFkB FIGURE 9 (i)

```
TGGAAGGGCTAATTCACTCACGGAAAAGACCAGTTGAACCAG
AAGAAGATAGAAGAGGCCATGAAGAAGAAACAACAGATTGT
TCTGCTTGCTCAGCTGGGGACTTTCCAGAAGGCGCGGCCTGA
GTGACTAAGCCCCGTTGGGGACTTTCCGAAGAGGCATGAAGG
GACTTTCCAAGGCAGGCGTGGCCTGGGCGGGACTGGGGAGTG
GCGAGCCCTCAGATGCTGCATATAAGCAGCTGCTTTCTGCCT
GTACTGGGTCTCTCTGGTTAGACCAGATCTGAGCCTGGGAGC
TCTCTGGCTAGCTAGGGAACCCACTGCTTAAGCCTCAATAAA
GCTTGCCTTGAGTGCTTCAAGTAGTGTGTGCCCGTCTGTTGT
GTGACTCTGGTATCTAGAGATCCCTCAGACCATTTAGTCCG
TGTGGAAATCTCTAGCAGTGGCGCCCGAACAGGGACTTGAA
AGCGAAAGGAAAACCAGAGGAGCTCTCTCGACGCAGGACTCG
GCTTGCTGAAGCGCGCACGGCAAGAGGCGAGGGGCGGCGACT
GGTGAGTACGCCGAAAATTTTGACTAGCGGAGGCTAGAAGGA
GAGAGATGGGTGCGAGAGCGTCAATATTAAGCGGGGAAAAT
TAGATAGATGGGAGAAATTCGGTTAAGGCCAGGAGGAAAGA
AAAGTATAAATTAAAACATATAGTATGGGCAAGCAGGGAGC
TAGAACGATTCGCAGTCAATCCTGGCCTGTTGGAAACATCAG
AAGGCTGTAGACAAATACTGGGACAGTTACACCCGTCCCTTC
AGACAGGATCAGAAGAACTTAAATCAGTATATAATGCAGTAG
CAGTCCTCTATTGTGTGCATCAAAACATAGACATAAAGGACA
CCAAGGAAGCTTTAGAAAAGATAGAGGAAGAGCAAAACAAAT
GTAAGAAAAAGCACAGCAAGCAGCAGCACAGCAAGCAGCAG
CTGGCACAGGAAACAGCAACCCGGTCAGCCAAAATTACCCTA
TAGTACAGAACATGCAGGGGCAAATGGTACATCAGGCCATAT
CACCTAGAACTTTAAATGCATGGGTAAAAGTAATAGAAGAGA
AGGCTTTCAGCCCAGAGGTAATACCCATGTTTTCAGCATTAT
CAGAAGGAGCCACCCCACAAGATTTAAACACCATGCTAAACA
CAGTGGGGGGACATCAAGCAGCTATGCAAATGTTAAAGAGA
CCATCAATGAGGAAGCTGCAGAATGGATAGATTACATCCAG
CGCAGGCAGGGCCTGTTGCACCAGGCCAGATGAGAGACCCAA
GGGGAAGTGACATAGCAGGAACTACTAGTACCCTTCAGGAAC
AAATAGGATGGATGACAGGTAATCCAGCTATCCCAGTAGGAG
AAATCTATAAAGATGGATAATCCTGGGATTAAATAAAATAG
TAAGGATGTATAGCCCTATCAGCATTCTGGACATAAAACAAG
GACCAAAGGAACCCTTTAGAGACTATGTAGACCGGTTCTATA
AAACTCTAAGAGCCGAGCAAGCTACACAGGAGGTAAAAATT
GGATGACAGAAACCTTGTTGGTCCAAAATGCAAACCCAGATT
GTAAGACTATTTTAAAAGCATTGGGACCAGCAGCTACACTAG
```

FIGURE 9(ii)

```
AAGAAATGATGACAGCATGTCAGGGAGTGGGAGGACCCAGCC
ATAAAGCAAGAGTTTTGGCAGAAGCAATGAGCCAAGCAACAA
ATGCAGCTACTGTAATGATGCAGAGAAGCAATTTTAGAAACC
AAAGAAAGAATGTTAAGTGTTTCAATTGTGGCAAAGAAGGGC
ACATAGCCAGAAATTGCAGGGCTCCTAGGAAAAGGGGCTGTT
GGAAATGTGGAAGGAAGGACACCAAATGAAAGATTGTACTG
AGAGACAGGCTAATTTTTAGGGAAAATCTGGCCTTCCCACA
AGGGGAGGCCAGGGAACTTTCTTCAGAGCAGGCCAGAACCAA
CAGCCCCTCTCCAGGGCAGGCCGGAGCCATCAGCCCCGCCAG
AAGAGAGCTTCAGGTTTGGGGAGGAGACAACAACTCCCTCTC
AGAAGCAGGAGCCGATAGACAGGGACAGGGATCTGTATCCTT
TAGCTTCCCTCAGATCACTCTTTGGCAACGACCCCTCGTCAC
AATAAAGATAGGGGGGCAGCTGAAGGAAGCTCTATTAGATAC
AGGAGCAGATGATACAGTATTAGAAGACATGCATTTGCCAGG
AAAATGGAAACCAAAAATGATAGGGGGAATTGGAGGTTTTAT
CAAAGTAAAACAATATGATGAAATTCTTGTAGAAATCTGTGG
ACATAAAGCTATAGGTACAGTATTAGTAGGACCTACACCTGT
CAACATAATTGGAAGAAATCTGTTGACTCAGATTGGTTGCAC
TTTAAATTTTCCCATTAGTCCTATTGAAACTGTACCAGTACA
ATTAAAGCCAGGAATGGATGGCCCAAAGGTTAAACAATGGCC
ATTGACAGAAGAGAAAATAAAAGCATTAGTAGAAATTTGTAC
AGAAATGGAAAAGGAAGGAAAGATTTCAAAAATTGGGCCTGA
AAATCCATACAATACTCCAGTATTTGCCATAAAGAAAAAGA
TGGTACTAAATGGAGAAATTAGTAGATTTCAGAGACCTTAA
TAAGAGAACTCAAGACTTCTGGGAAGTTCAATTAGGAATACC
ACATCCCTCAGGATTAAAAAGAAAAATCAGTAACAGTACT
GGATGTGGGTGATGCATACTTTTCAGTTCCCTTAGATGAAAA
CTTCAGGAAGTATACTGCATTTACCATACCTAGTATAAATAA
TGAGACACCAGGGATTAGATATCAGTACAATGTGCTTCCACA
GGGATGGAAAGGATCACCAGCAATATTCCAAAGTAGCATGAC
AAGAATCTTAGAGCCTTTTAGAAGACAAAATCCAGACATAGT
TATCTATCAATACATGGATGACTTGTATGTAGGATCTGATTT
AGAAATAGGACAGCATAGAATAAAAATAGAGGAACTGAGACA
ACATCTGTTGAAGTGGGGATTTACCACACCAGACAAAAAGCA
TCAGAAAGAACCCCCATTCCTTTGGATGGGTTATGAACTCCA
TCCTGATAAATGGACAGTGCAACCTATAGTACTGCCAGAAAA
AGACAGCTGGACTGTCAATGACATACAGAAGTTAGTGGGTAA
ATTAAATTGGGCAAGTCAGATTTACCCAGGAATTAAAGTAAG
GCAATTATGTAAACTCCTTAGGGGAACCAAAGCACTAACAGA
```

FIGURE 9 (iii)

```
AGTAATACCACTAACAGAAGAAGCAGAGCTAGAACTGGCAGA
AAACAGGGAAATTCTAAGAGAACCAGTACATGGAGTGTATTA
TGACCCATCAAAAGACTTAATAGCAGAAATACAGAAGCAGGA
GCAAGGCCAATGGACATATCAAATTTATCAAGATCAATTTAA
AAATCTAAAAACAGGAAAGTATGCAAGATTGAGGGGTGCCCA
CACTAATGATGTAAAACAATTTCCAGAGGCAGTGCAAAAAT
AGCCACAGAAGCATAGTAATATGGGAAAGACTCCTAAATT
TAGACTACCCATACAAAAGAAACATGGGACGCATGGTGGAC
AGAGTATTGGCAAGCCACCTGGATTCCTGAGTGGGAGTTTGT
CAATACCCCTCCCCTAGTAAATTATGGTACCAGTTAGAAAA
AGAACCCATAATAGGAGCAGAAACTTTCTATGTAGATGGGGC
AGCTAACAGAGAGACTAAATTAGGAAAAGCAGGATATGTTAC
TGACAGAGGAAGACAAAAGTTGTCTCCCTAACTGACACAAC
AAATCAGAAGACTGAGTTACAAGCAATTCATCTAGCTTTGCA
GGATTCAGGATTAGAAGTAAACATAGTAACAGACTCACAGTA
TGCATTAGGAATCATTCAAGCACAACCAGATAAAAGTGAATC
AGAAATAGTCAATCAAATAATAGAGCAATTAATAAAAAGGA
AAAGGTCTACCTGGCATGGGTACCAGCACACAAGGAATTGG
AGGGAATGAACAAGTAGATAAATTAGTCAGTGCTGGAATCAG
GAAAATACTATTTTAGATGGAATAGATAAGGCACAAGAAGG
CCATGAGAAATATCACAGTAATTGGAGAGCAATGGCTAGTGG
TTTTAACCTGCCACCTATAGTAGCAAAAGAAATAGTAGCCAG
CTGTGATAAATGTCAGCTAAAAGGAGAAGCCATGCATGGACA
AGTAGACTGTAGTCCAGGAATATGGCAACTAGATTGTACACA
TCTAGAAGGAAAAATTATCCTGGTAGCAGTTCATGTAGCCAG
TGGATATATAGAAGCAGAAGTTATTCCAGCAGAGACAGGGCA
GGAAACAGCATACTTTATCTTAAAATTAGCAGGAAGGTGGCC
AGTAAACACAATACATACAGACAATGGCGGCAATTTCATCAG
TACCACGGTTAAGGCCGCCTGTTGGTGGGCAGGGATCAAGCA
GGAATTTGGCATTCCCTACAATCCCCAAAGCCAAGGAGTAGT
GGAATCTATGAATAGAGAATTAAAGAAATTATAGGACAGGT
AAGAGATCAGGCTGAACATCTTAAGACAGCAGTACAAATGGC
AGTATTCATCCACAATTTTAAAAGAAAGGGGGGATTGGGGG
ATACAGTGCAGGGGAAGAATAGTAGACATAATAGCAACAGA
CATACAAACTAAAGAATTACAAAGCAAATTACAAAAATTCA
AAATTTTCGGGTTTATTACAGGGACAGCAGAGATCCACTTTG
GAAAGGACCAGCAAAACTTCTCTGGAAAGGCGAAGGGCAGT
AGTAATACAAGATAATAGTGACATAAAAGTAGTGCCAAGAAG
AAAAGTAAAGATCATTAGGGATTATGGAAAACAGATGGCAGG
```

FIGURE 9 (iv)

```
TGATGATTGTGTGGCAAGTAGACAGGATGAGGATTAGAACAT
GGAACAGTTTAGTGAAACACCATATGTATGTTTCAAAGAAAG
CTAAGGGATGGATTTATAGACATCACTATGAAAACACTCATC
CAAAAATAAGCTCAGAAGTACACATCCCACTAGGGGAAGCTA
GATTGGTAATAACAACATATTGGGGTCTACATACAGGAGAAA
GAGACTGGCATTTGGGTCAGGGAGTCTCCATAGAATGGAGGG
AAAGGACATATAGAACACAAGTAGACCCCGAACTAGCAGACC
AACTAATTCATATACATTACTTTGATTGTTTTTCAGAATCTG
CCATAAGAAGTGCCATATTAGGATATAGAGTTAGGCATAGGT
GTGAATATCAAGCAGGACATAACAAGGTAGGATCTCTACAGT
ACTTGGCACTAACAGCATTAATAACACCAAAGAAGATAAAGC
CACCTTTGCCTAGTGTTGCGAAACTGACAGAGGATAGATGGA
ACAAGCCCCAGAAGACCAAGGGCCACAGAGGCAGCCATACAA
TGAATGGACACTAGAACTTTTAGAGGAGCTTAAGAATGAAGC
TGTTAGGCATTTTCCTAGGGTATGGCTCCATGGCTTAGGGCA
ACATATCTATGAAACTTATGGGGATACTTGGGAAGGAGTGGA
GGCCATAACAAGAACTCTGCAACAACTGCTGTTTATTCATTT
CAGAATTGGGTGTCAACATAGCAGAATAGGCATTATTCGACA
GAGGAGAGCAAGAAATGGAGCCAGTAGATCCTAGACTAGAGC
CCTGGAAGCATCCAGGAAGTCAGCCTAAGACTGCGTGTACCA
CTTGCTATTGTAAAAGTGCTGCTTTCATTGCCAAGTTTGTT
TTATGACAAAAGGCTTAGGCATCTCCTATGGCAGGAAGAAGC
GGAGACAGCGACGAAGAGCTCCTCAAGACAGTCAGACTCATC
AAGCTTATCTATCAAAGCAGTAAGTAATATATGTAATGCAAC
CTTTACAAATAGTAGCAATAGTAGCATTAGTAGTAGCAGGAA
TAATAGCAATAGTTGTGTGGACCATAGTATTCATAGAATATA
AGAAAATATTAAGACAAAGAAAATAGACAGGTTGATTGATA
GAATAAGAGAAAGAGCAGAAGACAGTGGCAATGACAGTGAAG
GGGATCAGGAAGAATTATCGGCACTTGTGGACATGGGGCACC
ATGATCCTTGGGATATTAATGATCTGTAGAGCTGCAAACAAT
TTGTGGGTCACAGTCTATTATGGGGTACCTGTGTGGAGAGAA
GCAACCACCACTCTATTTTGTGCATCAGATGCCAAGGCATAT
GATGCAGAGGTACATAATGTTTGGGCCACACATGCCTGTGTA
CCCACAGACCCTAACCCACAAGAAGTAGAATTGAAAAATGTG
ACAGAAAATTTTAACATGTGGAAAATAACATGGTAGAACAG
ATGCATGAGGATATAATCAGTTTATGGATCAAAGCCTGAAG
CCATGTGTAAAATTAACCCCACTCTGTGTTTCTTTAAATTGC
ACTGATGCTACTAATACCACTAATAGTAATACCACTAGCAGC
AGCGAGAAACCGAAGGGGACAGGGGAAATAAAAACTGCTCT
```

FIGURE 9 (v)

```
TTCAATATCACCACAAGCATAAGAGATAAGGTGCAGAAACAA
TATGCACTTTTTTATAGCCTTGATGTAGTACCAATGGATGAT
AATGATAATAGTACAAGCTATAGGTTAATAAGTTGTAACACC
TCAATCATTACACAGGCCTGTCCAAGATATCCTTTGAGCCA
ATTCCCATACATTATTGTGCCCGGCTGGTTTTGCGATTCTA
AAGTGTAAAGATAAAAGGTTCAATGGAAAGGACCATGTACA
AGTGTCAGCACAGTACAGTGTACATGGAATTAGGCCAGTA
GTATCAACTCAACTGTTGTTAAATGGCAGTCTAGCAGAAGAA
GAGGTAGTAATTAGATCTGACAATTTACGAACAATGCTAAA
ACCATAATAGTACAGCTGAGCAAATCTGTAGAATTACTTGT
GTAAGACCCAACAACAATACAAGAAAAGTATAAGTATGGGA
CCAGGGAGAGCATTTTATACAACAGAAATAATAGGAGATATA
AGACAAGCATATTGTAACATTAGTAAAGCAAACTGGACTGAC
ACTTTAGAACAGATAGCTAGAAAATTAAGAGAACAATTTGAG
AATAAAACAATAGTCTTTAAGCCATCCTCAGGAGGGGACCCA
GAAATTGTAACACAGTTTTACAGTTTTAATTGTGGAGGGGAA
TTTTTCTACTGTAATTCAACACAACTGTTTAATGGTACTTGG
AATGGTACTTGGGTTAATGGTACTTGGAGTAGTAATAATACG
ACTGATACTGCAAATATCACACTCCCATGCAGAATAAAACAA
TTTATAAACATGTGGCAGGAAGTAGGAAAAGCAATGTATGCC
CCTCCCATCAAAGGACAAATTAAATGTACATCAAATATTACA
GGGCTGATATTAACAAGAGATGGTGGTAACAATAACACCACG
AACGACAACGAGACCGAGACCTTCAGACCTGGAGGAGGAGAT
ATGAGGGACAATTGGAGAAGTGAATTATATAAATATAAAGTA
GTACAAGTTGAACCATTAGGAGTAGCACCCACCAAGGCAAAG
AGAAGAGTGGTGCAAAGAGAAAAAGAGCAGTGGGAATAGGA
GCTATGTTCCTTGGGTTCTTAGGAGCAGCAGGAAGCACTATG
GGCGCAGCGTCAGTGACGCTGACGGTACAAGCCAGACAATTA
TTGTCTGGTATAGTGCAGCAGCAGAACAATCTGCTGAGGGCT
ATTGAGGCGCAACAGCATCTGTTGCAACTCACAGTCTGGGGC
ATCAAACAGCTCCAGGCAAGAGTCCTGGCTGTGGAAAGATAC
CTAAGGGATCAACAGCTCCTGGGACTTTGGGGTTGCTCTGGA
AAACTCATTTGCACCACTACTGTGCCTTGGAACAATAGCTGG
AGTAATAAATCTCTGGAACAATTTGGGATAACATGACCTGG
ATGCAGTGGGAAAGAGAAATTGACAATTACACAAACATAATA
TACACCTTAATTGAAGAATCGCAGAACCAACAAGAAAAAAAT
GAACTAGAATTATTGGAATTGGATAAATGGGCAAATTTGTGG
AATTGGTTTAGTATATCAAACTGGCTATGGTATATAAAATTA
TTCATAATGGTAGTAGGAGGCTTGGTAGGTTTAAGAATAGTT
```

FIGURE 9 (vi)

TTTACTGTACTTTCTATAGTTAATAGAGTTAGGCAGGGATAC
TCACCATTATCGTTTCAGACCCACCTCCCAACCCCGAAGGGA
CCCGACAGGCCAGAAGGAATCGAAGAAGAAGGTGGAGAGA
GACAGAGGCAGCTCCACTCGATTAGTGCACGGATTCTTAGCA
CTTTTCTGGGACGACCTGAGGAGTCTGTGCCTCTTCAGCTAC
CACCACTTGAGAGACTTACTCTTGATTGTAACGAGGATTGTG
GAACTTCTGGGACGCAGGGGATGGGAAGCCCTCAAATACTGG
TGGAATCTCCTGCAGTATTGGAGGCAGGAACTACAGAAGAGT
GCTGTTAGCTTGTTCAATGGCACGGCCATAGCAGTAGCTGAG
GGGACAGATAGAGTTATAGAAGCTTTACGAAGGGCTTATAGA
GCTATTCTCCACATACCTAGAAGAATAAGACAGGGCTTAGAA
AGGGCTTTGCTATAAATGGGTGGCAAGTGGTCAGAAAGTAG
TGTGGTTAGAAGGCATGTACCTTTAAGACAAGGCAGCTATAG
ATCTTAGCCGCTTTTTAAAAGAAAAGGGGGACTGGAAGGGC
TAATTCACTCACGGAAAGACCAGTTGAACCAGAAGAAGATA
GAAGAGGCCATGAAGAAGAAACAACAGATTGTTCTGCTTGC
TCAGCTGGGGACTTTCCAGAAGGCGCGGCCTGAGTGACTAAG
CCCCGTTGGGGACTTTCCGAAGAGGCATGAAGGGACTTTCCA
AGGCAGGCGTGGCCTGGGCGGGACTGGGGAGTGGCGAGCCCT
CAGATGCTGCATATAAGCAGCTGCTTTCTGCCTGTACTGGGT
CTCTCTGGTTAGACCAGATCTGAGCCTGGGAGCTCTCTGGCT
AGCTAGGGAACCCACTGCTTAAGCCTCAATAAAGCTTGCCTT
GAGTGCTTCAAGTAGTGTGTGCCCGTCTGTTGTGTGACTCTG
GTATCTAGAGATCCCTCAGACCATTTTAGTCCGTGTGGAAAA
TCTCTAGCA

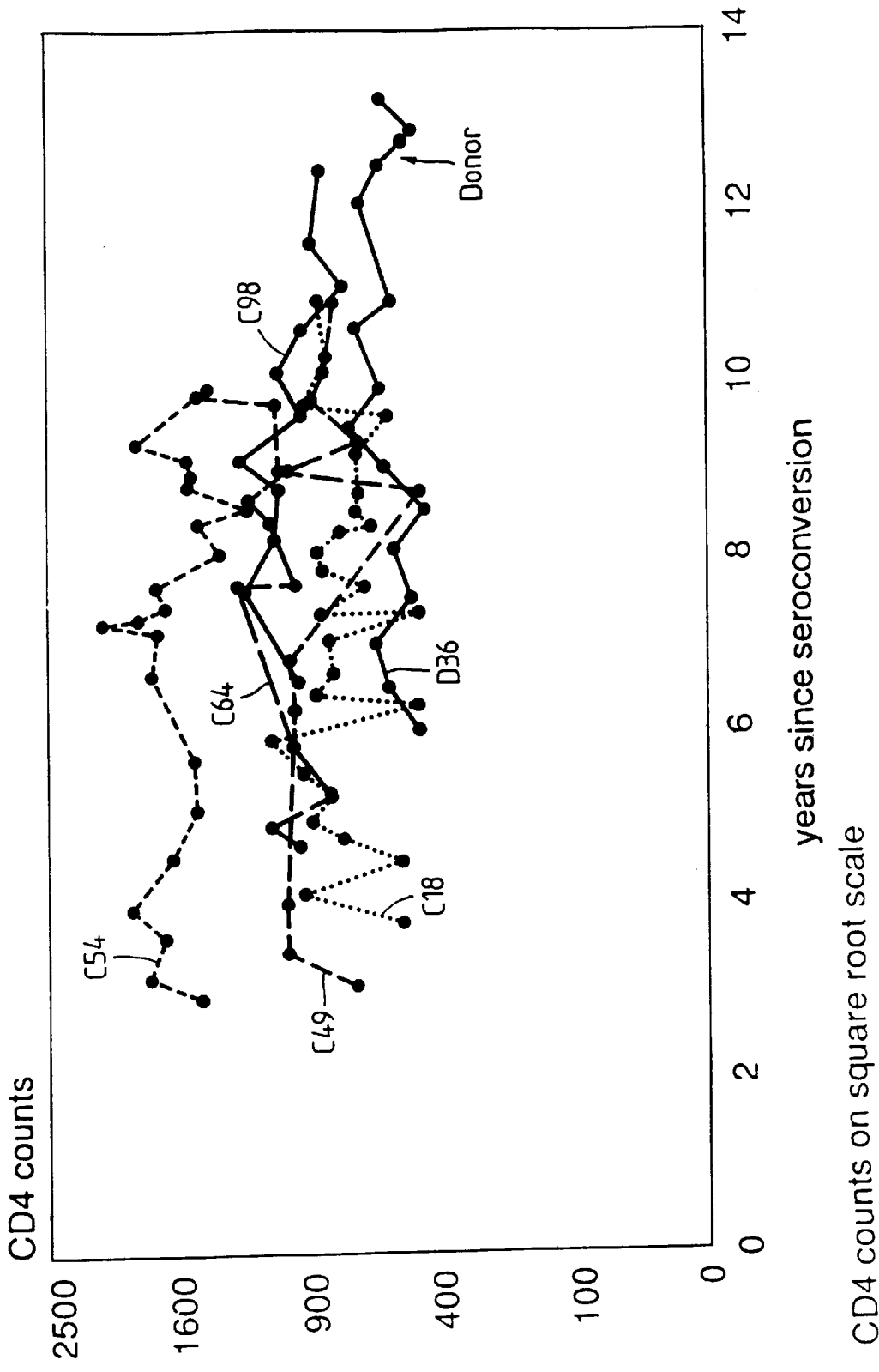

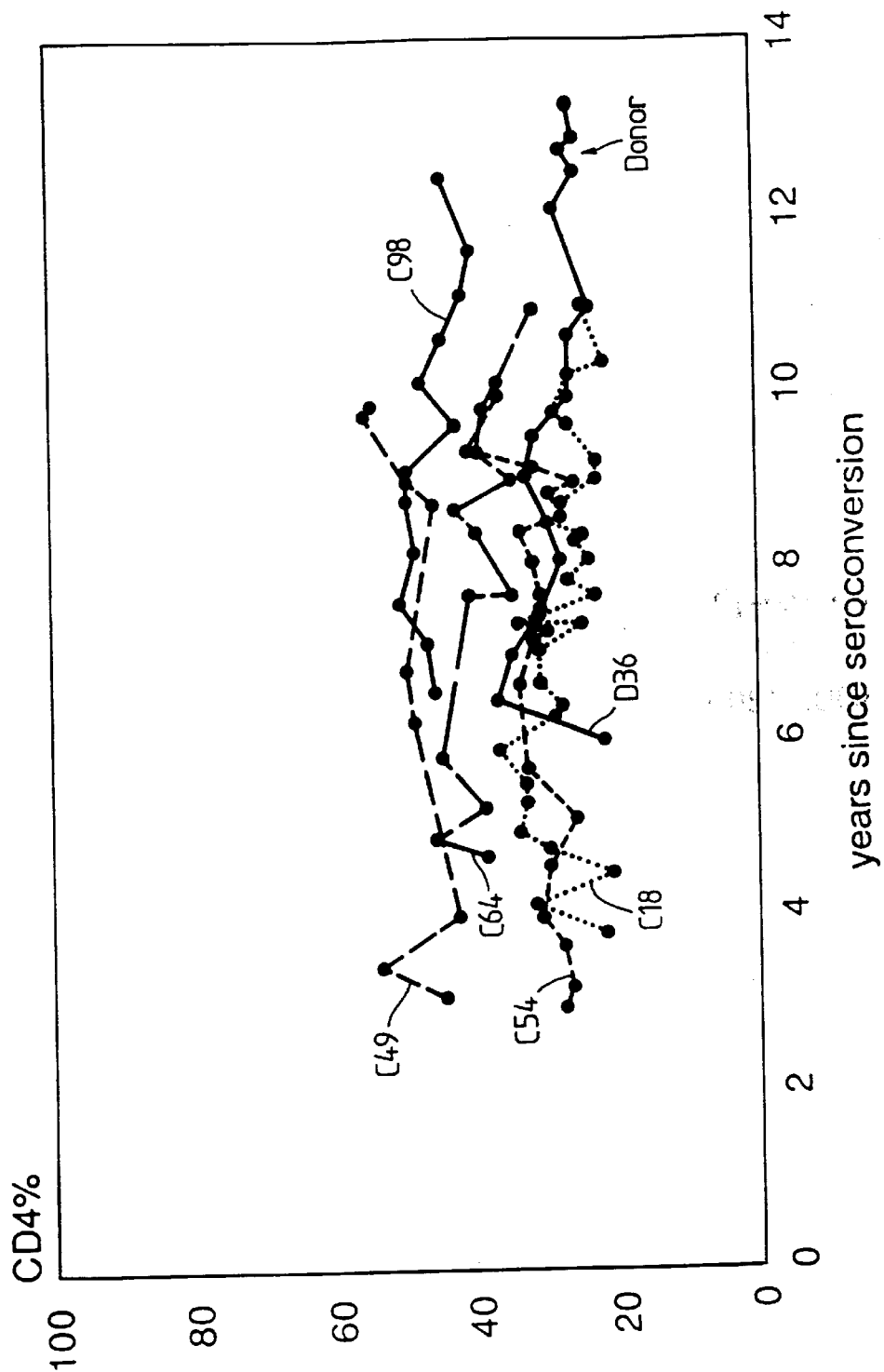
FIG 10(b)(ii)

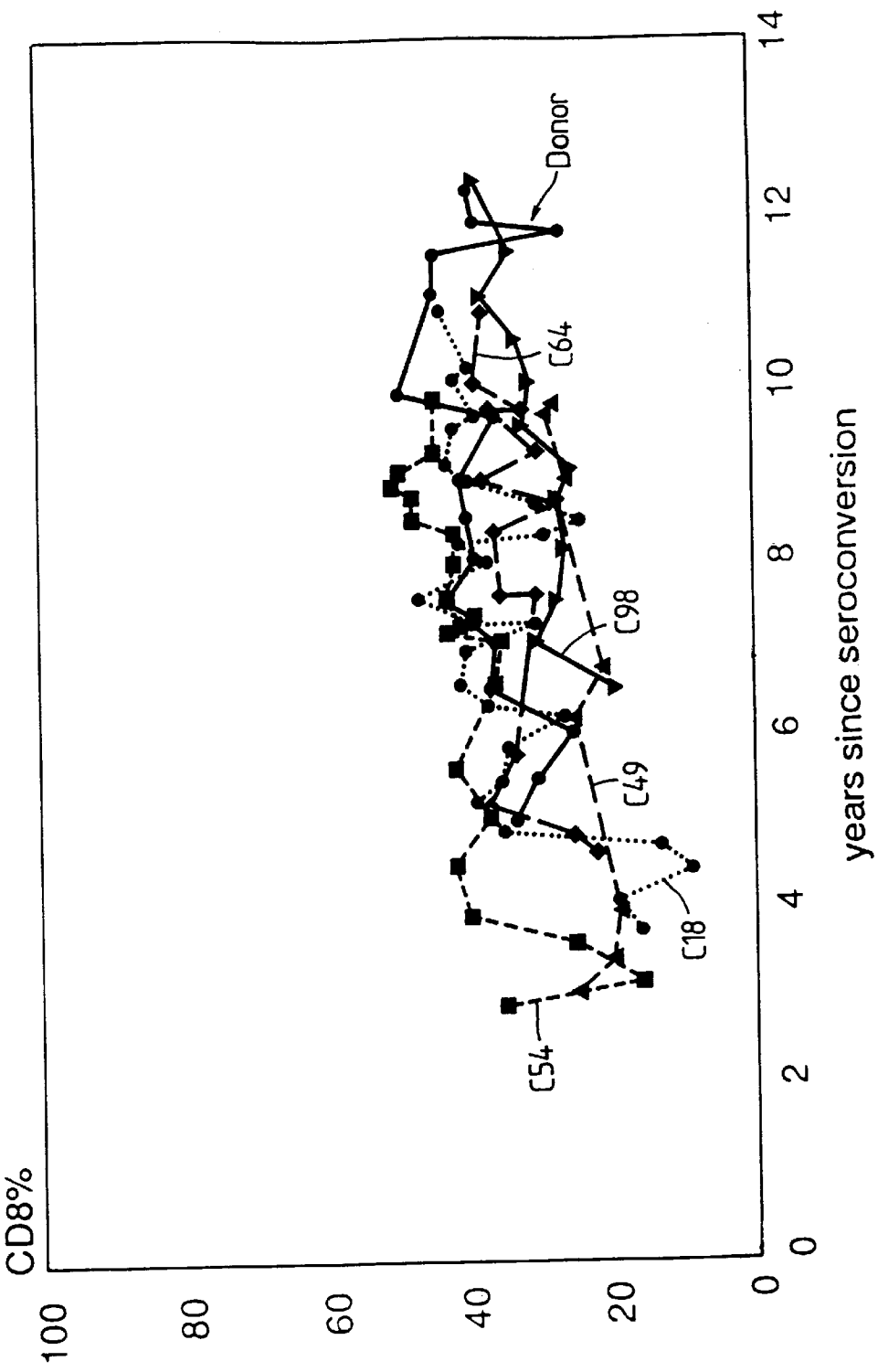
FIG 10 (c)(ii)

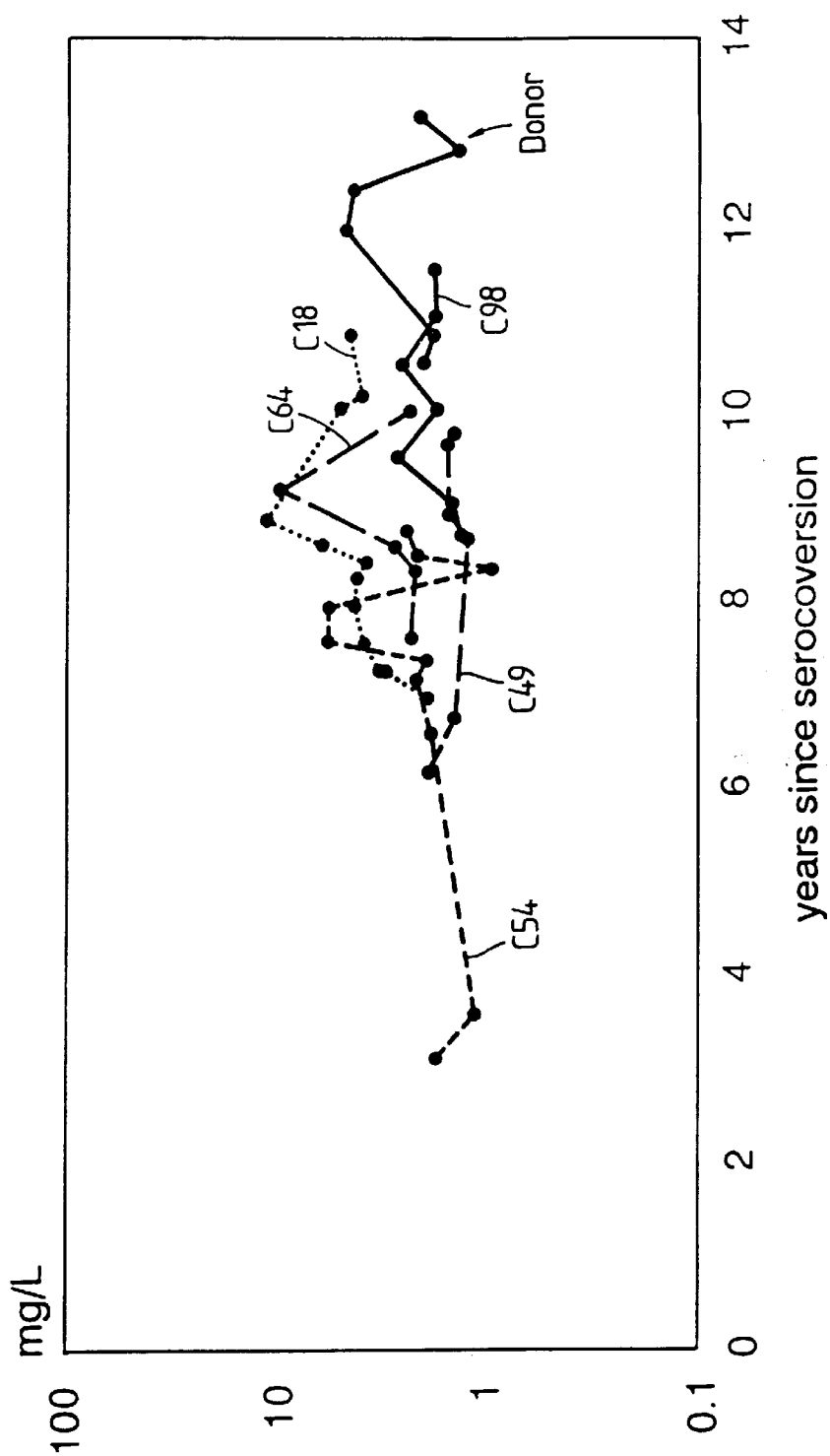
FIG 10(f) trends in beta-2 microglobulin since seroconversion

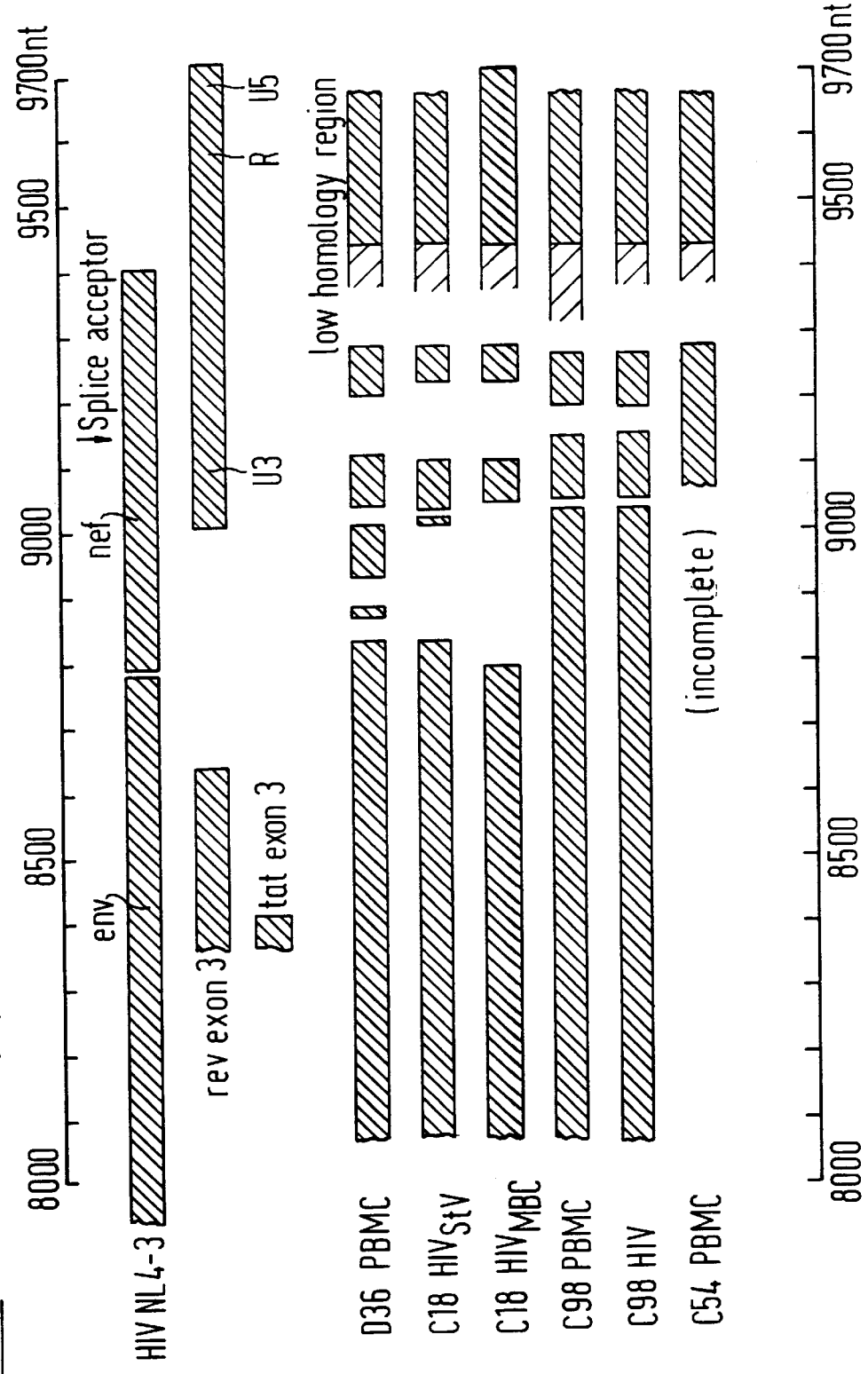

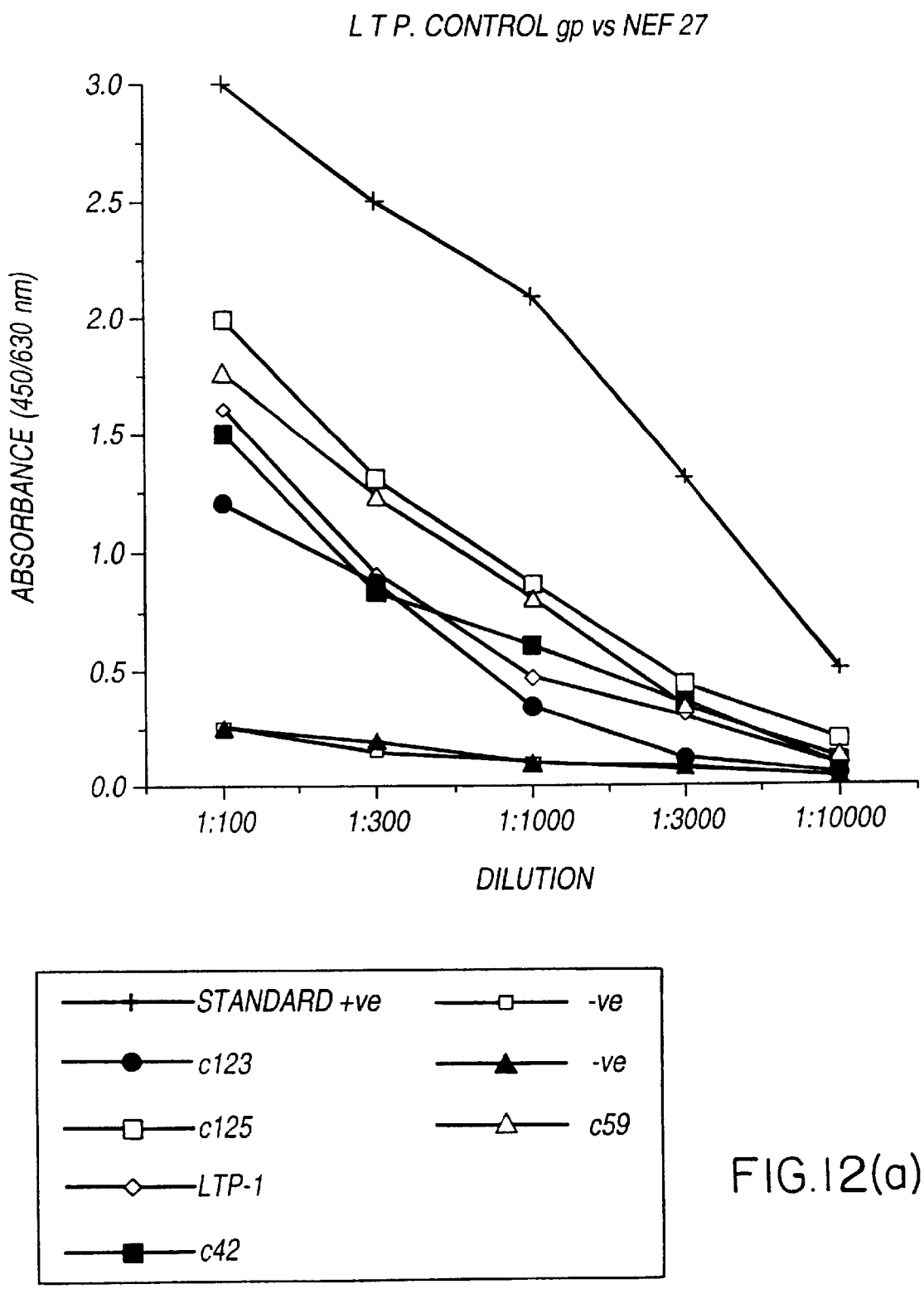

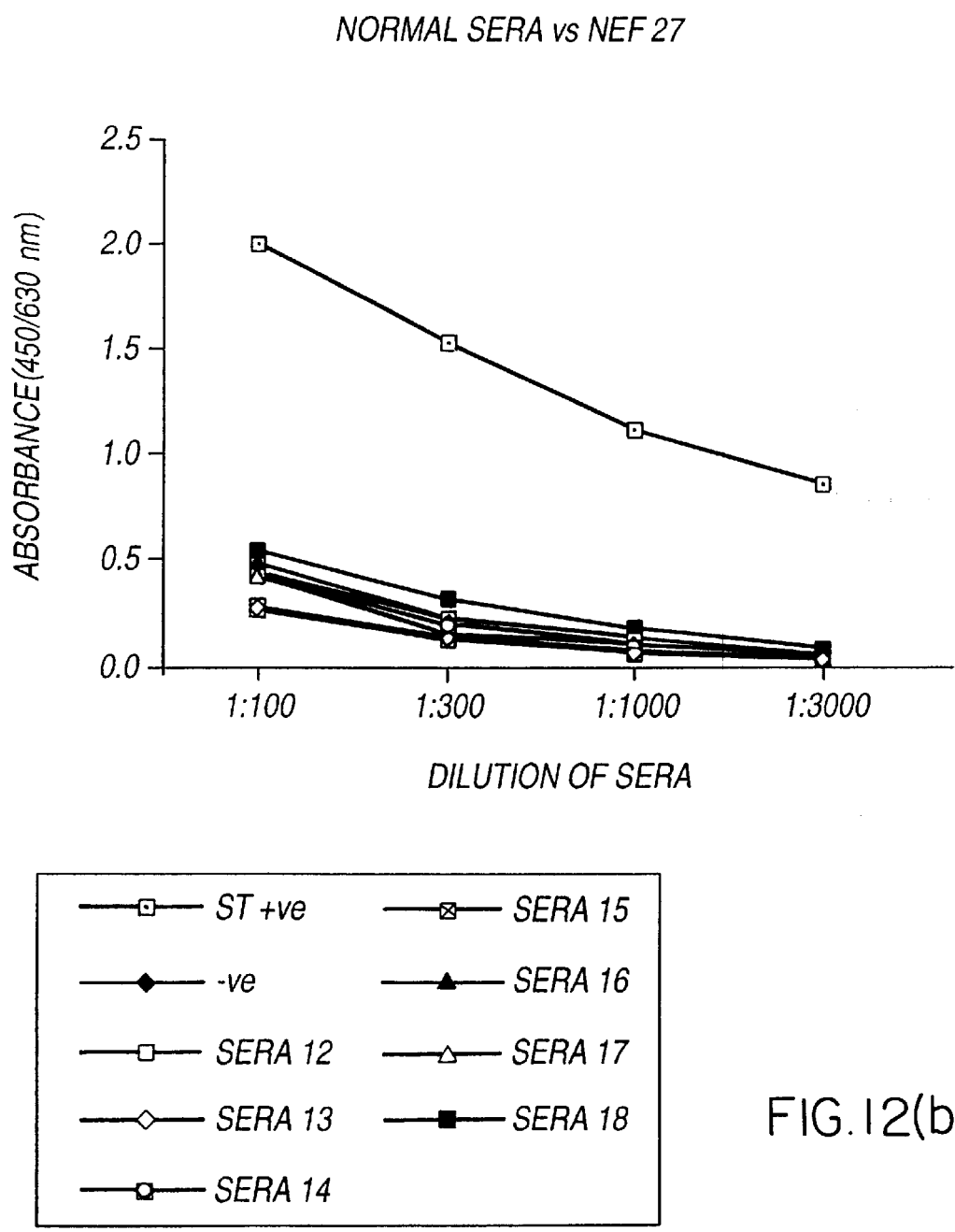
FIG.12(b)(ii)

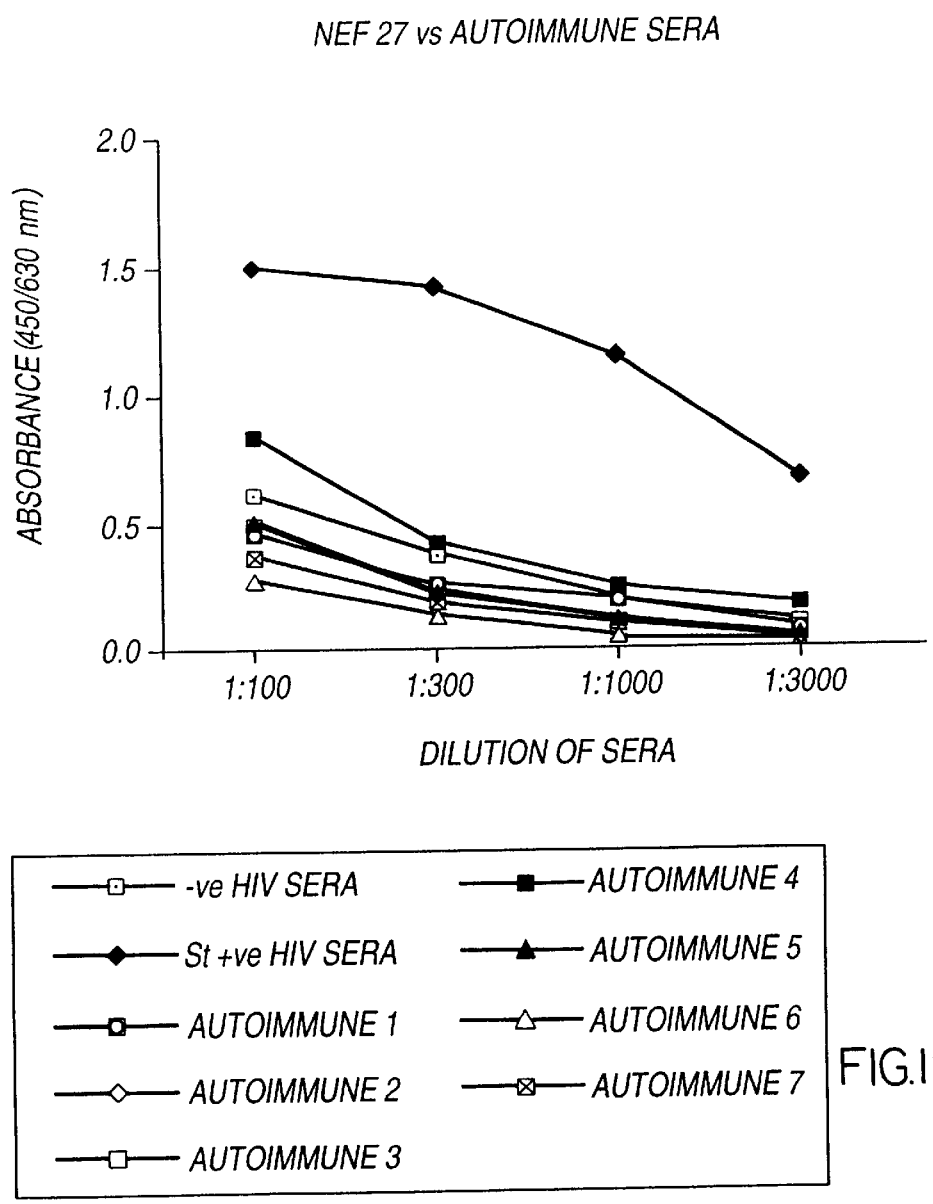
FIG.12(b)(iii)

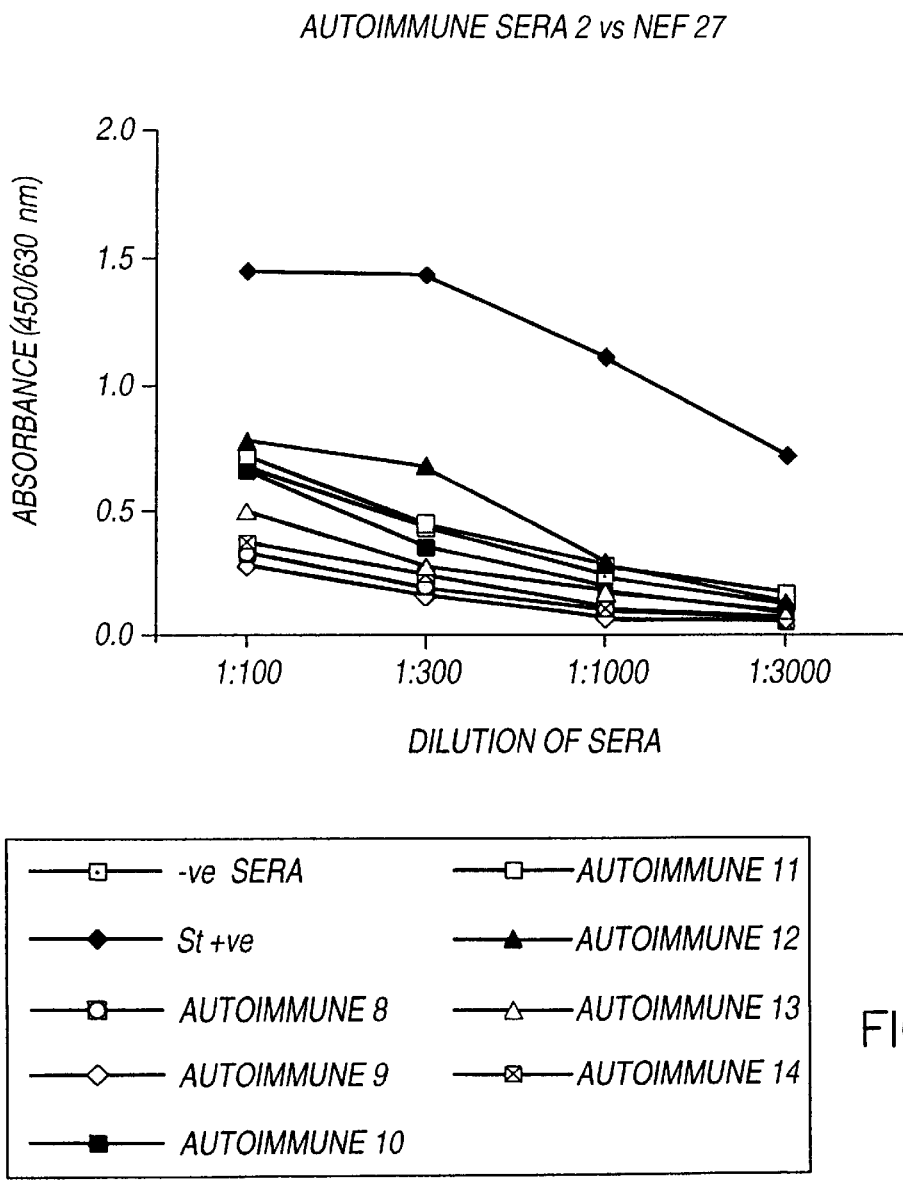
FIG.12(b)(iii) cont.

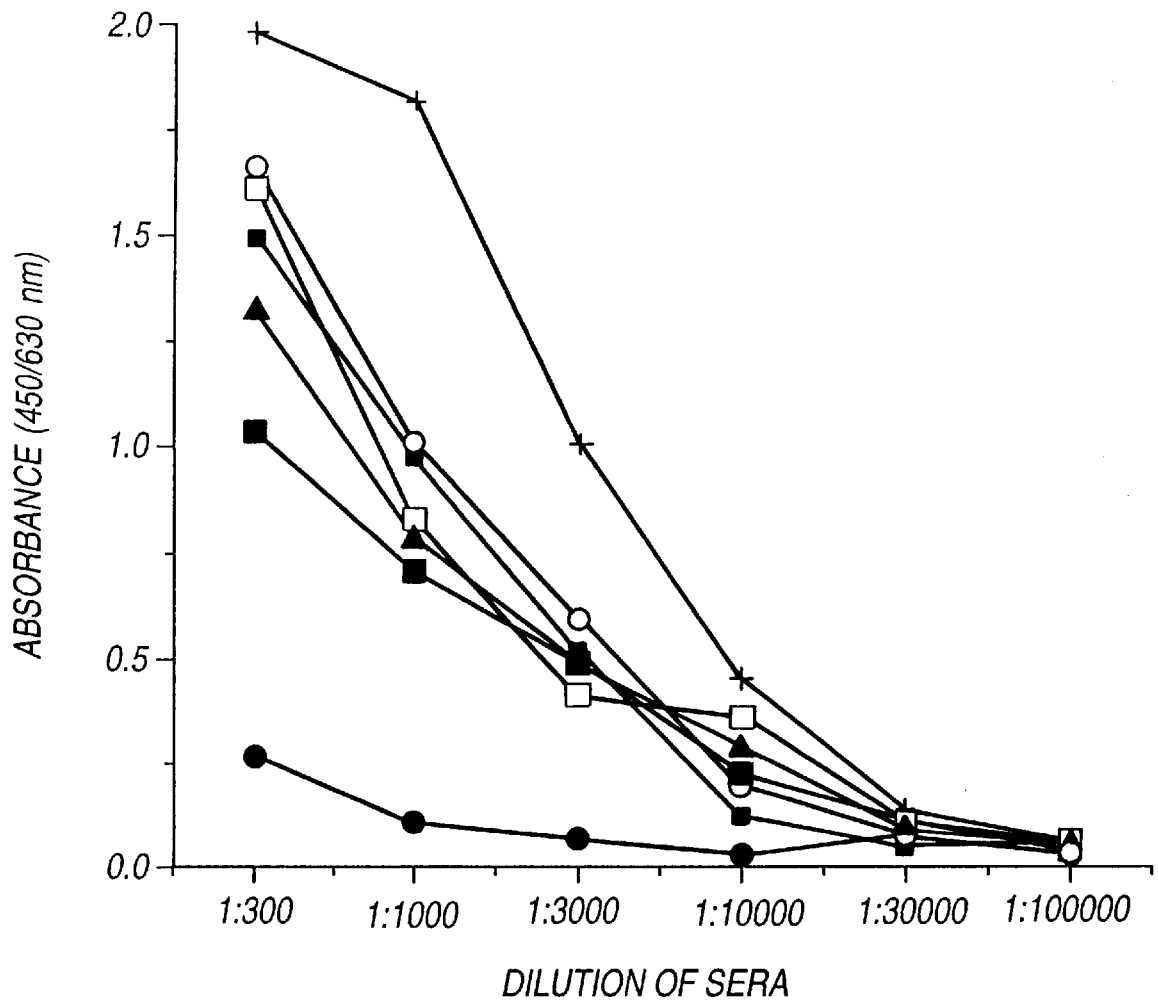
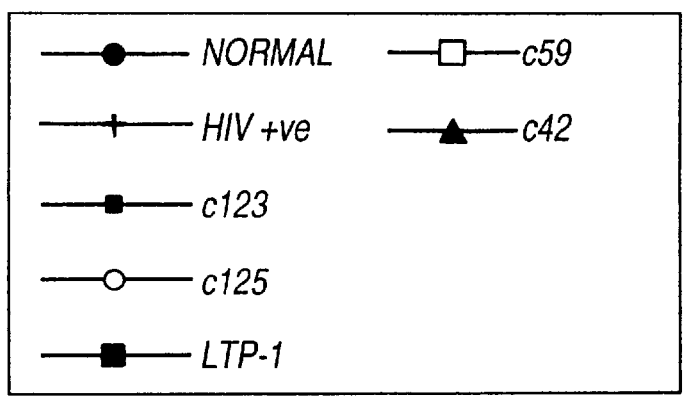
FIG.13(a)(i)

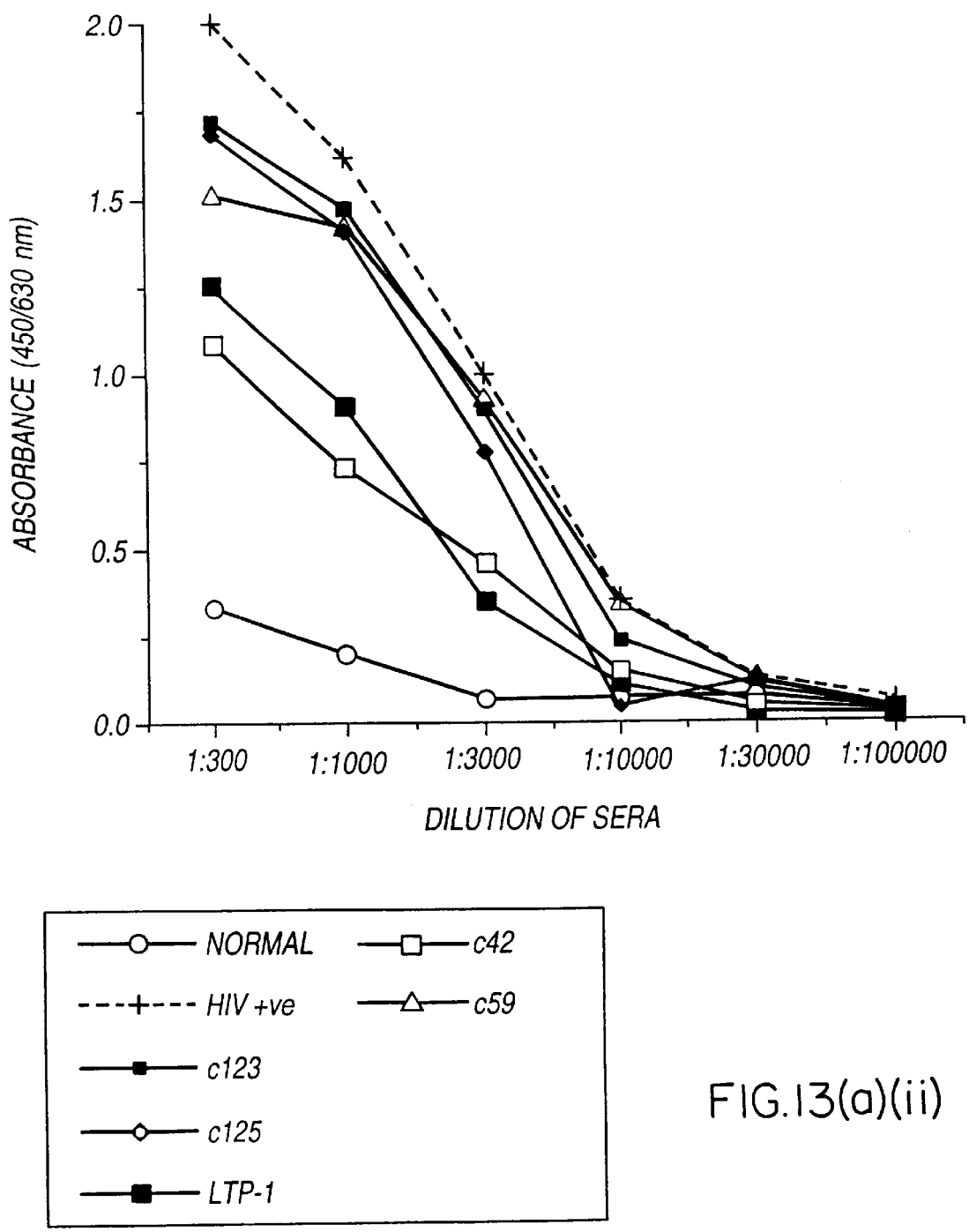
FIG.13(a)(ii)

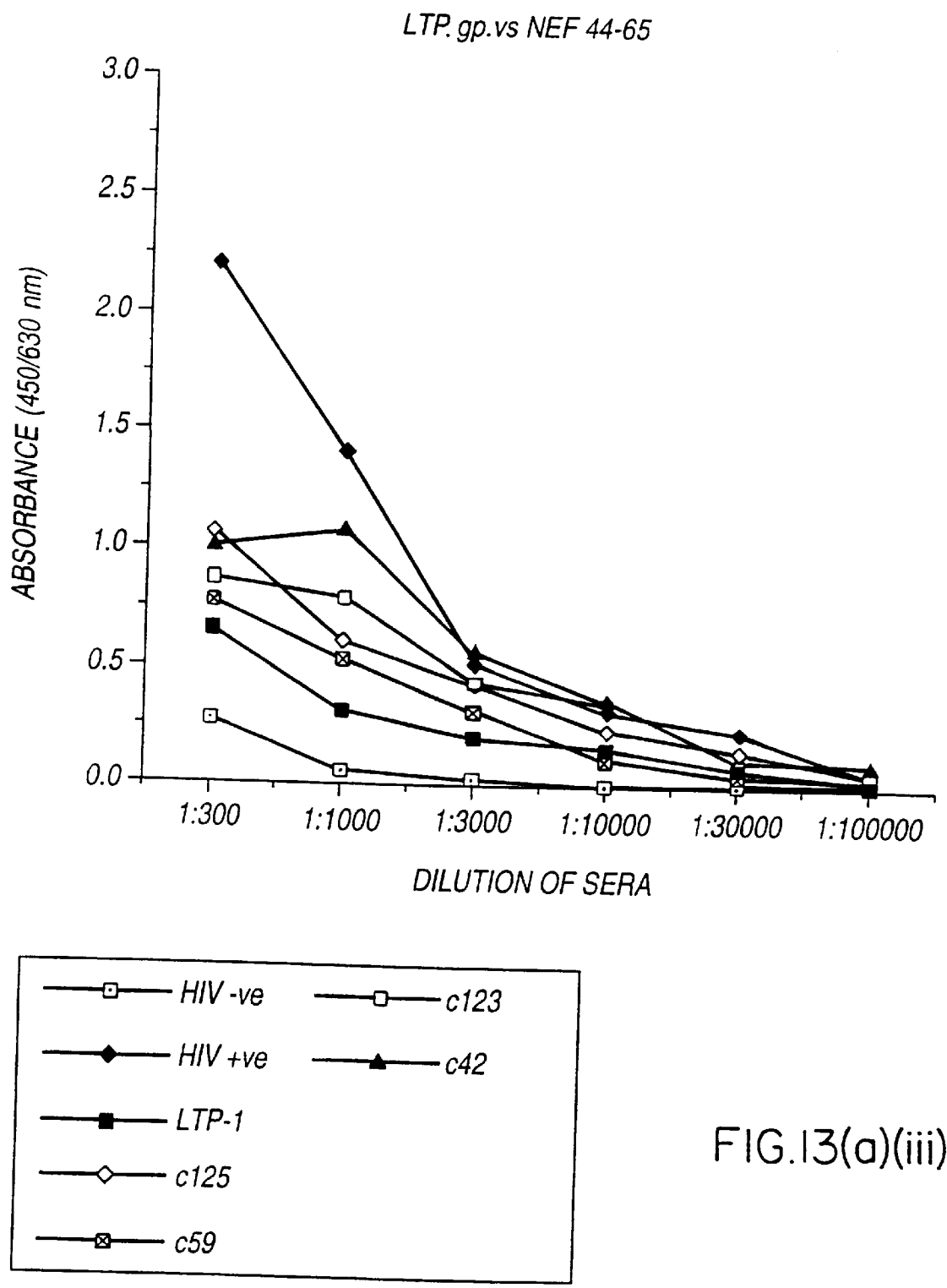
FIG.13(a)(iii)

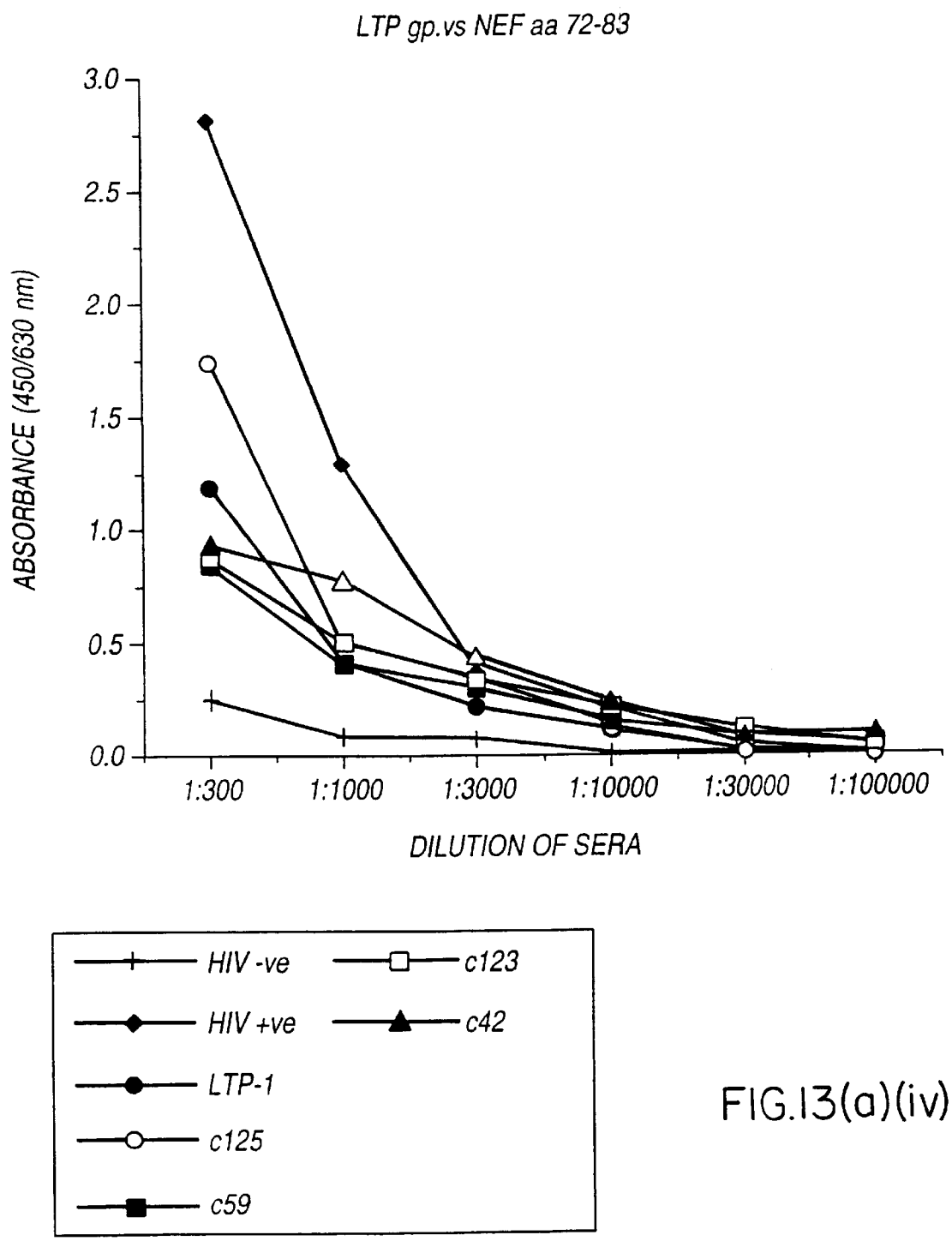
FIG.13(a)(iv)

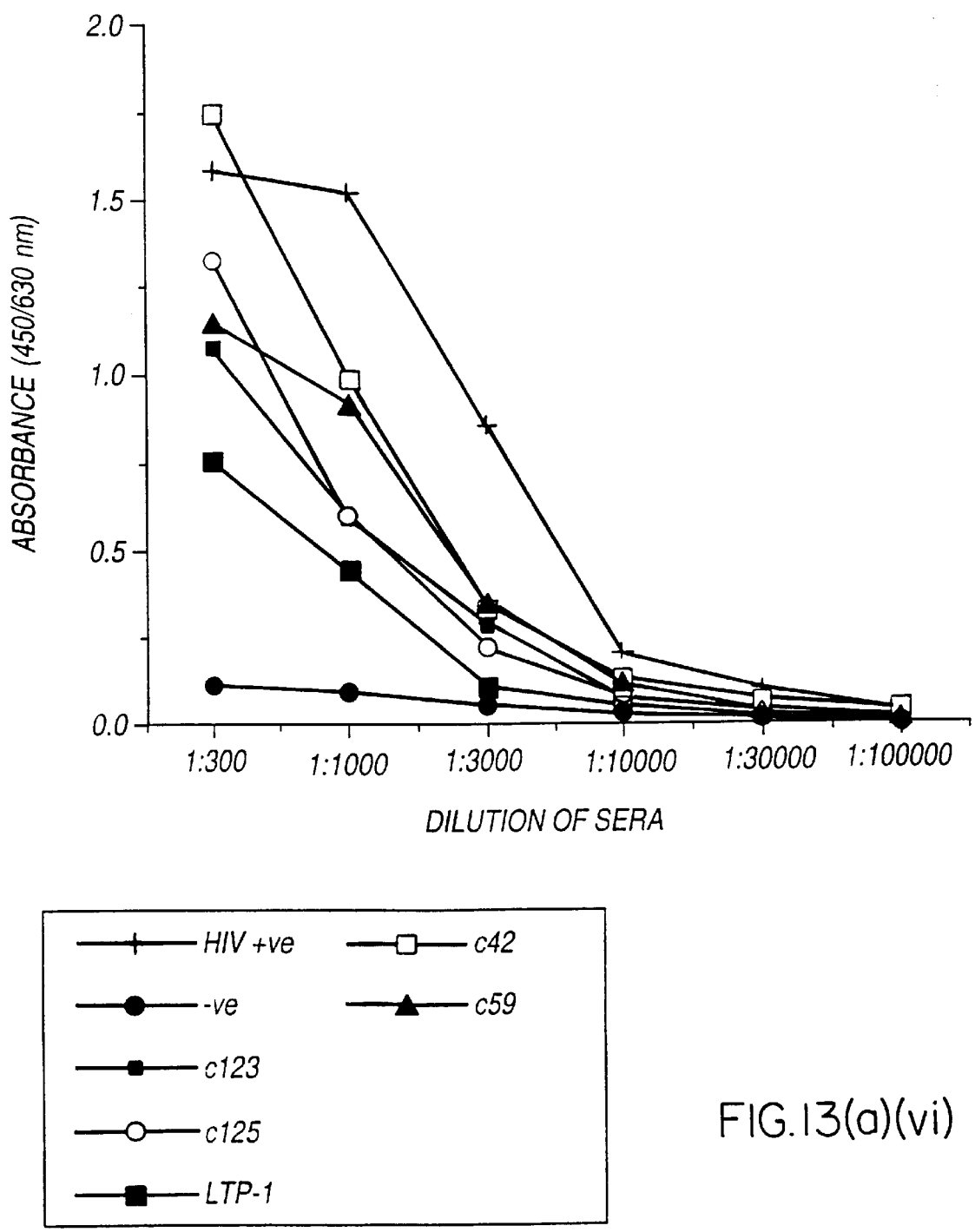
FIG.13(a)(vi)

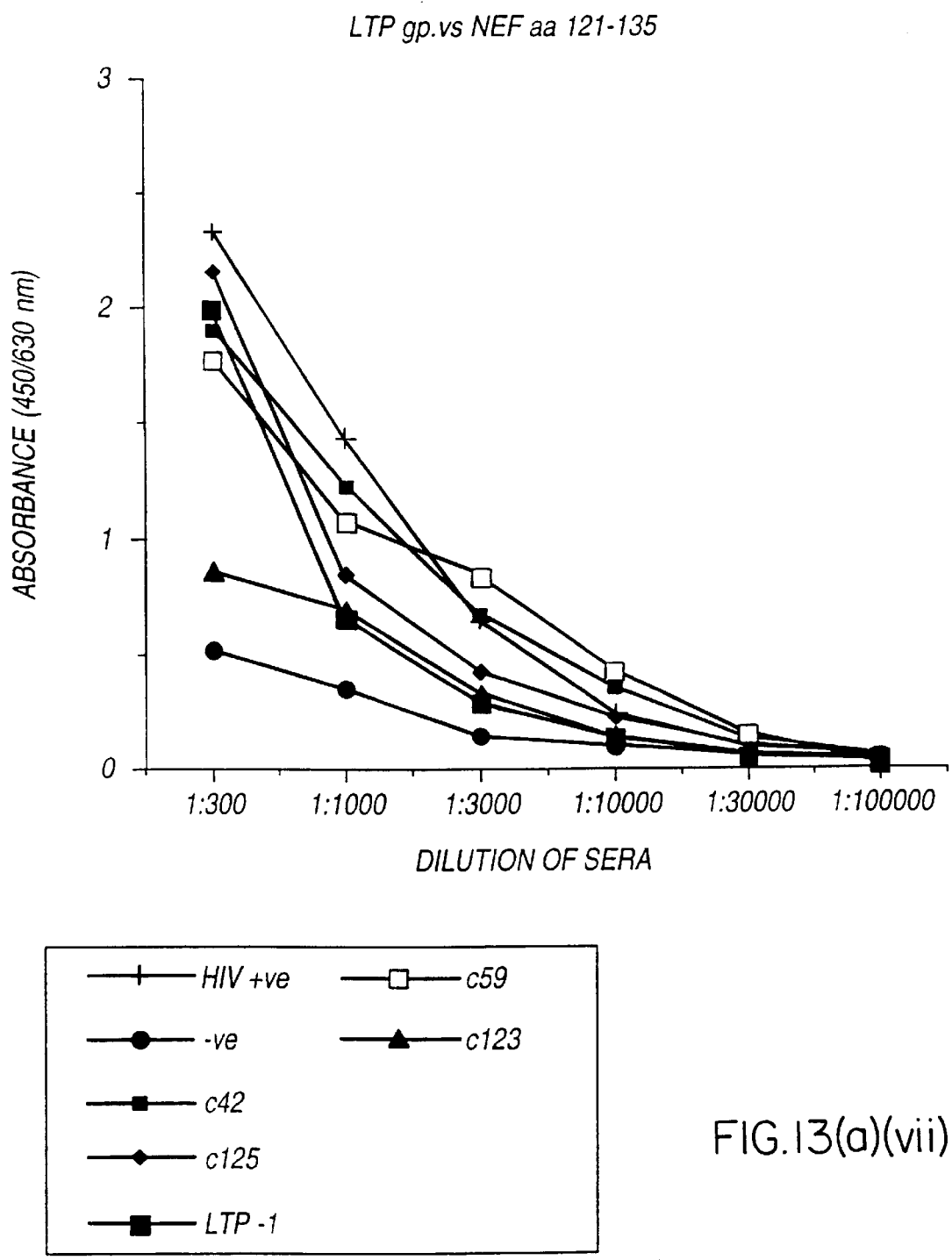
FIG.13(a)(vii)

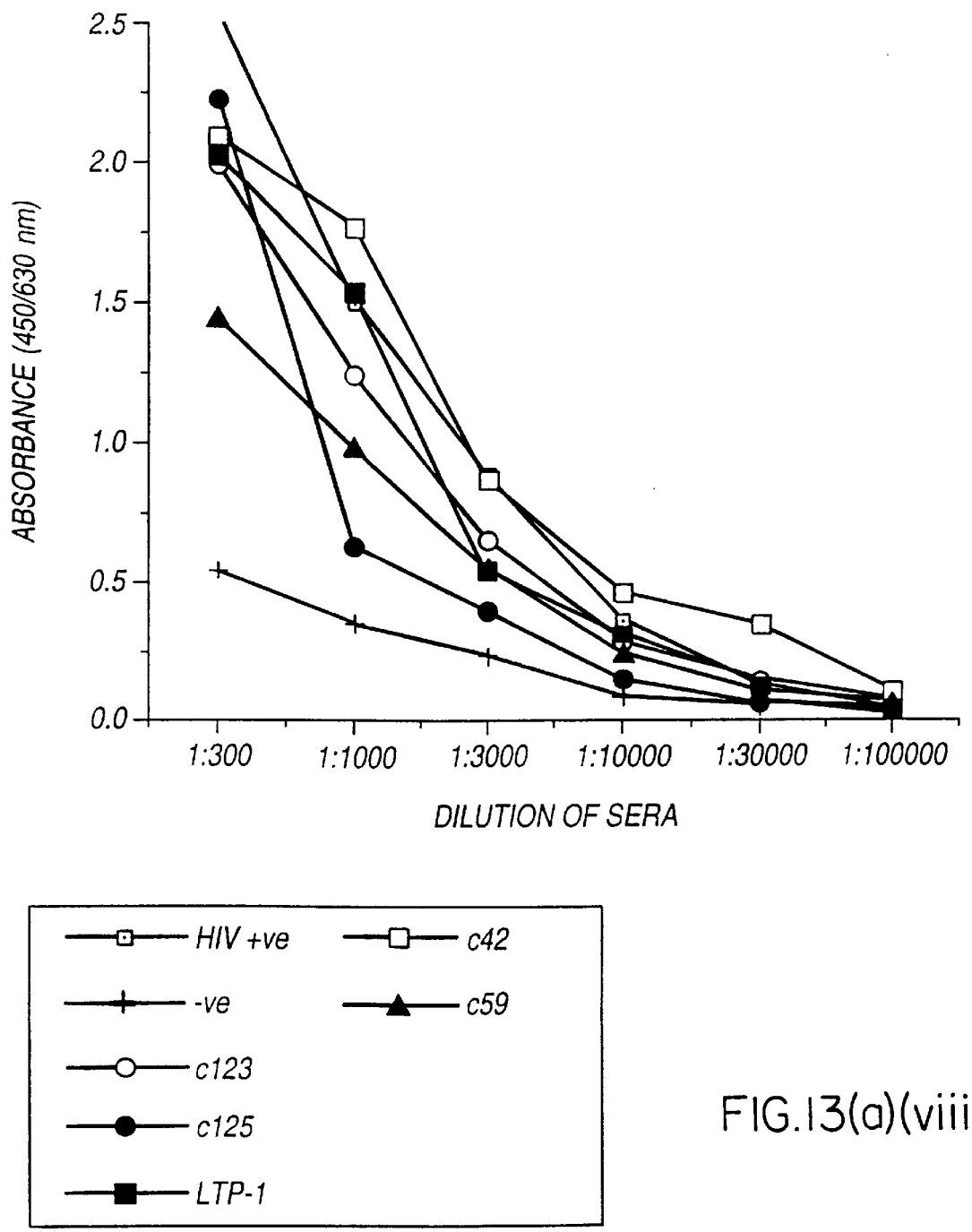
FIG.13(a)(viii)

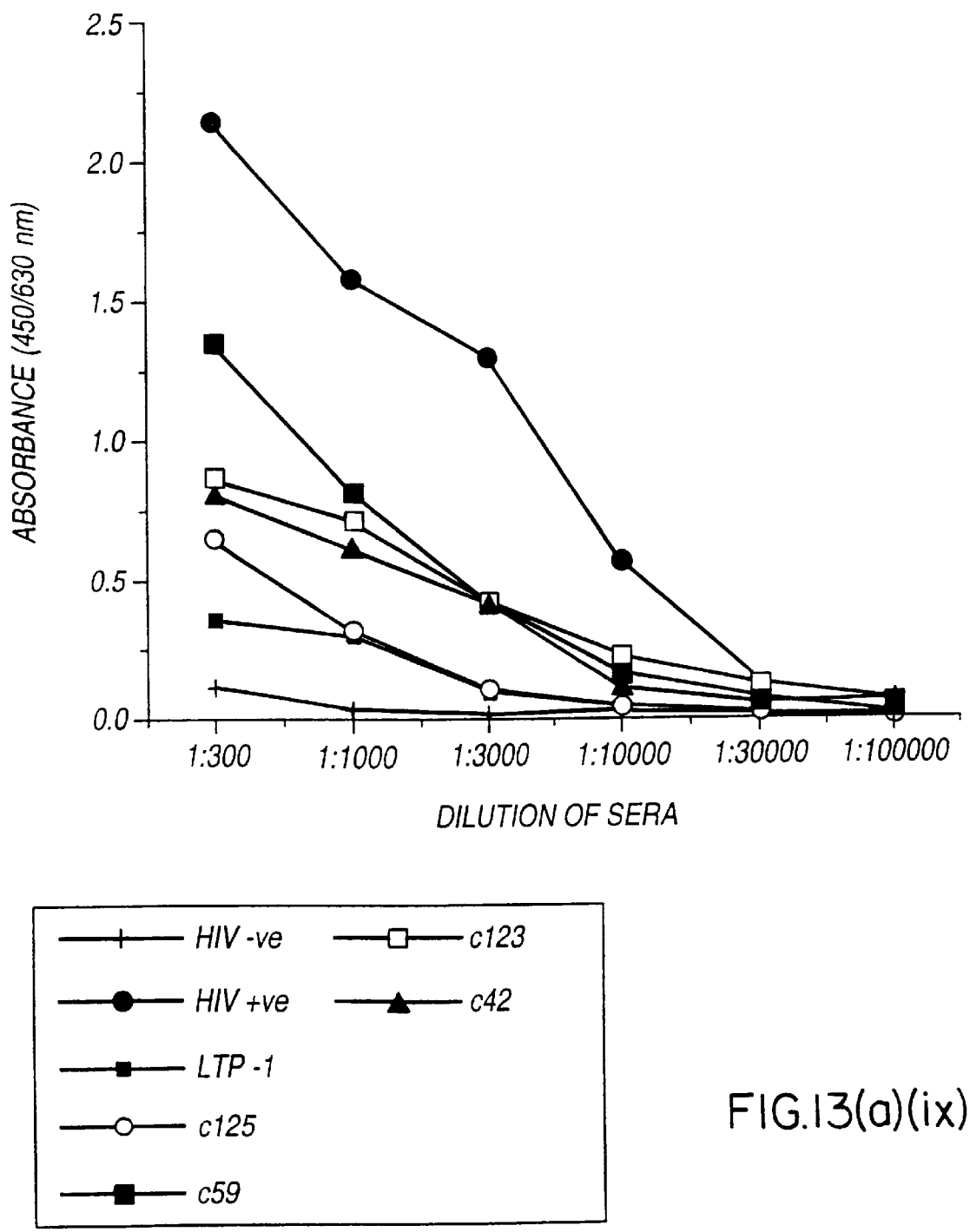
FIG.13(a)(ix)

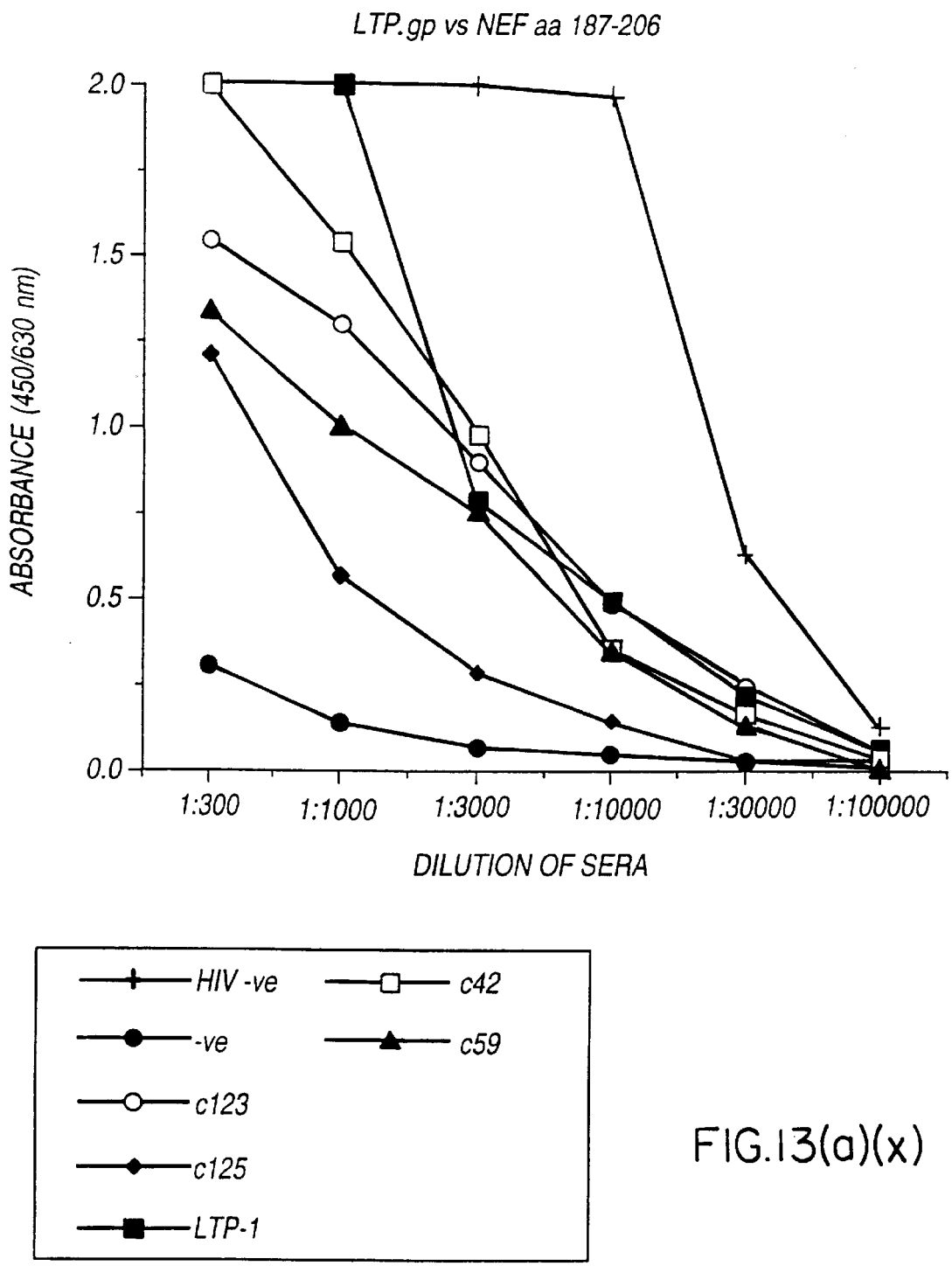

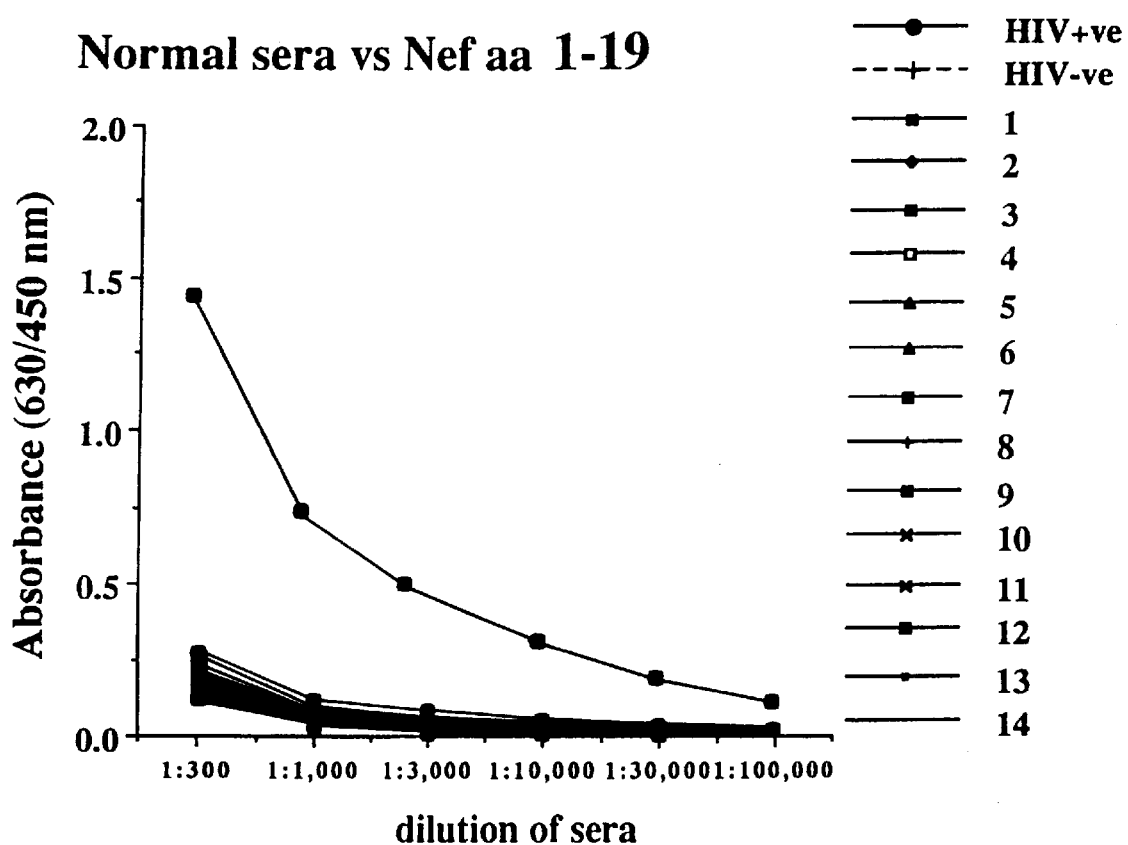
FIG.13(b)(i)(i)

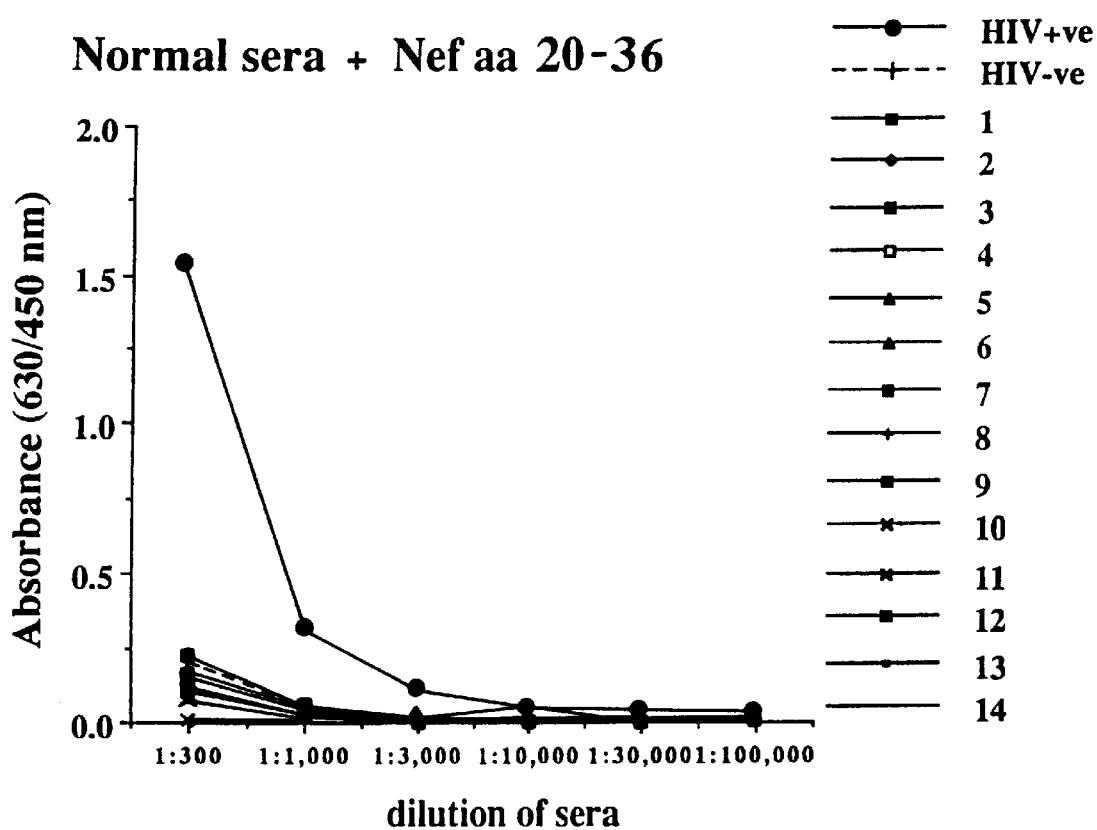
FIG.13(b)(i)(ii)

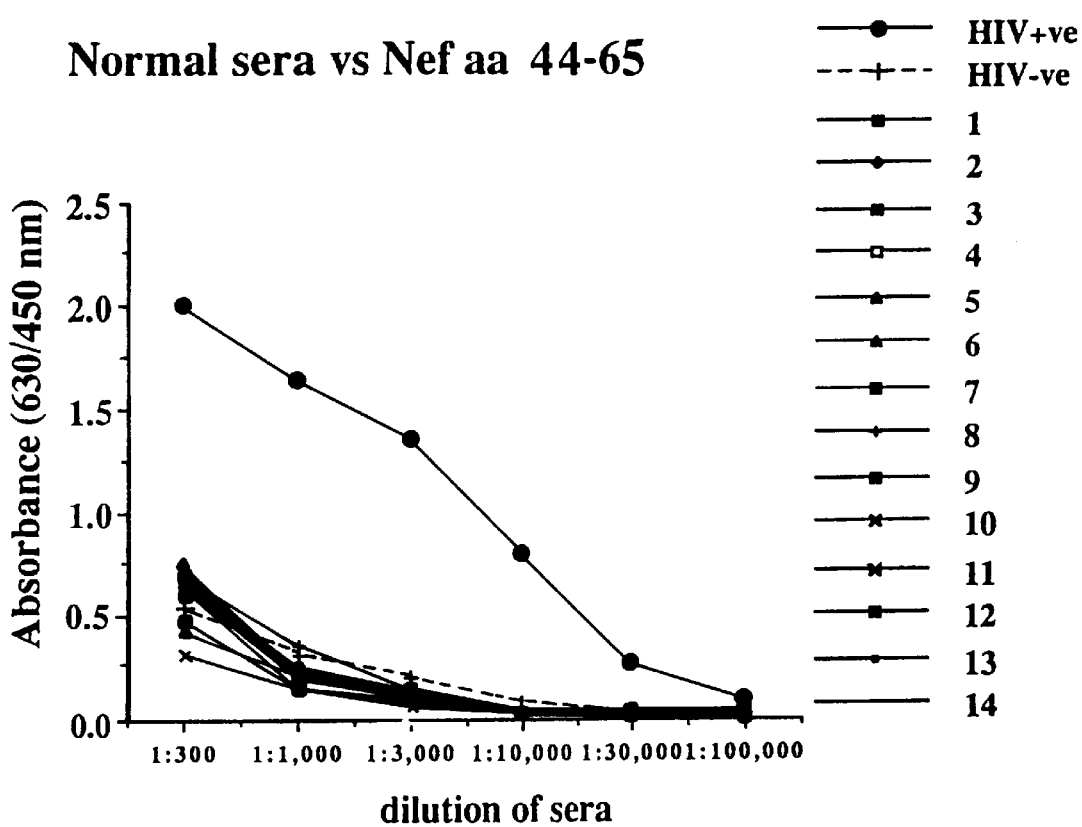
FIG.13(b)(i)(iii)

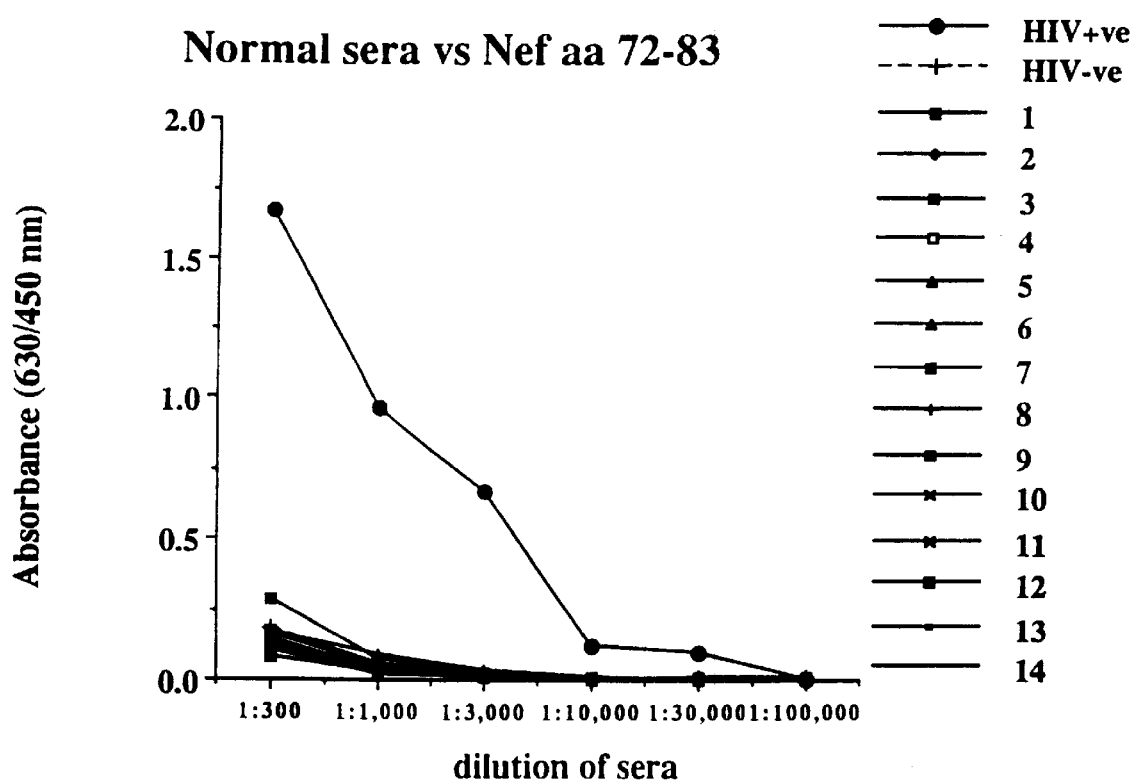
FIG.13(b)(i)(iv)

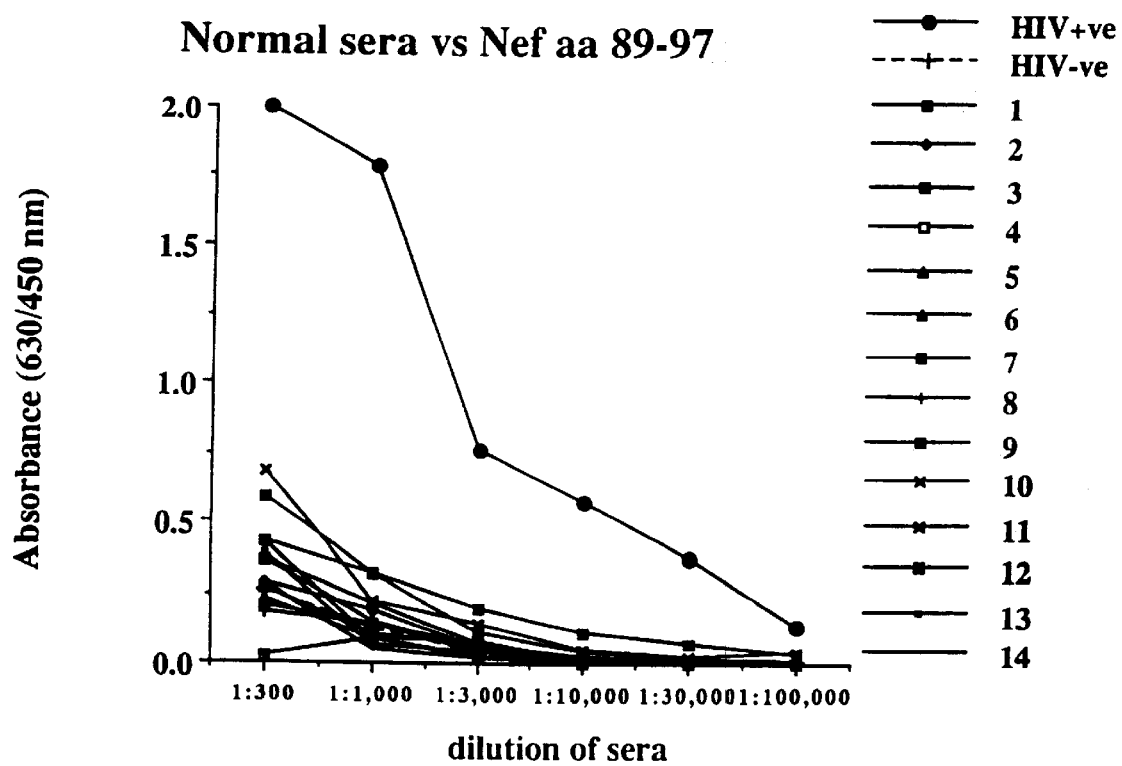
FIG.13(b)(i)(v)

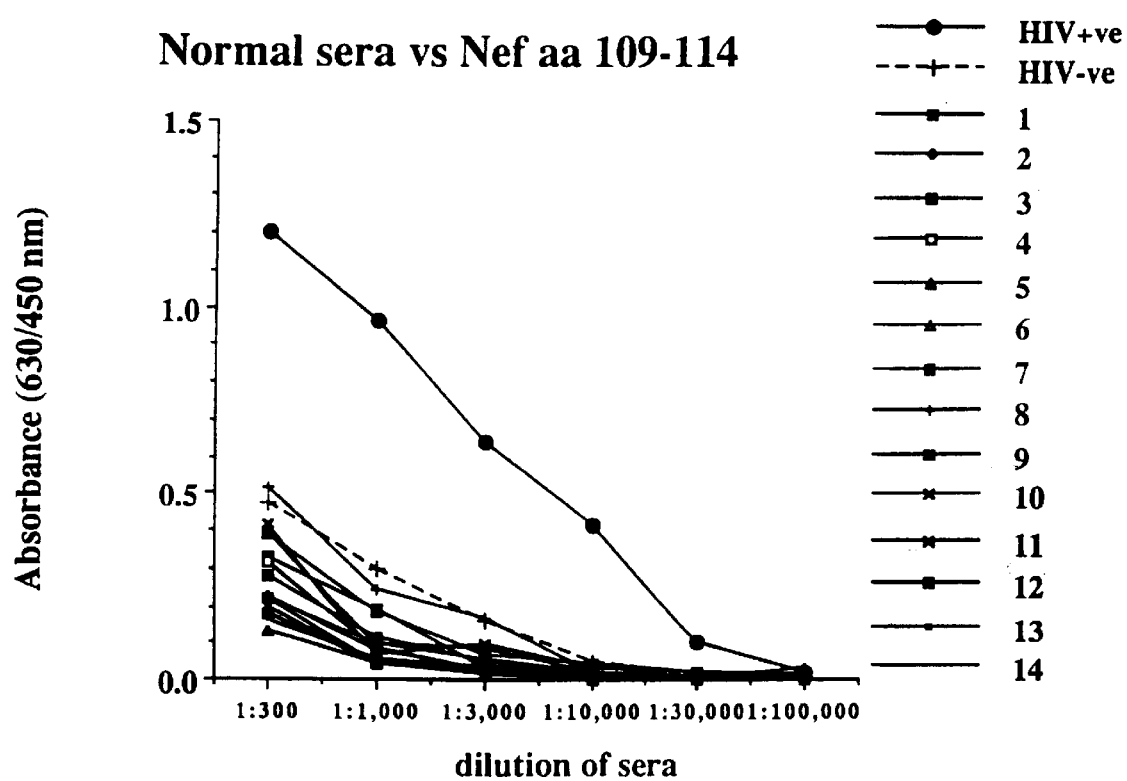
FIG.13(b)(i)(vi)

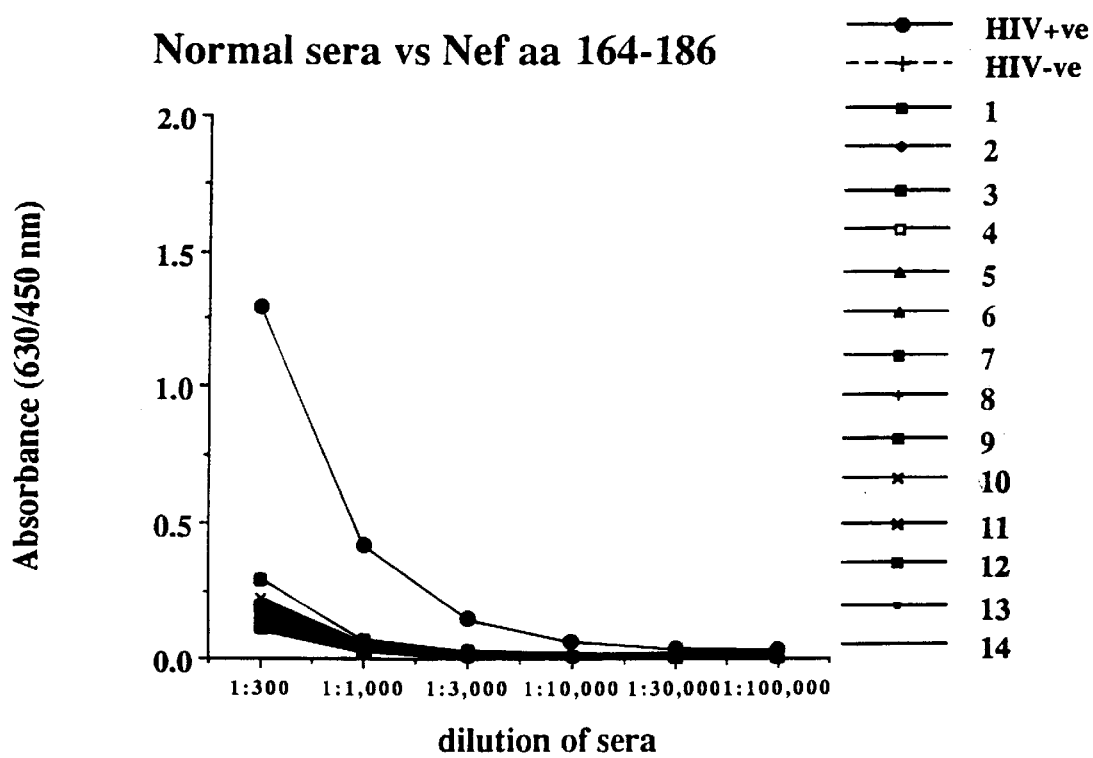
FIG.13(b)(i)(vii)

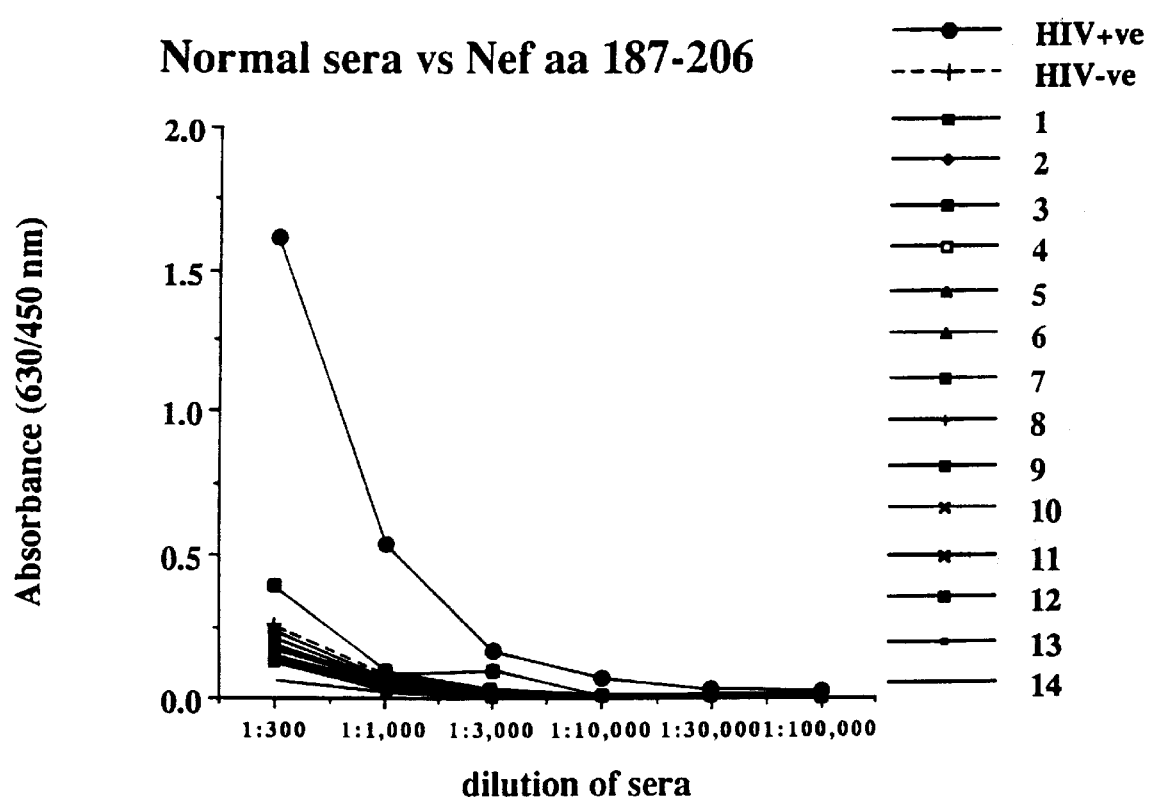
FIG.13(b)(i)(viii)

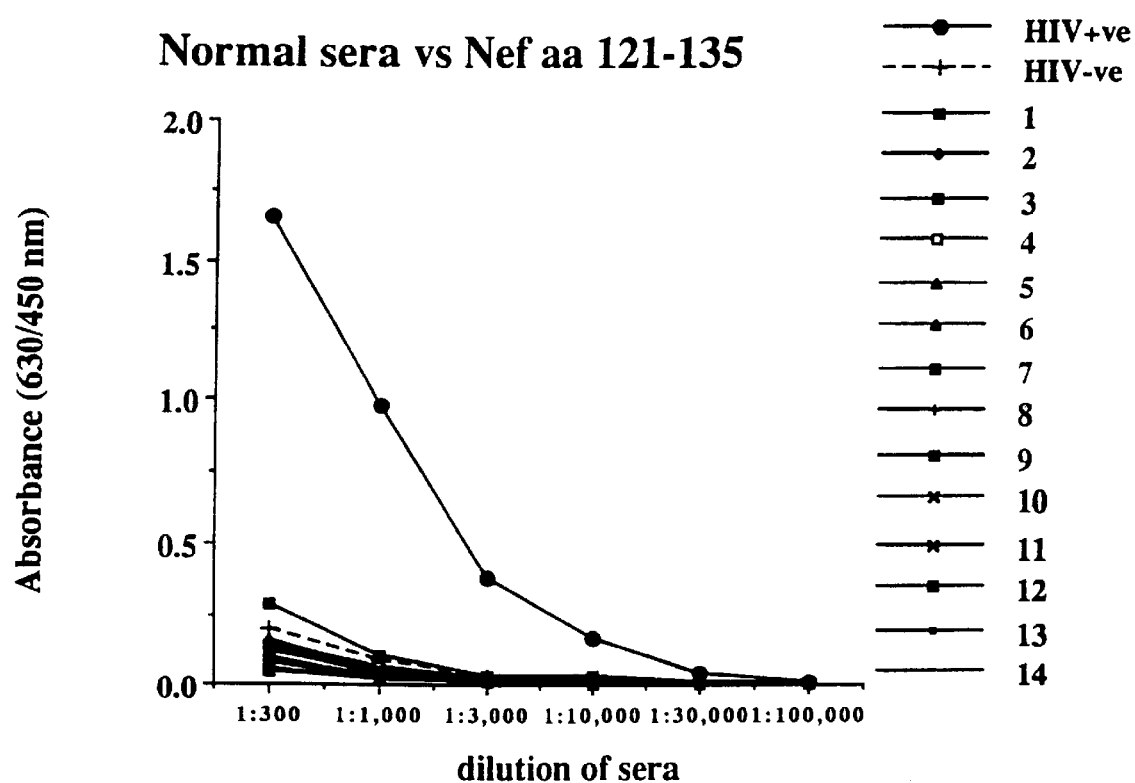
FIG.13(b)(i)(ix)

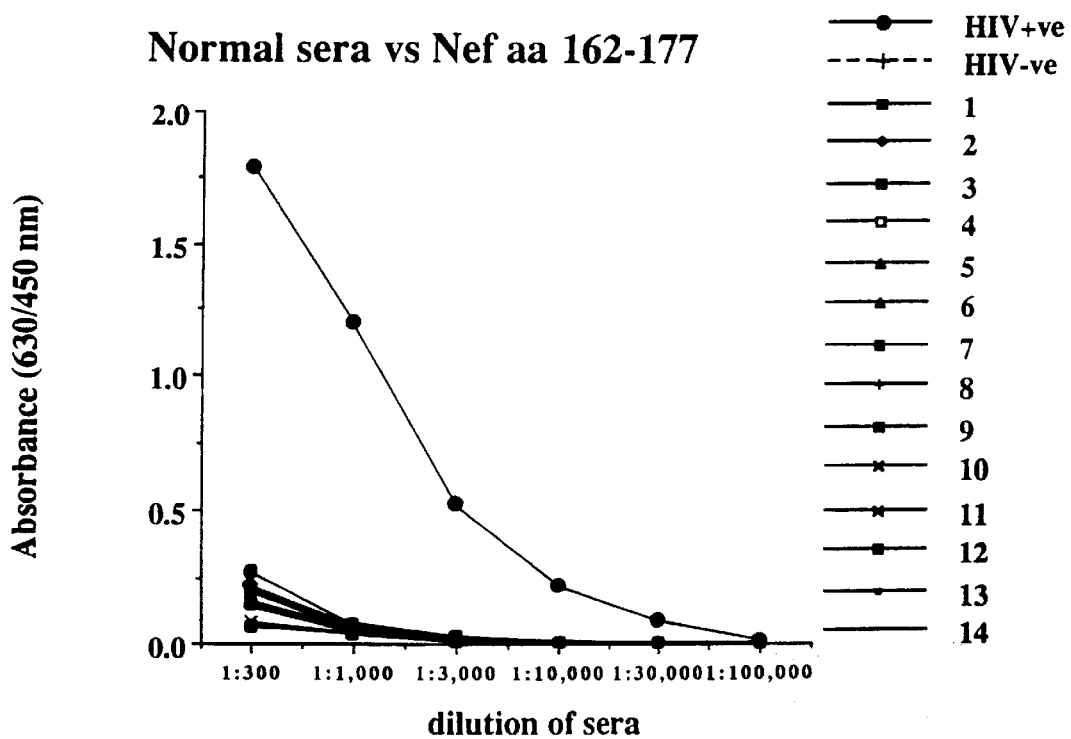
FIG.13(b)(i)(x)

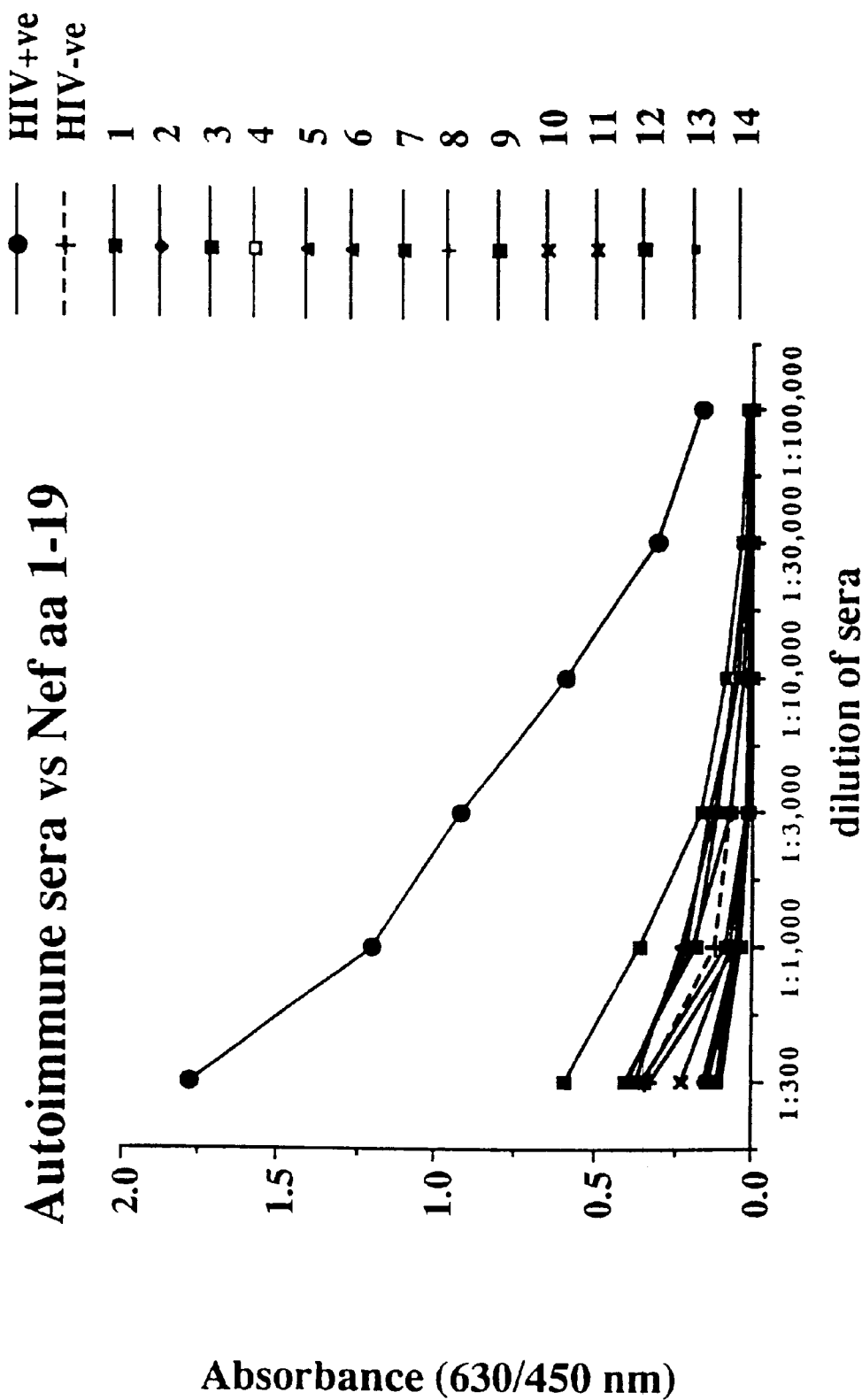
FIG.13(b)(ii)(i)

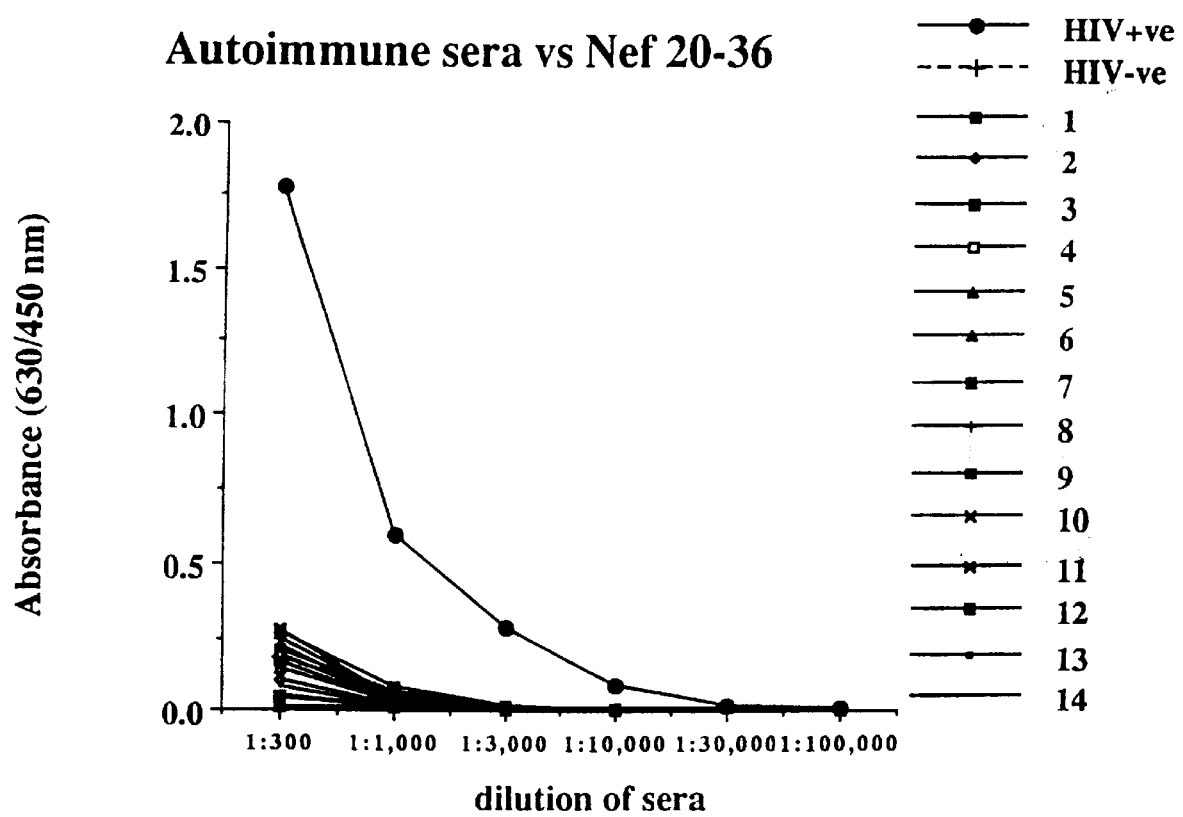
FIG.13(b)(ii)(ii)

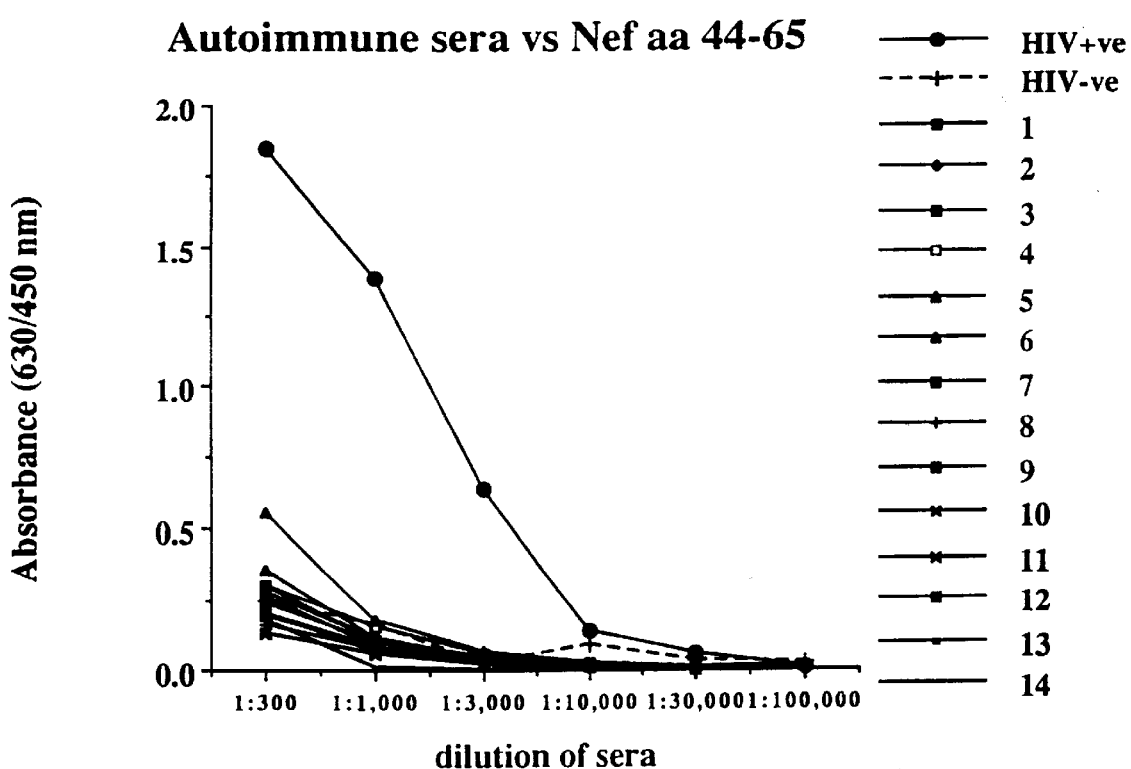
FIG.13(b)(ii)(iii)

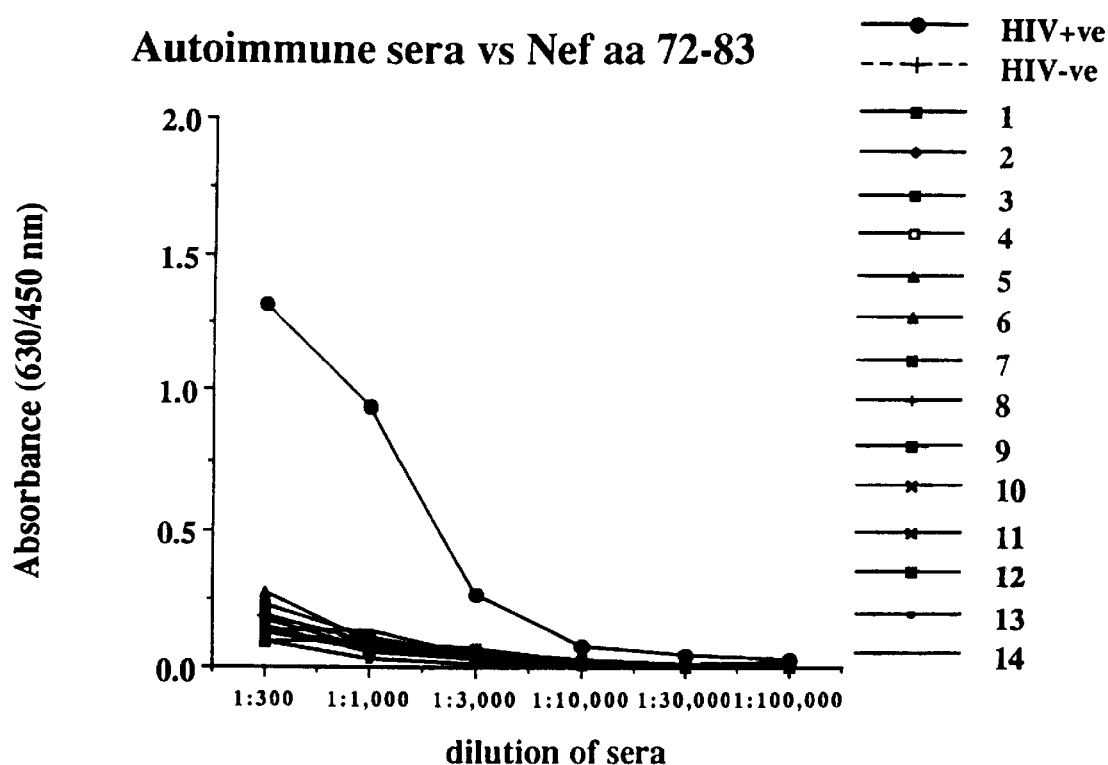
FIG.13(b)(ii)(iv)

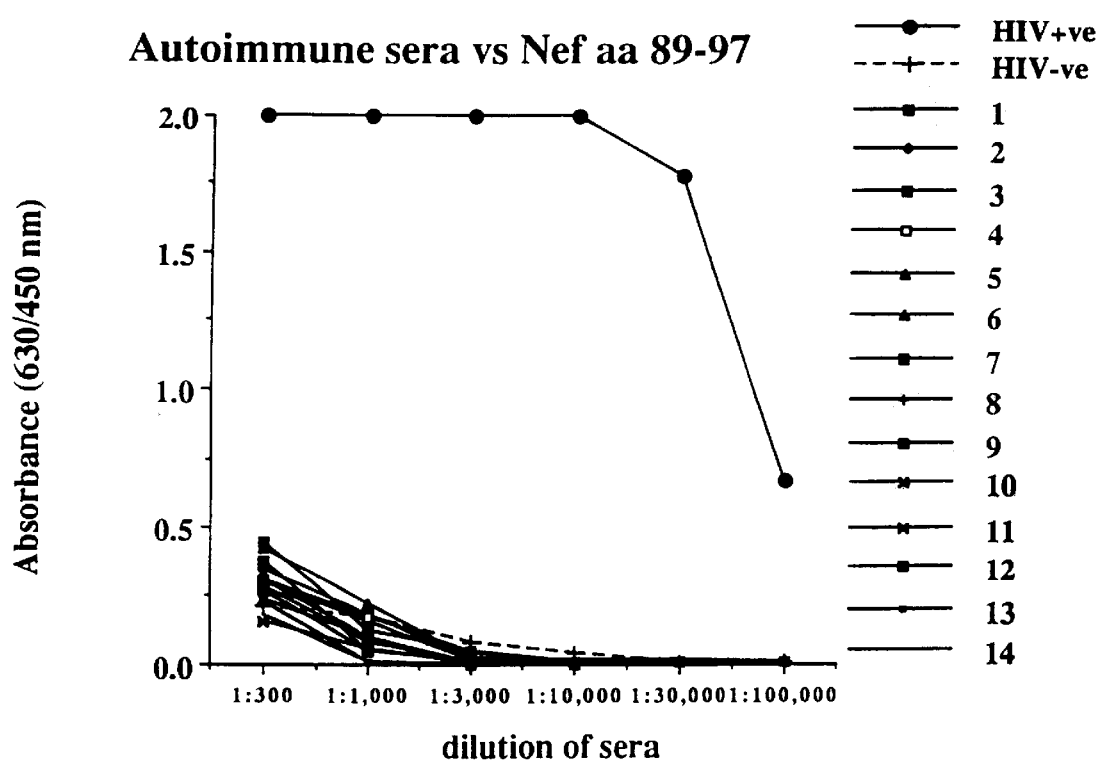
FIG.13(b)(ii)(v)

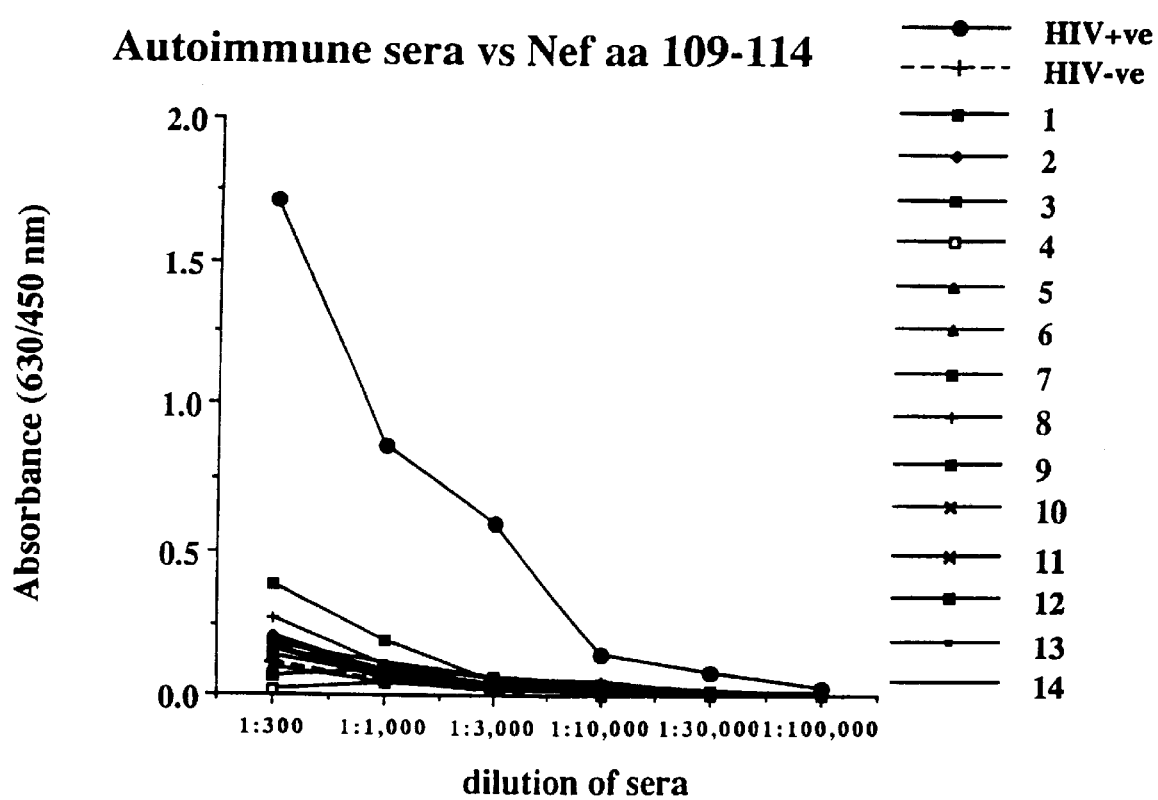
FIG.13(b)(ii)(vi)

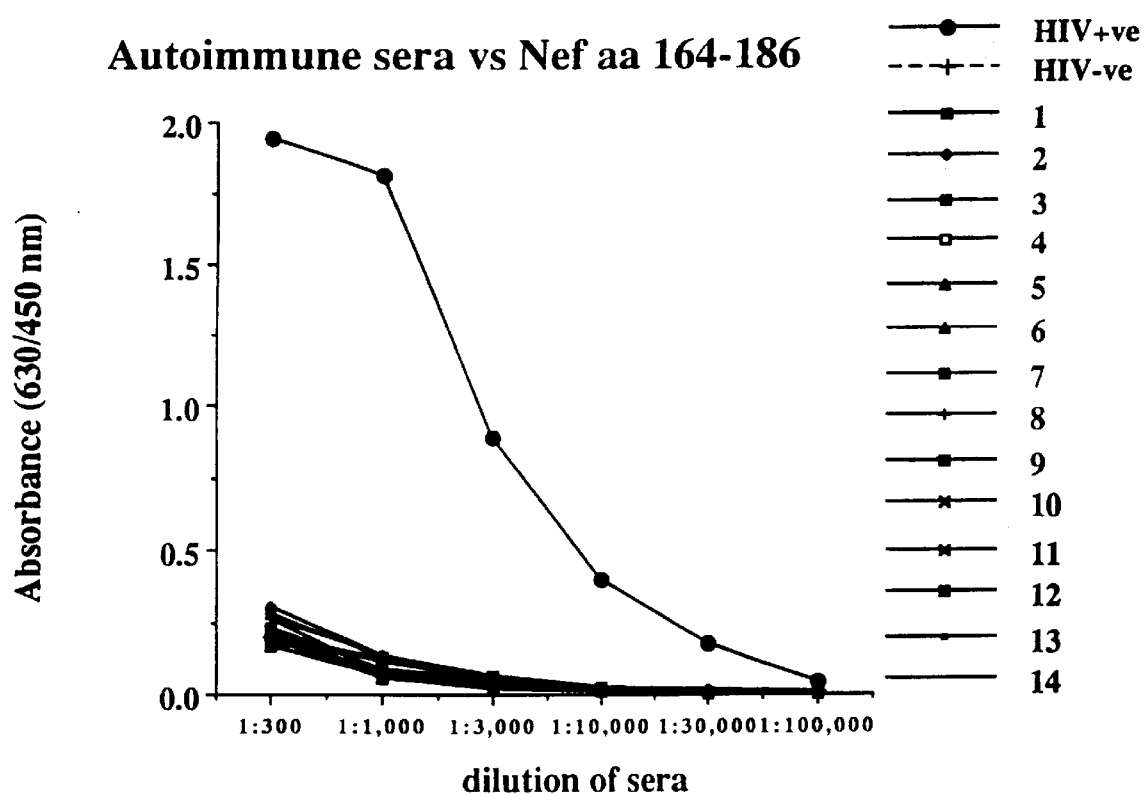
FIG.13(b)(ii)(vii)

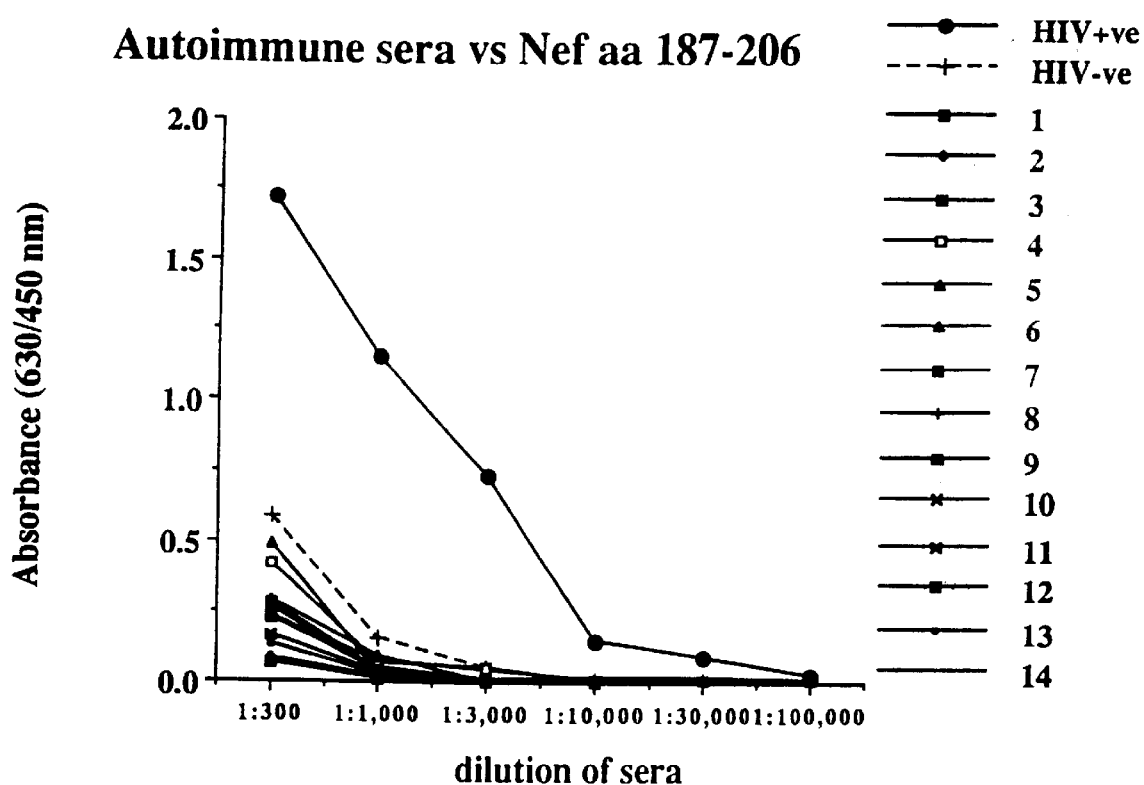
FIG.13(b)(ii)(viii)

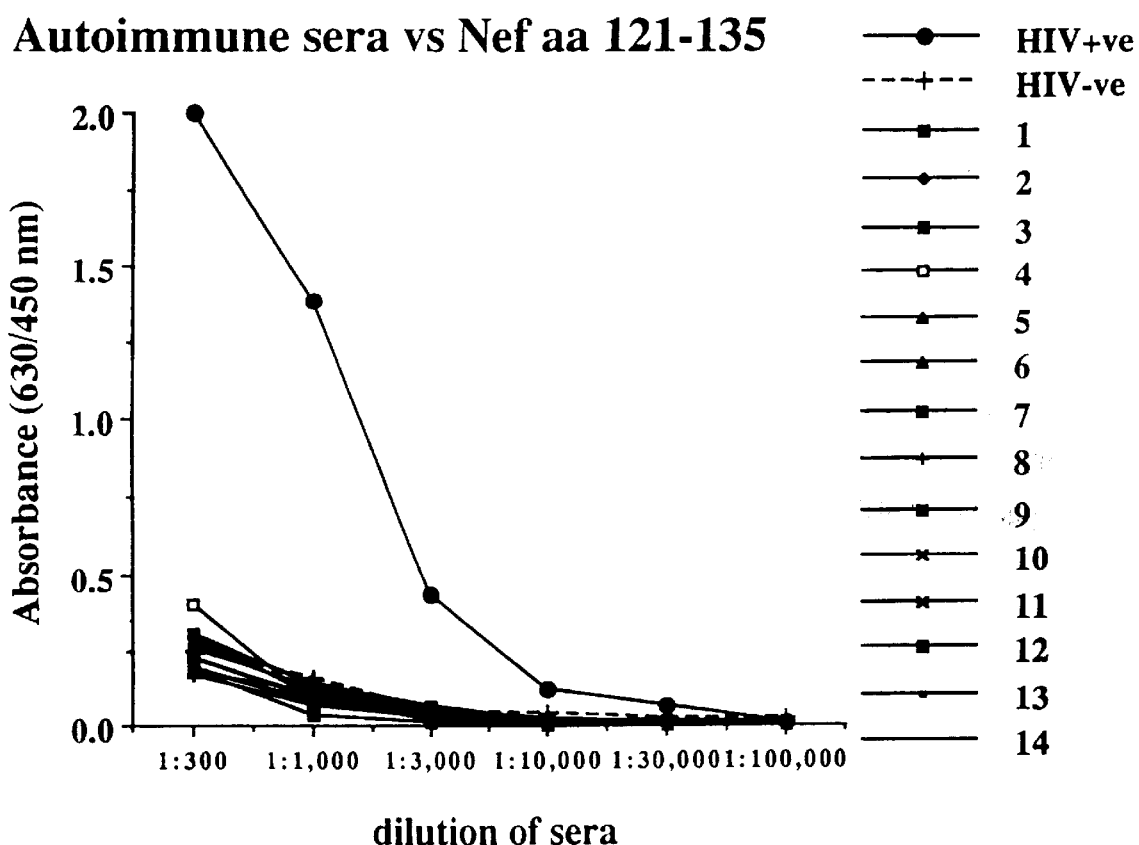
FIG.13(b)(ii)(ix)

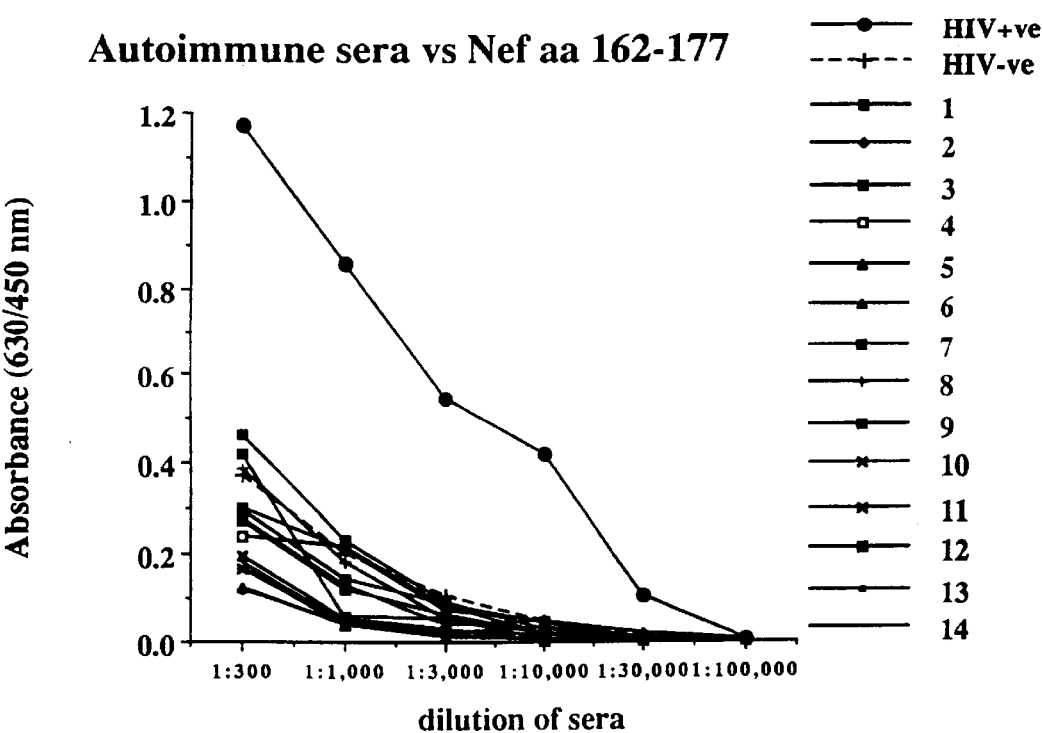
FIG.13(b)(ii)(x)

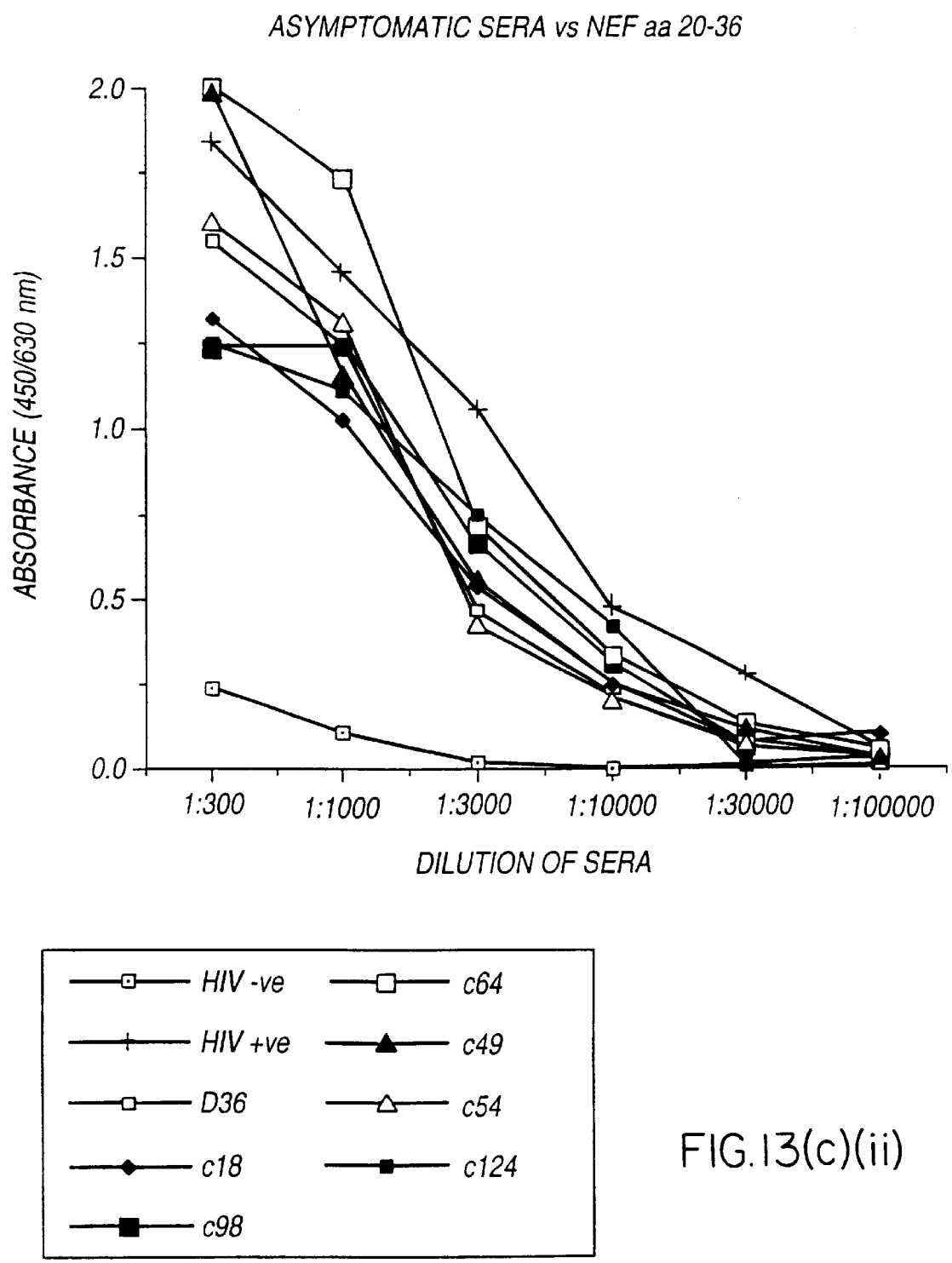
FIG.13(c)(ii)

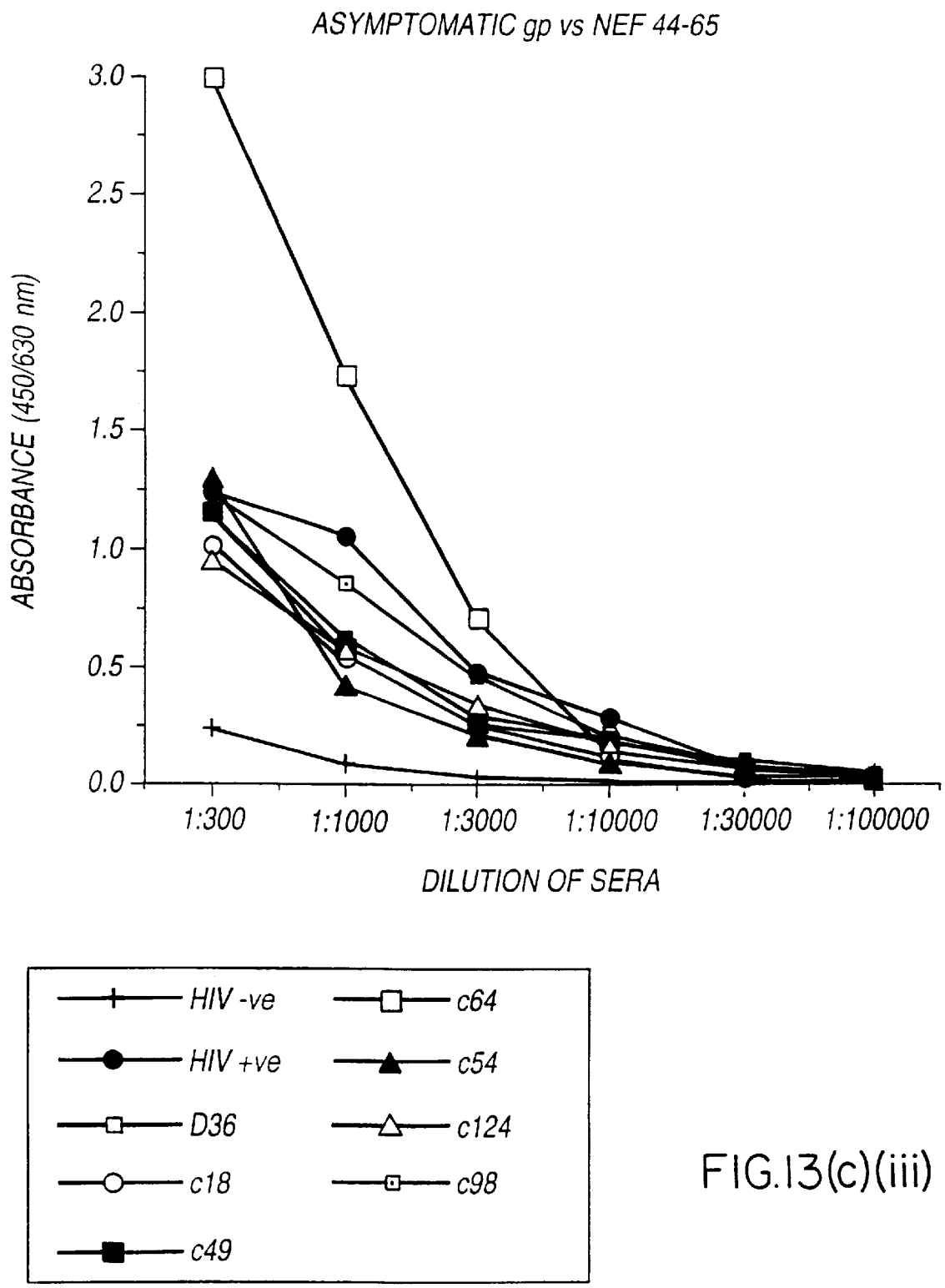
FIG.13(c)(iii)

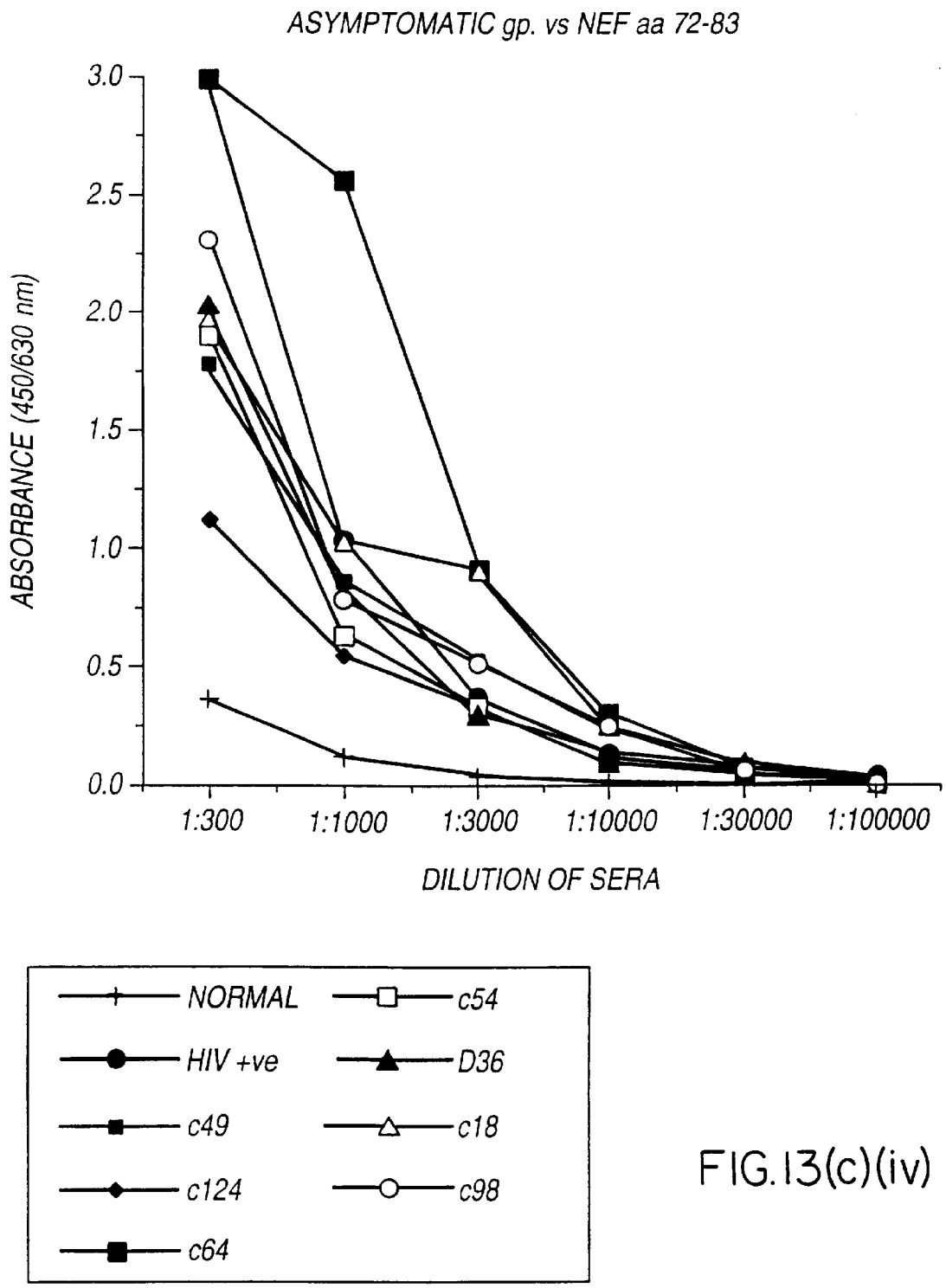

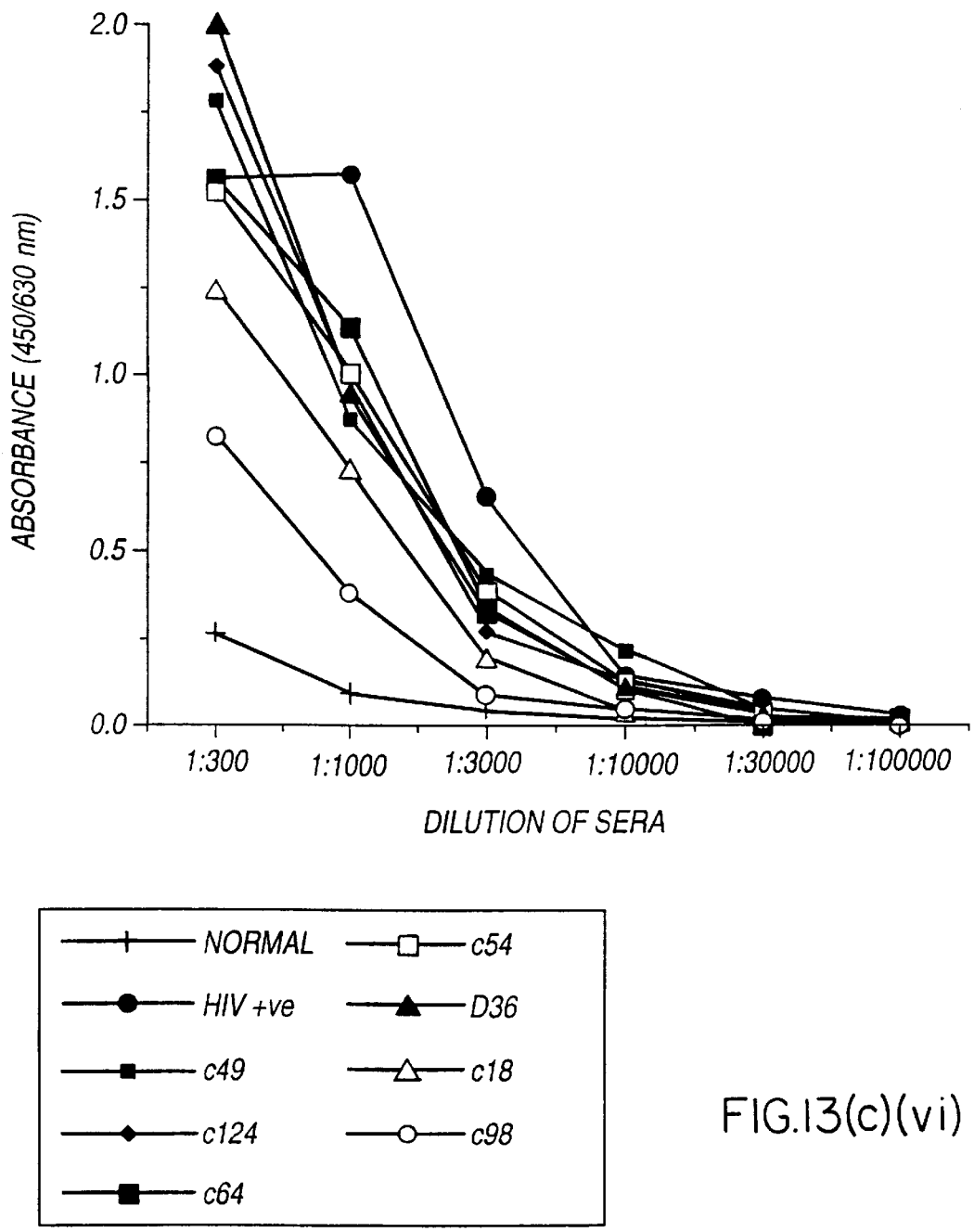
FIG.13(c)(vi)

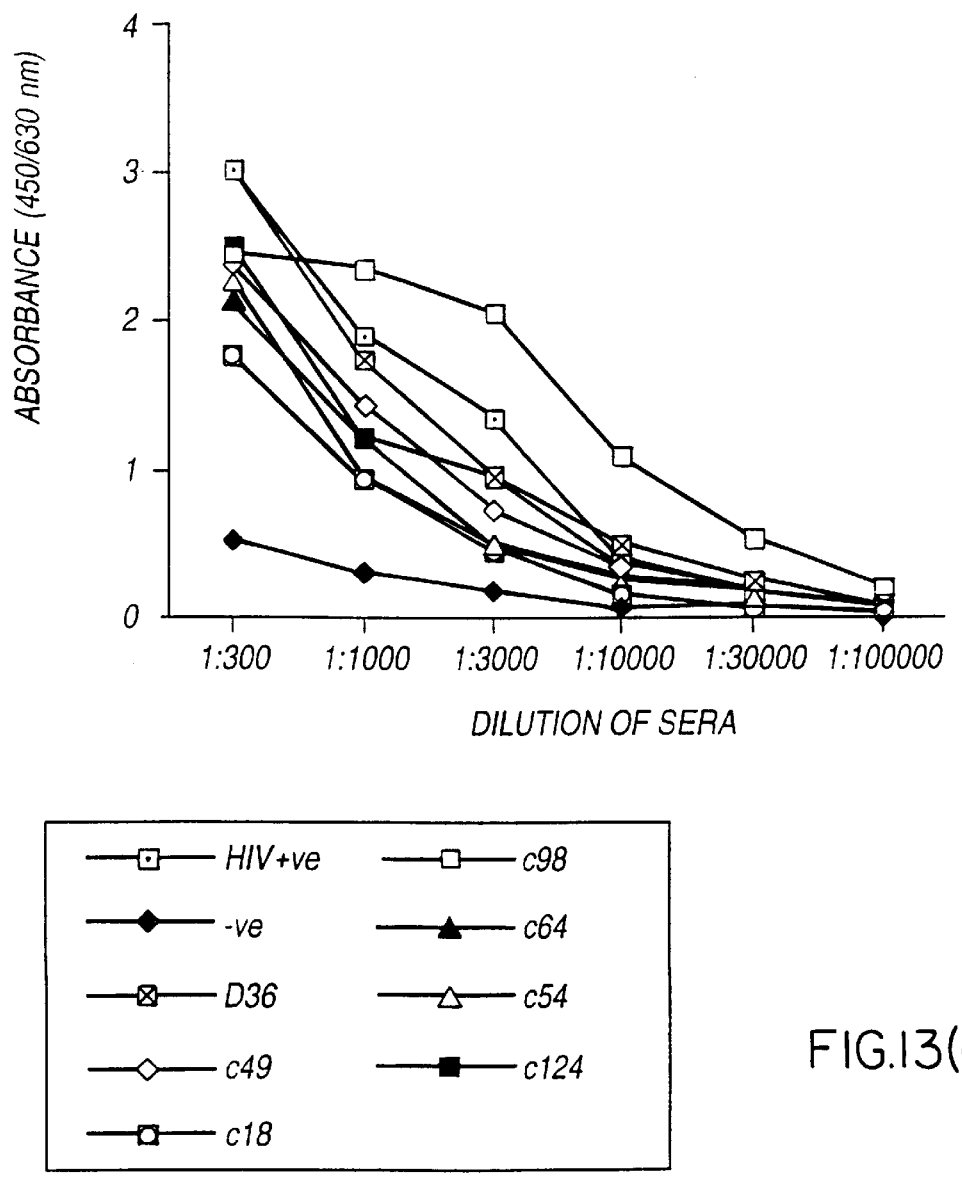
FIG.13(c)(vii)

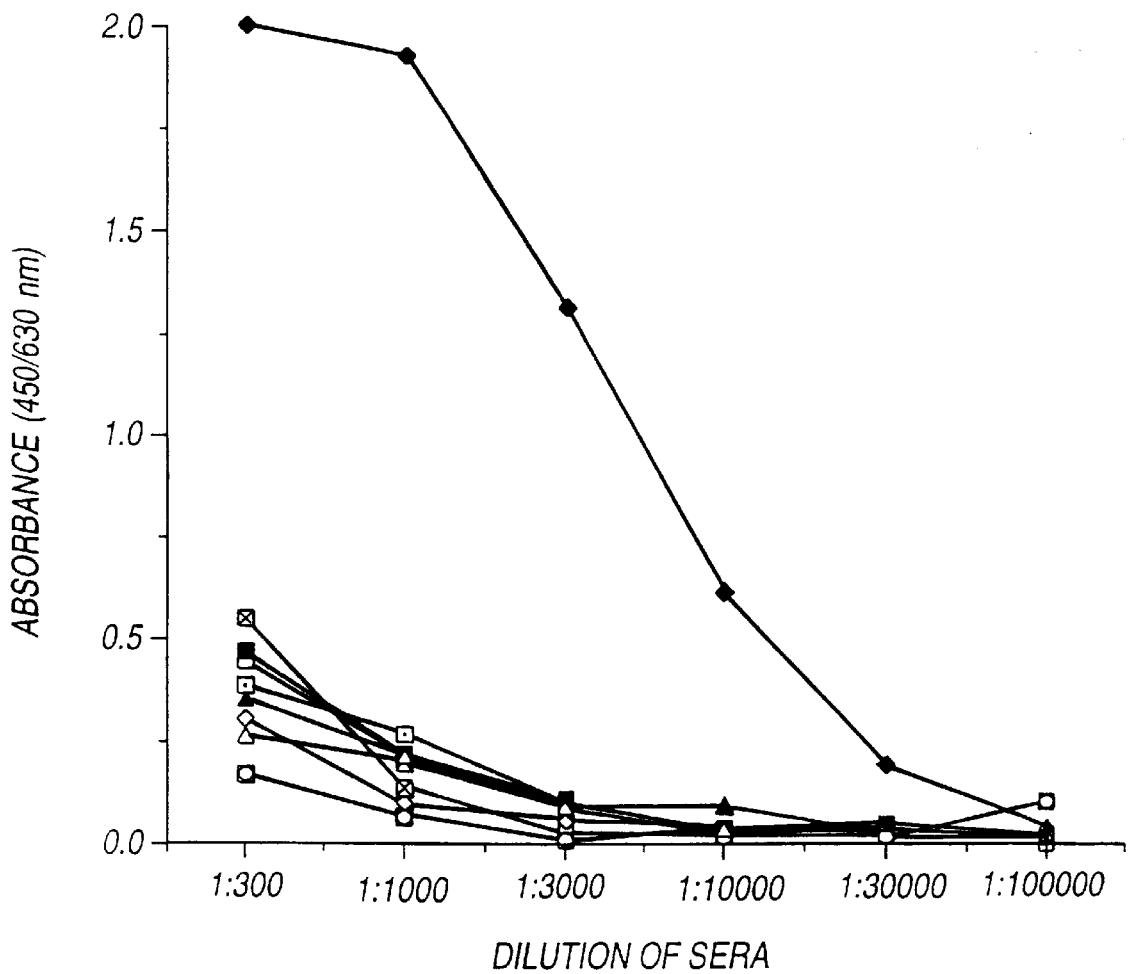
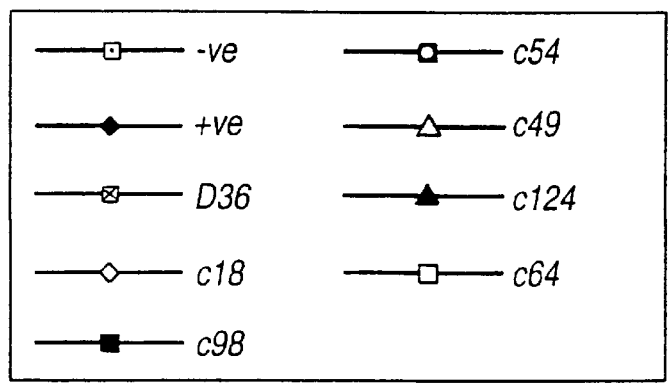
FIG.13(c)(viii)

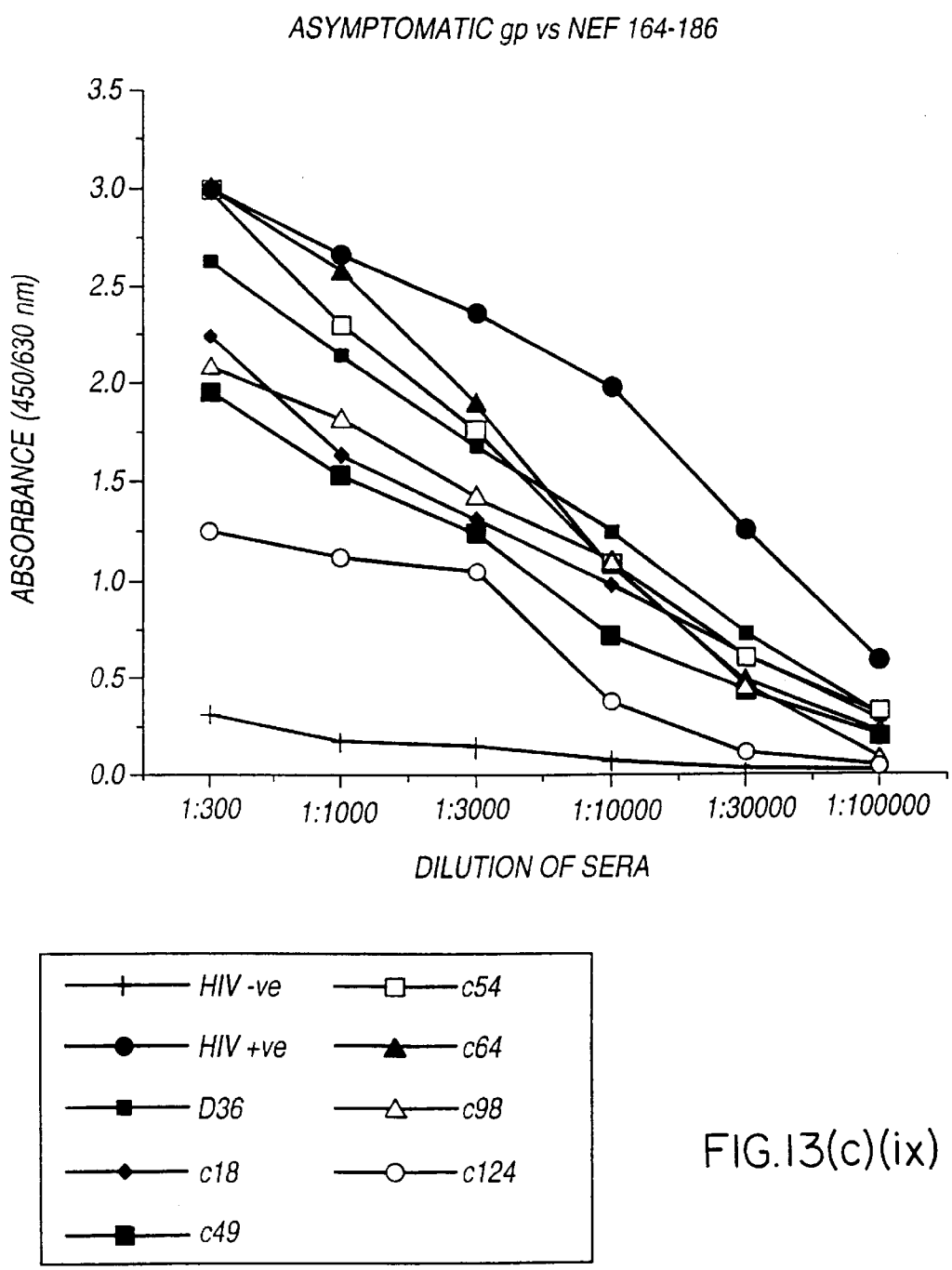
FIG.13(c)(ix)

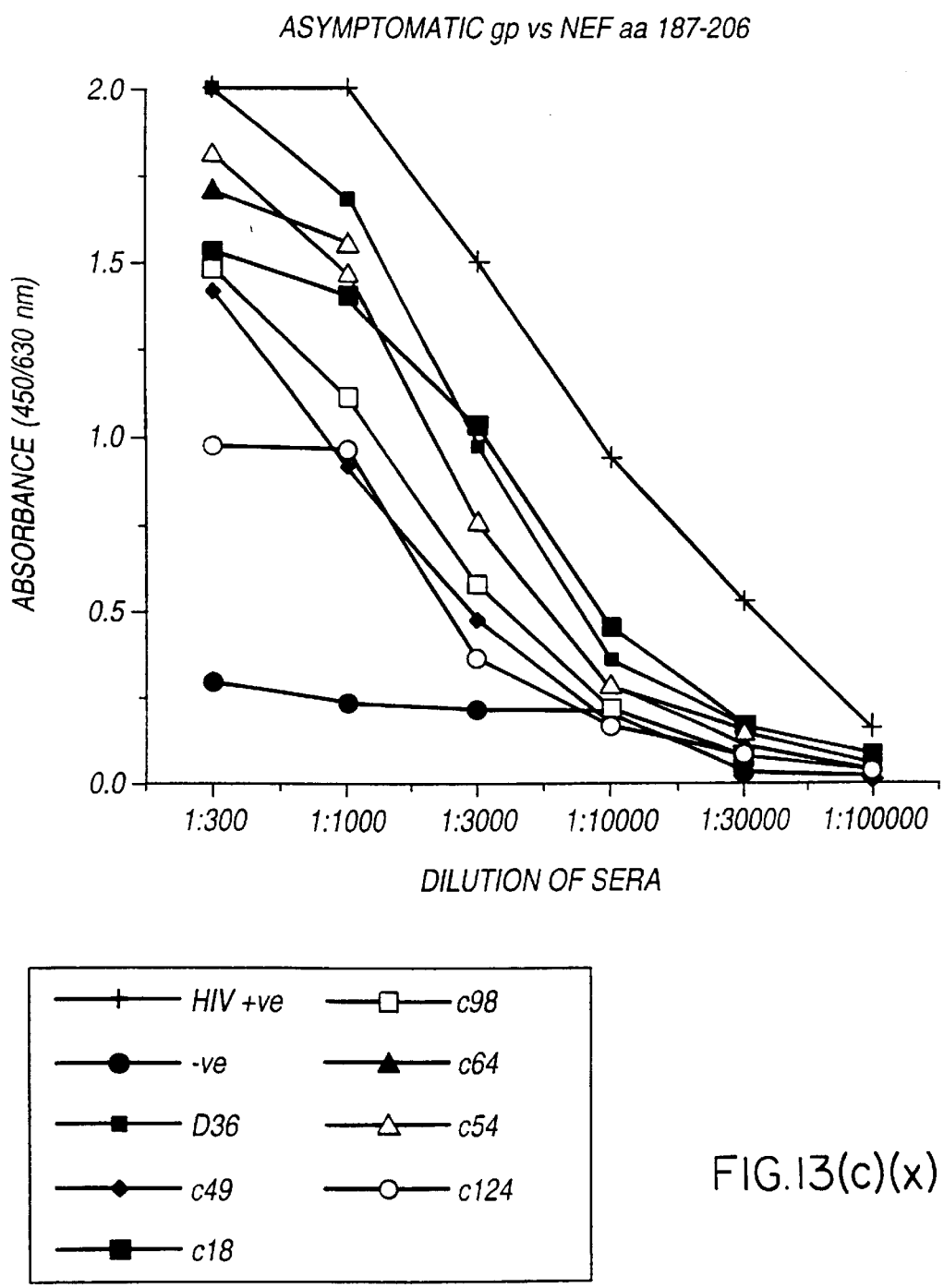

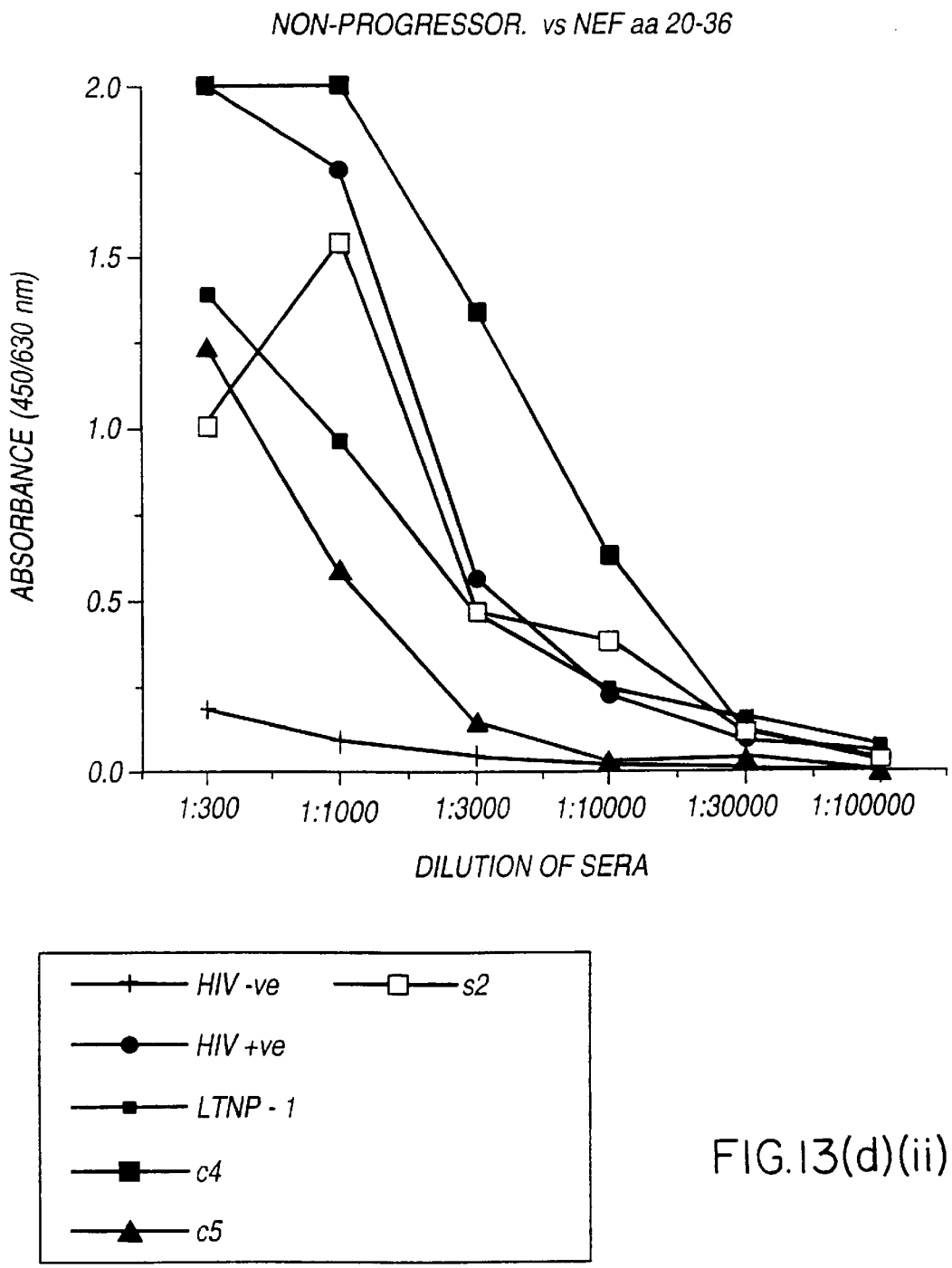
FIG.13(d)(ii)

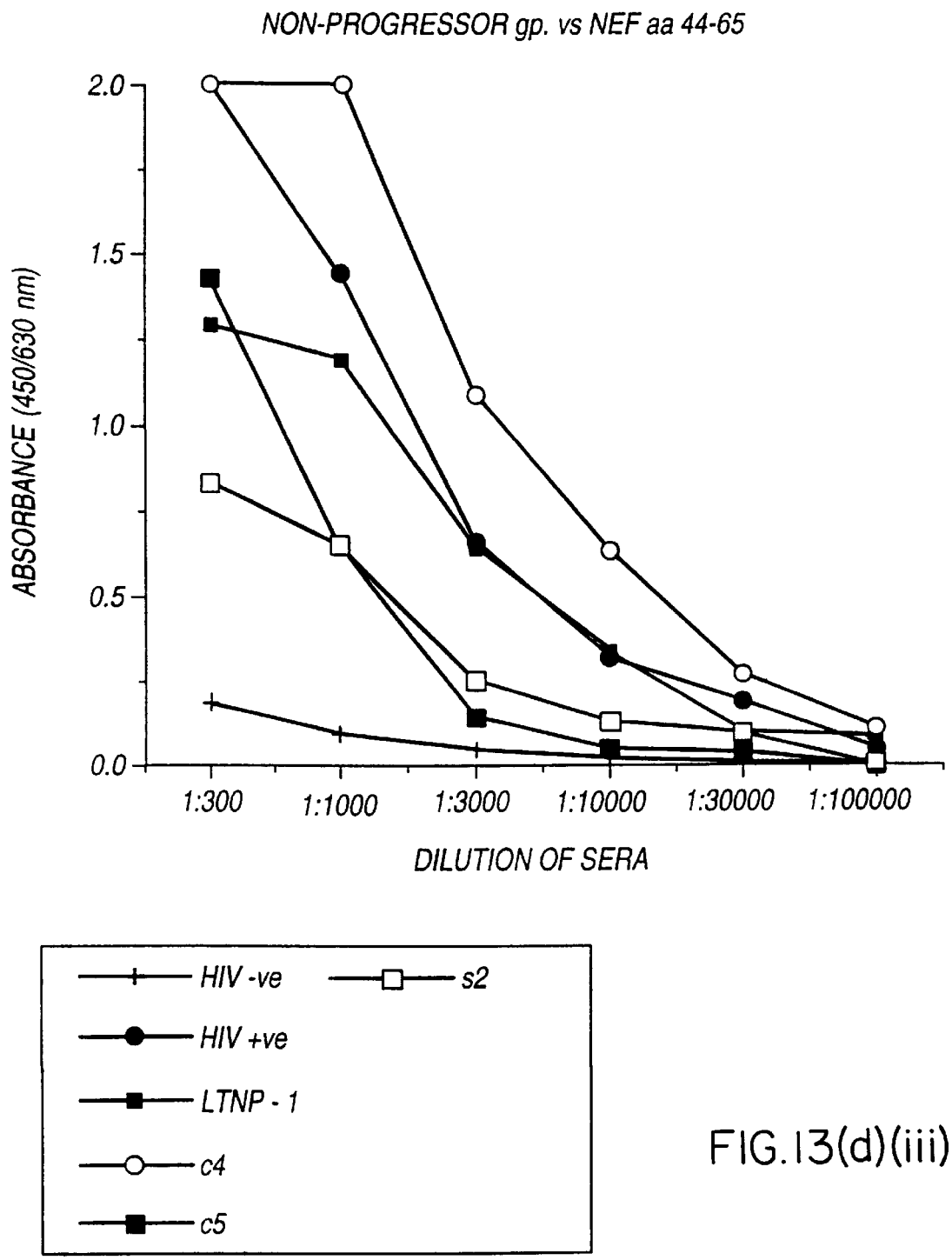
FIG.13(d)(iii)

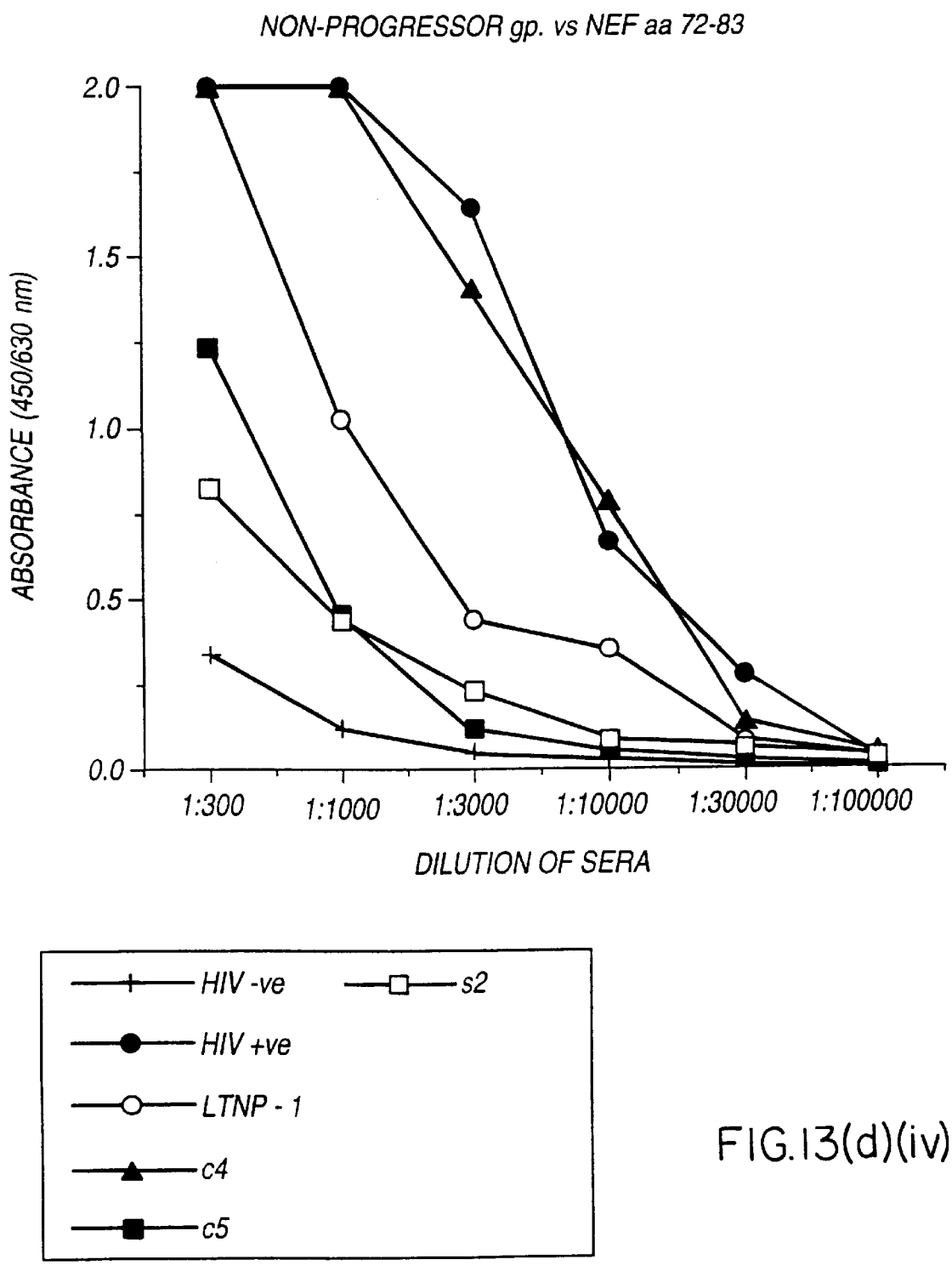
FIG.13(d)(iv)

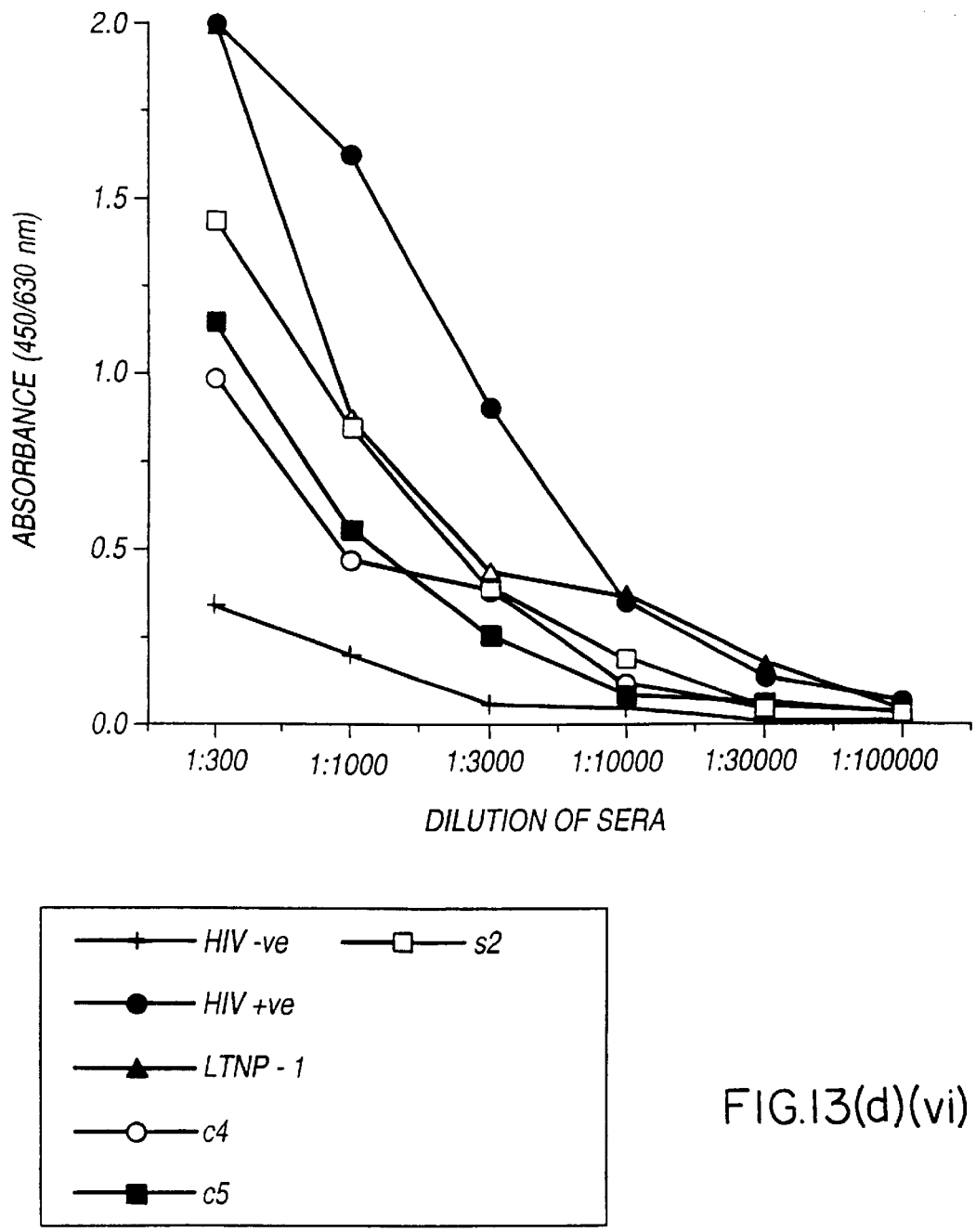
FIG.13(d)(vi)

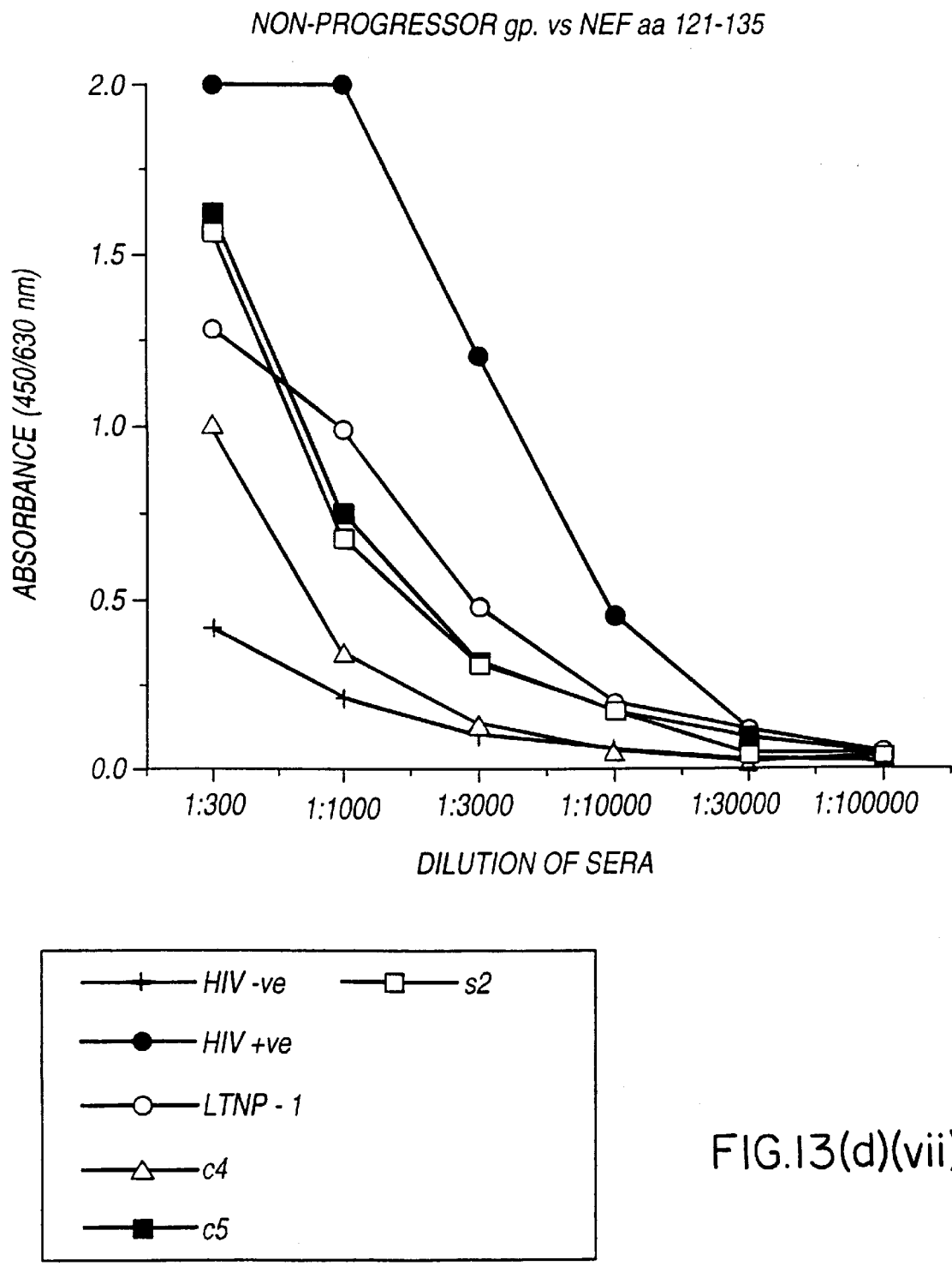
FIG.13(d)(vii)

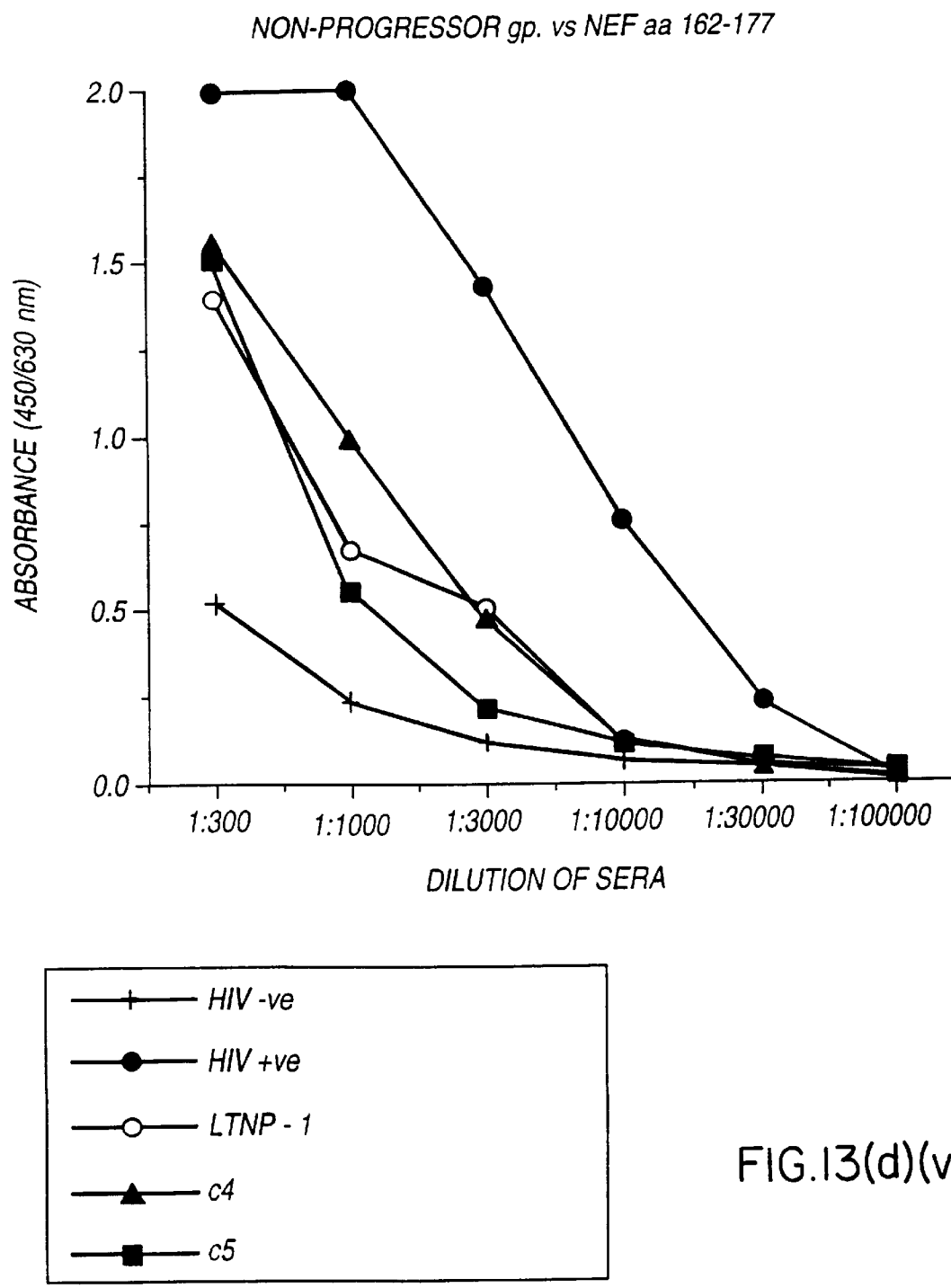
FIG.13(d)(viii)

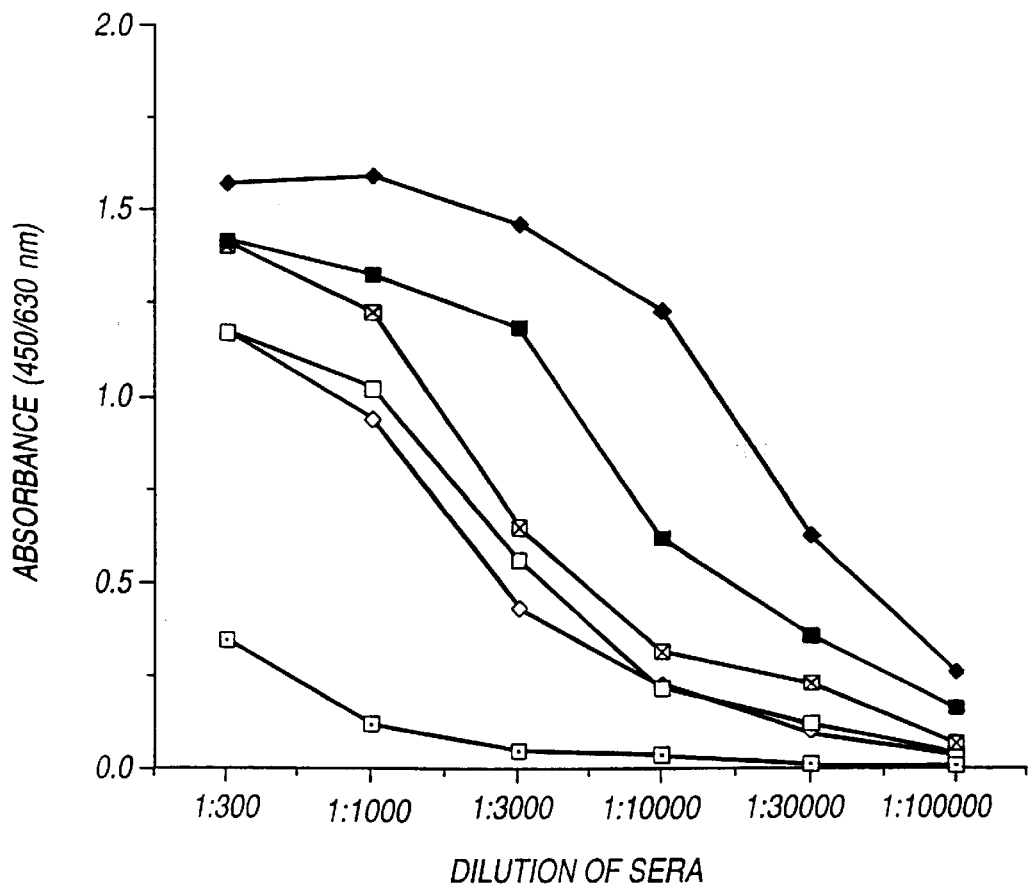
FIG.13(d)(ix)

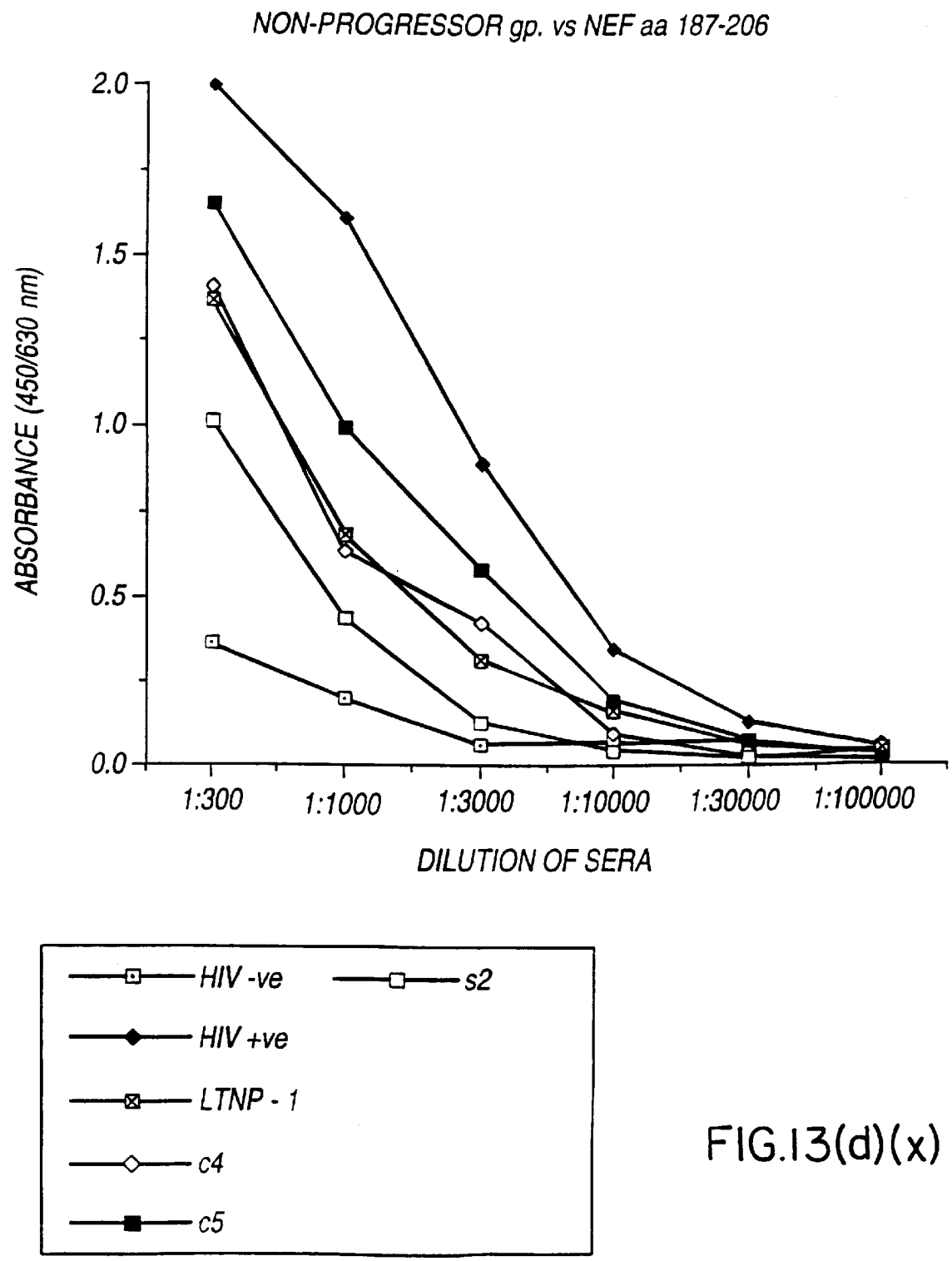

METHODS FOR THE DETECTION OF NON-PATHOGENIC HIV-1 STRAINS CONTAINING DELETIONS IN THE NEF CODING REGION AND U3 REGION OF THE LTR

CROSS REFERENCE TO RELATED APPLICATION

This application is a continuation-in-part application of U.S. Ser. No. 08/388,353 filed on Feb. 14, 1995.

FIELD OF THE INVENTION

The present invention relates to non-pathogenic strains of HIV-1 and to components, parts, fragments and derivatives thereof and to genetic sequences derived therefrom and their use in the development of diagnostic and therapeutic compositions for the treatment and prophylaxis of AIDS and AIDS-related disorders. The present invention also relates to a method for attenuating pathogenic strains of HIV-1 by mutagenizing particular regions of the HIV-1 genome. A particularly useful aspect of the print invention is a method for determining the likelihood or otherwise of an individual who is seropositive for HIV-1 developing AIDS or AIDS-related symptoms. Another aspect of the present invention is directed to strains of HIV-1 cable of synthesizing a modified Nef protein or having a wild-type Nef protein modified after synthesis thereby rendering those strains of HIV-1 substantially non-pathogenic.

BACKGROUND OF THE INVENTION

Bibliographic details of the publications referred to in this specification are collected at the end of the description. Sequence Identity Numbers (SEQ ID NOs.) for the nucleotide and amino acid sequences referred to in the specification are defined following the bibliography.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Genomic nucleotide sequences of HIV-1 strains referred to herein are represented by their corresponding DNA sequence.

Exemplary viral isolates referred to herein as "C18" and "C98" were deposited at the PHLS Centre for Applied Microbiology and Research, European Collection of Animal Cell Cultures (ECACC), Division of Biologies, Porton Down, Salisbury, Wiltshire SP4 OJG. C18 was deposited on Oct. 17, 1994 under Provisional Accession Number V94101706 and C98 was deposited on Oct. 31, 1994 under Provisional Accession Number V941031169. Viral isolate "C54" was deposited at ECACC on Mar. 10, 1995 under Provisional Accession Number V95031022.

A summary of particular deletion mutants of HIV-1 of the present invention referred to herein is given in FIG. 11.

Acquired Immune Deficiency Syndrome (AIDS) and AIDS related disorders are the clinical result of infection by Human Immunodeficiency Virus type 1 (Barre-Sinoussi et al, 1983). Infection by HIV-1 is generally characterised by progressive immune system damage (Teeuwsen et al, 1990; Clerici et al, 1989) leading to opportunistic infections, malignancies or wasting syndrome that constitute clinically-defined AIDS (Busch et at, 1991; Klaslow et al, 1990).

The high mortality rate of individuals infected with HIV-1 together with the social and economic consequences of the continuing HIV-1 epidemic has created an urgent need for a safe and effective treatment and/or prophylaxis against the devastating effects of AIDS. However, despite over a decade of high level scientific research into the pathogenesis of HIV-1 and the clinical manifestations of the disease, together with a detailed molecular analysis of the virus, there has been little success in the development of an effective vaccine. To date, the most effective therapy is treatment with zidovudine (AZT) which delays the onset of full blown AIDS and alleviates to some extent the symptoms of HIV-1 infection. However, AZT is not an innocuous compound and AZT, metabolic products thereof or impurities therein can cause a number of side effects which limit long term treatment with the drug. Furthermore, AZT resistant isolates have been reported during treatment. Clearly, therefore, a need exists to develop alternative strategies in preventing and treating HIV-1 infection.

The initial phases of HIV-1 infection are summarised by Levy (1993) as involving attachment, fussion and nucleo-capsid entry. These phases have been the traditional foci in research into development of antiviral strategies. The molecular events at the virus genomic level have also been the subject of intense scientific research with an aim being the development of a live attenuated vaccine as a possible approach for the treatment or prophylaxis of HIV-1 infection.

There is a high variable rate of progression from initial HIV-1 infection to AIDS which reflects a rapidly changing pathogen and variable immune response of the host to infection (Sheppard et at, 1993). With regards to the latter, HIV-1 can be considered as a heterogenous group of viruses differing at the genetic level with concomitant variable pathogenicity. For example, HIV-1 strains can differ in their capacity to kill cells. Furthermore, it appears that HIV-1 strains evolve in a host after infection and that the evolution varies depending on the tissues infected by the virus. The major sites in the genome apparently responsible for biological and pathological variation are the highly variable envelope region (Cheng-Mayer et al, 1991; Shioda et al, 1992; Hwang, et al 1991; Sullivan et al, 1993; Groenink et al, 1993) and the viral regulatory regions such as tat (Leguern et al, 1993). The genetic complexity of the HIV-1 group of viruses together with their variable pathogenicity, are major difficulties in the development of live vaccines, genetic vaccines or component vaccines.

Notwithstanding the highly pathogenic nature of HIV-1, there are some reports of long term survival of subjects infected with the virus (Learmont et al, 1992; Levy, 1993; Sheppard et at, 1993; Lifson et al 1991). It is not always clear, however, whether a benign course following HIV-1 infection is due to host factors, viral factors or other unknown factors. There are reports that most infected people have at least laboratory evidence of progressive immune system damage in the form of CD4+ cell loss (Lang et al, 1989) and defective immune responses (Clerici et at, 1989).

Although simian monkeys have been used as an in vivo model for HIV and Simian Immunodeficiency Virus (SIV) infection, a moor handicap in AIDS research has been the absence of suitable in vivo models to study the pathogenesis of the disease and, in particular, to study the viruses involved in benign infection. The need for a suitable in vivo model is heightened by the fact that results obtained in vitro cannot necessarily be extrapolated to what occurs in vivo. This was clearly observed by Mosier et at (1993) where conflicting results were obtained in animals compared to cell cultures.

Despite the absence of suitable in vivo models, considerable scientific research has been directed to attenuating HIV-1 strains by mutagenesis of the virus genome. Deletions in the nef gene have been implicated in attenuated strains of SIV and their use in providing protective effects in monkeys (Daniel et al, 1992). However, there are conflicting reports on the possible negative influence the nef gene product has on the rate or extent of virus replication (Terwilliger et al, 1986; Luciw et al, 1987; Niederman et al, 1989; Kim et al, 1989; Hammes et al, 1989). In fact, Kim et al (1989) found that nef did not affect HIV-1 replication or HIV-1 long terminal repeat (LTR)-driven CAT expression. Kestler III et al (1991) found that the nef gene is required for full pathogenic potential in SiV. However, such is the complexity of the HIV-1 group of viruses and the variability of immune responses between individuals let alone different species that it is far from clear whether nef deleted strains of HIV-1 would behave similarly to nef deleted strains of SIV-I. There is a need, therefore, in order to investigate the possibility of nef deleted HIV-1 strain as a vaccine candidate, to identify individuals infected with such modified viruses.

Learmont et at (1992) reported that a cohort of five persons infected with blood products from a single HIV-1 infected donor have remained asymptomatic from up to about 10–14 years after infection. Subsequently, a sixth person has been identified as being part of the cohort. Both the donor and recipients were HIV-1 seropositive but with no indications of clinical symptoms of HIV-1 related disease and CD4+ cell number and $\beta_2$-microglobulin levels have remained in the normal range. The identification of this cohort of benignly infected individuals provides a unique in vivo model in which the pathogenesis of HIV-1 infection can be studied at the clinical and molecular biological levels.

However, it has not always been possible using conventional isolation procedures to routinely and reproducibly isolate viral strains from the above mentioned donor or recipients which has frustrated efforts to investigate the cause of the asymptomatic individuals. In accordance with the present invention, methods have now been established to isolate viruses from the above individuals. It has been determined, in accordance with the present invention, that individuals of the cohort are infected by non-pathogenic strains of HIV-1. Furthermore, the non-pathogenic strains of HIV-1 carry one or more nucleotide mutations. The non-pathogenic strains of the present invention enable the generation of a range of therapeutic, diagnostic and targeting agents against HIV-1 infection. The present invention also enables the attenuation of previously pathogenic strain of HIV-1. Additionally, an investigation of the immunological profiles of cohort individuals has revealed that a non-pathogenic strain of HIV-1 is indicated by a particular deletion in the coding region of a protein resulting in an altered immunological profile for the expressed protein. An example of an altered immunological profile results from a deletion of certain amino acids in the Nef protein.

SUMMARY OF THE INVENTION

One aspect of the invention is directed to an isolated HIV-1 strain or a component, part, fragment or derivative thereof which is substantially non-pathogenic.

Another aspect of the invention is directed to an isolated strain of HIV-1 or a biological source thereof, said HIV-1 having the following characteristics:
  (i) is substantially non-pathogenic in human subjects; and
  (ii) carries a modified nef gene which encodes a nef gene product substantially immunologically non-interactive with antibodies to amino acids 162 to 177 of Nef in wild-type HIV-1.

Yet another aspect of the invention is directed to an isolated non-pathogenic strain of HIV-1 comprising a genome which is substantially incapable of hybridizing under medium stringent conditions to a nucleic acid molecule comprising a sequence of nucleotides which encodes all or part of amino acids 162 to 177 of wild-type HIV-1 Nef.

Still another aspect of the invention provides a non-pathogenic HIV-1 isolate which:
  (i) induces an immune response in a human or primate subject;
  (ii) does not substantially produce a proliferative response or cytokine production to a mitogen, alloantigen and/or recall antigen relative to a healthy, non-infected subject; and
  (iii) is substantially incapable of inducing an antibody response to amino acids 162 to 177 of wild-type HIV-1 Nef protein.

Still yet another aspect of the invention contemplates a viral isolate which:
  (i) is interactive to antibodies to a glycoprotein from HIV-1 selected from gp41–45, gp120 and gp160;
  (ii) is substantially non-pathogenic in human subjects; and
  (iii) carries a deletion mutation of at least ten nucleotide in a region corresponding to all or part of a acids 162 to 177 encoded by the nef gene of a pathogenic strain of HIV-1.

Another aspect of the invention provides an isolated strain of HIV-1 which is reactive to antibodies to a glycoprotein of HIV-1, is capable of inducing an immune response to at least one of gag, pol and/or env and which is incapable of directing synthesis of a nef gene product or a full length nef gene product.

A further aspect of the invention contemplates a method for inhibiting or reducing productive infection of an individual by a pathogenic strain of HIV-1, said method comprising administering to a subject a non-pathogenic isolate of HIV-1 in an amount effective to infect target cells and to generate target cells carrying DNA derived from said non-pathogenic HIV-1.

In yet another aspect of the invention there is contemplated a method for vaccinating an individual against the development of AIDS or AIDS related diseases, said method comprising administering to said individual a non-pathogenic isolate of HIV-1 in an amount effective to infect target cells and to generate target cells carrying DNA derived from said non-pathogenic HIV- 1.

In still yet another aspect of the invention there is provided a method for obtaining a preparation of non-pathogenic HIV-1 from a biological sample, said method comprising co-culturing PBMCs from said biological sample from an individual putatively infected with said non-pathogenic HIV-1 with HIV-1 seronegative donor PBMCs depleted for CD8+Cells, harvesting the PBMCs and supernatant fluid every from about 5 to about 10 days and adding fresh medium with CD8+depleted PBMCs with said fresh medium and isolating said virus from the supernatant fluid.

Another aspect of the invention contemplates a method for obtaining a preparation of non-pathogenic HIV-1 from a biological sample, said method comprising co-culturing monocytes from said biological sample from an individual putatively infected with said non-pathogenic HIV-1 with HIV-1 seronegative donor PBMCs depleted for CD8+cells, harvesting the monocytes and PBMCs and supernatant fluid every from about 5 to about 10 days and adding fresh medium with CD8+depleted PBMCs with said fresh medium and isolating ad virus from the supernatant fluid.

In yet a further aspect of the invention there is contemplated a method for identifying or screening for compounds capable of reducing or otherwise interfering with HIV-1 replication, said method comprising containing a compound to be tested with a cell or cell extract containing or capable of containing a nef gene product fused to a reporter molecule capable of giving an identifiable signal and screening for a compound which inhibits said signal.

In still yet a further aspect of the invention there is provided a viral isolate which:
(i) is genetically or immunologically related to a pathogenic strain of HIV-1;
(ii) is substantially non-pathogenic in human subjects;
(ii) comprises a first nucleotide sequence constituting its gemone which is capable of hybridising under medium stringency conditions to SEQ ID NO: 1 or a complementary form thereof; and
(iv) comprises a second nucleotide sequence within said first nucleotide sequence and which second nucleotide sequence directs expression of a mRNA molecule capable of inhibiting, reducing or otherwise down-regulating translation of a protein or polypeptide encoded by a pathogenic strain of HIV-1 or inhibit, reduce or otherwise down regulate operation of a non-protein encoding a region of a pathogenic strain of HIV-1.

Still yet another aspect of the invention is directed to a method for determining the pathogenicity of an HIV-1 strain after said HIV-1 strain infects cells of an individual, said med comprising determining the presence of a deletion mutation in the genome of said HIV-1 wherein said deletion mutation results in said genome being unable to synthesize a polypeptide or protein from a pathogenic strain of HIV-1 or directing the synthesis of a truncated form of said polypeptide or protein wherein the presence of a such a mutation is indicative of the presence of a non-pathogenic strain of HIV-1.

A further aspect of the invention contemplates a method for determining the pathogenicity of a strain of HIV-1 after said HIV-1 strain infects cells of an individual, said method comprising contacting a biological sample from said individual with a peptide corresponding to a deleted or truncated region of an HIV-1-derived protein and screening for the absence of antibody binding to said peptide, wherein the absence of antibody binding is indicative of a deletion or truncation in that protein and further indicative of th non-pathogenicity of said strain of HIV-1.

Another aspect of the invention is directed to a method for determining the pathogenicity of a strain of HIV-1 after said HIV-1 strain infects cells of an individual, said method comprising contacting a biological sample from said individual with an effective amount of a peptide having an amino acid sequence comprising or within a acids 162–177 of wild-type HIV-$1_{NL43}$ Nef, said contact being for a time and under conditions sufficient for an antibody if present in said biological sample to form a complex with said peptide and then detecting the presence of said complex wherein the absence of a complex in an individual seropositive for HIV-1 is indicative of that individual being infected with a non-pathogenic strain of HIV-1.

Still another aspect of the invention provides a method for determining the pathogenicity of an HIV-1 strain after said HIV-1 strain infects cells of an individual, said method comprising determining the presence of a mutation in the genome of said HIV-1 wherein the presence of the mutation results in a Nef protein substantially lacking amino acids 162 to 177 of Nef of a wild-type strain of HIV-1 and wherein said mutation is indicative of a non-pathogenic strain of HIV-1.

Still yet another aspect of the invention is directed to a synthetic peptide comprising a sequence of amino acids defined by SEQ ID NO:801 or a part or fragment thereof.

In yet a further aspect of the invention there is contemplated a method for determining the risk of an individual seropositive for HIV-1 developing symptoms of AIDS, said method comprising contacting antibodies from said patient with a synthetic peptide defined by SEQ ID NO:801 or a part or derivative thereof and detecting non-binding of antibodies to said peptide wherein the substantial absence of antibodies to said peptide is indicative of a low risk of the individual developing AIDS.

BRIEF DESCRIPTION OF THE FIGURES

FIG. 1 is a representation showing the alignment of the nucleotide sequences from donor D36 peripheral blood mononuclear cell (PBMC) [D36P] and non-pathogenic HIV-1 from recipient C18 HIV$_{StV}$ [C18S], C18 HIV$_{MBC}$ [C18M] and C98 HIV [C98H] and C54 PBMC [C54P] with the equivalent region of HIV-$1_{NL43}$. Sequences labelled PBMC are from patient PBMC, those labelled HIV are from virus isolated from patient PBMC and grown in culture. Numbering for HIV-$1_{NL43}$ is as per Myer et al (1992; 1994) whom nucleotide 1 is the first nucleotide of the complete proviral DNA sequence. D36P, C18S, C18M, C98H and C54P are numbered from the start of the region sequence. Identity with NL43 sequence is shown by (*). Deleted nucleotides are shown by (-). Spaces introduced to maximise alignment are shown by (,). Features in HIV-$1_{NL43}$ are marked by overlining the sequence, features in D36 and C18 are marked by umderlining the sequence.

FIG. 2 shows the alignment of encoded amino acid sequences of (a) tat exon 3 and (b) rev exon 3 from HIV-$1_{NL43}$, D36 PBMC, C18 HIV$_{StV}$ and C98 HIV. In-phase termination codons (*) and NL43 encoded amino acid numbers are shown.

FIG. 3 is a representation showing the alignment of C-terminal envelope glycoprotein gp41 amino acid sequences encoded by D36 PMBC, C18 HIV$_{StV}$. C18 HIV$_{MBC}$ and C98 HIV. Numbering is that of the amino acid sequence of the mature envelope glycoprotein of HIV-$1_{NL43}$. Termination in shown by (#).

FIG. 4 is a presentation showing alignment of amino acid sequences encoded by the nef genes of HIV-$1_{NL43}$, D36 PBMC, C18 HIV$_{StV}$, C18 HIV$_{MBC}$ and C98 HIV. In phase termination codons are shown by (#). Identical amino acids are shown by (*). Residues underlined are those immediately before a deletion.

FIG. 5 shows a duplication of NFKB nd Sp1 sequences in D36 PBMC, C18 HIV$_{StV}$, C18 HIV$_{MBC}$ and C98 HIV demonstrated by alignment of their low homology region sequences with the NFKB-Sp1 region of HIV-$1_{NL43}$. Nucleotide numbering according to FIG. 1. Identity with NL43 sequence shown by (*) and NFKB and Sp1 sites in NL43 overlined. Position of nef/LTR region sequence deletion shown by ($\Delta$).

FIG. 6 is a graphical representation showing replication of C18 and C98 viral isolates and D36 PBMCs from asymptomatic patients in PHA-stimulated PBMCs.

FIG. 7 is a graphical representation showing replication of viral isolates from asymptomatic patients in non-PHA stimulated PBMCs.

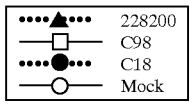

228200 is an Australian isolate of HIV-1 described by Kiernan, R et al (990). Its characteristics include being T cell trophic, with fast kinetics, high producer of HIV-1 and/or SI phenotype.

FIG. 8 is a graphical representation of cell surface receptor expression for syncytia-inducing (SI)/non-syncytia-inducing (NSI)/asymptomatic patient isolates.

228200 is defined in the legend to FIG. 7. 243925 is a viral isolate of HIV-1 which is monocyte/macrophage trophic and exhibits NSI phenotype (Dr Karen Coats-Fryer, PhD thesis entitled "Viral determinants of HIV-1 syncytium formation", the University of Melbourne, Parkville, Victoria, Australia.

FIG. 9 is a representation of the nucleotide sequence of C18 HIV-1$_{MBC}$ (SEQ ID NO: 800).

FIGS. 10(a)–(g) are graphical representations showing clinical immunology of cohort; (a) CD3; (b)(i) CD4 (ii) CD4%; (c)(i) CD8; (ii) CD8%; (d) lymphocyte count; (e) CD4/CD8 ratio; (f) β-2-microglobulin; and (g) Kaplan-Meier estimates of time to disease progression (Cox & Oakes, 1989).

FIG. 11 is a schematic representation of the deletion mutants of the present invention.

FIG. 12 shows reactivity of sera from LTP individuals (1a); HIV-1-ve individuals (1bi, 1bii); individuals with autoimmune disease (A/HIV-1) (1biii); LTNP1 (1c) and LTNP2 (1d) with full length Nef 27 derived from HIV-1$_{NL43}$ (referred to heren as "Nef 27"). The term "LTNP" is an abbreviation for "Long Term Non-Progessor". NTNP1 and LTNP2 are defined in Example 16.

Wells of 96-well polystyrene microtitre plates with purified Nef 27 (100 ng/well) were incubated with sera (titrated from 1:100 to 1:10,000) obtained from LTP individuals, HIV-1-ve individuals, individuals with autoimmune disease, LTNP1 and LTNP2. The presence of antibodies in the sera which recognise Nef 27 were detected using a biotin-streptavidin HRP system with o-phenylenediamine as substrate. Absorbance was measured using a Titertek plate reader at wavelengths of 630 and 450 nm.

FIG. 13a shows reactivity of sara from LTP individuals against Nef-derived peptides. Synthetic peptides corresponding to amino acid residues 1 to 19 (i), 20 to 36 (ii), 44 to 65 (iii); 72 to 83 (iv), 89 to 97 (v9); 109 to 114 (vi), 164 to 186 (vii), 187 to 206 (viii), 121 to 135 (ix) and 162 to 177 (x) of HIV-1$_{NL43}$ Nef27 were coated onto wells of 96-well microtitre plates at a concentration of 500 ng/well. Sera (titrated from 1:300 to 1;100,000) from the LTP individuals were then incubated with the immobilised peptides and the present of antibodies in the sera which recognise the Net-derived peptide were detected using a biotin-steptavidin HRP system with o-phenylenediamine as substrate. Absorbance was measured using a Titertek plate reader at wavelengths of 630 and 450 nm.

FIG. 13b(i) shows reactivity of sera from HIV-1-ve individuals against Nef-derived peptides. Synthetic peptides corresponding to amino acid residues 1 to 19(i), 20 to 36 (ii), 44 to 65 (iii), 72 to 83 (iv), 89 to 97 (v), 109 to 114 (vi) 164 to 186 (vii), 187 to 206 (viii), 121 to 135 (ix) and 162 to 177 (x) of HIV-1$_{NL43}$ Nef were=coated onto wells of 96-well microtitre plates at a concentration of 500 ng/well. Sera (titrated from 1:300 to 1:100,000) from A/HIV-1 -ve individuals with autoimmune disease was then incubated with the immobilised peptide and the presence of antibodies in the sera which recognise the Nef-derived peptides were detected using a biotin-steptavidin HRP system with o-phenylenediamine as substrate. Absorbance was measured using a Titertek plate reader at wavelengths of 630 and 450 nm.

FIG. 13b(ii) shows reactivity of sera from autoimmune A/HIV-1-ve individuals against Nef-derived peptides. Synthetic peptides corresponding to amino acid residues 1 to 19 (i), 20 to 36 (ii), 44 to 65 (i), 72 to 83 (iv), 89 to 97 (v), 109 to 114 (vi), 164 to 186 (vii), 187 to 206 (viii), 121 to 135 (ix) and 162 to 177 (x) of HIV-1$_{NL43}$ Nef were coated onto wells of 96-well microtitre plates at a concentration of 500 ng/well. Sera (titrated from 1:300 to 1:100,000) from A/HIV-1-ve individuals with autoimmune disease was then incubated with the immobilised peptides and the present of antibodies in the sera which recognise the Nef-derived peptides were detected using a biotin-streptavidin HRP system with o-phenylenediamine as substrate. Absorbance was measured using a Titerek plate reader at wavelengths of 630 and 450 nm.

FIG. 13c shows reactivity of sera from LTNP1 individual Nef-derived peptides. Synthetic peptides corresponding to amino acid residues 1 to 19 (i), 20 to 36 (ii), 44 to 65 (iii), 72 to 33 (iv), 89 to 97 (v), 109 to 114 (v), 164 to 186 (vii), 187 to 206 (viii), 121 to 135 (ix) and 162 to 177 (x) of HIV-1$_{NL43}$ Nef were coated onto wells of 96-well microtitre plates at a concentration of 500 ng/well. Sera (titrated from 1:300 to 1:100,000) from the LTNP1 individuals were then incubated with the immobilised peptides and the presence of antibodies in the sera which recognise the Nef-derived peptides were detected using a biotin-streptavidin HRP system wit o-phenylenediamine as substrate. Absorbance was measured using a Titertek plate reader at wavelengths of 630 and 450 nm.

FIG. 13d shows reactivity of sera of LTNP2 individuals Nef-derived peptides. Synthetic peptides corresponding to amino acid residues 1 to 19 (i), 20 to 36 (ii), 44 to 65 (iii), 72 to 83 (iv), 89 to 97 (v), 109 to 114 (vi), 164 to 186 (vii), 187 to 206 (viii), 121 to 135 (ix) and 162 to 177 (x) of HIV-1$_{NL43}$ Nef were coated onto wells of 96-well microtitre plates at a concentration of 500 ng/well. Sera (titrated from 1:300 to 1:100,000) from the LTNP2 individuals were then incubated with the immobilised peptides and the presence of antibodies in the sera which recognise the Nef-derived peptides were detected using a biotin-streptavidin HRP system with o-phenylenediamine as substrate. Absorbance was measured using a Titertek plate reader at wavelengths of 630 and 450 nm.

A summary of the SEQ ID Nos. used in the subject specification is shown below:

| SEQ ID NO: | DESCRIPTION |
|---|---|
| 1 | Nucleotide sequence of HIV-1$_{NL43}$ genome |
| 2–613 | Decanucleotides of nef gene from HIV-1$_{NL43}$ |
| 614 | Partial nucleotide sequence of D36 HIV-1 isolate |
| 615 | Partial nucleotide sequence of C18 HIV-1$_{MBC}$ isolate |
| 616–625 | PCR primers shown in Table 1 |
| 626–633 | Sequence primers shown in Table 2 |
| 634 | Amino acid residues 15–27 of HIV-1$_{NL43}$ nef protein |
| 635 | HIV-1$_{NL43}$ tat exons (FIG. 2) |
| 636 | HIV-1 D36 tat exons (FIG. 2) |
| 637 | HIV-1 C18 tat exons (FIG. 2) |
| 638 | HIV-1$_{NL43}$ rev exons (FIG. 2) |
| 639 | HIV-1 D36 rev exons (FIG. 2) |
| 640 | HIV-1 C18 rev exons (FIG. 2) |
| 641 | HIV-1$_{NL43}$ C-terminal of gp41 (FIG. 3) |
| 642 | HIV-1 D36 C-terminal of gp41 (FIG. 3) |
| 643 | HIV-1 C18 C-terminal of gp41 (FIG. 3) |
| 644 | HIV-1$_{NL43}$ nef gene (FIG. 4) |
| 645 | HIV-1 D36 nef gene (FIG. 4) |
| 646 | HIV-1 C18 nef gene (FIG. 4) |
| 647 | HIV-1$_{NL43}$ NFKB/SP1 sequence (FIG. 5) |
| 648 | HIV-1 D36 NFKB/SP1 sequence (FIG. 5) |
| 649 | HIV-1 C18 NFKB/SP1 sequence (FIG. 5) |
| 650 | Nucleotide sequence of nef gene from HIV-1$_{NL43}$ |
| 651 | Nucleotide sequence of env and nef regions of HIV-1$_{NL43}$ |
| 652–799 | Decanucleotides of LTR region from HIV-1$_{NL43}$ |
| 800 | Nucleotide sequence of C18 HIV-1$_{MBC}$ |
| 801 | Amino acids 162 to 177 of wild-type HIV-1$_{NL43}$ Nef |
| 802 | Nucleotide sequence encoding amino acids 162 to 177 of wild-type HIV-1$_{NL43}$ Nef |
| 803–841 | Decanucleotide deletion of Nef gene covering amino acids 162 to 177 |

DETAILED DESCRIPTION OF THE PREFERRED EMBODIMENTS

Figure 2:
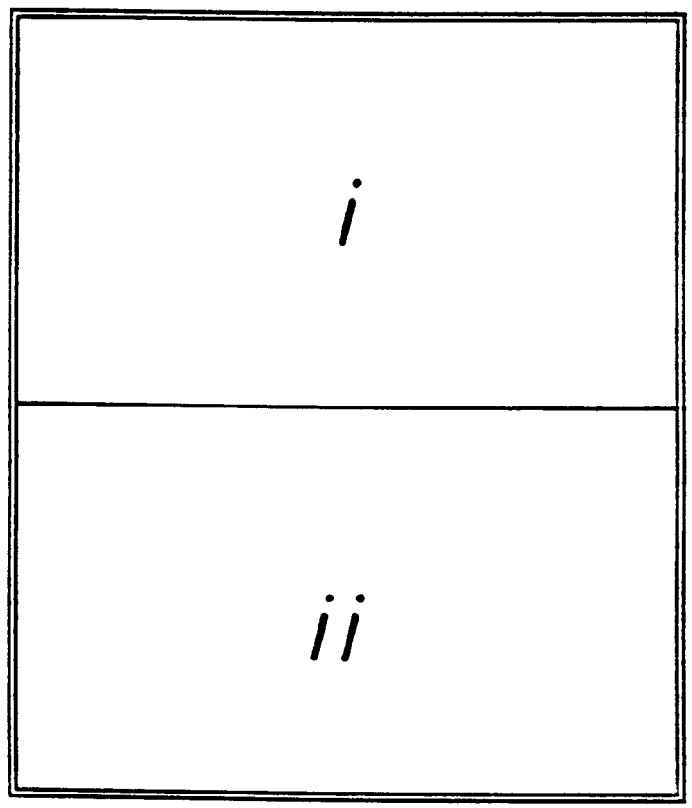

One aspect of the present invention contemplates a non-pathogenic isolates of HIV-1 or a component, part, fragment or derivative thereof.

In a related embodiment, there is provided a novel isolate of HIV-1 or a component, part fragment or derivative thereof wherein said HIV-1 isolate is capable of stimulating in a human or primate subject an immune response such as humoral immune response to at least one HIV-1 glycoprotein such as but not limited to gp41–45, gp120 and/or gp160 while not substantially reducing in said human or primate subject proliferative responses and cytokine production to a mitogen, alloantigen and/or recall antigen compared to a healthy, non-infected human or primate subject. Preferable, the cytokine is IL-2. Preferably, the mitogen is ConA or PHA and the recall antigen is influenza or tetanus toxoid. Preferably, the HIV-1 isolate is non-pathogenic.

More particularly, the present invention relates to an isolated HIV-1 in which:

(i) is substantially non-pathogenic in human subjects; and (ii) carries one or more mutations in its genome resulting in the inability to direct synthesis of at least one pathogenic HIV-1-derived polypeptide or protein.

Even more particularly, the present invention provides an isolated HIV-1 strain which:

(i) is substantially non-pathogenic in human subjects; and (ii) carries a mutation in the nef gene and/or a long terminal repeat (LTR) region or in a functionally equivalent location in the HIV-1 genome.

Still even more particularly, the preset invention is direct to an isolated virus which:

(i) has a genome which is capable of hybridising under medium stringency conditions to complementary nucleic acid from a pathogenic strain of HIV-1;

(ii) is substantially non-pathogenic in human subjects;

(iii) carries one or more deletion mutations in a region of its genome corresponding to a nef gene in said pathogenic strain of HIV-1; and (iv) optionally carries a mutation in one or both LTR regions.

In a related embodiment, there is provided an isolated virus which:

(i) has a genome which is capable of hybridising under medium stringency conditions to complementary nucleic acid from a pathogenic strain of HIV-1;

(ii) is substantially non-pathogenic in human subjects;

(iii) carries one or more deletion mutations in an LTR region of its genome; and (iv) optionally carries a mutation in a region corresponding to a nef gene in said pathogenic strain of HIV-1.

In a further related embodiment, there is provided an isolated virus which:

(i) has a genome which is capable of hybridising under medium stringency conditions to complementary nucleic acid from a pathogenic strain of HIV-1;

(ii) is substantially non-pathogenic in human subjects; and (iii) carries one or more deletion mutations in a region of its genome corresponding to a region which contains nef coding sequences and LTR nucleotide sequences.

Another aspect of the present invention is directed to an isolated strain of HIV-1 or a biological source thereof, wherein said HIV-1 has the following characteristics:

(i) is substantially non-pathogenic in human subjects; and (ii) carries a modified nef gene which encodes a nef gene product substantially immunologically non-interactive with antibodies to amino acids 162 to 177 of Nef in wild-type HIV-1.

Amino acids of 162–177 of wild-type HIV-1$_{NL43}$ strain (Myers et al, 1994) [hereinafter referred to as "HIV-1$_{NL43}$"] are as follows:

Thr Ser Leu Leu His Pro Val Ser Leu His Gly Met Asp Asp Pro Glu [SEQ ID NO:801].

This aspect of the present invention relates in part to amino acid sequence SEQ ID NO:801 from HIV-1$_{NL43}$ or from the functionally equivalent region of other pathogenic strains of HIV-1.

A further aspect of the present invention contemplates an isolated strain of HIV-1 or a biological source thereof, wherein said HIV-1 has the following characteristics:

(i) is substantially non-pathogenic in human subjects; and (ii) encodes an Nef protein or portion thereof which is interactive with wild HIV-1 Nef antibodies but which is substantially non-interactive with antibodies to amino acids 162 to 177 of wild-type HIV-1 Nef protein.

Still another aspect of the present invention relate to an isolated strain of HIV-1 or a biological source thereof which is substantially non-pathogenic in human subjects and which is substantially incapable of directing synthesis of a Nef protein or portion thereof comprising amino acids 162 to 177 of wild-type HIV-1 Nef protein.

In still yet another aspect of the present invention, there is provided an isolated strain of HIV-1 or a biological source thereof, said HIV-1 being substantially non-pathogenic in humans and comprising a mutation in its genome corresponding to amino acids 162 to 177 of wild-type HIV-1 Nef such that these amino acids are substantially not represented in a Nef protein or derivative thereof produced by said located HIV-1 strain, or insufficient of the amino acid sequence is represented to induce an immune response to that region of Nef.

In a related embodiment, the genomic mutation in the non-pathogenic strain of HIV-1 is a mutation in one or more of nucleotides 9271 to 9317 relative to HIV-1$_{NL43}$ or in a functionally equivalent region in another pathogenic strain of HIV-1.

In a related embodiment, there is provided a non-pathogenic strain of HIV-1 comprising a genome which is substantially incapable of hybridising under medium stringent conditions a nucleic acid molecule comprising that sequence of nucleotides which encodes all or part of amino acids 162 to 177 of wild-type HIV-1. Preferably, the nucleic acid molecule is a synthetic oligonucleotide.

In a particularly preferred embodiment, the present invention provides non-pathogenic HIV-1 isolate C18 deposited at the ECACC on Oct. 17, 1994 under Provisional Accession Number V94101706.

In a related embodiment, the present invention provides non-pathogenic HIV-1 isolate C98 deposited at the ECACC on Oct. 31, 1994 under Provisional Accession Number V941031169.

In another embodiment, the present invention provides non-pathogenic HIV-1 isolate C54 deposited at ECACC on Mar. 10, 1995 under Provisional Accession No. V95031022.

Although pathogenicity is a relative term, it is used herein in relation to the capacity of a strain of HIV-1 to induce AIDS or AIDS-related disorders in an individual over time. Accordingly, a "non-pathogenic" strain of HIV-1 is a strain which, at the clinical level, does not lead to the development of AIDS, at least within the median time of 6–10 years following infection with HIV-1. At the laboratory level, a non-pathogenic strain of HIV-1 is considered not to alter CD4+ cell counts or $\beta_2$-microglobulin concentrations. In addition, a non-pathogenic strain of HIV-1 may not alter CD8+ and CD3+ cell counts and would not alter lymphocyte counts. CD4+:CD8+ ratios also remain unchanged relative to normal non-infected individuals. Furthermore, generally, a non-pathogenic strain of HIV-1 does not induce p24 antigenaemia. A non-pathogenic HIV-1 of the present invention is generally still infectious but individuals infected with the virus remain free of symptoms for at least 6–10 years after infection.

A laboratory classified non-pathogenic strain of HIV-1 may be determined at any time after infection. The term "non-pathogenic" is not to be considered as a strain that is never pathogenic under any conditions as this might depend on the host individual, the level of immune responsiveness in that individual and the extent or otherwise of other, for example, immune comprising disorders. Accordingly, a "non-pathogenic" HIV-1 isolate of the present invention may also be considered a "low virulent" strain of the virus. A non-pathogenic strain of HIV-1 as contemplated herein may be isolated from an asymptomatic individual or may be derived from a pathogenic strain by mutation. Although the present invention is not to be limited to any particular pathogenic strain of HIV-1, for reference purposes, an example of a pathogenic strain is HIV-1$_{NL43}$ strain as described by Myers et al (1992; 1994).

The non-pathogenic nature of the HIV-1 of the present invention is conveniently evidenced by the cohort of seven individuals comprising one donor and six recipients which have remained free of symptoms or signs of HIV-1 infection for greater than the median time of 6–10 years. However, the individuals of the cohort are seropositive for HIV-1 following infection with the virus as determined by Western blot analysis and genetic analysis (e.g. using PCR techniques). A seropositive individual is one showing reactivity to at least one HIV-1 glycoprotein (such as but not limited to gp41–45, gp120, gp160) and at least three other virus-specific bands.

In accordance with the present invention, a non-pathogenic HIV-1 isolate is also a strain of HIV-1 which:

(i) induces an immune response in a human or primate subject; and (ii) does not substantially reduce proliferative responses or cytokine production to a mitogen, alloantigen and/or recall antigen relative to a healthy, non-infected subject.

Preferably, the immune response such as to a glycoprotein, for example gp41–45, gp120 and/or gp160. Preferably, the cytokine monitored is an interleukin, such as IL-2. Preferably, the recall antigen is influenza or tetanus toxoid. A non-pathogenic HIV-1 isolate is also one which:

(iii) does not substantially alter proliferative responses or cytokine production to allorgeneic mononuclear cells.

Furthermore, a non-pathogenic strain of HIV-1 carries a deletion in a HIV-1-derived protein which results in an altered immunological profile. In a particularly preferred embodiment, the non-pathogenic strain of HIV-1 is substantially incapable of inducing an antibody response to amino acids 162 to 177 to wild-type HIV-1 Nef protein. According to this preferred aspect of the present invention, there is provided a non-pathogenic HIV-1 isolate which:

(i) induces an immune response in a human or primate subject;

(ii) does not substantially reduce proliferative responses or cytokine production to a mitogen, alloantigen and/or recall antigen relative to a healthy, non-infected subject; and (iii) is substantially incapable of inducing an antibody response to amino acids 162 to 177 of wild-type HIV-1 Nef protein.

The genomes or complementary DNA therefrom of the non-pathogenic HIV-1 isolates of the present invention are capable of hybridising under medium stringency conditions to the corresponding genome or complementary DNA of a pathogenic strain of HIV-1 (e.g. HIV-1 strain HIV-1$_{NL43}$). The ability to hybridize to a pathogenic strain of HIV-1 only applies to a comparison of the entire genome/complementary DNA of a non-pathogenic strain or a fragment which includes genetic material corresponding to a region in the genome 3' of the nef gene in a pathogenic strain of HIV-1.

Reference herein to "wild-type HIV-1" is mean to include reference to architypal pathogenic strain HIV-1$_{NL43}$ (Myers et al, 1992; 1994). For the purposes of reference only, a suitable genomic nucleotide sequence from HIV-1$_{NL43}$ is set forth in SEQ ID NO: 1 (Myers et al, 1992; 1994):

1 TGGAAGGGCTAATTTGGTCCCAAAAAA-
GACAAGAGATCCTTGATCTGTGG
51 ATCTACCACACACAAGGCTACTTCCCT-
GATTGGCAGAACTACACACCAGG
101 GCCAGGGATCAGATATCCACTGAC-
CTTTGGATGGTGCTTCAAGTTAGTAC
151 CAGTTGAACCAGAGCAAGTAGAAGAGGC-
CAAATAAGGAGAGAAGAACAGC
201 TTGTTACACCCTATGAGCCAGCATGG-
GATGGAGGACCCGGAGGGAGAAGT
251 ATTAGTGTGGAAGTTTGACAGCCTC-
CTAGCATTTCGTCACATGGCCCGAG
301 AGCTGCATCCGGAGTACTACAAAGACT-
GCTGACATCGAGCTTTCTACAAG
351 GGACTTTCCGCTGGGGACTTTCCAGG-
GAGGTGTGGCCTGGGCGGGACTGG
401 GGAGTGGCGAGCCCTCAGATGCTA-
CATATAAGCAGCTGCTTTTTGCCTGT

```
 451 ACTGGGTCTCTGGTTAGACCAGATCT-
     GAGCCTGGGAGCTCTCTCTGGCTA
 501 ACTAGGGAACCCACTGCTTAAGCCT-
     CAATAAAGCTTGCCTTGAGTGCTCA
 551 AAGTAGTGTGTGCCCGTCTGTTGTG-
     TGACTCTGGTAACTAGAGATCCCTC
 601            AGACCCTTTTAGTCAGTGTG-
     GAAAATCTCTAGCAGTGGCGCCCGAACAGG
 651 GACTTGAAAGCGAAAGTAAAGCCAGAG-
     GAGATCTCTCGACGCAGGACTCG
 701 GCTTGCTGAAGCGCGCACGCAAGAGGC-
     GAGGGGCGGCGACTGGTGAGTA
 751 CGCCAAAAATTTTGACTAGCGGAGGCTA-
     GAAGGAGAGAGATGGGTGCGAG
 801 AGCGTCGGTATTAAGCGGGGGAGAATTA-
     GATAAATGGGAAAAATTCGGT
 851           TAAGGCCAGGGGGAAAGAAA-
     CAATATAAACTAAAACATATAGTATGGGCA
 901 AGCAGGGAGCTAGAACGATTCGCAGT-
     TAATCCTGGCCTTTTAGAGACATC
 951 AGAAGGCTGTAGACAAATACTGGGA-
     CAGCTACAACCATCCCTTCAGACAG
1001          GATCAGAAGAACTTAGATCAT-
     TATATAATACAATAGCAGTCCTCTATTGT
1051 GTGCATCAAAGGATAGATGTAAAAGA-
     CACCAAGGAAGCCTTAGATAAGAT
1101 AGAGGAAGACGAAACAAAAGTAA-
     GAAAAAGGCACAGCAAGCAGCAGCTG
1151 ACACAGGAAACAACAGCCAGGTCAGC-
     CAAAATTACCCTATAGTGCAGAAC
1201 CTCCAGGGGCAAATGGTACATCAGGC-
     CATATCACCTAGAACTTTAAATGC
1251 ATGGGTAAAAGTAGTAGAAGAGAAG-
     GCTTTCAGCCCAGAAGTAATACCCA
1301 TGTTTTCAGCATTATCAGAAGGAGCCAC-
     CCCACAAGATTTAAATACCATG
1351 CTAAACACAGTGGGGGACATCAAG-
     CAGCCATGCAAATGTTAAAAGAGAC
1401 CATCAATGAGGAAGCTGCAGAATGG-
     GATAGATTGCATCCAGTGCATGCAG
1451      GGCCTATTGCACCAGGCCAGAT-
     GAGAGAACCAAGGGGAAGTGACATAGCA
1501 GGAACTACTAGTACCCTTCAGGAA-
     CAAATAGGATGGATGACACATAATCC
1551      ACCTATCCCAGTAGGAGAAATC-
     TATAAAAGATGGATAATCCTGGGATTAA
1601 ATAAAATAGTAAGAATGTATAGCCCTAC-
     CAGCATTCTGGACATAAGACAA
1651 GGACCAAAGGAACCCTTTAGAGACTATG-
     TAGACCGATTCTATAAAACTCT
1701 AAGAGCCGAGCAAGCTTCACAAGAGG-
     TAAAAAATTGGATGACAGAAACCT
1751 TGTTGGTCCAAAATGCGAACCCAGATTG-
     TAAGACTATTTTAAAAGCATTG
1801 GGACCAGGAGCGACACTAGAAGAAAT-
     GATGACAGCATGTCAGGGAGTGGG
1851 GGGACCCGGCCATAAAGCAAGAGTTTTG-
     GCTGAAGCAATGAGCCAAGTAA
1901 CAAATCCAGCTACCATAATGATACA-
     GAAAGGCAATTTTAGGAACCAAAGA
1951 AAGACTGTTAAGTGTTTCAATTGTG-
     GCAAAGAAGGGCACATAGCCAAAAA
2001 TTGCAGGGCCCCTAGGAAAAAGGGCTGT-
     TGGAAATGTGGAAAGGAAGGAC
2051 ACCAAATGAAAGATTGtACTGAGAGA-
     CAGGCTAATTTTTTAGGGAAGATC
2101 TGGCCTTCCCACAAGGGAAGGCCAGG-
     GAATTTTCTTCAGAGCAGACCAGA
2151 GCCAACAGCCCCACCAGAAGAGAGCT-
     TCAGGTTTGGGGAAGAGACAACAA
2201 CTCCCTCTCAGAAGCAGGAGCCGATAGA-
     CAAGGAACTGTATCCTTTAGCT
2251 TCCCTCAGATCACTCTTTGGCAGCGAC-
     CCCTCGTCACAATAAAGATAGGG
2301 GGGCAATTAAAGGAGCTCTATTAGATA-
     CAGGAGACAGATGATACAGTATT
2351 AGAAGAAATGAATTTGCCAGGAAGATG-
     GAAACCAAAAATGATAGGGGGAA
2401 TTGGAGGTTTTATCAAAGTAGGACAG-
     TATGATCAGATACTCATAGAAATC
2451 TGCGGACATAAAGCTATAGGTACAG-
     TATTAGTAGGACCTACACCTGTCAA
2501 CATAATTGGAAGAAATCTGTTGACTCA-
     GATTGGCTGCACTTTAAATTTTC
2551 CCATTAGTCCTATTGAGACTYGTACCA-
     GAAAATTAAAGCCAGGAATGGAT
2601 GGCCCAAAAGTTAAACAATGGCCATTGA-
     CAGAAGAAAAAATAAAAGCATT
2651 AGTAGAAATTTGTACAGAAATGGAAAAG-
     GAAGGAAAAATTTCAAAAATTG
2701 GGCCTGAAAATCCATACAATACTCCAG-
     TATTTGCCATAAAGAAAAAAGAC
2751 AGTACTAAATGGAGAAAATTAGTA-
     GATTTCAGAGAACTTAATAAGAGAAC
2801 TCAAGATTTCTGGGAAGTTCAATTAG-
     GAATACCACATCCTGCAGGGTTAA
2851 AACAGAAAAAATCAGTAACAGTACTG-
     GATGTGGGCGATGCATATTTTTCA
2901 GTTCCCTTAGATAAAGACTTCAGGAAG-
     TATACTGCATTTACCATACCTAG
2951 TATAAACAATGAGACACCAGGGATTA-
     GATATCAGTACAATGTGCTTCCAC
3001 AGGGATGGAAAGGATCACCAGCAATAT-
     TCCAGTGTAGCATGACAAAAATC
3051 TTAGAGCCTTTTAGAAAACAAAATCCA-
     GACATAGTCATCTATCAATACAT
3101 GGATGATTTGTATGTAGGATCTGACTTA-
     GAAATAGGGCAGCATAGAACAA
3151 AAATAGAGGAACTGAGACAACATCTGT-
     TGAGGTGGGGATTTACCACACCA
3201 GACAAAAAACATCAGAAAGAACCTCCAT-
     TCCTTTGGATGGGTTATGAACT
3251 CCATCCTGATAAATGGACAGTACAGC-
     CTATAGTGCTGCCAGAAAAGGACA
3301 GCTGGACTGTCAATGACATACAGAAATT-
     AGTGGGAAAATTGAATTGGGCA
3351 AGTCAGATTTATGCAGGGATTAAAG-
     TAAGGCAATTATGTAAACTTCTTAG
3401 GGGAACCAAAGCACTAACAGAAGTAG-
     TACCACTAACAGAAGAAGCAGAGC
3451 TAGAACTGGCAGAAAACAGGGAGAT-
     TCTAAAAGAACCGGTACATGGAGTG
3501 TATTATGACCCATCAAAAGACTTAATAG-
     CAGAAATACAGAAGGAGGGGCA
3551 AGGCCAATGGACATATCAAATTTATCAA-
     GAGCCATTTAAAAATCTGAAAA
3601 CAGGAAAATATGCAAGAATGAAGGGTGC-
     CCACACTAATGATGTGAAACAA
3651 TTAACAGAGGCAGTACAAAAAATAGCCA-
     CAGAAAGCATAGTAATATGGGG
3701 AAAGACTCCTAAATTTAAATTACCCATA-
     CAAAAGGAAACATGGGAAGCAT
3751 GGTGGACAGAGTATTGGCAAGCCACCTG-
     GATTCCTGAGTGGGAGTTTGTC
3801 AATACCCCTCCCTTAGTGAAGTTATGG-
     TACCAGTTAGAGAAAGAACCCAT
```

3851 AATAGGAGCAGAAACTTTCTATGTA-
GATGGGGCAGCCAATAGGGAAACTA
3901 AATTAGGAAAAGCAGGATATGTAACTGA-
CAGAGGAAGACAAAAAGTTGTC
3951 CCCCTAACGGACACAACAAATCAGAA-
GACTGAGTTACAAGCAATTCATCT
4001 AGCTTTGCAGGATTCGGGATTAGAAG-
TAAACATATGGACAGACTCACAAT
4051 ATGCATTGGGAATCATTCAAGCACAAC-
CAGATAAGAGTGAATCAGAGTTA
4101 GTCAGTCAAATAATAGAGCAGT-
TAATAAAAAAGGAAAAAGTCTACCTGGC
4151 ATGGGTACCAGCACACAAGGAATTG-
GAGGAAATGAACAAGTAGATGGGT
4201 TGGTCAGTGCTGGAATCAGGAAAGTAC-
TATTTTTAGATGGAATAGATAAG
4251 GCCCAAGAAGAACATGAGAAATATCA-
CAGTAATTGGAGAGCAATGGCTAG
4301 GATTTTAACCTACCACCTGTAGTAG-
CAAAAGAAATAGTAGCCAGCTGTG
4351 ATAAATGTCAGCTAAAAGGGGAAGCCAT-
GCATGGACAAGTAGACTGTAGC
4401 CCAGGAATATGGCAGCTAGATTGTACA-
CATTTAGAAGGAAAAGTTATCTT
4451 GGTAGCAGTTCATGTAGCCAGTG-
GATATATAGAAGCAGAAGTAATTCCAG
4501 CAGAGACAGGGCAAGAAACAGCATACT-
TCCTCTTAAAATTAGCAGGAAGA
4551 TGGCCAGTAAAAACAGTACATACAGA-
CAATGGCAGCAATTTCACCAGTAC
4601 TACAGTTAAGGCCGCCTGTTG-
GTGGGCGGGGATCAAGCAGGAATTTGGCA
4651 TTCCCTACAATCCCCAAAGTCAAGGAG-
TAATAGAATCTATGAATAAAGAA
4701 TTAAAGAAAATTATAGGACAGGTAA-
GAGATCAGGCTGAACATCTTAAGAC
4751 AGCAGTACAAATGGCAGTATTCATCCA-
CAATTTTAAAAGAAAAGGGGGGA
4801 TTGGGGGGTACAGTGCAGGGGAAAGAAT-
AGTAGACATAATAGCAACAGAC
4851 ATACAAACTAAAGAATTACAAAAA-
CAAATTACAAAAATTCAAAATTTTCG
4901 GGTTTATTACAGGGACAGCAGAGATC-
CAGTTTGGAAAGGACCAGCAAAGC
4951 TCCTCTGGAAAGGTGAAGGGGCAGTAG-
TAATACAAGATAATAGTGACATA
5001 AAAGTAGTGCCAAGAAGAAAAGCAAA-
GATCATCAGGGATTATGGAAAACA
5051 GATGGCAGGTGATGATTGTGTGGCAAG-
TAGACAGGATGAGGATTAACACA
5101 TGGAAAAGATTAGTAAAACACCATATG-
TATATTTCAAGGAAAGCTAAGGA
5151 CTGGTTTTATAGACATCACTATGAAAG-
TACTAATCCAAAAATAAGTTCAG
5201 AAGTACACATCCACTAGGGGAT-
GCTAAATTAGTAATAACAACATATTGG
5251 GGTCTGCATACAGGAGAAAGAGACTG-
GCATTTGGGTCAGGGAGTCTCCAT
5301 AGAATGGAGGAAAAAGAGATATAGCACA-
CAAGTAGACCCTGACCTAGCAG
5351 ACCAACTAATTCATCTGCAC-
TATTTTGATTGTTTTTCAGAATCTGCTATA
5401 AGAAATACCATATTAGGACGTATAGT-
TAGTCCTAGGTGTGAATATCAAGC
5451 AGGACATAACAAGGTAGGATCTCTACAG-
TACTTGGCACTAGCAGCATTAA
5501 TAAAACCAAAACAGATAAAGCCAC-
CTTTGCCTAGTGTTAGGAAACTGACA
5551 GAGGACAGATGGAACAAGCCCCAGAA-
GACCAAGGGCCACAGAGGGAGCCA
5601 TACAATGAATGGACACTAGAGCTTTTA-
GAGGAACTTAAGAGTGAAGCTGT
5651 TAGACATTTTCCTAGGATATGGCTCCAT-
AACTTAGGACAACATATCTATG
5701 AAACTTACGGGGATACTTGGGCAG-
GAGTGGAAGCCATAATAAGAATTCTG
5751 CAACAACTGCTGTTTATCCATTTCA-
GAATTGGGTGTCACATAGCAGAAT
5801 AGGCGTTACTCGACAGAGGAGAGCAA-
GAAATGGAGCCAGTAGATCCTAGA
5851 CTAGAGCCCTGGAAGCATCCAGGAAGT-
CAGCCTAAAACTGCTTGTACCAA
5901 TTGCTATTGTAAAAAGTTTTGCTTTCAT-
TGCCAAGTTTGTTTCATGACAA
5951 AAGCCTTAGGCATCTCCTATGGCAGGAA-
GAAGCGGAGACAGCGACGAAGA
6001 GCTCATCAGAACAGTCAGACTCAT-
CAAGCTTCTCTATCAAAGCAGTAAGT
6051 AGTACGTAATGCAACCTATAATAG-
TAGCAATAGTAGCATTAGTAGTAG
6101 CAATAATAATAGCAATAGTTGTGTGGTC-
CATAGTAATCATAGAATATAGG
6151 AAAATATTAAGACAAAGAAAAATAGA-
CAGGTTAATTGATAGACTAATAGA
6201 AAGAGCAGAAGACAGTGGCAATGAGAGT-
GAAGGAGAAGTATCAGCACTTG
6251 TGGAGATGGGGGTGGAAATGGGGCAC-
CATGCTCCTTGGGATATTGATGAT
6301 CTGTAGTGCTACAGAAAAATTGTGGGT-
CACAGTCTATTATGGGGTACCTG
6351 TGTGGAAGGAAGCAACCACCACTC-
TATTTTGTGCATCAGATGCTAAAGCA
6401 TATGATACAGAGGTACATAAT-
GTTTGGGCCACACATGCCTGTGTACCCAC
6451 AGACCCCAACCCACAAGAAGTAGTATTG-
GTAAATGTGACAGAAAATTTTA
6501 ACATGTGGAAAAATGACATGGTAGAACA-
GATGCATGAGGATATAATCAGT
6551 TTATGGGATCAAAGCCTAAAGCCATGTG-
TAAAATTAACCCCACTCTGTGT
6601 TAGTTTAAAGTGCACTGATTTGAAGAAT-
GATACTAATACCAATAGTAGTA
6651 GCGGGAGAATGATAATGGAGAAAG-
GAGAGATAAAAAACTGCTCTTTCAAT
6701 ATCAGCACAAGCATAAGAGATAAGGTG-
CAGAAAGAATATGCATTCTTTTA
6751 TAAACTTGATATAGTACCAATA-
GATAATACCAGCTATAGGTTGATAAGTT
6801 GTAACACCTCAGTCATTACACAGGCCT-
GTCCAAAGGTATCCTTTGAGCCA
6851 ATTCCCATACATTATTGTGCCCCGGCTG-
GTTTTGCGATTCTAAAATGTAA
6901 TAATAAGACGTTCAATGGAACAGGAC-
CATGTACAAATGTCAGCACAGTAC
6951 AATGTACACATGGAATCAGGCCAGTAG-
TATCAACTCAACTGCTCTTAAAT
7001 GGCAGTCTAGCAGAAGAAGATGTAG-
TAATTAGATCTGCCAATTTCACAGA
7051 CAATGCTAAAACCATAATAGTACAGCT-
GAACACATCTGTAGAAATTAATT
7101 GTACAAGACCCAACAACAATACAA-
GAAAAAGTATCCGTATCCAGAGGGGA
7151 CCAGGGAGAGCATTTGTTACAATAG-
GAAAAATAGGAAATATGAGACAAGC
7201 ACATTGTAACATTAGTAGAGCAAAATG-
GAATGCCACTTTAAAACAGATAG

7251 CTAGCAAATTAAGAGAACAATTTG-GAAATAATAAAACAATAATCTTTAAG
7301 CAATCCTCAGGAGGGGACCCAGAAATTG-TAACGCACAGTTTTAATTGTGG
7351 AGGGGAATTTTTCTACTGTAATTCAACA-CAACTGTTTAATAGTACTTGGT
7401 TTAATAGTACTTGGAGTACTGAAGGGT-CAAATAACACTGAAGGAAGTGAC
7451 ACAATCACACTCCCATGCAGAATAAAA-CAATTTATAAACATGTGGCAGGA
7501 AGTAGGAAAAGCAATGTATGCCCCTC-CCATCAGTGGACAAATTAGATGTT
7551 CATCAAATATTACTGGGCTGCTATTAA-CAAGAGATGGTGGTAATAACAAC
7601 AATGGGTCCGAGATCTTCAGACCTGGAG-GAGGCGATATGAGGGACAATTG
7651 GAGAAGTGAATTATATAAATATAAAG-TAGTAAAAATTGAACCATTAGGAG
7701 TAGCACCCACCAAGGCAAAGAGAA-GAGTGGTGCAGAGAGAAAAAGAGCA
7751 GTGGGAATAGGAGCTTTGTTCCTTGGGT-TCTTGGGAGCAGCAGGAAGCAC
7801 TATGGGCTGCACGTCAATGACGCTGACG-GTACAGGCCAGACAATTATTGT
7851 CTGATATAGTGCAGCAGCAGAA-CAATTTGCTGAGGGCTATTGAGGCGCAA
7901 CAGCATCTGTTGCAACTCA-CAGTCTGGGGCATCAAACAGCTCCAGGCAAG
7951 AATCCTGGCTGTGGAAAGATACCTAAAG-GATCAACAGCTCCTGGGGATTT
8001 GGGGTTGCTCTGGAAAACTCATTTGCAC-CACTGCTGTGCCTTGGAATGCT
8051 AGTTGGAGTAATAAATCTCTGGAACA-GATTTGGAATAACATGACCTGGAT
8101 GGAGTGGGACAGAGAAATTAACAATTA-CACAAGCTTAATACACTCCTTAA
8151 TTGAAGAATCGCAAAACCAGCAAGAAAA-GAATGAACAAGAATTATTGGAA
8201 TTAGATAAATGGGCAAGTTTGTGGAAT-TGGTTTAACATAACAAATTGGCT
8251 GTGGTATATAAAATTATTCATAATGAT-AGTAGGAGGCTTGGTAGGTTTAA
8301 GAATAGTTTTTGCTGTACTTTCTATAGT-GAATAGAGTTAGGTAGGGATAT
8351 TCACCATTATCGTTTCAGACCCACCTC-CCAATCCCGAGGGGACCCGACAG
8401 GCCCGAAGGAATAGAAGAAGAAGGTG-GAGAGAGAGACAGAGACAGATCCA
8451 TTCGATTAGTGAACGGATCCTTAGCACT-TATCTGGGACGATCTGCGGAGC
8501 CTGTGCCTCTTCAGCTACCACCGCT-TGAGAGACTTACTCTTGATTGTAAC
8551 GAGGATTGTGGAACTTCTGGGACG-CAGGGGGTGGGAAGCCCTCAAATATT
8601 GGTGGAATCTCCTACAGTATTGGAGT-CAGGAACTAAAGAATAGTGCTGTT
8651 AACTTGCTCAATGCCACAGCCATAGCAG-TAGCTGAGGGACAGATAGGGT
8701 TATAGAAGTATTACAAGCAGCTTATA-GAGCTATTCGCCACATACCTAGAA
8751 GAATAAGACAGGGCTTGGAAAG-GATTTTGCTATAAGATGGGTGGCAAGTG
8801 GTCAAAAAGTAGTGTGATTGGATGGCCT-GCTGTAAGGGAAAGAATGAGAC
8851 GAGCTGAGCCAGCAGCAGATGGGGTGG-GAGCAGTATCTCGAGACCTAGAA
8901 AAACATGGAGCAATCACAAGTAGCAATA-CAGCAGCTAACAATGCTGCTTG
8951 TGCCTGGCTAGAAGCACAAGAGGAGGAA-GAGGTGGGTTTTCCAGTCACAC
9001 TCTAGGTACCTTTAAGACCAATGACTTA-CAAGGCAGCTGTAGATCTTAGC
9051 CACTTTTTAAAAGAAAAGGGGGGACTG-GAAGGGCTAATTCACTCCCAAAG
9101 AAGACAAGATATCCTTGATCTGTGGATC-TACCACACACAAGGCTACTTCC
9151 CTGATTGGCAGAACTACACACCAGGGC-CAGGGGTCAGATATCCACTGACC
9201 TTTGGATGGTGCTACAAGCTAGTAC-CAGTTGAGCCAGATAAGGTAGAAGA
9251 GGCCAATAAAGGAGAGAACACCAGCT-TGTTACACCCTGTGAGCCTGCATG
9301 GAATGGATGACCCTGAGAGAGAAGTGT-TAGAGTGGAGGTTTGACAGCCGC
9351 CTAGCATTTCATCACGTGGC-CCGAGAGCTGCATCCGGAGTACTTCAAGAA
9401 CTGCTGACATCGAGCTTGTCACAAGG-GACTTTCCGCTGGGGACTTTCCAG
9451 GGAGGCGTGGCCTGGGCGGGACTGGG-GAGTGGCGAGCCCTCAGATGCTGC
9501 ATATAAGCAGCTGCTTTTTGCCTG-TACTGGGTCTCTCTGGTTAGACCAGA
9551 TCTGAGCCTGGGAGCTCTCTGGCTAAC-TAGGGAACCCACTGCTTAAGCCT
9601 CAATAAAGCTTGCCTTGAGTGCTTCAAG-TAGTGTGTGCCCGTCTGTTGTG
9651 TGACTCTGGTAACTAGAGATCCCTCA-GACCCTTTTAGTCAGTGTGGAAAA
9701 TCTCTAGCA

However, for the purposes of comparing the nucleotide sequence of non-pathogenic HIV-1 strains including the ability to hybridize to a reference strain, the present invention extends to a genomic nucleotide sequence from any pathogenic strain of HIV-1.

Reference to a biological source includes blood or blood-related products or components such as lymphocytes, plasma, tissue fluid and time extracts.

Accordingly, in a particularly preferred embodiment, there is provided a viral isolate which:

(i) carries a genome which is capable of hybridising under medium stringency conditions to SEQ ID NO: 1 or a complementary form thereof or an analogous sequence from another pathogenic strain of HIV-1; and (ii) carries a deletion mutation in a region corresponding to the nef gene and/or in an LTR region. Generally, such an HIV-1 isolate is non-pathogenic as hereinbefore defined.

In a related embodiment, there is provided an isolated virus which:

(i) has a genome which is capable of hybridising under medium stringency conditions to complementary nucleic acid from a pathogenic strain of HIV-1; and (ii) carries one or more deletion mutations in a region of its genome corresponding to a region which contains nef coding sequence and LTR nucleotide sequences.

For the purposes of defining the level of stringency, reference can conveniently be made to Maniatis et al (1982) at pages 387–389 which is herein incorporated by reference where the washing steps disclosed are considered high stringency. A low stringency is defined herein as being in 1–3× SSC/0.1–0.5% w/v SDS at 37–50° C. for 2–3 hours. Depending on the source and concentration of nucleic acid involved in the hybridisation, alterative conditions of stringency may be employed such as medium stringent conditions which are considered herein to be 0.1–1× SSC/

0.2–0.5% w/v SDS at ≧45° C. for 2–3 hours or high stringent conditions considered herein to be 0.1–1× SSC/ 0.1% w/v SDS at 60° C. for 1–3 hours.

In a particularly preferred embodiment of the present invention, the non-pathogenic strain of HIV-1 carries a mutation in the nef gene and/or LTR region of the genome.

In an even more preferred embodiment, the non-pathogenic strain of HIV-1 carries a mutation in the nef gene such that a Nef protein is not produced or a modified Nef protein is produced substantially not carrying amino acids 162 to 177 or a portion thereof from wild-type Nef.

A "mutation" is considered herein to include a single or multiple nucleotide substitution, deletion and/or addition. Most preferred mutations are single or multiple deletions of at least one, most preferably at least ten and even more preferably at least twenty contiguous nucleotides from a region corresponding to the nef gene and/or the LTR region. When the non-pathogenic virus carries a mutation in the LTR region, this generally occurs 5' of the Sp1 sites. A particularly preferred deletion is from a region within the nef gene corresponding to a acids 162 to 177 of the Nef protein.

According to a preferred aspect of the present invention, there is provided a viral isolate which:

(i) is reactive to antibodies to a glycoprotein from HIV-1 such as at least one of gp41–45, gp120 and/or gp160;

(ii) is substantially non-pathogenic in human subjects; and (iii) carries a deletion mutation of at least ten nucleotides in a region corresponding to the nef gene and/or LTR region of a pathogenic strain of HIV-1.

In another embodiment, there is provided a viral isolate which:

(i) is capable of inducing an immune response to at least one of gag, pol and/or env;

(ii) is substantially non-pathogenic in human subjects; and (iii) carries a deletion mutation of at least ten nucleotides in a region corresponding to the nef gene and/or LTR region of a pathogenic of HIV-1.

Preferably, in respect of the latter embodiment, the immune response is an antibody or a cell mediated response. In a most preferred embodiment, the immune response is a humoral immune response.

In another aspect of the present invention, there is provided a viral isolate which:

(i) is interactive to antibodies to a glycoprotein from HIV-1 such as at least one of gp41–45, gp120 and/or gp160;

(ii) is substantially non-pathogenic in human subjects; and (iii) carries a deletion mutation of at least ten nucleotides in a region corresponding to all or part of amino acids 162 to 177 encoded by the nef gene of a pathogenic strain of HIV-1.

The nucleotide sequence of the nef gene in HIV-$1_{NL43}$ is defined in SEQ ID NO: 650:

ATGGGTGGCAAGTGGTCAAAAAGTAGT-GTGATTGGATGGCCTGCTGTAAGGGAAAGAAT GAGACGAGCTGAGCCAGCAGCA-GATGGGGTGGGAGCAGTATCTCGAGAC-CTAGAAAAAC ATGGAGCAATCACAAGTAGCAATA-CAGCAGCTAACAATGCTGCTTGTGCCTGGCTAGAA GCACAAGAGGAGGAAGAGGTGGGTTTTC-CAGTCACACCTCAGGTACCTTTAAGACCAAT GACT-TACAAGGCAGCTGTAGATCTTAGC-CACTTTTTAAAAGAAAAGGGGGGACTGGAAG GGCTAATTCACTCCCAAAGAAGACAA-GATATCCTTGATCTGTGGATCTACCACACACAA GGCTACTTCCCTGATTGGCAGAACTACA-CACCAGGGCCAGGGGTCAGATATCCACTGAC CTTTGGATGGTGCTACAAGCTAGTAC-CAGTTGAGCCAGATAAGGTAGAAGAGGCCAATA AAGGAGAGAACACCAGCTTGTTACAC-CCTGTGAGCCTGCATGGAATGGATGACCCTGAG AGAGAAGTGTTAGAGTGGAGGTTTGA-CAGCCGCCTAGCATTTCATCACGTGGCCCGAGA GCTGCATCCGGAGTACTTCAAGAACTGCTGA.

The nucleotide sequence encoding amino acids 162–177 of wild-type HIV-$1_{NL43}$ Nef is as follows:

ACCAGCTTSETTACACCCTrTGAGCCTG-CATGGATGACCCMM [SEQ ID NO:8021].

The present invention extends to any or all single or multiple nucleotide deletions to a contiguous series of at least ten nucleotides from the nef gene which render the strain avirulent. The deletions may encompass the entire gene or parts thereof and may represent a single deletion or two or more deletions. Put in alternative terms, the non-pathogenic HIV-1 isolates of the present invention comprise a nucleotide sequence at the corresponding nef gene region non-identifiable to SEQ ID NO: 650, said non-identity comprising at least 5%, more preferably at least 10% and even more preferably at least 20% variation thereon. The present invention particularly extends to any or all single or multiple nucleotide deletions to a contiguous series of at least ten nucleotides from the region of the nef gene corresponding to all or part of amino acids 162 to 177 and which render the strain avirulent. Although this aspect of the present invention is exemplified by specific reference to amino acids 162 to 177, the present invention also extends to a functionally analogous sequence where, for example, amino acids are substituted by structurally or functionally similar amino acids. In addition, the present invention extends to any deletion or other mutation in an HIV-1 derived protein which renders that strain non-pathogenic.

In a preferred embodiment, therefore, the present invention contemplates a viral isolate which:

(i) is reactive to antibodies to a glycoprotein from HIV-1 such as at least one of gp41–45, gp120 and/or gp160;

(ii) carries a genome or a part or fragment thereof capable of hybridising under medium stringency conditions to a nucleotide sequence as set forth in SEQ ID NO: 1 or a complementary form thereof or an analogous sequence from another pathogenic strain of HIV-1;

(iii) carries a deletion of at least ten nucleotides in a region corresponding to the nef gene in HIV-$1_{NL43}$; and wherein said deletion encompasses one or more of the following decanucleotides from the nef gene of HIV-$1_{NL43}$ or corresponding sequences from another pathogenic strain of HIV-1:

| | |
|---|---|
| ATGGGTGGCA (SEQ ID NO: 2); | TGGGTGGCAA (SEQ ID NO: 3); |
| GGGTGGCAAG (SEQ ID NO: 4); | GGTGGCAAGT (SEQ ID NO: 5); |
| GTGGCAAGTG (SEQ ID NO: 6); | TGGCAAGTGG (SEQ ID NO: 7); |
| GGCAAGTGGT (SEQ ID NO: 8); | GCAAGTGGTC (SEQ ID NO: 9); |

-continued

| | |
|---|---|
| CAAGTGGTCA (SEQ ID NO: 10); | AAGTGGTCAA (SEQ ID NO: 11); |
| AGTGGTCAAA (SEQ ID NO: 12); | GTGGTCAAAA (SEQ ID NO: 13); |
| TGGTCAAAAA (SEQ ID NO: 14); | GGTCAAAAAG (SEQ ID NO: 15); |
| GTCAAAAAGT (SEQ ID NO: 16); | TCAAAAAGTA (SEQ ID NO: 17); |
| CAAAAAGTAG (SEQ ID NO: 18); | AAAAAGTAGT (SEQ ID NO: 19); |
| AAAAGTAGTG (SEQ ID NO: 20); | AAAGTAGTGT (SEQ ID NO: 21); |
| AAGTAGTGTG (SEQ ID NO: 22); | AGTAGTGTGA (SEQ ID NO: 23); |
| GTAGTGTGAT (SEQ ID NO: 24); | TAGTGTGATT (SEQ ID NO: 25); |
| AGTGTGATTG (SEQ ID NO: 26); | GTGTGATTGG (SEQ ID NO: 27); |
| TGTGATTGGA (SEQ ID NO: 28); | GTGATTGGAT (SEQ ID NO: 29); |
| TGATTGGATG (SEQ ID NO: 30); | GATTGGATGG (SEQ ID NO: 31); |
| ATTGGATGGC (SEQ ID NO: 32); | TTGGATGGCC (SEQ ID NO: 33); |
| TGGATGGCCT (SEQ ID NO: 34); | GGATGGCCTG (SEQ ID NO: 35); |
| GATGGCCTGC (SEQ ID NO: 36); | ATGGCCTGCT (SEQ ID NO: 37); |
| TGGCCTGCTG (SEQ ID NO: 38); | GGCCTGCTGT (SEQ ID NO: 39); |
| GCCTGCTGTA (SEQ ID NO: 40); | CCTGCTGTAA (SEQ ID NO: 41); |
| CTGCTGTAAG (SEQ ID NO: 42); | TGCTGTAAGG (SEQ ID NO: 43); |
| GCTGTAAGGG (SEQ ID NO: 44); | CTGTAAGGGA (SEQ ID NO: 45); |
| TGTAAGGGAA (SEQ ID NO: 46); | GTAAGGGAAA (SEQ ID NO: 47); |
| TAAGGGAAAG (SEQ ID NO: 48); | AAGGGAAAGA (SEQ ID NO: 49); |
| AGGGAAAGAA (SEQ ID NO: 50); | GGGAAAGAAT (SEQ ID NO: 51); |
| GGAAAGAATG (SEQ ID NO: 52); | GAAAGAATGA (SEQ ID NO: 53); |
| AAAGAATGAG (SEQ ID NO: 54); | AAGAATGAGA (SEQ ID NO: 55); |
| AGAATGAGAC (SEQ ID NO: 56); | GAATGAGACG (SEQ ID NO: 57); |
| AATGAGACGA (SEQ ID NO: 58); | ATGAGACGAG (SEQ ID NO: 59); |
| TGAGACGAGC (SEQ ID NO: 60); | GAGACGAGCT (SEQ ID NO: 61); |
| AGACGAGCTG (SEQ ID NO: 62); | GACGAGCTGA (SEQ ID NO: 63); |
| ACGAGCTGAG (SEQ ID NO: 64); | CGAGCTGAGC (SEQ ID NO: 65); |
| GAGCTGAGCC (SEQ ID NO: 66); | AGCTGAGCCA (SEQ ID NO: 67); |
| GCTGAGCCAG (SEQ ID NO: 68); | CTGAGCCAGC (SEQ ID NO: 69); |
| TGAGCCAGCA (SEQ ID NO: 70); | GAGCCAGCAG (SEQ ID NO: 71); |
| AGCCAGCAGC (SEQ ID NO: 72); | GCCAGCAGCA (SEQ ID NO: 73); |
| CCAGCAGCAG (SEQ ID NO: 74); | CAGCAGCAGA (SEQ ID NO: 75); |
| AGCAGCAGAT (SEQ ID NO: 76); | GCAGCAGATG (SEQ ID NO: 77); |
| CAGCAGATGG (SEQ ID NO: 78); | AGCAGATGGG (SEQ ID NO: 79); |
| GCAGATGGGG (SEQ ID NO: 80); | CAGATGGGGT (SEQ ID NO: 81); |
| AGATGGGGTG (SEQ ID NO: 82); | GATGGGGTGG (SEQ ID NO: 83); |
| ATGGGGTGGG (SEQ ID NO: 84); | TGGGGTGGGA (SEQ ID NO: 85); |
| GGGGTGGGAG (SEQ ID NO: 86); | GGGTGGGAGC (SEQ ID NO: 87); |
| GGTGGGAGCA (SEQ ID NO: 88); | GTGGGAGCAG (SEQ ID NO: 89); |
| TGGGAGCAGT (SEQ ID NO: 90); | GGGAGCAGTA (SEQ ID NO: 91); |
| GGAGCAGTAT (SEQ ID NO: 92); | GAGCAGTATC (SEQ ID NO: 93); |
| AGCAGTATCT (SEQ ID NO: 94); | GCAGTATCTC (SEQ ID NO: 95); |
| CAGTATCTCG (SEQ ID NO: 96); | AGTATCTCGA (SEQ ID NO: 97); |
| GTATCTCGAG (SEQ ID NO: 98); | TATCTCGAGA (SEQ ID NO: 99); |
| ATCTCGAGAC (SEQ ID NO: 100); | TCTCGAGACC (SEQ ID NO: 101); |
| CTCGAGACCT (SEQ ID NO: 102); | TCGAGACCTA (SEQ ID NO: 103); |
| CGAGACCTAG (SEQ ID NO: 104); | GAGACCTAGA (SEQ ID NO: 105); |
| AGACCTAGAA (SEQ ID NO: 106); | GACCTAGAAA (SEQ ID NO: 107); |
| ACCTAGAAAA (SEQ ID NO: 108); | CCTAGAAAAA (SEQ ID NO: 109); |
| CTAGAAAAAC (SEQ ID NO: 110); | TAGAAAAACA (SEQ ID NO: 111); |
| AGAAAAACAT (SEQ ID NO: 112); | GAAAAACATG (SEQ ID NO: 113); |
| AAAAACATGG (SEQ ID NO: 114); | AAAACATGGA (SEQ ID NO: 115); |
| AAACATGGAG (SEQ ID NO: 116); | AACATGGAGC (SEQ ID NO: 117); |
| ACATGGAGCA (SEQ ID NO: 118); | CATGGAGCAA (SEQ ID NO: 119); |
| ATGGAGCAAT (SEQ ID NO: 120); | TGGAGCAATC (SEQ ID NO: 121); |
| GGAGCAATCA (SEQ ID NO: 122); | GAGCAATCAC (SEQ ID NO: 123); |
| AGCAATCACA (SEQ ID NO: 124); | GCAATCACAA (SEQ ID NO: 125); |
| CAATCACAAG (SEQ ID NO: 126); | AATCACAAGT (SEQ ID NO: 127); |
| ATCACAAGTA (SEQ ID NO: 128); | TCACAAGTAG (SEQ ID NO: 129); |
| CACAAGTAGC (SEQ ID NO: 130); | ACAAGTAGCA (SEQ ID NO: 131); |
| CAAGTAGCAA (SEQ ID NO: 132); | AAGTAGCAAT (SEQ ID NO: 133); |
| AGTAGCAATA (SEQ ID NO: 134); | GTAGCAATAC (SEQ ID NO: 135); |
| TAGCAATACA (SEQ ID NO: 136); | AGCAATACAG (SEQ ID NO: 137); |
| GCAATACAGC (SEQ ID NO: 138); | CAATACAGCA (SEQ ID NO: 139); |
| AATACAGCAG (SEQ ID NO: 140); | ATACAGCAGC (SEQ ID NO: 141); |
| TACAGCAGCT (SEQ ID NO: 142); | ACAGCAGCTA (SEQ ID NO: 143); |
| CAGCAGCTAA (SEQ ID NO: 144); | AGCAGCTAAC (SEQ ID NO: 145); |
| GCAGCTAACA (SEQ ID NO: 146); | CAGCTAACAA (SEQ ID NO: 147); |
| AGCTAACAAT (SEQ ID NO: 148); | GCTAACAATG (SEQ ID NO: 149); |
| CTAACAATGC (SEQ ID NO: 150); | TAACAATGCT (SEQ ID NO: 151); |
| AACAATGCTG (SEQ ID NO: 152); | ACAATGCTGC (SEQ ID NO: 153); |
| CAATGCTGCT (SEQ ID NO: 154); | AATGCTGCTT (SEQ ID NO: 155); |
| ATGCTGCTTG (SEQ ID NO: 156); | TGCTGCTTGT (SEQ ID NO: 157); |
| GCTGCTTGTG (SEQ ID NO: 158); | CTGCTTGTGC (SEQ ID NO: 159); |
| TGCTTGTGCC (SEQ ID NO: 160); | GCTTGTGCCT (SEQ ID NO: 161); |
| CTTGTGCCTG (SEQ ID NO: 162): | TTGTGCCTGG (SEQ ID NO: 163); |
| TGTGCCTTGC (SEQ ID NO: 164); | GTGCCTGGCT (SEQ ID NO: 165); |
| TGCCTGGCTA (SEQ ID NO: 166); | GCCTGGCTAG (SEQ ID NO: 167); |
| CCTGGCTAGA (SEQ ID NO: 168); | CTGGCTAGAA (SEQ ID NO: 169); |

TGGCTAGAAG (SEQ ID NO: 170); GGCTAGAAGC (SEQ ID NO: 171);
GCTAGAAGCA (SEQ ID NO: 172); CTAGAAGCAC (SEQ ID NO: 173);
TAGAAGCACA (SEQ ID NO: 174); AGAAGCACAA (SEQ ID NO: 175);
GAAGCACAAG (SEQ ID NO: 176); AAGCACAAGA (SEQ ID NO: 177);
AGCACAAGAG (SEQ ID NO: 178); GCACAAGAGG (SEQ ID NO: 179);
CACAAGAGGA (SEQ ID NO: 180); ACAAGAGGAG (SEQ ID NO: 180);
CAAGAGGAGG (SEQ ID NO: 182); AAGAGGAGGA (SEQ ID NO: 183);
AGAGGAGGAA (SEQ ID NO: 184); GAGGAGGAAG (SEQ ID NO: 185);
AGGAGGAAGA (SEQ ID NO: 186); GGAGGAAGAG (SEQ ID NO: 187);
GAGGAAGAGG (SEQ ID NO: 188); AGGAAGAGGT (SEQ ID NO: 189);
GGAAGAGGTG (SEQ ID NO: 190); GAAGAGGTGG (SEQ ID NO: 191);
AAGAGGTGGG (SEQ ID NO: 192); AGAGGTGGGT (SEQ ID NO: 193);
GAGGTGGGTT (SEQ ID NO: 194); AGGTGGGTTT (SEQ ID NO: 195);
GGTGGGTTTT (SEQ ID NO: 196); GTGGGTTTTC (SEQ ID NO: 197);
TGGGTTTTCC (SEQ ID NO: 198); GGGTTTTCCA (SEQ ID NO: 199);
GGTTTTCCAG (SEQ ID NO: 200); GTTTTCCAGT (SEQ ID NO: 201);
TTTTCCAGTC (SEQ ID NO: 202); TTTCCAGTCA (SEQ ID NO: 203);
TTCCAGTCAC (SEQ ID NO: 204); TCCAGTCACA (SEQ ID NO: 205);
CCAGTCACAC (SEQ ID NO: 206); CAGTCACACC (SEQ ID NO: 207);
AGTCACACCT (SEQ ID NO: 208); GTCACACCTC (SEQ ID NO: 209);
TCACACCTCA (SEQ ID NO: 210); CACACCTCAG (SEQ ID NO: 211);
ACACCTCAGG (SEQ ID NO: 212); CACCTCAGGT (SEQ ID NO: 213);
ACCTCAGGTA (SEQ ID NO: 214); CCTCAGGTAC (SEQ ID NO: 215);
CTCAGGTACC (SEQ ID NO: 216); TCAGGTACCT (SEQ ID NO: 217);
CAGGTACCTT (SEQ ID NO: 218); AGGTACCTTT (SEQ ID NO: 219);
GGTACCTTTA (SEQ ID NO: 220); GTACCTTTAA (SEQ ID NO: 220);
TACCTTTAAG (SEQ ID NO: 222); ACCTTTAAGA (SEQ ID NO: 223);
CCTTTAAGAC (SEQ ID NO: 224); CTTTAAGACC (SEQ ID NO: 225);
TTTAAGACCA (SEQ ID NO: 226); TTAAGACCAA (SEQ ID NO: 227);
TAAGACCAAT (SEQ ID NO: 228); AAGACCAATG (SEQ ID NO: 229);
AGACCAATGA (SEQ ID NO: 230); GACCAATGAC (SEQ ID NO; 231);
ACCAATGACT (SEQ ID NO: 232); CCAATGACTT (SEQ ID NO: 233);
CAATGACTTA (SEQ ID NO: 234); AATGACTTAC (SEQ ID NO: 235);
ATGACTTACA (SEQ ID NO: 236); TGACTTACAA (SEQ ID NO: 237);
GACTTACAAG (SEQ ID NO: 238); ACTTACAAGG (SEQ ID NO: 239);
CTTACAAGGC (SEQ ID NO: 240); TTACAAGGCA (SEQ ID NO: 241);
TACAAGGCAG (SEQ ID NO: 242); ACAAGGCAGC (SEQ ID NO: 243);
CAAGGCAGCT (SEQ ID NO: 244); AAGGCAGCTG (SEQ ID NO: 245);
AGGCAGCTGT (SEQ ID NO: 246); GGCAGCTGTA (SEQ ID NO: 247);
GCAGCTGTAG (SEQ ID NO: 248); CAGCTGTAGA (SEQ ID NO: 249);
AGCTGTAGAT (SEQ ID NO: 250); GCTGTAGATC (SEQ ID NO: 251);
CTGTAGATCT (SEQ ID NO: 252); TGTAGATCTT (SEQ ID NO: 253);
GTAGATCTTA (SEQ ID NO: 254); TAGATCTTAG (SEQ ID NO: 255);
AGATCTTAGC (SEQ ID NO: 256); GATCTTAGCC (SEQ ID NO: 257);
ATCTTAGCCA (SEQ ID NO: 258); TCTTAGCCAC (SEQ ID NO: 259);
CTTAGCCACT (SEQ ID NO: 260); TTAGCCACTT (SEQ ID NO: 261);
TAGCCACTTT (SEQ ID NO: 262); AGCCACTTTT (SEQ ID NO: 263);
GCCACTTTTT (SEQ ID NO: 264); CCACTTTTTA (SEQ ID NO: 265);
CACTTTTTAA (SEQ ID NO: 266); ACTTTTTAAA (SEQ ID NO: 267);
CTTTTTAAAA (SEQ ID NO: 268); TTTTTAAAAG (SEQ ID NO: 269);
TTTTAAAAGA (SEQ ID NO: 270); TTTAAAAGAA (SEQ ID NO: 271);
TTAAAAGAAA (SEQ ID NO: 272); TAAAAGAAAA (SEQ ID NO: 273);
AAAAGAAAAG (SEQ ID NO: 274); AAAGAAAAGG (SEQ ID NO: 275);
AAGAAAAGGG (SEQ ID NO: 276); AGAAAAGGGG (SEQ ID NO: 277);
GAAAAGGGGG (SEQ ID NO: 278); AAAAGGGGGG (SEQ ID NO: 279);
AAAGGGGGGA (SEQ ID NO: 280); AAGGGGGGAC (SEQ ID NO: 281);
AGGGGGGACT (SEQ ID NO: 282); GGGGGGACTG (SEQ ID NO: 283);
GGGGGACTGG (SEQ ID NO: 284); GGGGACTGGA (SEQ ID NO: 285);
GGGACTGGAA (SEQ ID NO: 286); GGACTGGAAG (SEQ ID NO: 287);
GACTGGAAGG (SEQ ID NO: 288); ACTGGAAGGG (SEQ ID NO: 289);
CTGGAAGGGC (SEQ ID NO: 290); TGGAAGGGCT (SEQ ID NO: 291);
GGAAGGGCTA (SEQ ID NO: 292); GAAGGGCTAA (SEQ ID NO: 293);
AAGGGCTAAT (SEQ ID NO: 294); AGGGCTAATT (SEQ ID NO: 295);
GGGCTAATTC (SEQ ID NO: 296); GGCTAATTCA (SEQ ID NO: 297);
GCTAATTCAC (SEQ ID NO: 298); CTAATTCACT (SEQ ID NO: 299);
TAATTCACTC (SEQ ID NO: 300); AATTCACTCC (SEQ ID NO: 301);
ATTCACTCCC (SEQ ID NO: 302); TTCACTCCCA (SEQ ID NO: 303);
TCACTCCCAA (SEQ ID NO: 304); CACTCCCAAA (SEQ ID NO: 305);
ACTCCCAAAG (SEQ ID NO: 306); CTCCCAAAGA (SEQ ID NO: 307);
TCCCAAAGAA (SEQ ID NO: 308); CCCAAAGAAG (SEQ ID NO: 309);
CCAAAGAAGA (SEQ ID NO: 310); CAAAGAAGAC (SEQ ID NO: 311);
AAAGAAGACA (SEQ ID NO: 312); AAGAAGACAA (SEQ ID NO: 313);
AGAAGACAAG (SEQ ID NO: 314); GAAGACAAGA (SEQ ID NO: 315);
AGGACAAGAT (SEQ ID NO: 316); AGACAAGATA (SEQ ID NO: 317);
GACAAGATAT (SEQ ID NO: 318); ACAAGATATC (SEQ ID NO: 319);
CAAGATATCC (SEQ ID NO: 320); AAGATATCCT (SEQ ID NO: 321);
AGATATCCTT (SEQ ID NO: 322); GATATCCTTG (SEQ ID NO: 323);
ATATCCTTGA (SEQ ID NO: 324); TATCCTTGAT (SEQ ID NO: 325);
ATCCTTGATC (SEQ ID NO: 326); TCCTTGATCT (SEQ ID NO: 327);
CCTTGATCTG (SEQ ID NO: 328); CTTGATCTGT (SEQ ID NO: 329);

TTGATCTGTG (SEQ ID NO: 330); TGATCTGTGG (SEQ ID NO: 331);
GATCTGTGGA (SEQ ID NO: 332); ATCTGTGGAT (SEQ ID NO: 333);
TCTGTGGATC (SEQ ID NO: 334); CTGTGGATCT (SEQ ID NO: 335);
TGTGGATCTA (SEQ ID NO: 336); GTGGATCTAC (SEQ ID NO: 337);
TGGATCTACC (SEQ ID NO: 338); GGATCTACCA (SEQ ID NO: 339);
GATCTACCAC (SEQ ID NO: 340); ATCTACCACA (SEQ ID NO: 341);
TCTACCACAC (SEQ ID NO: 342); CTACCACACA (SEQ ID NO: 343);
TACCACACAC (SEQ ID NO: 344); ACCACACACA (SEQ ID NO: 345);
CCACACACAA (SEQ ID NO: 346); CACACACAAG (SEQ ID NO: 347);
ACACACAAGG (SEQ ID NO: 348); CACACAAGGC (SEQ ID NO: 349);
ACACAAGGCT (SEQ ID NO: 350); CACAAGGCTA (SEQ ID NO: 351);
ACAAGGCTAC (SEQ ID NO: 352); CAAGGCTACT (SEQ ID NO: 353);
AAGGCTACTT (SEQ ID NO: 354); AGGCTACTTC (SEQ ID NO: 355);
GGCTACTTCC (SEQ ID NO: 356); GCTACTTCCC (SEQ ID NO: 357);
CTACTTCCCT (SEQ ID NO: 358); TACTTCCCTG (SEQ ID NO: 359);
ACTTCCCTGA (SEQ ID NO: 360); CTTCCCTGAT (SEQ ID NO: 361);
TTCCCTGATT (SEQ ID NO: 362); TCCCTGATTG (SEQ ID NO: 363);
CCCTGATTGG (SEQ ID NO; 364); CCTGATTGGC (SEQ ID NO: 365);
CTGATTGGCA (SEQ ID NO: 366); TGATTGGCAG (SEQ ID NO; 367);
GATTGGCAGA (SEQ ID NO: 368); ATTGGCAGAA (SEQ ID NO: 369);
TTGGCAGAAC (SEQ ID NO; 370); TGGCAGAACT (SEQ ID NO: 371);
GGCAGAACTA (SEQ ID NO: 372); GCAGAACTAC (SEQ ID NO: 373),
CAGAACTACA (SEQ ID NO: 374); AGAACTACAC (SEQ ID NO: 375);
GAACTACACA (SEQ ID NO: 376); AACTACACAC (SEQ ID NO: 377);
ACTACACACC (SEQ ID NO: 378); CTACACACCA (SEQ ID NO: 379);
TACACACCAG (SEQ ID NO: 380); ACACACCAGG (SEQ ID NO: 381);
CACACCAGGG (SEQ ID NO: 382); ACACCAGGGC (SEQ ID NO: 383);
CACCAGGGCC (SEQ ID NO: 384); ACCAGGGCCA (SEQ ID NO: 385);
CCAGGGCCAG (SEQ ID NO: 386); CAGGGCCAGG (SEQ ID NO: 387);
AGGGCCAGGG (SEQ ID NO: 388); GGGCCAGGGG (SEQ ID NO; 389);
GGCCAGGGGT (SEQ ID NO: 390); GCCAGGGGTC (SEQ ID NO: 391);
CCAGGGGTCA (SEQ ID NO: 392); CAGGGGTCAG (SEQ ID NO: 393);
AGGGGTCAGA (SEQ ID NO: 394); GGGGTCAGAT (SEQ ID NO: 395);
GGGTCAGATA (SEQ ID NO: 396); GGTCAGATAT (SEQ ID NO: 397);
GTCAGATATC (SEQ ID NO: 398); TCAGATATCC (SEQ ID NO: 399);
CAGATATCCA (SEQ ID NO: 400); AGATATCCAC (SEQ ID NO: 401);
GATATCCACT (SEQ ID NO: 402); ATATCCACTG (SEQ ID NO: 403);
TATCCACTGA (SEQ ID NO: 404); ATCCACTGAC (SEQ ID NO: 405);
TCCACTGACC (SEQ ID NO: 406); CCACTGACCT (SEQ ID NO: 407);
CACTGACCTT (SEQ ID NO: 408); ACTGACCTTT (SEQ ID NO: 409);
CTCACCTTTG (SEQ ID NO: 410); TGACCTTTGG (SEQ ID NO: 411);
GACCTTTGGA (SEQ ID NO: 412); ACCTTTGGAT (SEQ ID NO: 413);
CCTTTGGATG (SEQ ID NO: 414); CTTTGGATGG (SEQ ID NO: 415);
TTTGGATGGT (SEQ ID NO: 416); TTGGATGGTG (SEQ ID NO: 417);
TGGATGGTGC (SEQ ID NO: 418); GGATGGTGCT (SEQ ID NO: 419);
GATGGTGCTA (SEQ ID NO: 420); ATGGTGCTAC (SEQ ID NO: 421);
TGGTGCTACA (SEQ ID NO: 422); GGTGCTACAA (SEQ ID NO: 423);
GTGCTACAAG (SEQ ID NO: 424); TGCTACAAGC (SEQ ID NO: 425);
GCTACAAGCT (SEQ ID NO: 426); CTACAAGCTA (SEQ ID NO: 427);
TACAAGCTAG (SEQ ID NO: 428); ACAAGCTAGT (SEQ ID NO: 429);
CAAGCTAGTA (SEQ ID NO: 430); AAGCTAGTAC (SEQ ID NO; 431);
AGCTAGTACC (SEQ ID NO: 432); GCTAGTACCA (SEQ ID NO: 433);
CTAGTACCAG (SEQ ID NO: 434); TAGTACCAGT (SEQ ID NO: 435);
AGTACCAGTT (SEQ ID NO: 436); GTACCAGTTG (SEQ ID NO: 437);
TACCAGTTGA (SEQ ID N6: 438); ACCAGTTGAG (SEQ ID NO: 439);
CCAGTTGAGC (SEQ ID NO: 440); CAGTTGACCC (SEQ ID NO: 441);
AGTTGAGCCA (SEQ ID NO: 442); GTTGAGCCAG (SEQ ID NO: 443);
TTGAGCCAGA (SEQ ID NO: 444); TGAGCCAGAT (SEQ ID NO: 445);
GAGCCAGATA (SEQ ID NO: 446); AGCCAGATAA (SEQ ID NO: 447);
GCCAGATAAG (SEQ ID NO: 448); CCAGATAAGG (SEQ ID NO: 449);
CAGATAAGGT (SEQ ID NO: 450); AGATAAGGTA (SEQ ID NO: 451);
GATAAGGTAG (SEQ ID NO: 452); ATAAGGTAGA (SEQ ID NO: 453);
TAAGGTAGAA (SEQ ID NO: 454); AAGGTAGAAG (SEQ ID NO: 455);
AGGTAGAAGA (SEQ ID NO: 456); GGTAGAAGAG (SEQ ID NO: 457);
GTAGAAGAGG (SEQ ID NO: 458); TAGAAGAGGC (SEQ ID NO: 459);
AGAAGAGGCC (SEQ ID NO: 460); GAAGAGGCCA (SEQ ID NO: 461);
AAGAGGCCAA (SEQ ID NO: 462); AGAGGCCAAT (SEQ ID NO: 463);
GAGGCCAATA (SEQ ID NO: 464); AGGCCAATAA (SEQ ID NO: 465);
GGCCAATAAA (SEQ ID NO: 466); GCCAATAAAG (SEQ ID NO: 467);
CCAATAAAGG (SEQ ID NO: 468); CAATAAAGGA (SEQ ID NO: 469);
AATAAAGGAG (SEQ ID NO: 470); ATAAAGGAGA (SEQ ID NO: 471);
TAAAGGAGAG (SEQ ID NO: 472); AAAGGAGAGA (SEQ ID NO: 473);
AAGGAGAGAA (SEQ ID NO: 474); AGGAGAGAAC (SEQ ID NO: 475);
GGAGAGAACA (SEQ ID NO: 476); GAGAGAACAC (SEQ ID NO: 477);
AGAGAACACC (SEQ ID NO: 478); GAGAACACCA (SEQ ID NO: 479);
AGAACACCAG (SEQ ID NO: 480); GAACACCAGC (SEQ ID NO: 481);
AACACCAGCT (SEQ ID NO: 482); ACACCAGCTT (SEQ ID NO. 483);
CACCAGCTTG (SEQ ID NO; 484); ACCAGCTTGT (SEQ ID NO: 485);
CCAGCTTGTT (SEQ ID NO: 486); CAGCTTGTTA (SEQ ID NO: 487);
AGCTTGTTAC (SEQ ID NO: 488); GCTTGTTACA (SEQ ID NO: 489);

-continued

| | |
|---|---|
| CTTGTTACAC (SEQ ID NO 490); | TTGTTACACC (SEQ ID NO: 491); |
| TGTTACACCC (SEQ ID NO: 492); | GTTACACCCT (SEQ ID NO: 493); |
| TTACACCCTG (SEQ ID NO: 494); | TACACCCTGT (SEQ ID NO: 495); |
| ACACCCTGTG (SEQ ID NO: 496); | CACCCTGTGA (SEQ ID NO: 497); |
| ACCCTGTGAG (SEQ ID NO: 498); | CCCTGTGAGC (SEQ ID NO: 499); |
| CCTGTGAGCC (SEQ ID NO: 500); | CTGTGAGCCT (SEQ ID NO: 501); |
| TGTGAGCCTG (SEQ ID NO: 502); | GTGAGCCTGC (SEQ ID NO: 503); |
| TGAGCCTGCA (SEQ ID NO: 504); | GAGCCTGCAT (SEQ ID NO: 505); |
| AGCCTGCATG (SEQ ID NO: 506); | GCCTGCATGG (SEQ ID NO: 507); |
| CCTGCATGGA (SEQ ID NO: 508); | CTGCATGGAA (SEQ ID NO: 509); |
| TGCATGGAAT (SEQ ID NO: 510); | GCATGGAATG (SEQ ID NO: 511); |
| CATGGAATGG (SEQ ID NO: 512); | ATGGAATGGA (SEQ ID NO: 513); |
| TGGAATGGAT (SEQ ID NO: 514); | GGAATGGATG (SEQ ID NO: 515); |
| GAATGGATGA (SEQ ID NO: 516); | AATGGATGAC (SEQ ID NO: 517); |
| ATGGATGACC (SEQ ID NO: 518); | TGGATGACCC (SEQ ID NO: 519); |
| GGATGACCCT (SEQ ID NO: 520); | GATGACCCTG (SEQ ID NO: 521); |
| ATGACCCTGA (SEQ ID NO: 522); | TGACCCTGAG (SEQ ID NO: 523); |
| GACCCTGAGA (SEQ ID NO: 524) | ACCCTGAGAG (SEQ ID NO: 525); |
| CCCTGAGAGA (SEQ ID NO: 526); | CCTGAGAGAG (SEQ ID NO: 527); |
| CTGAGAGAGA (SEQ ID NO: 528); | TGAGAGAGAA (SEQ ID NO: 529); |
| GAGAGAGAAG (SEQ ID NO: 530); | AGAGAGAAGT (SEQ ID NO: 531); |
| GAGAGAAGTG (SEQ ID NO. 532); | AGAGAAGTGT (SEQ ID NO: 533); |
| GAGAAGTGTT (SEQ ID NO: 534); | AGAAGTGTTA (SEQ ID NO: 535); |
| GAAGTGTTAG (SEQ ID NO: 536); | AAGTGTTAGA (SEQ ID NO: 537); |
| AGTGTTAGAG (SEQ ID NO: 538); | GTGTTAGAGT (SEQ ID NO: 539); |
| TGTTAGAGTG (SEQ ID NO: 540); | GTTAGAGTGG (SEQ ID NO: 541); |
| TTAGAGTGGA (SEQ ID NO: 542); | TAGAGTGGAG (SEQ ID NO: 543); |
| AGAGTGGAGG (SEQ ID NO: 544); | GAGTGGAGGT (SEQ ID NO: 545); |
| AGTGGAGGTT (SEQ ID NO: 546); | GTGGAGGTTT (SEQ ID NO: 547); |
| TGGAGGTTTG (SEQ ID NO: 548); | GGAGGTTTGA (SEQ ID NO: 549); |
| GAGGTTTGAC (SEQ ID NO: 550); | AGGTTTGACA (SEQ ID NO: 551); |
| GGTTTGACAG (SEQ ID NO: 552); | GTTTGACAGC (SEQ ID NO: 553); |
| TTTGACAGCC (SEQ ID NO: 554); | TTGACAGCCG (SEQ ID NO: 555); |
| TGACAGCCGC (SEQ ID NO: 556); | GACAGCCGCC (SEQ ID NO: 557); |
| ACAGCCGCCT (SEQ ID NO: 558); | CAGCCGCCTA (SEQ ID NO: 559); |
| AGCCGCCTAG (SEQ ID NO: 560); | GCCGCCTAGC (SEQ ID NO: 561); |
| CCGCCTAGCA (SEQ ID NO: 562); | CGCCTAGCAT (SEQ ID NO: 563); |
| GCCTAGCATT (SEQ ID NO: 564); | CCTAGCATTT (SEQ ID NO: 565); |
| CTAGCATTTC (SEQ ID NO: 566); | TAGCATTTCA (SEQ ID NO: 567); |
| AGCATTTCAT (SEQ ID NO: 568); | GCATTTCATC (SEQ ID NO: 569); |
| CATTTCATCA (SEQ ID NO: 570); | ATTTCATCAC (SEQ ID NO: 571); |
| TTTCATCACG (SEQ ID NO: 572); | TTCATCACGT (SEQ ID NO: 573); |
| TCATCACGTG (SEQ ID NO: 574); | CATCACGTGG (SEQ ID NO: 575); |
| ATCACGTGGC (SEQ ID NO: 576); | TCACGTGGCC (SEQ ID NO: 577); |
| CACGTGGCCC (SEQ ID NO: 578); | ACGTGGCCCG (SEQ ID NO: 579); |
| CGTGGCCCGA (SEQ ID NO: 580); | GTGGCCCGAG (SEQ ID NO: 581); |
| TGGCCCGAGA (SEQ ID NO: 582); | GGCCCGAGAG (SEQ ID NO: 583); |
| GCCCGAGAGC (SEQ ID NO: 584); | CCCGAGAGCT (SEQ ID NO: 585); |
| CCGAGAGCTG (SEQ ID NO: 586); | CGAGAGCTGC (SEQ ID NO: 587); |
| GAGAGCTGCA (SEQ ID NO: 588); | AGAGCTGCAT (SEQ ID NO: 589); |
| GAGCTGCATC (SEQ ID NO: 590); | AGCTGCATCC (SEQ ID NO: 591); |
| GCTGCATCCG (SEQ ID NO: 592); | CTGCATCCGG (SEQ ID NO; 593); |
| TGCATCCGGA (SEQ ID NO: 594); | GCATCCGGAG (SEQ ID NO: 595); |
| CATCCGGAGT (SEQ ID NO: 596); | ATCCGGAGTA (SEQ ID NO: 597); |
| TCCGGAGTAC (SEQ ID NO: 598); | CCGGAGTACT (SEQ ID NO: 599); |
| CGGAGTACTT (SEQ ID NO: 600); | GGAGTACTTC (SEQ ID NO: 601); |
| GAGTACTTCA (SEQ ID NO: 602); | AGTACTTCAA (SEQ ID NO: 603); |
| GTACTTCAAG (SEQ ID NO: 604); | TACTTCAAGA (SEQ ID NO: 605); |
| ACTTCAAGAA (SEQ ID NO: 606); | CTTCAAGAAC (SEQ ID NO: 607); |
| TTCAAGAACT (SEQ ID NO: 608); | TCAAGAACTG (SEQ ID NO: 609); |
| CAAGAACTGC (SEQ ID NO: 610); | AAGAACTGCT (SEQ ID NO: 611); |
| AGAACTGCTG (SEQ ID NO: 612); | GAACTGCTGA (SEQ ID NO: 613). |

In a preferred embodiment the present invention contemplates a viral isolate which:

(i) is reactive to antibodies to a glycoprotein from HIV-1 such as at least one of gp41–45, gp120 and/or gp160;

(ii) carries a deletion of at least ten nucleotides in a region corresponding to the nef gene in HIV-1$_{NL43}$; and wherein said deletion encompasses one or more decanucleotides from the nef gene of HIV-1$_{NL43}$ or corresponding sequences from another pathogenic strain of HIV-1 defined in (or substantially analogous to) SEQ ID NOs:803 to 841:

| | |
|---|---|
| ACCAGCTTGT [SEQ ID NO: 803] | CCAGCTTGTT [SEQ ID NO: 804] |
| CAGCTTGTTA [SEQ ID NO: 805] | AGCTTGTTAC [SEQ ID NO: 806] |
| GCTTGTTACA [SEQ ID NO :807] | CTTGTTACAC [SEQ ID NO: 808] |
| TTGTTACACC [SEQ ID NO: 809] | TGTTACACCC [SEQ ID NO: 810] |

-continued

| | |
|---|---|
| GTTACACCCT [SEQ ID NO: 811] | TTACACCCTG [SEQ ID NO: 812] |
| TACACCCTGT [SEQ ID NO: 813] | ACACCCTGTG [SEQ ID NO: 814] |
| CACCCTGTGA [SEQ ID NO: 815] | ACCCTGTGAG [SEQ ID NO: 816] |
| CCCTGTGAGC [SEQ ID NO: 817] | CCTGTGAGCC [SEQ ID NO: 818] |
| CTGTGAGCCT [SEQ ID NO: 819] | TGTGAGCCTG [SEQ ID NO: 820] |
| GTGAGCCTGC [SEQ ID NO: 821] | TGACCCTGCA [SEQ ID NO: 822] |
| GAGCCTGCAT [SEQ ID NO: 823] | AGCCTGCATG [SEQ ID NO: 824] |
| GCCTGCATGG [SEQ ID NO: 825] | CCTGCATGGA [SEQ ID NO: 826] |
| CTGCATGGAA [SEQ ID NO: 827] | TGCATGGAAT [SEQ ID NO: 828] |
| GCATGGAATG [SEQ ID NO: 829] | CATGGAATGG [SEQ ID NO: 830] |
| ATGGAATGGA [SEQ ID NO: 831] | TGGAATGGAT [SEQ ID NO: 832] |
| CGAATGGATG [SEQ ID NO: 833] | GAATGGATGA [SEQ ID NO: 834] |
| AATGGATGAC [SEQ ID NO: 835] | ATGGATGACC [SEQ ID NO: 836] |
| TGGATGACCC [SEQ ID NO: 837] | GGATGACCCT [SEQ ID NO: 838] |
| GATGACCCTG [SEQ ID NO: 839] | ATGACCCTGA [SRG ID NO: 840] |
| TGACCCTGAG [SEQ ID NO: 841] | |

Generally, the subject HIV-1 isolate is non-pathogenic as hereinbefore defined. Additionally, reference herein to "a deletion" includes reference to a contiguous or non-contiguous series of two or more deletions.

The non-pathogenic isolate may carry a single decanucleotide deletion or may carry more than one decanucleotide deletion. Where it carries multiple deletions these may all correspond to a contiguous sequence or be from different part of the nef gene. Furthermore, the terminal end portions of a deletion may lie within a decanucleotide as defined above. It is emphasised at the present invention extends to analogous sequences from other pathogenic strains of HIV-1 which might carry nef genes with a slightly altered sequence relative to HIV-$1_{NL43}$.

In a most preferred embodiment of the present invention, there is provided a non-pathogenic strain of HIV-1 carrying a nucleotide sequence in its genome as set forth in SEQ ID No. 614:

GAAGAGATTTGGGAGAACATGACCTG-
GATGCAGTGGGAAAAAGAAATTCACAATCACAC
AAAATACATATACTCCTTACT-
TGAAAAATCGCAGAACCAACAAGAAAA-
GAATGAACAAG AACTATTGGAATTGGATCAA-
TGGG CAAGTTTGTGGAATTGGTTTGACATAAC-
AAAATGG CTGTGGTATATAAAAATATTCATAATGG-
TAGTAGGAGGCTTGATAGGTTTAAGAATAGT
TTTTGCTGTACTTTCTATAGTGAATA-
GAGTTAGGCAGGGATACTCACCATTGTCGTTTC
AGACCCTCCTCCCAACCCCGAGGGGAC-
CCGACAGGCCCGAAGGAATCGAAGAAGAAGGT
GGAGAGAGAGGACAGAGCAGATCCACTC-
GATTAGTACACGGATTCTTAGCACTTTTCTG GGAC-
GACCTGAGGAGCCTGTGCCTCTTCCTC-
TACCACCACTTGAGAGACTTACTCTTGA
TTGTAACAAGGATTGTGGAACTTCTGG-
GACGCAGGGGATGGGAAGCCCTCAAATATTGG
TGGAACCTCCTAAAGTATTGGAGCCAG-
GAACTGCAGAAGAGTGCTGTTATCTTGCTCAA
TGCCACCGCCATAGCAGTAGCTGAGGG-
GACAGATAGAGTTTTAGAAGTATTACAAAGAG
CTTATAGAGCTATCCTCCACATACCTA-
GAAGAATAAGACAGGGCCTCGAAATGGCTTTG
CTATAAAATGGGTGGCAAGTGAG-
CAAAAAGTAGTGTAGTCAGATAGCATG-
CATCATAAG GGGTGGGGGCCAACAACTAACAAT-
GCTGATCGTGCCTGGCTAGAAGCACAAGAGAAGGA
AGAATCGGGTTTTCCAGTCAAACCTCAG-
GTAGCTGTAGATCTTAGCCACTTTTTAAAAG
AAAAGGGGGGACTGGAAGGGCTAAT-
TCACTCCCAAAGAAGACAAGATACACAGTGCTGC
AAACTATTACCAGTGGAGTCAGCGAA-
GATAGAAGAGGCCAATGGAGGAGAAAACCACAG
ATTGTTCTGTTGGGGACTTTCCATCCGT-
TGGGGACTTTCCAAGGCGGCGTGGCCTGGGT GAC-
TAGTTCCGGTGGGGACTTTCCAAGAAG-
GCGCGGCCTGGGCGGGACTGGGGAGTGGC
GAGCCCTCAGATGCTGCATATAAG-
CAGCTGCTTTCTGCTGTTACTGGGTCTCTCGGGTT
AGACCAGATCTGAGCCTGG-
GAGCTCTCTGGCTAACTAGGGAAC-
CCACTGCTTAAGCCTC AATAAAGCTTGCCTT-
GAGTGCTTCAAGTAGTGTGTGCCCGTCTGTTGTGT-
GACT- CTGGT ATCTAGA;

and/or SEQ ID NO: 615:

GAAACAATTTGGGATAACATGACCTG-
GATGCAGTGGGAAAGAGAAATTGACAATTACAC
AAACATAATATACACCTTAATTGAA-
GAATCGCAGAACCAACAAGAAAAAAATGAACTAG
AATTATTGGAATTG-
GATAAATGGGCAAATTTGTGGAATTG-
GTTTAGTATATCAAACTGG CTATGGTATATAAAA-
TTATTCATAATGGTAGTAGGAGGCTTGGTAGGTTTA-
AGAATAGT TTTTACTGTACTTTCTATAGTGAATA-
GAGTTAGGCAGGGATACTCACCATTGTCGTTTC
AGACCCACCTCCCAACCCCGAAGGGAC-
CCAGCAGGCCAGAAGGAATCGAAGAAGAAGGT
GGAGAGAGAGACAGAGGCAGCTCCACTC-
GATTAGTGCACGGATTCTTAGCACTTTTCTG GGAC-
GACCTGAGGAGTCTGTGCCTCTTCAGC-
TACCACCACTTGAGAGACTTACTCTTGA
TTGTAACGAGGATTGTGGAACTTCTGG-
GACGCAGGGGATGGGAAGCCCTCAAATACTGG
TGGAATCTCCTGCAGTATTGGAGGCAG-
GAACTACAGAAGAGTGCTGTTAGCTTGTTCAA
TGGCACGGCCATAGCAGTAGCTGAGGG-
GACAGATAGAGTTATAGAAGCTTTACGAAGGG
CTTATAGAGCTATTCTCCACATACCTA-
GAAGAATAAGACAGGGCTTAGAAAGGGCTTTG
CTATAAAATGGGTGGCAAGTGGTCA-
GAAAGTAGTGTGGTTAGAAGGCATGTACCTTTAA
GACAAGGCAGCTATAGATCTTAGC-
CGCTTTTTAAAAGAAAAGGGGGGACTG-
GAAGGGCT AATTCACTCACAGAG-
AAGATCAGTTGAACCAGAAGAAGATAGAAGAGG-
CCATGAAGA- AG AAAACAACAGATTGTTC-
CGTTTGTTCCGTTGGGGACTTTCCAG-
GAGACGTGGCCTGAGT GATAAGCCGCT-
GGGGACTTTCCGAAGAGGCGTGACGGGACTTTCC-
AAG- GCGACGTGGCC TGGGCGGGACTGGG-
GAGTGGCGAGCCCTCAGATGCTG-

CATATAAGCAGCTGCTTTCTGC TGGGC-
GGGACTGGGGAGTGGCGAGCCCTCAGATGCTGCA-
TATAAGCAGCTGCTTTCTGCCTG-
TACTGGGTCTCTCTGGTTAGACCA-
GATCTGAGCCTGGGAGCTCTCTGGCTAACTAG
GGAACCCACTGCTTAAGCCT-
CAATAAAGCTTGCCTTGAGTGCTTCAAG-
TAGTGTGTGCC CGTCTGTTGTGTGACTCTGG-
TATCTAGA.

The present invention, however, extends to HIV-1 isolates which are non-pathogenic; carry genomes capable of hybridising under low stringency conditions to SEQ ID NO: 614 or SEQ ID NO: 615; and which do not direct the synthesis of a full length nef gene product.

In a further embodiment the present invention contemplates a viral isolate which:

(i) is reactive to antibodies to a glycoprotein from HIV-1 such as at least one of gp41–45, gp120 and/or gp160;

(ii) carries a genome or a part or fragment thereof capable of hybridising under medium stringency conditions to a nucleotide sequence as set forth in SEQ ID NO: 1 or a complementary form thereof or an analogous sequence from another pathogenic strain of HIV-1;

(iii) carries a deletion of at least ten nucleotides in a region corresponding to the LTR region in HIV-$1_{NL43}$; and wherein said deletion encompasses one or more of the following decanucleotides from the LTR region of HIV-$1_{NL43}$ or corresponding sequences from another pathogenic strain of HIV-1:

| | |
|---|---|
| GCTTTTTGCC (SEQ ID NO: 652); | CTTTTTGCCT (SEQ ID NO: 653); |
| TTTTTGCCTG (SEQ ID NO: 654); | TTTTGCCTGT (SEQ ID NO: 655); |
| TTTGCCTGTA (SEQ ID NO: 656); | TTGCCTGTAC (SEQ ID NO: 657); |
| TGCCTGTACT (SEQ ID NO: 658); | GCCTGTACTG (SEQ ID NO: 659); |
| CCTGTACTGG (SEQ ID NO: 660); | CTGTACTGGG (SEQ ID NO: 661); |
| TGTACTGGGT (SEQ ID NO: 662); | GTACTGGGTC (SEQ ID NO: 663); |
| TACTGGGTCT (SEQ ID NO: 664); | ACTGGGTCTC (SEQ ID NO: 665); |
| CTGGGTCTCT (SEQ ID NO: 666); | TGGGTCTCTC (SEQ ID NO: 667); |
| GGGTCTCTCT (SEQ ID NO: 668); | GGTCTCTCTG (SEQ ID NO: 669); |
| GTCTCTCTGG (SEQ ID NO: 670); | TCTCTCTGGT (SEQ ID NO: 671); |
| CTCTCTGGTT (SEQ ID NO: 672); | TCTCTGGTTA (SEQ ID NO: 673); |
| CTCTGGTTAG (SEQ ID NO: 674); | TCTCTGOTTA (SEQ ID NO: 675); |
| CTGGTTAGAC (SEQ ID NO: 676); | TGGTTAGACC (SEQ ID NO: 677); |
| GGTTAGACCA (SEQ ID NO: 678); | GTTAGACCAG (SEQ ID NO: 679); |
| TTAGACCAGA (SEQ ID NO: 680); | TAGACCAGAT (SEQ ID NO: 681); |
| AGACCAGATC (SEQ ID NO: 682); | GACCAGATCT (SEQ ID NO: 683); |
| ACCAGATCTG (SEQ ID NO: 684); | CCAGATCTGA (SEQ ID NO: 685); |
| CAGATCTGAG (SEQ ID NO; 686); | AGATCTGAGC (SEQ ID NO: 687); |
| GATCTGAGCC (SEQ ID NO; 688); | ATCTGAGCCT (SEQ ID NO: 689); |
| TCTGAGCCTG (SEQ ID NO: 690); | CTGAGCCTGG (SEQ ID NO: 691); |
| TGAGCCTGGG (SEQ ID NO: 692), | GAGCCTGGGA (SEQ ID NO: 693); |
| AGCCTGGGAG (SEQ ID NO: 694); | GCCTGGGAGC (SEQ ID NO: 695); |
| CCTGGGAGCT (SEQ ID NO: 696); | CTGGGAGCTC (SEQ ID NO: 697); |
| TGGGAGCTCT (SEQ ID NO: 698); | GGGAGCTCTC (SEQ ID NO: 699); |
| GGAGCTCTCT (SEQ ID NO: 700); | GAGCTCTCTG (SEQ ID NO: 701); |
| AGCTCTCTGG (SEQ ID NO: 702); | GCTCTCTGGC (SEQ ID NO: 703); |
| CTCTCTGGCT (SEQ ID NO: 704); | TCTCTGGCTA (SEQ ID NO: 705); |
| CTCTGGCTAA (SEQ ID NO: 706); | TCTGGCTAAC (SEQ ID NO: 707); |
| CTGGCTAACT (SEQ ID NO: 708); | TGGCTAACTA (SEQ ID NO: 709); |
| GGCTAACTAG (SEQ ID NO: 710); | GCTAACTAGG (SEQ ID NO: 711); |
| CTAACTAGGG (SEQ ID NO: 712); | TAACTAGGGA (SEQ ID NO: 713); |
| AACTAGGGAA (SEQ ID NO: 714); | ACTAGGGAAC (SEQ ID NO: 715); |
| CTAGGGAACC (SEQ ID NO: 716); | TAGGGAACCC (SEQ ID NO: 717); |
| AGGGAACCCA (SEQ ID NO: 718); | GGGAACCCAC (SEQ ID NO: 719); |
| GGAACCCACT (SEQ ID NO: 720); | GAACCCACTG (SEQ ID NO: 721); |
| AACCCACTGC (SEQ ID NO: 722); | ACCCACTGCT (SEQ ID NO: 723); |
| CCCACTGCTT (SEQ ID NO: 724); | CCACTGCTTA (SEQ ID NO: 725); |
| CACTGCTTAA (SEQ ID NO: 726); | ACTGCTTAAG (SEQ ID NO: 727); |
| CTGCTTAAGC (SEQ ID NO; 728); | TGCTTAAGCC (SEQ ID NO: 729); |
| GCTTAAGCCT (SEQ ID NO: 730); | CTTAAGCCTC (SEQ ID NO: 731); |
| TTAAGCCTCA (SEQ ID NO; 732); | TAAGCCTCAA (SEQ ID NO: 733); |
| AAGCCTCAAT (SEQ ID NO: 734); | AGCCTCAATA (SEQ ID NO: 735); |
| GCCTCAATAA (SEQ ID NO: 736); | CCTCAATAAA (SEQ ID NO: 737); |
| CTCAATAAAG (SEQ ID NO: 738); | TCAATAAAGC (SEQ ID NO: 739); |
| CAATAAAGCT (SEQ ID NO: 740); | AATAAAGCTT (SEQ ID NO: 741); |
| ATAAAGCTTG (SEQ ID NO: 742); | TAAAGCTTGC (SEQ ID NO: 743); |
| AAAGCTTGCC (SEQ ID NO; 744); | AAGCTTGCCT (SEQ ID NO: 745); |
| AGCTTGCCTT (SEQ ID NO; 746); | GCTTGCCTTG (SEQ ID NO: 747); |
| CTTGCCTTGA (SEQ ID NO: 748); | TTGCCTTGAG (SEQ ID NO: 749); |
| TGCCTTGAGT (SEQ ID NO: 750); | GCCTTGAGTG (SEQ ID NO: 751); |
| CCTTGAGTGC (SEQ ID NO: 752); | CTTGAGTGCT (SEQ ID NO: 753); |
| TTGAGTGCTT (SEQ ID NO: 754); | TGAGTGCTTC (SEQ ID NO: 755); |
| GAGTGCTTCA (SEQ ID NO: 756); | AGTGCTTCAA (SEQ ID NO: 757); |
| GTGCTTCAAG (SEQ ID NO: 758); | TGCTTCAAGT (SEQ ID NO: 759); |
| GCTTCAAGTA (SEQ ID NO: 760); | CTTCAAGTAG (SEQ ID NO: 761); |
| TTCAAGTAGT (SEQ ID NO: 762); | TCAAGTAGTG (SEQ ID NO: 763); |
| CAAGTAGTGT (SEQ ID NO: 764); | AAGTAGTGTG (SEQ ID NO: 765); |
| AGTAGTGTGT (SEQ ID NO: 766); | GTAGTGTGTG (SEQ ID NO: 767); |
| TAGTGTGTGC (SEQ ID NO: 768); | AGTGTGTGCC (SEQ ID NO: 769); |
| GTGTGTGCCC (SEQ ID NO. 770); | TGTGTGCCCG (SEQ ID NO: 771); |

-continued

| | |
|---|---|
| GTGTGCCCGT (SEQ ID NO: 772); | TGTGCCCGTC (SEQ ID NO: 773); |
| GTGCCCGTCT (SEQ ID NO: 774); | TGCCCGTCTG (SEQ ID NO: 775); |
| GCCCGTCTGT (SEQ ID NO: 776); | CCCGTCTGTT (SEQ ID NO: 777); |
| CCGTCTGTTG (SEQ ID NO: 778); | CGTCTGTTGT (SEQ ID NO: 779); |
| GTCTGTTGTG (SEQ ID NO: 780); | TCTGTTGTGT (SEQ ID NO: 781); |
| CTGTTGTGTG (SEQ ID NO: 782); | TGTTGTGTGA (SEQ ID NO: 783); |
| GTTGTGTGAC (SEQ ID NO: 784); | TTGTGTGACT (SEQ ID NO: 785); |
| TGTGTGACTC (SEQ ID NO: 786); | GTGTGACTCT (SEQ ID NO: 787); |
| TGTGTGACTC (SEQ ID NO: 768); | GTGTGACTCT (SEQ ID NO: 789); |
| TGTGACTCTG (SEQ ID NO: 790); | GTGACTCTGG (SEQ ID NO: 791); |
| TGACTCTGGT (SEQ ID NO: 792); | GACTCTGGTA (SEQ ID NO: 793); |
| ACTCTGGTAA (SEQ ID NO: 794); | CTCTGGTAAC (SEQ ID NO: 795); |
| TCTGGTAACT (SEQ ID NO: 796); | CTGGTAACTA (SEQ ID NO: 797); |
| TGGTAACTAG (SEQ ID NO: 798); | GGTAACTAGA (SEQ ID NO: 799). |

The non-pathogenic isolate may carry a single decanucleotide deletion in the LTR region or may carry multiple deletions in the same region or in the LTR region and another region such as the nef gene. In particular, the mutation may be in the LTR/nef overlap region. Where it carries multiple deletions, these may correspond to a contiguous sequence or be from different parts of the LTR region and/or nef gene. Furthermore, the terminal end portions of a deletion may lie within a decanucleotide as defined above.

Yet another aspect of the present invention provides an infectious molecular clone comprising genetic sequences derived from the non-pathogenic HIV-1 isolates as hereinbefore described and includes genetic sequences encoding major structural proteins such as gag, env and pol. Infectious molecular clones are particularly useful as genetic compositions capable of "infecting" host cells without need of viral coat. The infectious molecular clones of the present invention may also be derived from pathogenic HIV-1 strains rendered non-pathogenic as herein described.

According to this latter embodiment, there is contemplated a method of attenuating a pathogenic strain of HIV-1, said method comprising inducing a mutation in the nef gene and/or an LTR region to generate a non-pathogenic HIV-1 strain as hereinbefore described. Preferred mutations are deletions of at least ten nucleotides such as one or more of the decanucleotides as hereinbefore described. Particularly preferred mutations result in modified Nef protein carrying a deletion substantially corresponding to amino acids 162 to 177 of Nef from wild-type HIV-1. The mutation may also constitute substitutions and/or insertions of heterologous nucleic acid molecules in the nef and/or LTR regions such as the incorporation of a sense (i.e. co-suppression) or antisense molecule.

In still yet another embodiment of the present invention, there is provided an isolated, non-pathogenic strain of HIV-1 comprising a deletion in its genome of at least 10 nucleotide within the region of nucleotide 8787 and 9709 and more particularly within the region 8800 and 9700 and even more preferably within the region 8800 and 9410, using the nucleotide numbering of HIV-$1_{NL43}$.

In one embodiment, the deletion of at least 10 nucleotides is from within a region selected from the list consisting of (using the nucleotide numbers of HIV-$1_{NL43}$):

nucleotide (i) 8830–8862;
(ii) 9009–9035;
(iii) 9019–9029; and
(iv) 9033–9049.

In another embodiment, the deletion of at least 10 nucleotides is from within a region selected from the list consisting of (using the nucleotide numbers of HIV-$1_{NL43}$):

nucleotide (v) 9281–9371;
(vi) 9281–9362;
(vii) 9105–9224; and
(viii) 9271–9370.

In yet another embodiment, the deletion of at least 10 nucleotides is from within a region selected from the list consisting of (using the nucleotide numbers of HIV-$1_{NL43}$):

nucleotide (ix) 8882–8928;
(x) 8850–9006;
(xi) 8792–9041; and
(xii) 9112–9204.

In still yet another embodiment, the deletion of at least 10 nucleotides is from within a region selected from the list consisting of (using the nucleotide numbers of HIV-$1_{NL43}$):

nucleotide (xiii) 9105–9224;
(xiv) 9389–9395; and
(xv) 9281–9366.

The above embodiments including any combinations thereof or functional equivalents thereof. Most preferred variants of HIV-1 are defined in Table 3.

Reference herein to the non-pathogenic HIV-1 strains of the present invention includes reference to components, parts, fragments and derivatives thereof including both genetic and non-genetic material. Furthermore, the non-pathogenic HIV-1 strains may be in isolated form or resident in peripheral blood mononuclear cells (PBMCs) or other like cells where the genome of the HIV-1 strains is integrated as DNA from said HIV-1 strains such as proviral DNA. In addition, the present invention extends to recombinant virus such as from (or resident in) prokaryotes or eukaryotes as well as in the form of infectious molecular clones.

Accordingly, the present invention provides for the non-pathogenic HIV-1 isolate, genomic material therefrom, complementary proviral DNA, molecular infectious clones recombinant viral particles or genetic sequences therefrom or cells expressing same or blood cells carrying proviral DNA or to any mutants, derivatives, components, fragments, part, homologues or analogues of the foregoing.

Another aspect of the present invention contemplates a synthetic peptide comprising a sequence of amino acids as defined in SEQ ID NO:699 or a part or a fragment thereof. The synthetic peptide generally comprises at least four, preferably at least five, more preferably at least six and even more preferably at least seven or more of the amino acids as defined in SEQ ID NO:699. Furthermore, the synthetic peptides may comprise chemically modified amino acids or structurally, functionally and/or stereochemically equivalent substitute amino acids. Such synthetic peptides are useful in diagnostic protocols or in therapeutic regimums, such as in generating antibodies to that particular region of the Nef protein. By administering the synthetic peptides of this aspect of the present invention, higher titres of antibodies to a particular region of Nef may be obtained compared to what would be stimulated if a larger portion of Nef is used.

The non-pathogenic HIV-1 strains of the present invention are particularly useful in the development of therapeutic compositions, therapeutic molecules and/or diagnostic reagents. With regards to the former, the non-pathogenic HIV-1 strain may be considered as a live attenuated vaccine where individuals carrying DNA derived from said non-pathogenic HIV-1 strain such as proviral DNA in target cells are protected from infection by a corresponding pathogenic strain. The term "vaccine" is used in its broadest sense as a therapeutic composition or molecule which prevents or reduces HIV-1 infection or risk of infection or which ameliorates the symptoms of infection. It may involve the stimulation of an immune response or may involve blocking HIV-1 cells receptors and/or the use of genetic compositions, for example, to introduce ribozymes or anti-sense molecules to HIV-1 directed genetic sequences or to prepare infectious molecular clones. For convenience, all such compositions a referred hereinafter to "therapeutic compositions".

Accordingly, the present invention contemplates a method for inhibiting or reducing the risk of infection by a pathogenic strain of HIV-1, said method comprising administering to a subject a non-pathogenic HIV-1 as hereinbefore defined in an amount effective to infect target cells and to generate target cells carrying proviral DNA from said non-pathogenic HIV-1. More particularly, the present invention contemplates a method for inhibiting or reducing productive infection of an individual by a pathogenic strain of HIV-1, said method comprising administering to a subject a non-pathogenic isolate of HIV-1 in an amount effective to infect target cells and to generate target cells proviral DNA from said non-pathogenic HIV-1. By "productive infection" as used in the specification and claims herein is meant the infection of a cell or cells by a pathogenic strain of HIV-1 which leads ultimately to the symptomology of AIDS or AIDS related diseases. A cell infected productively produces pathogenic virions. By definition, infection of an individual by a non-pathogenic strain of HIV-1 would not lead to productive infection. Non-pathogenic HIV-1 strains generally replicate to a sufficient extent to protect cells against challenge by virulent or pathogenic strain. The methods of the present invention are applicable prophylactically (i.e. to prevent de novo infection) or therapeutically (i.e. to reduce or slow disease progression).

The present invention further provides a method for vaccinating an individual against the development of AIDS or AIDS-related diseases, said method comprising administering to said individual a non-pathogenic isolate of HIV-1 in an amount effective to infect target cells and to generate target cells carrying proviral DNA from said non-pathogenic HIV-1. The term "vaccinating" should not be taken as limiting the invention to the prevention of HIV-1 infection by solely immunological means. The term "vaccinating" includes any means of preventing productive infection of an individual by pathogenic HIV-1. Particularly, preferred non-pathogenic strains of HIV-1 according to these aspects of the present invention are generally defined as encoding a modified protein such as a modified Nef protein and in particular a modified Nef protein which is substantially non-interactive to antibodies to amino acids 162 to 177 of wild-type HIV-1 Nef.

As an alternative to the above methods, a therapeutic composition as hereinbefore defined is administered. The non-pathogenic isolate may be administered inter alia as an isolated viral preparation or via infected blood cells. Another aspect of the invention provides a therapeutic composition for inhibiting or reducing the risk of infection by a pathogenic strain of HIV-1 said therapeutic composition comprising a non-pathogenic strain of HIV-1 or genetic sequences derived therefrom as hereinbefore described and optionally one or more pharmaceutically acceptable carriers and/or diluents. In a further embodiment, the therapeutic compositions comprise the synthetic peptides comprising an amino acid sequence as set forth in SEQ ID NO:699 or a part, fragment or homologue thereof. Such a vaccine would generate high titre antibodies to a specific region of Nef protein.

The therapeutic composition of the present invention is generally suitable for intravenous, intraperitoneal, intramuscular, intramucosal (e.g. nasal spray, respiratory spray) or other forms of parenteral administration. The therapeutic composition might also be administered via an implant or rectally or orally. In addition to the mutations contemplated above, the non-pathogenic HIV-1 strain may also contain one or more other mutations to further reduce the risk of reversion to virulence and/or to insert a genetic sequence capable of providing directly or indirectly an identifiable signal, having further anti-HIV-1 properties and/or immunostimulatory or cell regulatory properties.

For example, the non-pathogenic HIV-1 isolate in the therapeutic composition may comprise additional genetic material capable of directing expression of antisense nucleotide sequences to inhibit expression of one or more proteins encoded by a pathogenic strain of HIV-1. Alternatively, sense co-suppression may be employed. Preferred sense or antisense molecules would reduce expression of the nef gene or affect normal functioning of the LTR region. In a particularly preferred embodiment, the nucleotide sequence encoding amino acids 162 to 177 is targetted by sense or antisense molecules.

According to this embodiment, the non-pathogenic HIV-1 strain may be considered as a targeting agent to introduce genetic constructs capable of reducing expression of one or more HIV-1 proteins or polypeptides. In this embodiment there is provided a viral isolate which:

(i) is genetically or immunologically related to a pathogenic strain of HIV-1;

(ii) is substantially non-pathogenic in human subjects;

(iii) comprises a first nucleotide sequence constituting its genome which is capable of hybridising under medium stringency conditions to SEQ ID NO: 1 or a complementary form thereof; and (iv) comprises a second nucleotide sequence within said first nucleotide sequence and which second nucleotide sequence directs expression of a mRNA molecule capable of inhibiting, reducing or otherwise down-regulating translation of a protein or polypeptide encoded by a pathogenic strain of HIV-1 or inhibit, reduce or otherwise down regulate operation of a non-protein encoding a region of a pathogenic strain of HIV-1.

Preferred proteins or polypeptides targeted for reduced expression are those encoded by one or more of the following: gag; pol, env, tat, rev, vpu, vpr, vif and/or nef genes. The most preferred protein or polypeptide targeted for reduced expression is the product of the nef gene. Alternatively, the target nucleotide sequence does not encode a polypeptide or protein but is required for other functions such a integration or excision from the human genome or expression of genes on the viral genome. An example of such a nucleotide sequence is the LTR region. Accordingly, the present invention extends to disruption to the function of such regions.

In a particularly preferred embodiment there is provided a viral isolate which:

(i) is genetically or immunologically related to a pathogenic strain of HIV-1;

(ii) is substantially non-pathogenic in human subjects; and (iii) comprises a nucleotide sequence which directs expression of a mRNA molecule capable of inhibiting, reducing or otherwise down-regulating translation of Nef.

Preferably, the nucleotide sequence reduces levels of amino acids 162 to 177 in Nef. The above aspect relates to use of antisense technology. The present invention extends, however, to use of ribozymes and/or co-suppression to achieve the same results. In an alternative embodiment, or in addition to, the second (or optionally a third) nucleotide sequence encodes an antiviral agent (e.g. interferon) and/or an immune enhancing agents The identification of deletions inter alia in the nef gene and/or LTR region in asymptomatic subjects provides a unique opportunity to study the in vivo effects of attenuated HIV-1 strains carrying one or more mutations in selected genetic regions. In particular, the present invention provides a means for designing therapeutic compositions directed to inhibiting expression of a nef gene and/or LTR region in a pathogenic HIV-1 strain (such as contemplated above) as well as developing a therapeutic regimem aimed at inhibiting the activity of the nef gene product for the function of the LTR region. According to this latter embodiment, the present invention provides a therapeutic composition comprising a molecule capable of inhibiting the intracellular activity of the nef gene product and/or LTR region, said composition further comprising one or more pharmaceutically acceptable carriers and/or diluents. In one preferred embodiment, the inhibition effects amino acids 162 to 177 of Nef.

The molecule contemplated by the above aspect of the subject invention may be a protein, polypeptide, peptide, chemical compound, sugar moiety or derivative of the nef gene product. The molecule will need to be capable of entering an infected cell. Where the molecule is a protein, polypeptide or peptide, it may be encoded by the second nucleotide sequence on the targeting vector as contemplated above. Alternatively, the molecule may be a nucleic acid molecule capable of targeting the nef gene or LTR region. Where the nef gene is targetted, the preferred region is the nucleotide sequence which encodes amino acids 162 to 177 of Nef.

The deletion mutants of the present invention may result in a modified nef gene product either having no readily discernable activity or having activity different to the naturally occurring nef protein. In any event if a mutant nef gene product is produced, it will generally have a lower molecular weight than the naturally occurring nef protein and will have a different overall amino acid sequence. Importantly, it will be immunologically distinguishable from wild-type Nef in that it will be substantially non-interactive with antibodies to a particular region of Nef, such as amino acids 162 to 177 of wild-type Nef. This provides, therefore, for a means for diagnosing individuals with ben HIV-1 infection by, for example, assaying for a modified nef protein or screening for a modified nef gene sequence. Alternatively, benign HIV-1 infection may be detected by assaying for a modified LTR region such as an altered nucleotide sequence.

These aforementioned aspects of the present invention apply to screening deletion, truncation or other mutants of HIV-1-derived proteins where such mutations result in a strain of HIV-1 being substantially non-pathogenic. Although a variety of procedures are available to detect a modified HIV-1-derived protein, a particularly convenient approach is to screen HIV-1 infected individuals for the absence of antibodies to the deleted or truncated portion of a target protein.

According to one embodiment there is provided a method for determining the pathogenicity of a strain of HIV-1 after said HIV-1 strain infers cells of an individual said method comprising contacting a biological sample from said individual with a peptide corresponding to a deleted or truncated region of an HIV-1-derived protein and screening for the absence of antibody binding to said peptide, wherein the absence of antibody binding is indicative of a deletion or truncation in that protein and further indicative of the non-pathogenicity of said strain of HIV-1.

Although this general methodology is applicable to any protein encoded by HIV-1 which is critical for pathogenicity in a host, it is particularly useful in screening deletions in the Nef protein. An exemplary deletion in the Nef protein is all or part of the sequence of amino acids 162 to 177 of Nef. Preferably, the assay would include a positive control such that where antibodies are present to Nef, such antibodies would bind to this positive control. When a Nef protein carries a deletion at or about amino acids 162 to 177, antibodies to this region would be absent in an individual infected by a non-pathogenic strain of HIV-1 and no binding would be detected to a peptide covering this region.

According to a particularly preferred embodiment, there is contemplated a method for determining the pathogenicity of an HIV-1 strain after said strain infects cells of an individual, said method comprising contacting a biological sample from said individual with an effective amount of a peptide having an amino acid sequence comprising or within amino acids 162 to 177 of wild-type HIV-1$_{NL43}$ Nef, said contact being for a time and under conditions sufficient for an antibody if present in sad biological sample to form a complex with said peptide and then detecting the present of said complex wherein the absence of a complex is an individual seropositive for HIV-1 is indicative of that the individual being infected with a non-pathogenic strain of HIV-1. The method may also comprise contacting the biological sample with one or more peptides derived from other regions of Nef such as flanking regions to amino acids 162 to 177 where antibodies to such other regions may be expected even in non-pathogenic HIV-1 strains. This would provide a suitable positive control. A biological sample according to this embodiment would be any source of antibodies such serum and whole blood. Preferably, the peptides are immobilized to a solid support as described below. This method of the present invention is also applicable for determining the risk of an individual seropositive for HIV-1 developing symptoms of AIDS. Again, substantial absence of antibodies to amino acids 162 to 177 of Nef in an HIV-1 seropositive individual would be indicative of a low risk of an individual developing AIDS.

Other methods of screening for the pathogenicity or otherwise of strains of HIV-1 readily become apparent as a result of the present invention. For example, antibodies may be first genera to modified Nef proteins from non-pathogenic strain of HIV-1 where such antibodies would not recognise wild-type Nef protein.

According to one embodiment, there is provided a method for determining the pathogenicity of an HIV-1 strain after said HIV-1 strain infects cells of an individual, said method comprising contacting a biological sample from said individual with an effective amount of an antibody specific to a nef protein from a non-pathogenic strain of HIV-1 (as hereinbefore defined) for a time and under conditions sufficient to form an antibody-modified nef protein complex and then detecting said complex. The presence of said complex is indicative of a modified nef gene product and of the non-pathogenicity of the strain of HIV-1. Alternatively, the isolated Nef could be tested against a panel of antibodies where certain antibodies are specific to a deleted region. The absence of antibody binding would be indicative of a deletion and, therefore, a modified Nef protein and in turn a putative non-pathogenic form of the virus. The biological sample is a sample likely to contain the modified gene product such as tissue extract or cell extract of an infected cell. However, where the modified nef gene product is capable of permeation or transport out of the cell, suitable biological fluid would include serum, whole blood, lymph and mucosal secretion amongst other fluids.

Many variations in the aforementioned assays are possible and are contemplated herein. For example, an assay could also be based on the inability for a nef specific antibody to bind to a modified nef protein. For the purposes of the present invention the term "contacting" including "mixing".

The presence of a modified nef molecule, such as a molecule carrying a deletion, or other suitable HIV-1 derived protein in biological fluid can be detected using a wide range of immunoassay techniques such as those described in U.S. Pat. Nos. 4,016,043, 4,424,279 and 4,018,653. These include both single-site and two-site, or "sandwich", assays of the non-competitive types, as well as in the traditional competitive binding assays and include ELISA and RIA techniques. Sandwich assays are among the most useful and commonly used assays and are favoured for use in the present invention. A number of variations of the sandwich assay technique exist, and all are intended to be encompassed by the present invention. Briefly, and by way of example only, in a typical forward assay, a modified nef product-specific antibody is immobilised onto a solid substrate to form a first complex and the sample to be tested for modified nef product brought into contact with the bound molecule. After a suitable period of incubation, for a period of time sufficient to allow formation of an antibody-modified nef product secondary complex, a second modified nef protein antibody, labelled with a reporter molecule cable of producing a detectable signal, is then added and incubated, allowing time sufficient for the formation of a tertiary complex of antibody-modified nef product-antibody. Any unreacted material is washed away, and the presence of the tertiary complex is determined by observation of a signal produced by the reporter molecule. The results may either be qualitative, by simple observation of the visible signal or may be quantitated by comparison with a control sample containing known amounts of hapten. Variations of the forward assay include a simultaneous assay, in which both sample and labelled antibody am added simultaneously to the bound antibody, or a reverse assay in which the labelled antibody and sample to be tested are first combined, incubated and then added simultaneously to the bound antibody. These techniques are well known to those skilled in the art, and the possibility of minor variations will be readily apparent. The antibodies used above may be monoclonal or polyclonal. In a preferred embodiment, antibodies to Nef in an individual's biological fluid are screened for using peptides derived from Nef. The absence of antibodies to specific regions of Nef such as amino acids 162 to 177 would be indicative of a non-pathogenic strain of HIV-1. All such assays and variations of such assays are encompassed by the present invention.

The solid substrate is typically glass or a polymer, the most commonly used polymers being cellulose, polyacrylamide, nylon, polystyrene, polyvinyl chloride or polypropylene. The solid supports may be in the form of tubes, discs or microplates, or any other surface suitable for conducting an immunoassay. The binding processes are well-known in the art and generally consist of cross-linking covalently binding or physically adsorbing the molecule to the insoluble carrier.

By "reporter molecule", as used in the present specification, is meant a molecule which, by its chemical nature, produces an analytically identifiable signal which allows the detection of antigen-bound antibody. Detection may be either qualitative or quantitative. The most commonly used reporter molecules in this type of assay are enzymes, fluorophores or radionuclide containing molecules (i.e. radioisotopes). In the case of an enzyme immunoassay, an enzyme is conjugated to the second antibody, generally by means of glutaraldehyde or periodate. As will be readily recognised, however, a wide variety of different conjugation techniques exist which are readily available to one skilled in the art. Commonly used enzymes include horseradish peroxidase, glucose oxidase, $\beta$-galactosidase and alkaline phosphatase, amongst others. The substrates to be used with the specific enzymes are generally chosen for the production, upon hydrolysis by the corresponding enzyme, of a detectable colour change. It is also possible to employ fluorogenic substrates, which yield a fluorescent product.

Alternatively, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. AS In the EIA, the fluorescent labelled antibody is allowed to bind to the first antibody-hapten complex. After washing off the unbound reagent, the remaining complex is then exposed to the light of the appropriate wavelength, the fluorescence observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed. It will be readily apparent to the skilled technician how to vary the procedure to suit the required purpose. It will also be apparent that the foregoing can be used to label a modified nef product and to use same directly in the detection of, for example, circulatory antibodies specific to said modified nef product.

Alternatively, genetic assays may be conducted to screen for abberations in the nef gene and/or LTR region. Such a genetic assay may be by Southern or Northern blot analysis, PCR analysis or the like using oligonucleotides specific to a deleted region of a nef gene and/or LTR region.

According to this embodiment there is provided a method for determining the pathogenicity of an HIV-1 strain after said HIV-1 strain infects cells of an individual, said method comprising determining directly or indirectly the presence of a deletion mutation in the genome of said HIV-1 wherein the presence of a such a mutation is indicative of the presence of a non-pathogenic strain of HIV-1. The deletion mutation may result in the genome being unable to synthesize a polypeptide or protein from a pathogenic strain of HIV-1 or may direct the synthesis of a truncated or deleted form of said polypeptide or protein. For example, a Nef protein with amino acids 162 to 177 deleted therefrom. The mutation may also lead to altered expression of a polypeptide detectable by, for example, decreased synthesis of a particular protein, such as the nef gene product. Alternatively, the deletion mutation affect the LTR region or a regulatory region of the HIV-1 genome. In either case, affected viruses may also be detected by, for example, observing low viral copy numbers such as low viral loads.

Preferably, said non-pathogenic HIV-1 carries a deletion in its genome of at least 10 nucleotides within the region from nucleotide 8787 to nucleotide 9709 using the nucleotide numbering of HIV-$1_{NL43}$.

Preferably, said non-pathogenic HIV-1 carries a deletion in its genome of at least 10 nucleotides from within a region selected from the list consisting of:
nucleotide (i) 8830–8862;
(ii) 9009–9035;
(iii) 9019–9029; and
(iv) 9033–9049.

Preferably, said non-pathogenic HIV-1 carries a deletion in its genome of at least 10 nucleotides from within a region selected from the list consisting of:
nucleotide (v) 9281–9371;
(vi) 9281–9362;
(vii) 9105–9224; and
(viii) 9271–9370.

Preferably, said non-pathogenic HIV-1 carries a deletion in its genome of at least 10 nucleotides from within a region selected from the list consisting of:
nucleotide (ix) 8882–8928;
(x) 8850–9006;
(xi) 8792–9041; and
(xii) 9112–9204.

Preferably, said non-pathogenic HIV-1 carries a deletion in its genome of at least 10 nucleotides from within a region selected from the list consisting of:
nucleotide (xiii) 9105–9224;
(xiv) 9389–9395; and
(xv) 9281–9366.

The above nucleotide numbers are based on the nucleotide numbering in the NL43 genome.

Particularly preferred oligonucleotides are based on the deleted regions of the nef gene and/or LTR region such as but not limited to one or more oligonucleotides based on SEQ ID NO: 2 to SEQ ID NO: 613 and/or SEQ ID NO: 652 to SEQ ID NO: 799.

Most preferred deletions include deletions of one or more of SEQ ID NO:803 to 841 which cover amino acids 162 to 177 of Nef. A particularly preferred genetic assay screens for this deletion.

The present invention further extends to kits for the diagnosis of infection by pathogenic strains of HIV-1 or for determining the pathogenicity of infecting virus. The kits would be in compartmental form each comprising one or more suitable reagents for conducting the assay.

The present invention is further described by the following non-limiting Examples.

EXAMPLE 1

Source Material

For the purposes of the following examples, non-pathogenic HIV-1 strains were isolated from recipients of HIV-1 infected blood. The recipients are designated "C18", "C54", "C98", "C49", "C64" and "C124". The donor is identified herein as "D36". The place of isolation may be indicated after the abbreviation of "HIV". For example, St Vincents Hospital, Sydney (HIV$_{StV}$) or Macfarlane Burnet Center of Medical Research, Melbourne (HIV$_{MBC}$).

Exemplary viral isolates referred to herein as "C18" and "C98" were deposited at the PHLS Center for Applied Microbiology and Research, European Collection of Animal Cell Cultures (ECACC), Division of Biologies, Porton Down, Salisbury. Wiltshire SP4 OJG. C18 was deposited on Oct. 17, 1994 under Provisional Accession Number V94101706 and C98 was deposited on Oct. 31, 1994 under Provisional Accession Number V941031169. Another isolate "C54" was deposited at ECACC on Mar. 10, 1995 under Provisional Accession Number V95031022.

FIG. 11 is a summary of the deletion mutant of the present invention.

Viruses are isolatable by the following procedures:

1. Infected peripheral blood mononuclear cells (PBMCs) were co-cultured with HIV-1 seronegative donor PBMCs. A convenient source of seronegative donor PBMCs is a blood bank. The supernatants and cells are harvested every 7 days and fresh medium added with CD8 depleted PBMCs. CD8 depletion promotes the ability to isolate HIV-1. The culture and procedure is continued for up to approximately 5 weeks;

2. The infected PBMCs are purified from whole blood and these cells are cultured alone for up to 5 weeks. PMBCs alone are used because the virus is more likely to be monocytotropic. Fresh medium is added weekly and supernatant fluid is harvested at this time;

3. Supernatant fluids are harvested every approximately 7 days, fresh medium and fresh HIV-1 seronegative CD8 depleted PBMCs are added at this time;

4. HIV-1 seronegative PBMCs are pretreated with with M-CSF for approximately 72 hours prior to the addition of infected PBMCs. M-CSF has been shown to enhance HIV-1 replication in monocytes (Gendelman et al, 1988); and 5. The supernatant fluid is harvested from the cultures of step 4 every approximately 7 days, fresh medium added together with HIV-1 seronegative stimulated CD8 depleted PBMCs. The virus is isolated from the infected PBMCs.

A particularly preferred method of isolation is as follows: HIV negative donor PBMC were stimulated by culture in RPMI 1640 containing 10% v/v fetal calf serum (FCS), 15 mM N-2-hydroxyethylpiperazine-N'-2-ethanesulfonic acid, 0.1% w/v sodium bicarbonate with 100 IU/ml penicillin and 100 µg/ml streptomycin with the addition of 10 µg/ml PHA (Wellcome, Temple Hill Dartford, England) for 72 h prior to co-culture. Fresh patient cells ($10 \times 10^6$ cells) were then co-cultured with the PHA-activated donor PBMC ($10 \times 10^6$ cells). Immediately on co-culture $2 \times 10^6$ of the mixed cell population were UV irradiated (254 nm, 300 µW/cm$^2$, 15 sec), added back to the remaining cells and cultured for 29 days. After UV treatment cells ware resuspended at $1 \times 10^6$ cells/ml in RPMI 1640 containing 10%. v/v FCS, 15 mM HEPES, 0.1% w/v sodium bicarbonate, 25 µg/ml glutamine, 100 IU/ml penicillin, 100 µg/ml streptomycin, 2 µg/ml polybrene; 4 µg/ml hydrocortisone (Sigma, St Louis, Mo., USA), 20 U/ml interleukin 2 (Boehringer Mannheim, Germany) and 120 nU/ml anti-interferon (ICN Biochemicals, Costa Mesa, Calif., USA). Cells were maintained by half medium changes every 3 to 4 days after PHA stimulation, with the addition of fresh stimulated donor PBMC on days 7, 14 and 21. Virus production was assayed for by cell-free reverse transcriptase activity (Neate et al, 1987) or p24 activity (Abbott Diagnostics assay).

EXAMPLE 2

DNA Preparation and PCR Amplification

Non-pathogenic HIV-1 (e.g. strain C18) infected peripheral blood mononuclear cells (PBMC) were harvested 4 days after infection of phytohaemagglutinin (PHA) stimulated HIV-1 negative donor PBMC culture by the method of Neate et al (1987) and washed in phosphate buffered saline (PBS). PBMC from Donor D36 and Recipients C18, C54 and C98 were prepared by Ficoll isopaque centrifugation of buffy coat cells and washed with PBS.

Approximately $10^7$ cells were lysed in 1 ml lysis solution (0.45% v/v NP40, 0.45% v/v Tween 20, 10 mM Tris-HCl pH 8.3, 40 mM KCl 2.5 mM $MgCl_2$) and digested with 60 μg/ml proteinase K (Boehringer Mannheim) at 55° C. for 1 hour followed by 100° C. for 10 minutes. Lysates were stored at −20° C.

All polymerase chain reaction (PCR) primers (Table 1) and sequencing primers (Table 2) were synthesized using an Applied Biosystem model 391 DNA synthesizer using phosphoramidite chemistry.

Strict physical separation was maintained for sample, PCR reagent mix and PCR reaction preparations as well as amplification and analysis. Final reaction mixes (50 μl) contained 2 μl neat or diluted cell lysate, 0.2 μM each primer, 200 mM dNTPs and 1.25 units Taq polymerase (Boehringer Mannheim) in PCR buffer, (10 mM Tris-HCl pH8.3, 50 mM KCl, 100 μg/ml gelatine) adjusted to the optimum $MgCl_2$ concentration for the primer pair (1.5–3.0 mM. Aliquoted reagent mix was overlaid with 50 μl mineral oil prior to addition of DNA template lysate. After template denaturation at 94° C. for 3 min amplification was achieved with 30 cycles of 94° C., 1 min; 55° C., 1 min; 72° C., 2 mins. A final elongation reaction was conducted at 72° C. for 7 minutes. For double PCR amplification 2 μl of first round product was added to the second reagent mix and amplified as before.

PCR amplified DNA was checked for quality, quantity and fragment size by agarose gel electrophoresis in Tris-Acetate-EDTA buffer (Sambrook et al, 1989) stained in ethidium bromide and viewed by UV transillumination.

EXAMPLE 3

DNA Sequence Analysis

DNA sequence of PCR amplified HIV-1 regions was determined by the dideoxynucleotide method (Sanger et al, 1997) using Sequenase T7 polymerase (United States Biochemicals).

PCR amplified DNA was purified by PCR Magic prep resin chromatography (Promega). Approximately 2 to 7 μg purified DNA plus 10 mg specific primer (table 2) were denatured by boiling for 3 mins and snap frozen to −20° C. The initial labelling reaction was for 3 minutes at 22° C. (room temperature) with $^{35}$SdNTP (500 Ci/mmol; Dupont) followed by dideoxynucleotide termination reaction at 37° C. for 5 minutes. NP40, to 0.45% v/v, was included in denaturation and reaction mixes (Bachman et al, 1990). Sequencing reaction products were denatured in formamide and resolved on a 6% w/v polyacrylamide gel containing 8M urea, fixed in 10% v/v acetic acid, 10% v/v methanol and dried. Following autoradiography on XK1 film (Kodak) the gel sequences were read assembled, translated to protein and aligned using the PC/GENE suite of programs (IntelliGenetics, USA).

TABLE 1

PCR PRIMERS

| PRIMER | SEQUENCE[1,3] | POSITION[2] |
|---|---|---|
| Cl-1 | TGGAAGGGCTAATTTGGT(616) | 1–18 |
| Cl-2 | ATCTTCCCTAAAAAATTAGCCTGTC(617) | 2099–2075 |
| LTR-3' | AGGCTCAGATCTGGTCTAAC(618) | 9559–9540 |
| SK68 | AGCAGCAGGAAGCACTATGG(619) | 7786–7805 |
| Cl-6 | TGCTAGAGATTTTCCACAC(620) | 9709–9691 |
| KS-2 | AGTGAATAGAGTTAGGCAGG(621) | 8326–8345 |
| RT5'-v3 | GTAAGACAGTATGATCAGATA(622) | 2418–2438 |
| RT3'-v2 | TTGTAGGGAATTCCAAATTCC(623) | 4660–4640 |
| RT5'-v2 | CAGGATCCTACACCTGTCAACATAAT(624) | 2487–2506 |
| RT3'-v1 | GGGAATTCCTTATTCCTGCTTG(625) | 4655–4634 |

[1.]Sequence is presented from 5' to 3' of the primer.
[2.]Position is according to the numbering of HIV-1 in Myers et al (1992).
[3.]SEQ ID NOs are given in parentheses.

TABLE 2

SEQUENCING PRIMERS

| PRIMER | SEQUENCE[1,3] | POSITION[2] |
|---|---|---|
| KS3 | CCAGAAGTTCCACAATCC(626) | 8570–8553 |
| KS4 | TTCTTCTAGGTATGTGGAG(627) | 8753–8735 |
| KS5 | AGTGAATTAGCCCTTCCAG(628) | 9093–9075 |
| KS6 | TGCTAGAGATTTTCCACAC(629) | 9709–9691 |
| SP2 | TGCTCTGGAAAACTCAT(630) | 8006–8022 |
| SP3 | CTTTCTATAGTGAATAGAG(631) | 8318–8336 |
| SP4 | TATTGGAGTCAGGAACT(632) | 8618–8634 |
| SPR | GGTCTAACCAGAGAGAC(633) | 9547–9531 |

[1.]Sequence is presented from 5' to 3' of the primer.
[2.]Position is according to the numbering of HIV-1 in Myers et al (1992).
[3.]SEQ ID NOs are given in parentheses.

EXAMPLE 4

Cells and Cell Culture

Peripheral blood was obtained from HIV-1 sero-negative volunteers ad mononuclear cells prepared by centrifugation on a Ficoll/Hypaque density gradient (Peper et al, 1968). PBMC were activated with phytohemagglutinin (PHA; 10 μg/$10^6$ cells) for 48 h at 37° C. washed and then cultured In RPMI 164 medium containing 10% v/v hat inactivated foetal calf serum, 15 mM HEPES, 0.1% v/v sodium bicarbonate, 25 μg/ml polybrene (Sigma), 10% v/v interleukin 2 (Boehringer Mannheim) and 1:1000 anti-interferon (Miles) (IL-2 medium). Non-PHA stimulated cells were prepared in similar manner except they were cultured in medium lacking PHA and IL-2.

EXAMPLE 5

Antipeptide antisera

Antibodies specific for HIV-1 Nef were raised against a peptide corresponding to the predicted amino acid residues 15–27 (AVRERMRRAEPAA SEQ ID NO: 634) of Nef encoded by the HIV-1 clone pNL4.3 (Kemp et al, 1988). The peptide was conjugated to keyhole limpet hemocyanin (KLH; Calbiochem, Behring Diagnostics, Calif.) via glutaraldehyde and this complex used to immunise sheep (0.5 mg peptide conjugate/sheep). Antibodies to the peptide were purified by affinity chromatography. Reactivity of the antibodies with recombinant HIV-1 Nef 25 ad 27 was demonstrated by immunoblotting.

EXAMPLE 6

Reactivity of anti-Nef $_{(15-27)}$ with HIV C18-infected Cells Immunoblotting Seven days post-infection HIV-1 C18-infected PBMCs and mock—infested cells were washed in PBS then lysed (0.5% w/v NP-40, 0.5% w/v sodium deoxycholate, 50 mM NaCl, 25 mM Tris-HCl, 10 mM EDTA, 0.01% w/v sodium azide and 10 mM phenylmethylsulphonylfluoride). After nuclei were spun out lysates were electrophoresed in a 13% w/v SDS-polyacrylamide gel (SDS-PAGE) and subsequently transferred to Hybond-C nitrocellulose (Amersham, Buckinghamshire, England) for 1 h at 100 V using a Bio-Rad protein transfer cell (Bio-Rad, Richmond, Calif.). Membranes were pre-incubated with 1% w/v BSA/PBS for 2 h at room temperature and then reacted with affinity purified sheep anti-Nef$_{(15-27)}$, diluted 1:100, overnight at room temperature. After three washes in 1% w/v BSA/PBS, the blots were incubated with donkey anti-sheep Ig conjugated to biotin (Amersham, diluted 1:500) for 1 h at room temperature. After extensive washing as described above the membranes were incubated with streptavidin-conjugated horse radish peroxidase (Amersham; diluted 1:1500 for 1 h at room temperature. All dilutions were made with 1% w/v BSA in PBS. After further washing the membrane was developed with phenylenediamine substrate (Dako, Dapopatts, Denmark). The antibody preparation used in the immunoblotting experiments was free of detectable antibodies to the immunogenic carrier protein and coupling reagent.

EXAMPLE 7

Analysis by Polymerase Chain Reaction Amplification

A 5' fragment defined by primers Cl-1 and Cl-2 containing the 5' LTR and part of the gag gene was amplified. DNA from HIV-1 C18 infected PBMC gave an amplified fragment (amplimer) of about 1.9 kb compared with 2.1 kb for pHXB2 control template, implying a deletion of about 200 bp from HIV C18. Further amplification of this fragment with primers defining the U3 region of the LTR (Cl-1 and LTR-3') gave amplimers of about 300 bp for HIV-1 C18 infected PBMC DNA compared with 340 bp for C18 and D36 PBMC DNA and 484 bp for pHXB2 control. This implies the loss of approximately 140 to 180 bp from the U3 region of these proviral DNAs.

To analyse the nef-gene-3' LTR region, the nested primer pairs SK68-Cl6 and KS-2-LTR-3' were used in a double PCR. Amplimers of approximately 830 bp were obtained for HIV-1 C18 infected PBMC DNA as well as for PBMC DNA form Donor D36 and Recipients C18, C54 and C98 compared with approximately 1230 bp for pHXB2 DNA. These results suggest that about 400 bp of DNA have been deleted from the Donor and Recipient proviral DNAs.

In comparison, amplification of the polymerase gene region by double PCR with the nested primer pairs RT5'-v3-RT3'-v2 and RT5'-v2-RT3'-v1 gave a fragment (approximately 2.1 kb) the same size as the molecular clone pHXB2 fragment for HIV-1 C18 infected PBMC DNA, suggesting that deletions from this region were unlikely.

EXAMPLE 8

Nucleotide Sequence of the nef-3' LTR Region

PCR amplification experiments indicated an approximately 200 bp nucleotide deletion from both the nef gene and LTR regions of Donor D36 PBMC and Recipient C18 HIV-1 proviral DNA. To further analyse these regions, the DNA sequence was determined for the PCR amplified nef-3'-LTR region of D36 PBMC, C18 isolates HIV$_{MBC}$ and HIV$_{StV}$ as well as isolate C98 HIV infected PBMC proviral DNA. The 3' region was amplified with outer primers (SK68-Cl16) and inner primers (SK68-LTR3' or KS2-Cl16) and sequenced directly using a number of internal sequencing primers based on the HIV-1$_{NL43}$ nucleotide sequence (Table 2).

Alignment of the nucleotide sequences of the amplified 3' region of donor D36 PBMC and recipient C18 isolates HIV$_{MBC}$ and HIV$_{StV}$ and C98 HIV (FIG. 1) showed a number of nucleotide sequences changes, including deletions, relative to the nucleotide sequence of wild-type infectious HIV-1 (HIV-1$_{NL43}$). In the region of alignment, D36 PBMC lacked 291 nucleotides, C18 HIV$_{StV}$ differed in size by 388 nucleotides (comprising deletions of 397 nucleotides and an insertion of 9 nucleotides), C18 HIV$_{MBC}$ differed by 456 nucleotides and C98 HIV lacked 158 nucleotides compared with HIV-1$_{NL43}$. The overall identity with HIV-1$_{NL43}$ nucleotide sequence of D36 PBMC, C18 HIV$_{StV}$, HIV$_{MBC}$ and C98 HIV nucleotide sequences, including deletion, was 73% (1157/1596), 67% (1459/1592), 62% (982/1592) and 79% (1105/1399), respectively.

Figure 3:
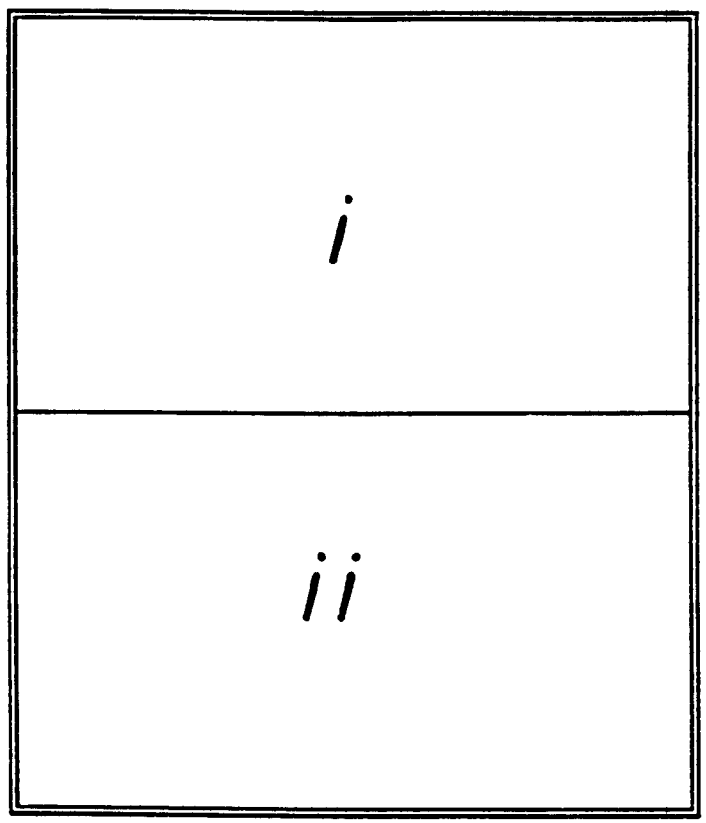

The D36 PBMC sequence differed from HIV-1$_{NL}$43 in a number of features. A change in the wild type tat termination codon from TAG to TCG (Ser) extended the third tat exon (which starts at splice acceptor 10) by a further 15 amino acids to terminate at a conserved TAG (FIG. 1). The resulting C-terminal peptide is rich in charged amino acids (8/15) (FIG. 2a). The wild type rev termination codon has also changed (TAG to GAG, Glu) and the third rev exon is extended for 14 codons to terminate at a conserved TAG (FIG. 2b). The encoded extra amino acids are mainly polar (11/14) and charged in nature (FIG. 2b). The sequence also encodes the C-terminal 237 amino acids of Env gp41 (FIG. 3) terminating at the normal termination codon. The D36 PBMC Env amino acid sequence has 85% identity with the HIV-1$_{NL43}$ sequence, increasing to 89% if similarities are included.

There are significant differences from HIV-1$_{NL43}$ downstream of the env (gp41) gene. A change in the fifth nef codon, from TGG (Trp) to TGA (FIG. 1), introduces an early termination in the D36 PBMC nef gene. The encoded Nef protein is identical to the N-terminal 4 amino acids of HIV-1$_{NL43}$ Nef (FIG. 4). Following the early termination there are deletions of 33. 47, 93 and 91 nucleotides and a region of low sequence homology, compared with HIV-1, prior to the wild type nef termination codon site (HIV-1 nts 9405–9407). As well as removing a significant part of the nef gene, these deletions also bring into phase a further 6 termination codons. While the polypurine tract (plus strand primer binding site) and the first 38 nucleotides of the LTR U3 region are perfectly conserved, downsteam U3 region sequences are disrupted by the 93 and 91 nucleotide deletions and the low homology region. The resulting U3 region lacks recognition sequences for the transcription factors c-myb, USF and TCF1α as well as one of the suggested NF-AT sites (Gaynor et al, 1992). Downstream from the 91 nucleotide deletion, a 59 nucleotide region of low homology contains two extra NFKB enhancer sites 19 nucleotides upstream of the usual site of a pair of NFKB sites, the upstream one of which is altered in its 5'-half in D36. Sequences further downstream are highly conserved with respect to HIV-1$_{NL43}$, including the position and number of Sp1 basal promoter sites, TATA box, TAR and polyadenylation signal sequences.

Similar to D36 PBMC, the C18 $HIV_{StV}$ and $HIV_{MBC}$ sequences show the tat third exon to be extended by 15 codons. All but two codons (altered by point mutations) are identical to those of D36 PBMC (FIG. 2a). The rev third exon of both C18 isolates is also extended (FIG. 2b) but by only three codons, identical to the first three codons of the D36 PBMC rev extension. The same 237 amino acid coding region of Env gp41 is found in both the C18 HIV DNA sequences (FIG. 3) and shows 85% identify, increasing to 88% if similarities are included, with the same region of the $HIV-1_{NL43}$ Env gp41.

It is in the nef gene and LTR regions that the major differences from wild-type HIV-1 arise, just as in D36 PBMC. The nef gene of C18 $HIV_{StV}$ encodes 24 amino acids with 9 of the 10 N-terminal being identical to the $HIV-1_{NL43}$ Nef protein (FIG. 4). Thereafter, deletions of 177 and 11 nucleotides cause a frameshift and termination at the 25th codon (FIG. 1). Downstream deletions of 120, 82 and 7 nucleotide cause he loss of wild type nef gene sequence and bring into phase a further three termination codons.

The nef gene of C18 $HIV_{MBC}$ encodes only 7 amino acids with only the initiator methionine identical to the $HIV-1_{NL43}$ Nef protein. This loss of identity and early termination is brought about by a 250 nucleotide deletion after the fifth nucleotide of the nef gene. Downstream deletions of 120 and 86 nucleotides cause further loss of wild-type nef gene sequences. In both C18 isolates there is perfect conservation of the polypurine tract and 29/31 nucleotides at the 5' end of the U3 region immediately before the 120 nucleotide deletion (FIG. 1). This deletion together with the downstream 82 and 7 nucleotide deletions in $HIV_{StV}$ and 86 nucleotide deletion in $HIV_{MBC}$ and the low homology region cause the loss of the 5' half of the NRT-1 site (Yamamoto et al 1992) and the downstream NFAT site. A third NFKB site is present 31 ($HIV_{StV}$) and 33 ($HIV_{MBC}$) nucleotides upstream of the expected pair of NFKB sites which are themselves separated by 13 nucleotides instead of the 4 nucleotides in $HIV-1_{NL43}$. The 5'-most Sp1 site sequence is slightly altered but sequences downstream including the other 2 Sp1 sites the TATA box, TAR and polyadenylation signal sequences are identical to $HIV-1_{NL43}$ sequence.

The three sequences, D36 PBMC, C18 $HIV_{StV}$ and C18 $HIV_{MBC}$ show a number of similarities consistent with the transmission of virus from person D36 to person C18 as well as a number of differences indicating post-transmission divergence of sequence. All three have tat open reading frames (ORFs) extended by 15 codons. All three have extended rev ORFs. The new rev termination codon in both C18 HIV-1 isolates, three codons downstream of the $HIV-1_{NL43}$ rev termination codon, has a point mutation in D36 PBMC to make a Glu codon so that it continues for a further 11 codons (FIG. 2b) to terminate at a conserved TGA. The partial Env gp41 amino acid sequences are more closely related to each other (86% identity or 90% including similarities) than to HIV-1 (85% and 89%, respectively).

The nucleotide sequence of the nef and LTR region of the HIV-1 isolate from recipient C98 (C98 HIV) is 90.3% identical (1264/1399) to the HIV-1 sequence, ignoring deletions. Similar to the D36 PBMC and C18 $HIV_{StV}$ and $HIV_{MBC}$ isolates the C98 HIV sequence shows the third exon of tat to be extended by 15 codons with all but one being identical to the D36 PBMC tat extension. Also, the rev gene is extended by 3 codons, 2 of which are identical to the first 2 codons of the D36 PBMC rev extension. The sequence also encodes the C-terminal 223 amino acids of Env gp41 >terminating at the normal termination codon. The C98 HIV Env amino acid sequence has 89% identity with HIV-1 Env sequence, increasing to 92% of similarities are included.

As with the D36 PBMC and the C98 HIV isolate sequences it is the nef gene and LTR regions that major differences from the HIV-1 sequence arise. The nef gene open reading frame of C98 HIV is much longer than in D36 PBMC, C18 $HIV_{STV}$ and $HIV_{MBC}$, encoding 85 amino acids compared with 206 amino acids for $HIV-1_{NL43}$. Sixty eight of those 85 amino acids are identical to the N-terminal sequence of $HIV-1_{NL43}$ Nef. The single, small deletion (16 nucleotides) in the C98 HIV nef-alone regions (Table 3) occurs after nef codon 82 causing a frameshift and termination after a further 3 codons at the start of the highly conserved polypurine tract sequence immediately before the 3'-LTR. The nef/LTR region has two deletions totalling 142 nucleotides. The 5'-most deletion of 42 nucleotides includes the splice acceptor 12 sequence. The NRT-1, dyad symmetry and myb response element sequences are all intact. However, the downstream 100 nucleotide deletion includes sequences from the 3' end of the 5'-NF-AT and all of the 3' NF-AT sequences as well as the USF transcription factor recognition sequence. The downstream low homology region of 77 nucleotides lacks the TCF-1α sequence but has two additional NFKB sites 13 nucleotides apart and 26 nucleotides upstream of the 3'-half-remmant of the normal 5'-NFKB site. Sequence downstream, including the 3'-NFKB site, the 3 Sp1 sites, TATA box TAR and polyadenylation signal sequences are all highly conserved.

The main feature of the sequences is the series of deletions, with respect to HIV-1, in the nef/gene 3'-LTR region. These can be grouped into two regions namely the nef-alone region, that part of the nef gene upstream of the LTR, and the nef/LTR region, where the nef gene and LTR U3 regions overlap. The deletions in these regions of each of the sequences start and end at the same or similar positions (Table 3). The deletions are larger in C18 $HIV_{StV}$ and C18 $HIV_{MBC}$ sequences where totals of 397 and 456 nucleotides have been deleted (relative to $HIV-1_{NL43}$) compared to 291 nucleotides, from D36 and 158 nucleotides from C98 HIV. In the nef-alone region the two deletions in C18 $HIV_{StV}$ and the single deletion in C18 $HIV_{MBC}$ occupy the same region as the three deletions in D36 PBMC. Similarly, the nef/LTR region in the three deletions in the C18 $HIV_{StV}$, the two deletions in the C18 $HIV_{MBC}$ and the D36 PBMC sequences occupy the same region. These findings indicate that mutant virus was transmitted from D36 to C18 after which further deletions and rearrangements occurred. Similarly, the sequence of C98 HIV in the nef/LTR region indicates two deletions occupying the same region as the nef/LTR deletions in D36 and the C18 sequences. However, the size (only 16 nucleotides) and the position of the deletion in the nef-alone region of C98 HIV are distinct from those of the D36 PBMC and C18 sequences.

The timing of transmission of virus by transfusion was that recipient C18 was transfused approximately 19 months after C98. Consistent with the relative timing of mission and the sequence similarities and differences is the suggestion that at the time of transmission to C98, the D36 sequence had deletions in the nef/LTR region but not in nef-alone region. After transmission to C98, the C98 virus developed further deletions and rearrangements, including the deletion in the nef-alone region. The D36 virus evolved so that at the time of transmission to C18, further deletions and rearrangements had occurred including deletion of sequence from the nef-alone region distinct from the C98 HIV nef-alone region deletion. After transmission to C18, further deletions and rearrangements occurred in the C18 virus giving rise to at least two sequences ($HIV_{StV}$ and $HIV_{MBC}$).

The nef-alone deletion region may be a mutation or recombination "hotspot" as it includes sequences that were found to be variably duplicated in 28 out of 54 Nef protein sequences derived from 8 of 12 patients analysed in a study (Shugars et at 1993). The sequence between the nef-alone and the nef/LTR region deletions is highly conserved and is important in provirus integration into the infected cell genome and interacts with a number of cellular proteins. It is interesting that the sequence equivalent to HIV-$1_{NL43}$ nucleotides 9209 to 9225 is retained in D36 and C98 HIV but lost in the C18 HIV sequences. This includes part of a sequence of dyad symmetry (9210 to 9231) and is a significant part of the binding site for NRT-1 (Yamamoto et al 1991) which has been shown to have a negative regulatory effect on HIV-1 expression. The presence of this sequence in D36 and C98 HIV and its absence from the C18 isolates may correlate with the inability to isolate virus from D36 PBMC and the poor replication of C98 HIV but the ability to isolate HIV-1 from C18 PBMC. The deletion of sequence equivalent to nucleotides 9281 to 9395 of HIV-$1_{NL43}$ causes the loss of some transcription factor binding sites including NFAT and USF from the D36, C18 HIV and C98 HIV sequences.

A further similarity between the D36, C18 HIV$_{SrV}$, C18 HIV$_{MBC}$ and C98 HIV sequences is a region of low homology to HIV-$1_{NL43}$ extending downstream of the nef/LTR deleted region to the NFKB enhancer/Sp1 promoter site region. This low homology region in fact consists of incomplete duplications of part of the NFKB/Sp1 region (FIG. 5) resulting in D36 and C98 HIV having 2 extra NFKB sites upstream of an altered 5' NFKB site while the C18 sequences have one extra NFKB site and altered spacing between the 5' and 3' wild type NFKB sites due to an insertion of 9 nucleotides.

Figure 6:
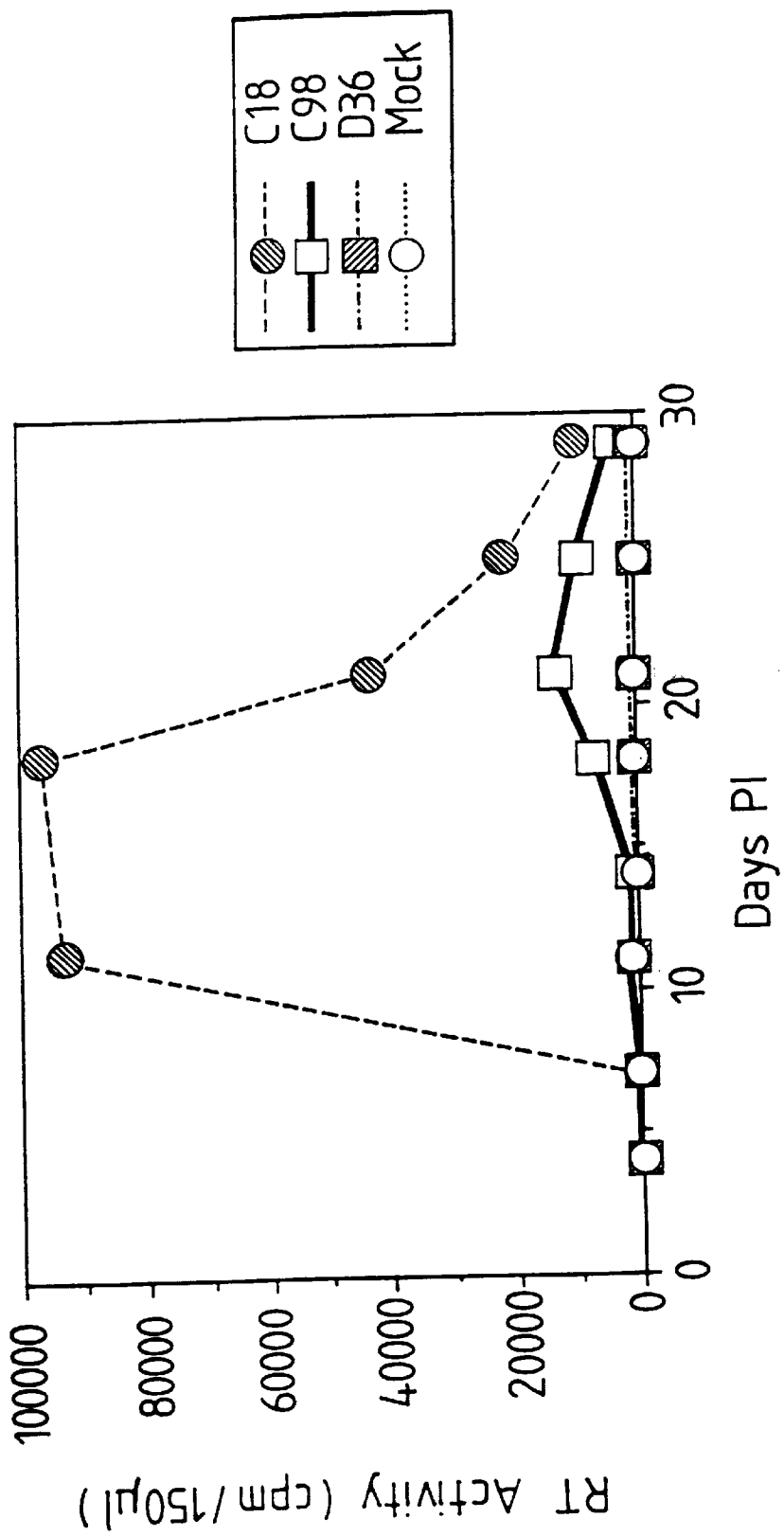
Figure 7:
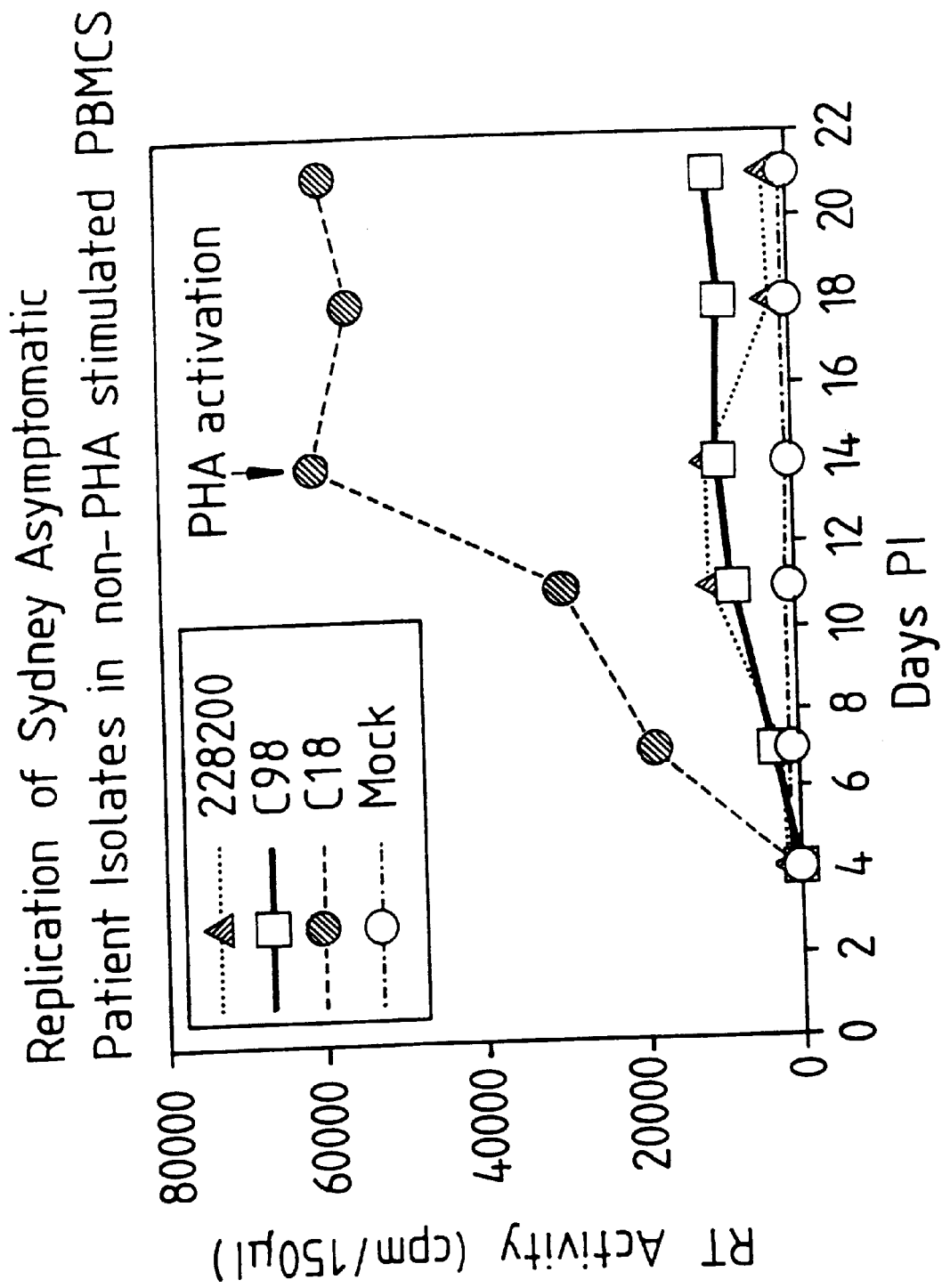
Figure 8:
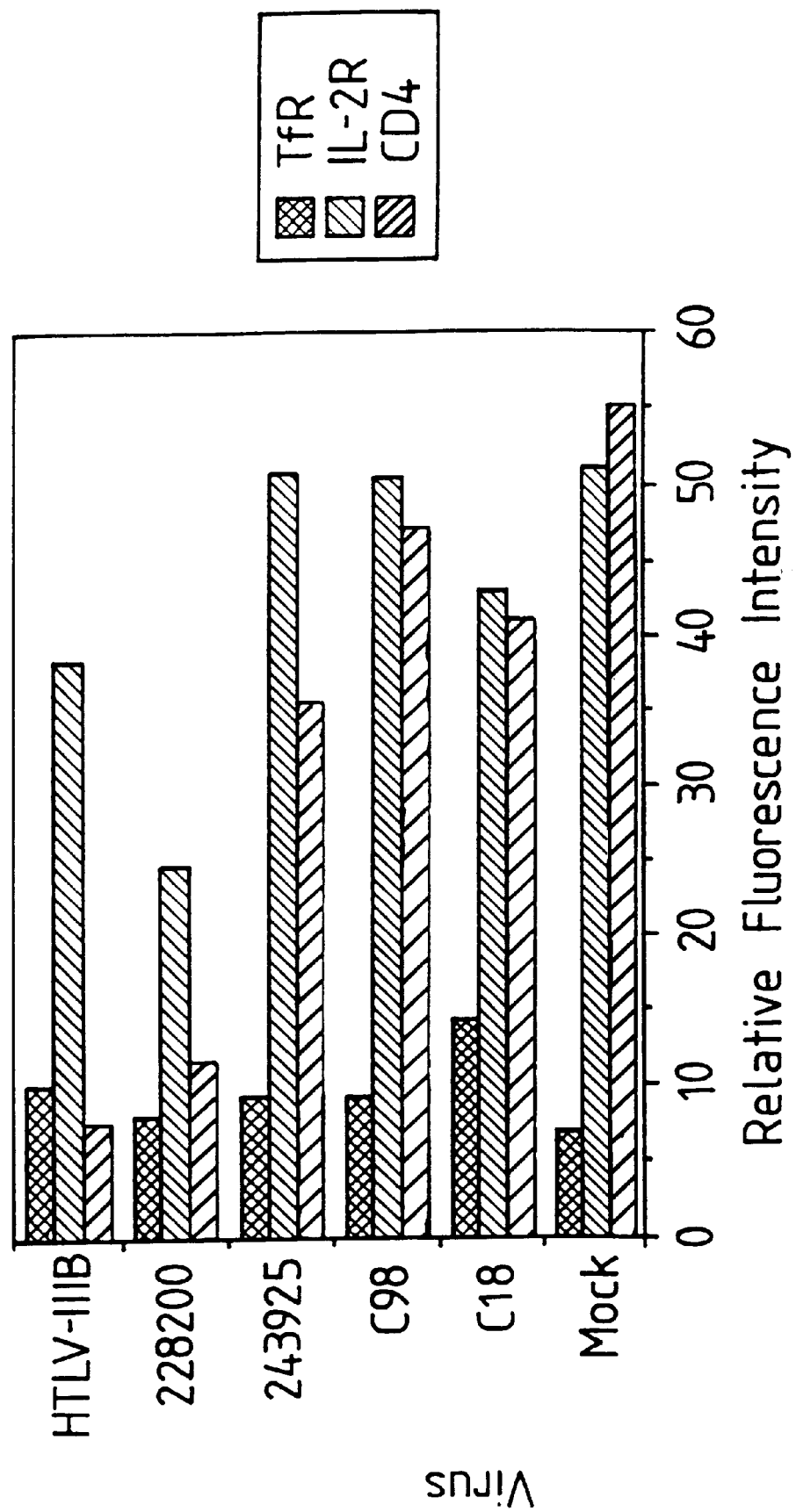

For the C18 and C98 HIV-1 isolates virus replication was a assessed in PHA-stimulated and non-stimulated PBMCs (FIGS. 6 and 7). In PHA-stimulated PBMCs we also studied cell surface CD4 and IL-2R expression (FIG. 8). In comparison with HIV-1 wild-type SI and NSI isolates clearly both C18 HIV$_{MBC}$ and C98 viruses are replication competent, though C98 HIV replicates more poorly than C18 HIV$_{MBC}$ and are of the NSI phenotype when syncytium formation and CD4 and IL-2 surface expression are taken into account. Additionally, and more surprisingly, these two replicated almost as efficiently in non-PHA stimulated PBMCs when compared to a typical local wild type SI isolate (HIV-1 228200, FIG. 7).

When protein expression was assessed for C18 HIV$_{MBC}$ and C98 HIV$_{MBC}$ although structural proteins were identified, no typical Nef protein was seen in infected cells. However, analysis of cell lysates prepared from PBMC infects with C18 HIV$_{MBC}$ or PBMC infected with C98 HIV$_{MBC}$ (which were subsequently stimulated by UV irradiation, see Valerie et al, 1988) by Western immunoblotting using two antibodies specific for the N-terminal region of Nef showed the presence of smaller proteins of 19 kDa and 21 kDa, respectively. These proteins were not observed in mock-injected control PBMC lysates and were not observed when the infected-cell lysates were probed were probed with antibodies reactive with the C-terminal of Nef.

Thus, although the C18 and C9 HIV isolates are replication competent in vitro they clearly replicate differently using different conditions for cell activation and from the known functions of HIV-1 Nef protein and the LTR show that the major deletion in the nef gene and/or the LTR is at least in part responsible for the outcome of infection, implicating the importance of Nef and/or the LTR in the clinical outcome of infection in vivo.

EXAMPLE 9

Determination of Degree of Relatedness Between Viruses

To determine degree of relatedness between viruses such as between mutants or between mutants and a wild-type virus and to ascertain putative infected patients, the method of Delwart et al was employed.

EXAMPLE 10

Immune responsiveness of subjects Infected by non-pathogenic HIV-1 isolate

In this example, the donor and recipients of the cohort were tissue typed and assessed for basic cellular immune responses. Proliferative responses and IL-2 production to the mitogens ConA and PHA, to allogeneic mononuclear cells (irradiated pooled mononuclear cells from 20 random donors) and to recall antigens (e.g. influenza and tetanus toxoid) were within normal ranges. While at the immunogenetic level, HLA typing failed to identify a consistently common allele or haplotype within the group.

The conservation of CD4+ counts observed in the cohort, the relative integrity of their immune system and the varied HLA types of the donor and recipients further supports the fact that the symptomless condition of the cohort members is due to a non-pathogenic strain of HIV-1 or a strain of low virulence.

Accordingly, this provides a screening procedure for subjects putatively infested by a non-pathogenic HIV-1 isolate where such subjects are seropositive for HIV-1 (e.g. have antibodies to an HIV-1 glycoprotein) yet have normal proliferative responses and cytokine production to mitogens, allogeneic mononuclear cells and to recall antigens.

EXAMPLE 11

Clinical Immunology of Cohort

To establish that the donor and the recipients belonging to the cohort exhibit normal immunological profiles, members of the cohort were assayed for CD3, CD4, CD5, lymphocyte count, CD4/CD8 ratio and β2-microglobulin over time since seroconversion.

Parameters considered normal in non-infected individuals range as follows:

| Parameter | | |
|---|---|---|
| CD3 | 55–82% | 620–2200 (×$10^6$/L) |
| CD4 | 29–58% | 420–1410 (×$10^6$/L) |
| CD8 | 12–43% | 200–980 (×$10^6$/L) |
| Lymphocyte Count | 1000–3500 (×$10^6$/L) | |
| CD4/CD8 | 0.7–3.7 | |
| β-2-microglobulin | 0.00–2.20 mg/L | |

Figure 10A:
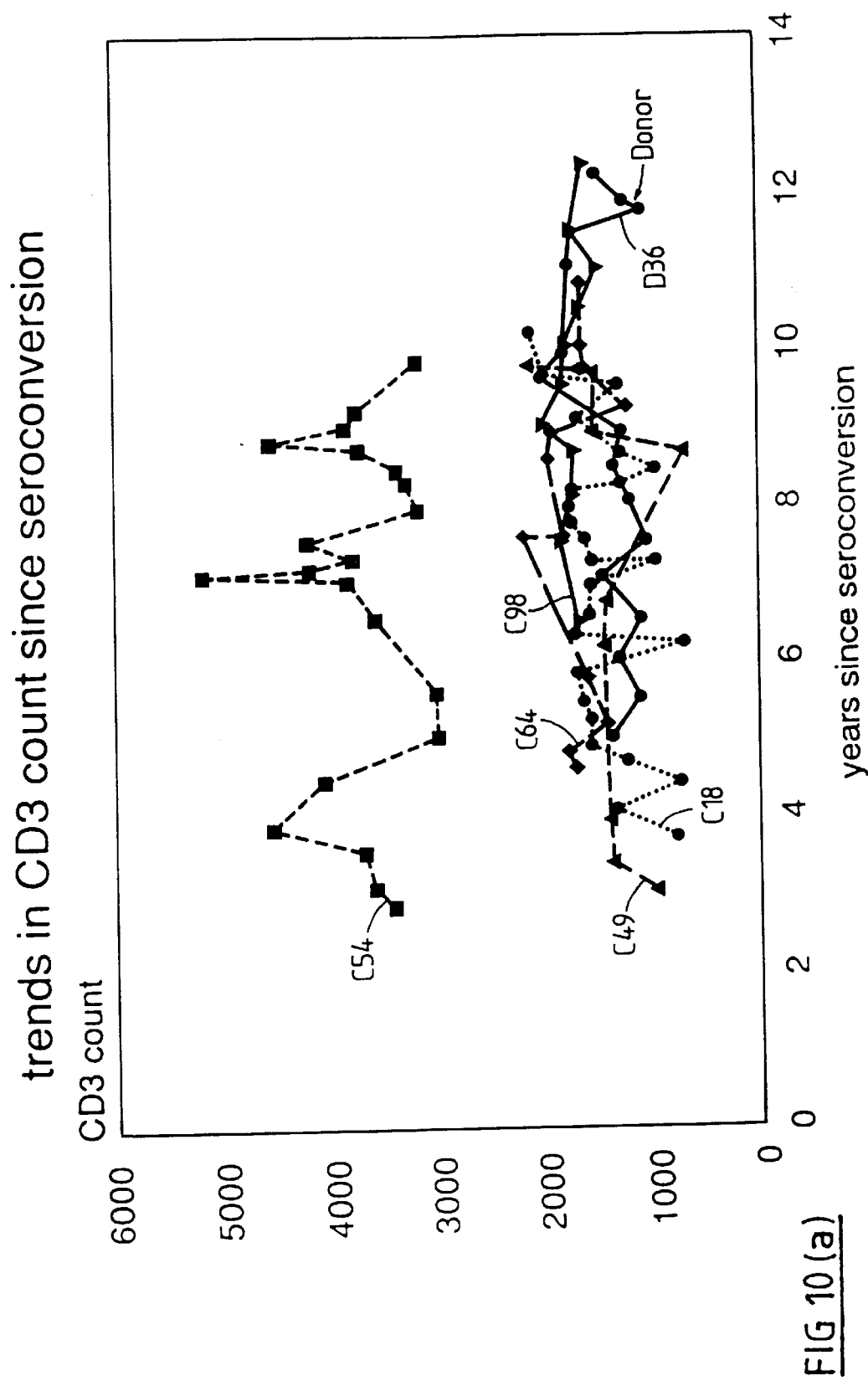
Figure 10C:
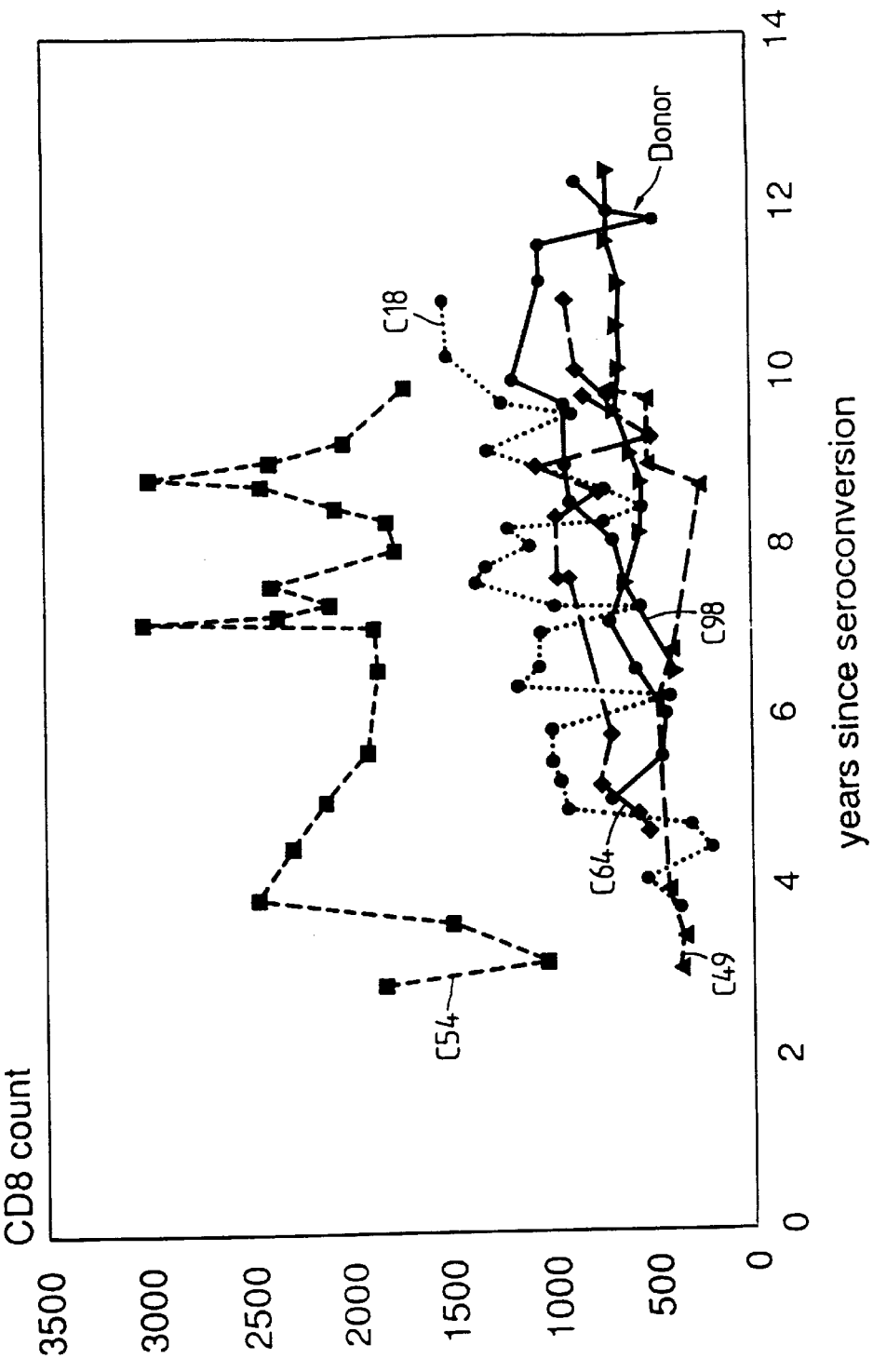
Figure 10D:
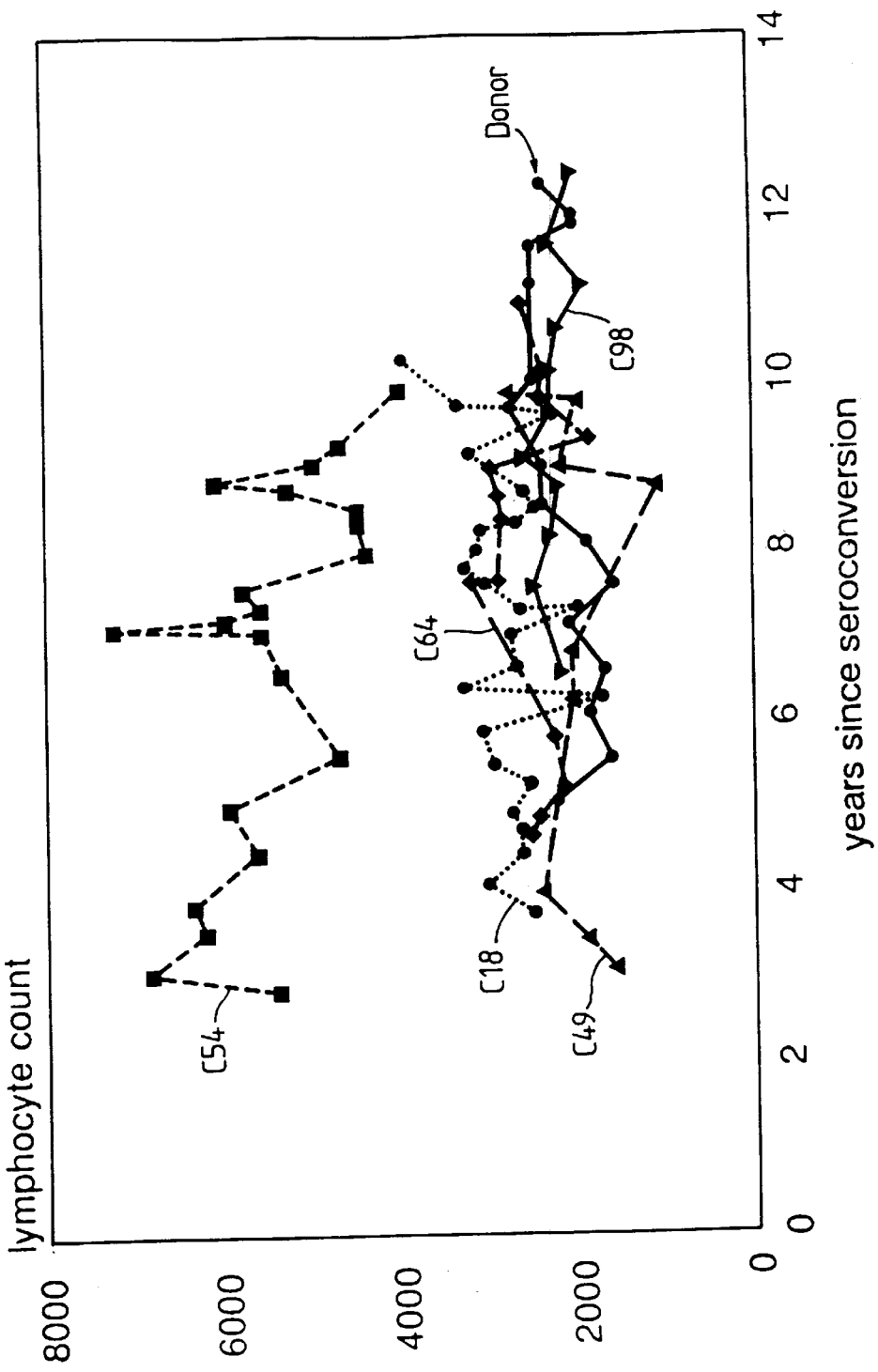
Figure 10E:
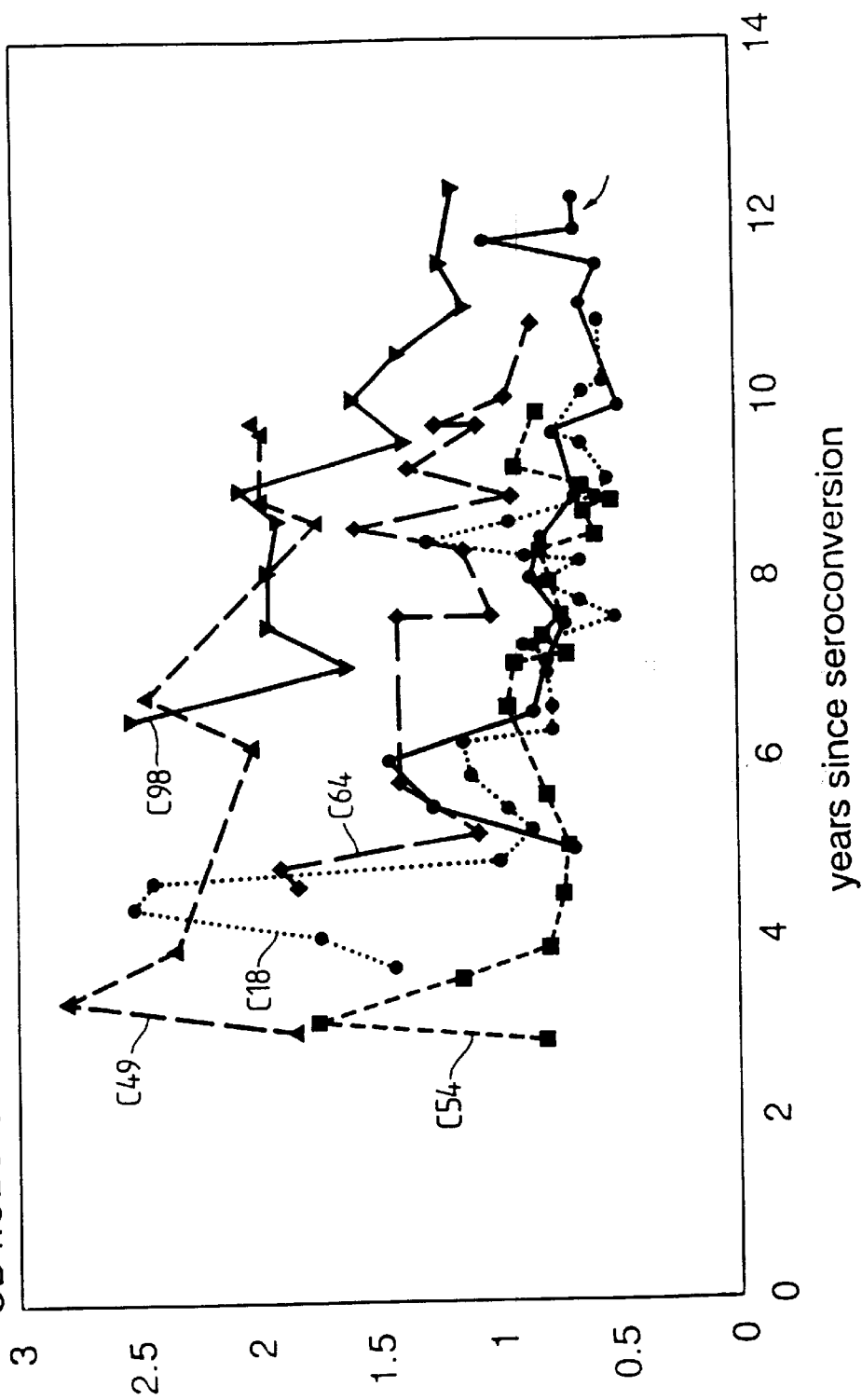
Figure 10G:
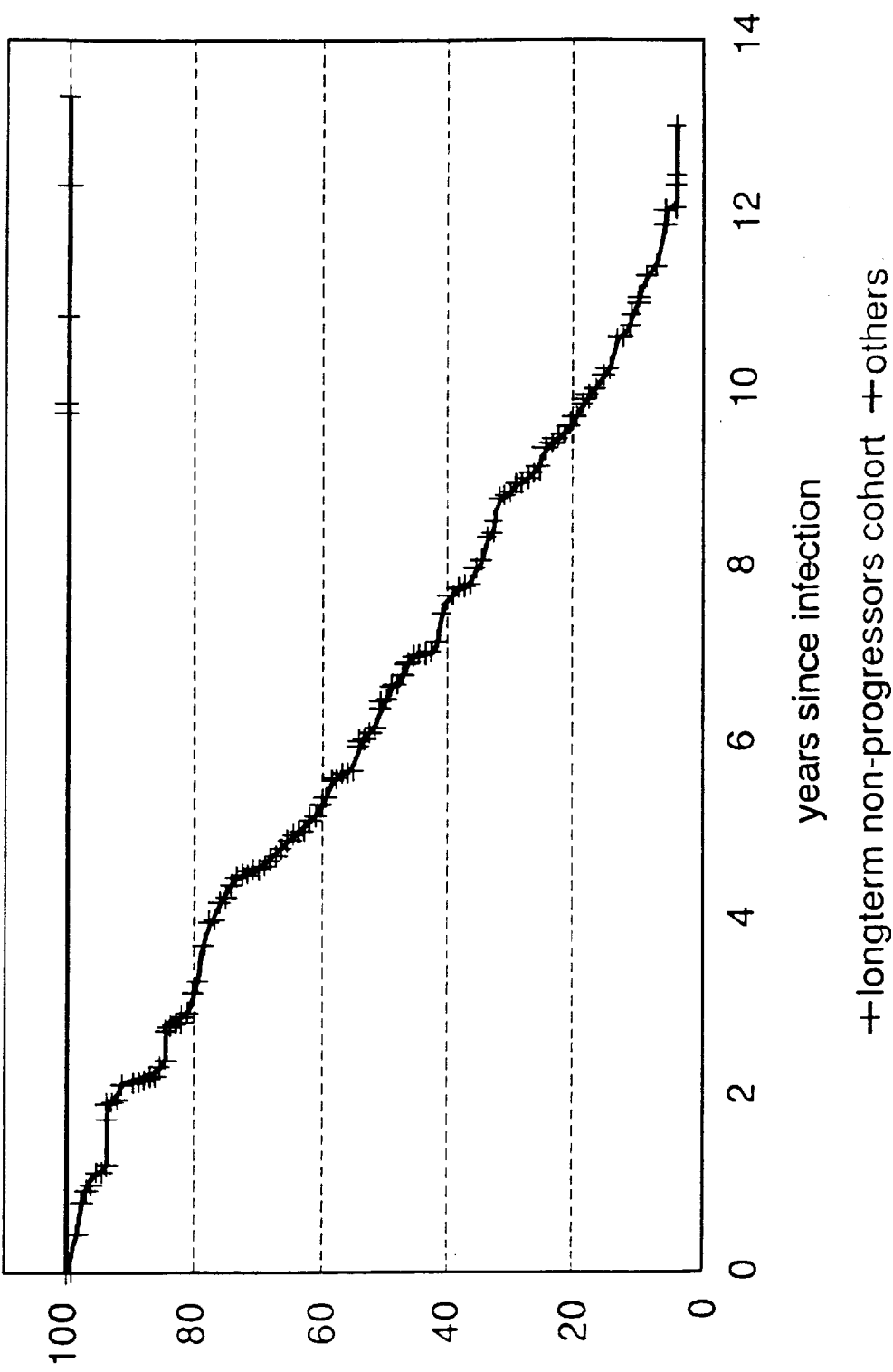

The results are shown in FIGS. 10(a)–(g) and clearly show that the immunological profiles of cohort members are substantially normal further highlighting the non-pathogenicity of the HIV-1 isolates of the present invention. FIG. 10(g) shows a graph of the Kaplan-Meier (Ox and Oates 1989) estimates of time to disease progression (AIDS or CD4>250). The results demonstrate that the difference is large in spite of conservative bias, with a median time to progression of 6.2 years in the main database. An exact logrank test (Cytel Software Corporation, 1989, StatXact: Statistical Software for Exact Nonparametric Inference.

Cambridge, Mass.) was performed, demonstrating that the difference between the groups was highly statistically significant (logrank statistic 11.8, p<0.0001).

nucleotides between the usual NFκKB sites. Downstream of the NFκB sites the sequence of the LTR has a high level of homology (96.2%) with the same region of HIV-1.

TABLE 3

Deletions and their sizes in the nef-alone and the nef/LTR regions of the Long-Term Asymptomatic HIV-1 Sequences

| Sequence | nef-alone Region | Region Deletion (nt) | nef/LTR Region | Region Deletion (nt) | Total Deletion (nt) |
| --- | --- | --- | --- | --- | --- |
| D36 PBMC | 8830–8862 (33) | | 9112–9204 (93) | | |
| | 8882–8928 (47) | | 9281–9371 (91) | 184 | 291 |
| | 9009–9035 (27) | 107 | | | |
| C18 HIV$_{SIV}$ | 8830–9006 (177) | | 9105–9224 (120) | | |
| | 9019–9029 (11) | 188 | 9281–9362 (82) | 202 | 390 |
| C18 HIV$_{MBC}$ | 8792–9041 (250) | 250 | 9105–9224 (120) | | |
| | | | 9281–9366 (86) | 206 | 456 |
| C98 HIV | 9033–9048 (16) | 16 | 9148–9189 (42) | | |
| | | | 9271–9370 (100) | 142 | 158 |
| C54 PBMC | incomplete | ? | 9281–9375 (95) | 95 | 95+ |

Sequence numbering relates to the equivalent position in HIV-1 NLA-3. Numbers in brackets are the delection sizes in nucleotides (nt).
The nef ORF starts at nt 8787 and the 3'-LTR starts at nt 9074 in HIV-1 NL4-3.

EXAMPLE 12

Sequencing of isolate HIV-1 C18$_{MBC}$

The genome of variant HIV-1 designated C18 HIV-1$_{MBC}$ was amplified by the polymerase chain reaction (PCR) as 7 overlapping fragments using the sets of inner and outer oligonucleotide primers, designed using the programme PCRPLAN (IntelliGenetics), listed in Table 5 and either UlTma (Applied Biosystems) or a mixture of KlenTaq and Pfu (KlenTaq LA, Ab Peptides Inc) polymerases (for faithful amplification of long fragments). The resulting fragments were cloned into the SmaI site of the plasmid vector pGEM7Zf+. Insert-containing clones representing each region of the full length variant HIV-1 were sequenced by a nested deletion strategy (Gou & Wu, 1982) and cycle sequencing with Taq polymerase and dye labelled primers complimentary to the T7 or SP6 sites within the cloning vector. Nucleotide sequences were entered and collated by ASSEMGEL and SEQIN (IntelliGenetics) and SEQED (Applied Biosystems) and translated to the encoded amino acid sequences using TRANSL (IntelliGenetics) programmes. Sequence alignments used NALIGN, CLUSTAL (IntelliGenetics) and SEQED programmes.

Figure 9:
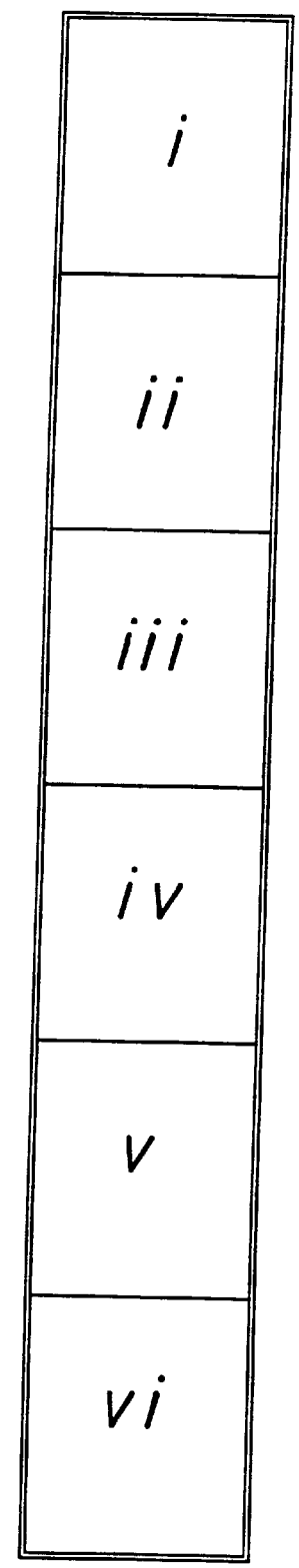

The full length sequence (FIG. 9; SEQ ID NO:800) of isolate HIV-1 C18$_{MBC}$ is 9207 nucleotides long which is 506 nucleotides shorter than the HIV-1 sequence. This size difference is comprised of 126 nucleotides of insertions and 632 nucleotides of deletions, see Table 6. The most extensive differences between the HIV-1 C18$_{MBC}$ sequence and HIV-1$_{NL43}$ are in the U3 region of the LTR and in the nef gene, as hereinafter described.

The 5' LTR has deletions of 120 and 87 nucleotides and a region of low sequence homology, which is the result of an imperfect duplication of the downstream NFκB and Sp1 response sequences. These result in the loss of sequence from a number sites important in the regulation of transcription of HIV-1 genes, including the negative response element (NRE) and the response elements for a number of transcription factors including NF-AT, NRT-1, USF and TCF-1α. Furthermore, the low homology region contains an extra NFκB and Sp1 sites as well as an insertion of 9

The gag gene contains 3 insertions, which represent direct repetitions of adjacent sequences. The first is a perfect repeat of 15 nucleotides after the equivalent of nucleotide 1134 of HIV-1$_{NL43}$ and adds 5 amino acids to the C-terminus region of $p^{17gag}$. The remaining 2 insertions are imperfect and perfect repeats of 30 and 6 nucleotides, respectively, after the equivalent of HIV-1 nucleotides 2163 and 2232, respectively. These encode an extra 12 amino acids in the C-terminus region of $p^{15gag}$ just downstream of the gag to pol frameshift sequences. The variation in sequence length of the gag gene at these two positions is unusual. The homology of the encoded amino acid sequence of HIV-1 C18$_{MBC}$ and HIV-1 for the gag p17, p24, and p15 proteins is 87.1%, 93.5% and 94.3%, respectively.

In the pol ORF, the encoded proteins have high homology with the HIV-1$_{NL43}$ sequences being 95.5% overall comprising p10 protease 92.9%, p66 reverse transcriptase 95.4% and p34 integrase 95.8%. The amino acid sequence of the p61 RT lacks the mutations associated with resistance to the nucleoside (AZT, ddI, ddC)and non-nucleotide Nevirapine) analogue drugs used in the treatment of HIV-1-infected persons.

The vif gene encodes a 192 amino acid protein with 88.0% homology with at of HIV-1. The vpr gene encodes a 96 amino acid protein with 89.6% homology with that of HIV-1$_{NL43}$.

There are 2 insertions and 1 deletion of sequences in the vpu gene. The insertions of 3 and 9 nucleotides are after the equivalent of nucleotide 6071 and 6234, respectively, of HIV-1$_{NL43}$. These add 1 amino acid after amino acid 3, and 3 amino acids after amino acid 59 of the encoded Vpu protein. The deletion of 12 nucleotides after the equivalent of HIV-1$_{NL43}$ nucleotide 6261 deletes 4 amino acids from the C-terminal region of Vpu as well as from the signal peptide of the env polyprotein, which is encoded by an overlapping reading frame. Amino acid sequence homology of HIV-1 C18$_{MBC}$ Vpu with HIV-1$_{NL43}$ is 85.2%.

The sequence encoding the env gp120 has 9 insertions totalling 45 nucleotides (encoding 15 amino acids) and the deletion of a total of 18 nucleotides (encoding 6 amino acids). These are listed in Table 6. All of these events (insertions and deletions) are at positions in the env gene.

This is within the env V3 coding region, immediately upstream of the sequence encoding the so called V3 tip (or loop) amino acid sequence, Gly Pro Gly Arg. The V3 region sequence is that of a typical clade B subtype (North America, Europe and Australia) being identical to the clade B consensus sequence (based on 186 env sequences) at 29/35 positions. The type of amino acid at positions 11 and 28 of the V3 loop region (where position 1 is the Cys at amino acid 266 of the env gp120) is predictive of the viral non-syncytium/syncytium forming phenotype (Fouchier et al, 1992). The HIV-1 C18$_{MBC}$ env gene encoded amino acid sequence has Ser at position 11 and Ile at position 28 of the V3 loop region. The lack of a positively charged amino acid at both positions is strongly indicative of a non-syncytium viral phenotype. The overall amino acid sequence homology with HIV-1$_{NL43}$ (ignoring deletions and insertions) is 86.1%, comprising 85.5% for the gp120 region and 87.6% for the gp41 region.

Both the tat and rev exon open reading frames (ORF) are longer than in HIV1$_{NL43}$. A change of the tat termination codon form TAG to TCG extends the tat ORF to a downstream in phase termination codon extending the encoded tat amino acid sequence by 15 residues, compared with the 86 amino acid long HIV-1$_{NL43}$ tat protein, to a total length of 101 amino acids. However, this is the usual length of the HIV-1 tat protein.

Similarly, the normal rev termination codon is changed from TAG to GAG. This extends the rev ORF to an in-phase termination codon 3 codons downstream so that the encoded Rev protein is 119 amino acids long instead of the usual 116.

As mentioned above the most extensive differences between the sequences of the isolate HIV-1 C18$_{MBC}$ and HIV-1$_{NL43}$ are in the nef gene and the LTR region. While the nef gene overlaps the 3' LTR, these differences are found in both the nef alone and the nef/LTR overlap regions. The HIV C18$_{MBC}$-encoded nef protein is only 24 amino acids long compared with the normal length of 206 amino acids. This severe shortening of the nef protein is due to the deletion of 188 nucleotides (the 177 and 11 nucleotide deletions) from the nef-alone region which also brings into phase a termination codon, TAG, at the resulting 25th codon. Downstream there is further loss of potential nef gene sequences by the 120 and 87 nucleotide deletions situated in the nef/LTR overlap region. The resulting 24 amino acid nef protein is identical to the N-terminus of the HIV-1$_{NL43}$ nef at 9 of the first 10 positions. Thereafter, homology is lost completely.

Some sequences used in the generation of mature mRNAs are altered or lost in C18$_{MBC}$. The dinucleotide immediately after the splice donor site 2 (SD2) at nts 4818–4819 (HIV-1$_{NL43}$ equivalent nts 4963–4964) is changed from the conserved GT to GC. It is expected that this change would lead to loss of function of this site as a splice donor. Splice donor 2 is used in the processing of HIV-1 transcripts to some of the mRNAs that encode Tat, Rev and nef proteins. Similarly the splice acceptor site 7 (SA7) sequence at nts 6477–6478 (HIV-1$_{NL43}$ equivalent nts 6602–6603) is changed from the conserved AG dinucleotide to TC. This change is expected to lead to loss of function of this site as a splice acceptor. While this SA site is used in HIV-1 mRNA processing it is not a major site and is not used in the production of the regulatory proteins (Tat, Rev or nef) mRNAs. The splice donor 12 site is absent form the C18$_{MBC}$ sequence (NL43 equivalent nts 9161–9162) as it is within the first deletion region in the nef/LTR overlap region which occurs at nt 8797 and results in the loss of NL43 nucleotides 9105 to 9224. It is significant that the SA12 site is absent from the sequence of all of the cohort virus isolates so far obtained as well as from the sequence of D36 PBMC, however, the C54 PBMC sequence does contain the SA12 site. SA12 is not used in the processing of mRNAs that encode the viral regulatory proteins. Normally SA12 is used in splicing in conjunction with SD1, 2, 3 and 4 and the resulting spliced RNA is probably not a mRNA but may have a regulatory role involving binding to cellular proteins (Smith et al, 1992).

An interesting feature of the sequence of the HIV-1 C18$_{MBC}$ isolate is the deletion and rearrangement of sequence from the 5'-LTR U3 region and the deletion of sequence from the nef gene (both nef alone and nef/3' LTR regions). These being the only features of the sequence distinct from disease-causing HIV-1. The lack of AIDS or AIDS-like symptoms in the patient C18 is attributed to the effects of the loss of LTR sequence and/or the loss of nef coding sequences and their role in the pathogenesis of AIDS.

TABLE 4

Primers used to Amplify Overlapping regions of HIV-1 C18$_{MBC}$

| Primer | 5'-Coordinate | Direction (+/-) | Primer Length (nt) | Sequence |
|---|---|---|---|---|
| CL 1A | 1 | + | 30 | TGGAAGGGCTAATTTACTCCCAAAAAAGAC |
| CL 14 | 896 | - | 25 | AATCGTTCTAGCTCCCTGCTTGCCC |
| CL 1B | 1 | + | 30 | AATCCCGGGTGGAAGGGCTAATTTACTCCC |
| CL 13 | 796 | - | 31 | CCTCTAGACCGCTTAATACTGACGCTCTCGC |
| CL 11 | 682 | + | 23 | TCTCTCGACGCAGGACTCGGCTT |
| CL 18 | 3440 | - | 30 | CTGTTTTCTGCCAGTTCTAGCTCTGCTTCT |
| CL 12A | 732 | + | 26 | TTTCCCGGGCGGCGACTGGTGAGTAC |
| CL 17 | 3330 | - | 32 | CCCTCTAGACTTGCCCAATTCAATTTTCCCAC |
| CL 26 | 3193 | + | 39 | CCACACCAGACAAAAAGCATCAGAAGAACCCCCATTCC |
| CL 6B | 9671 | - | 39 | TGCTAGAGATTTTCCACACGGACTAAAATGGTCTGACGG |
| CL 27 | 3251 | + | 39 | CCATCCTGATAAATGGACAGTACAACCCATAGTACTGCC |
| CL 28 | 639 | - | 37 | TGGCCCAAACATTATGTACCTCTGCATCATATGC |
| CL 19 | 5448 | + | 30 | AGCAGGACATAACAAGGTAGGATCTCTACA |
| CL 24 | 8422 | - | 28 | GGATCTGTCTCTGTCTCTCTCTCCACCT |

Underlined sequences depict added restriction enzyme site
+ and - orientations refer to sense and antisense strands of the double stranded DNA sequence

TABLE 5

Sequence Deletions and Insertions in HIV-1 C18$_{MBC}$
Compared with HIV-1$_{NL43}$

| Gene or Region | Position (nt) C18$_{MBC}$ | Position (nt) NL-43 | Deletions (nt) | Insertions (nt) |
|---|---|---|---|---|
| 5'-LTR U3 | 29 | 29 | 120 | — |
| 5'LTR U3 | 85 | 205 | 87 | — |
| 5'LTR U3 | 154 | 360 | — | 9 |
| gag p17 | 939 | 1134 | — | 15 |
| gag p15 | 1982 | 2163 | — | 30 |
| gag p15 | 2081 | 2232 | — | 6 |
| vpu | 5927 | 6062 | — | 3 |
| vpu/env | 6092 | 6234 | — | 9 |
| vpu/env | 6128 | 6261 | 12 | — |
| env | 6483 | 6628 | — | 6 |
| env | 6514 | 6653 | 2 | — |
| env | 6524 | 6665 | 1 | — |
| env | 6630 | 6772 | — | 9 |
| env | 6646 | 6778 | — | 3 |
| env | 7011 | 7141 | 6 | — |
| env | 7140 | 7276 | 3 | — |
| env | 7195 | 7334 | — | 6 |
| env | 7266 | 7399 | 3 | — |
| env | 7278 | 7414 | — | 6 |
| env | 7290 | 7420 | — | 2 |
| env | 7300 | 7429 | — | 1 |
| env | 7314 | 7441 | 3 | — |
| env | 7463 | 7593 | — | 3 |
| env | 7471 | 7598 | — | 9 |
| nef | 8711 | 8829 | 177 | — |
| nef | 8723 | 9018 | 11 | — |
| nef/LTR | 8798 | 9104 | 120 | — |
| nef/LTR | 8854 | 9280 | 87 | — |
| LTR U3 | 8923 | 9435 | — | 9 |
|  |  |  | 632 | 126 |

EXAMPLE 13

Macrophage Isolates of HIV-1 C18 and HIV-1 C98

HIV-1 has been isolated from the macrophages of patients C18 and C98.

Patient monocytes were prepared as follows. Whole blood was spun at 2000 rpm for 10 minutes. Plasma was removed into a separate tube and the remaining cells were diluted 1:2 in PBS$^-$ (magnesium and calcium free phosphate buffered saline). This was underlaid with 10 ml of Ficoll Isopaque and spun at 2000 rpm for 20 minutes. Cells were collected from the interphase and washed three times with PBS$^-$. These cells were then seeded into a 6 well Costar tray at a concentration of $1.0\times10^7$/ml and allowed to adhere for 1 hour. Any non-adherent cells were removed by aspiration.

Donor HIV-1 negative macrophages for use in co-cultivation were prepared as follows. Peripheral blood mononuclear cells were purified from whole blood using Ficoll/Isopaque density gradient. These cells were seeded at a concentration of $2.0\times10^6$/ml in teflon. PBMC were cultured in the presence of 3 μg/ml of PHA and 1000 U/ml of M-CSF 3 days prior to co-culture.

On day of co-culture, donor PBMC were CDS depleted. Dyna beads coated with anti-CD8 were used for this purpose. Dyna beads were washed once in PBS$^-$ and then applied to a magnet for 3 minutes. Supernatant was removed and the beads were then resuspended in 250 μl of RF-10. Aliquots of $2.0\times10^8$ patient cells were then added to 250 μl (3 beads: 1 CD8 T-cell) of Dyna beads and allowed to incubate for 30 minutes on ice with occasional mixing. After 30 minutes the cell suspension was placed onto a magnet for 3 minutes. The supernatant was then removed placed into a second tube containing 142 μl (1 bead: 1 CD8 T-cell) of Dyna beads. This suspension was placed on ice for an additional 30 minutes with occasional mixing. After 30 minutes cell suspension was placed onto a magnet for 3 minutes. Supernatant was removed and washed once in RF-10.

For co-culture, CD8 depleted PBMC were then added to patient monocytes. Half media changes were done every 7 days for a period of 21 days. Aliquots of 2.5 ml of medium was removed from these cultures and replaced with CD8 depleted donor PBMC in Iscoves containing 10% HuS (Human serum), 5% v/v FCS and 5% w/v IL-2 and 1000 μU/ml of M-CSF. Harvested supernatants were spun at 1400 rpm for 10 minutes and stored as 1 ml aliquots. Cell pellets were lysed in 200 μl of lysis buffer for PCR analysis. Infection was quantitated using a p24 EIA Kit.

Cells were harvested from the co-cultures and used to prepare DNA as described above. The nef/3'-LTR region of both virus isolates was amplified by PCR using the above described primer sets and conditions (Example 12). The resulting amplimers were cloned into the plasmid vector pT7T3U19 and the nucleotide sequence determined by the Taq cycle sequencing method with dye-labelled primers.

The C18 macrophage sequence has 3 deletions starting and finishing at positions within 3 nucleotides of the same deletions in C18$_{MBC}$. The encoded nef protein is 3 amino acids long compared with 7 amino acids for C18$_{MBC}$. The low homology region of the LTR U 3 region of C18 macrophage is very similar in sequence to C18$_{MBC}$ and similarly it has one extra upstream NFκB site.

On the other hand, the sequence of C98 macrophage has a number of differences from the C98 isolate. While it has exactly the same first deletion of 16 nucleotides just upstream of the polypurine tract (PPT), in the nef-alone region, and exactly the same second deletion (position and size) it has an extra deletion of 18 nucleotides at HIV-1$_{NL43}$ equivalent nucleotides 9206 to 9223. The final deletion is in approximately the same position as in the C98 isolate but is 5 nucleotides longer. The encoded nef protein is 34 amino acids long compared with 86 amino acids for the C98 isolate. The low homology region is very similar to the C98 isolate, having the same 2 extra upstream NFκB sites and completely lacking the normal 5'-NFκB site.

EXAMPLE 14

Construction and Use of an Infectious Molecular Clone

Molecular biological techniques can be used to construct a molecular clone of, for example, HIV-1 C18$_{MBC}$. Two schemes may be used. In the first scheme genomic DNA, extracted from either the CD4 positive PBMC of the patient C18 or donor PBMC that have been infected with the isolate HIV-1 C18$_{MBC}$, is used as the template for polymerase chain reaction amplification, using thermostable polymerase of high transcriptional fidelity (eg UlTma polymerase or KlenTaq/Pfu polymerase mixture), of long (6 to 7 kb) overlapping fragments representing the 5'- and 3'-parts of the HIV-1 C18$_{MBC}$ proviral genome of total length 9207 nts. The amplified fragments may then be ligated together after digestion with a restriction enzyme that cleaves at a unique site common to the overlapping region of the amplified fragments, for example the unique Bgl I or Nco I sites. Ligation of this full length proviral DNA into a plasmid vector will allow its propagation in E coli and the subsequent preparation of large (mg) quantities of this molecularly cloned proviral DNA.

In the second scheme donor PBMC that have been infected with the isolate HIV-1 C18$_{MBC}$ are used as a source of non-integrated proviral DNA which can be extracted from the infected cells by the Hirt extraction method (Hirt, 1967). Circular proviral DNA molecules may be linearised by digestion with a restriction enzyme that cleaves at a unique position in the genome (eg the Bgl I or Nco I sites). The resulting linearised molecules can be ligated into a plasmid Or, more usually, a bacteriophage lambda (λ) based vector (eg Charon 4a, λWES) after modification of the end to provide blunt or cohesive ends compatible with the vector. Transformation or transduction of *E coli* with the recombinant plasmid or bacteriophage material, respectively allows the propagation of the proviral DNA. Clones of *E coli* containing proviral DNA may be selected and DNA prepared. Molecular clones of retroviral genomes prepared in this way are often permuted. Rearrangement to the functional arrangement of sequence is achieved by restriction enzyme cleavage and religation of fragments to reconstruct the correctly permuted proviral genome.

The molecularly cloned DNA products of both schemes can be used to prepare variant proviral genomes that may be used as the basis of a biologically attenuated HIV-1 vaccine strain. Similarly, they may be modified to contain extra DNA sequences in the nef-alone deletion region that may deliver sequences that may be of therapeutic advantage (eg antisense or ribozyme sequences).

Infectious virus particles of HIV-1 C18$_{MBC}$, or modified virus, can be produced by transfection of human cells (eg HeLa cells) which will produce, and release to the culture medium, virus particles of HIV-1 $C18_{MBC}$, or modified virus. These virus particles can be used to infect a variety of CD4 positive cells for further propagation or experimentation.

EXAMPLE 15

In vivo Primate Model

Following construction of infectious molecular clones of the mutant HIV-1 strains, studies are then undertaken in primates to establish attenuation, immunogenicity and vaccine prophylactic efficacy. AU studies compare mutant clones of HIV-1 with isogenic wild-type (WT) virus. Initial studies are performed using the macaque (*M nemistrina*) model of HIV-1 infection. Macaque-infectious WT HIV-1 and mutant clones are compared with respect to duration of viremia, anatomic sites of replication, and cellular and humoral immune responses. Where the mutant HIV-1 clones induce an immune response in the macaques infected, challenge studies with WT virus are also performed. Studies are performed in a limited number of chimpanzees, generally in parallel with the macaque studies. Relevant mutations are engineered into WT HIV-1 clones previously shown to produce chronic infection in chimps, and the course of chimp infection with mutant clones compared with historical controls. If infection is established, WT challenge studies is also performed.

Examples 16 to 21 relate to the screening of antibodies in HIV-1 infected individuals to peptides covering regions of Nef.

EXAMPLE 16

Study Subjects

Serum samples were obtained from seven HIV+ve individuals, D-36, C-124, C-98, C-64, C-18, C-49 and C-54. Individuals C124, C-98, C-64, C18, C49 and C-54 (recipients) were infected through units of blood or blood products from donor D36, over a 2-year period. Long-term follow-up of the six recipients and the donor, shows persistent long term asymptomatic infection. This group is referred to herein as the long term non-progressor 1 (LTNP1) cohort. Members of this cohort have been infected for an average of 11 years (10.75 to 14 years) and it was established that the donor had been infected since April 1981 (Learmont et al, 1992). Regular follow-up includes history, physical examination, full blood count, T-cell subset counting and measurement of serum p24 antigen and β2-microglobulin concentrations (Learmont et al, 1992; Learmont et al, 1995). As controls, sera were obtained from 14 HIV-1 negative individuals (HIV-1-ve). 4 patients who were infected with HIV-1 through sexual activity or through blood transfusion and are also considered long-term non-progressors and 12 HIV-1 positive (HIV-1+ve) individuals that have developed clinical infections (long term progressors, LTP). Sera from patients with autoimmune disease and who were HIV-1-ve were also employed.

EXAMPLE 17

Peptide Synthesis

Peptides corresponding to amino acid residues 1 to 19, 20 to 36, 44 to 65, 72 to 83, 89 to 97, 109 to 114, 121 to 136, 162 to 177, 164 to 186 and 187 to 206 of HIV-1 nef (HIV-$1_{NL43}$) were synthesized using standard t-Boc chemistry and purified by high pressure chromatography as described elsewhere (Fecondo et al, 1993).

EXAMPLE 18

Expression of recombinant HIV-1 Nef protein in *E. coli*

The large scale expression of the 27 kDa form of HIV-$1_{NL43}$ in *E coli* and subsequent purification were as described by Azad et al (1994).

EXAMPLE 19

Screening of sera from HIV-1+ve individuals and control HIV-1-ve groups for reactivity against Nef protein and derived peptides by direct ElA For detecting antibodies that recognise the Nef protein or its peptide derivatives, highly purified full length Nef protein or peptides corresponding to the HIV-$1_{NL43}$ Nef amino acid sequence were coated onto the wells of 96-well polysyrene microtitre plates at 100 ng/well or 500 ng/well in PBS, respectively. Peptides and proteins were allowed to coat for 2 h at 37° C. After this incubation period the wells were washed three times with PBS containing 0.05% v/v Tween 20 (PBS-Tween) and any remaining available sites on the wells blocked by incubation of 150 μl of gelatine (1% w/v) in PBS for 1 h at 37° C. Following washing with PBS-Tween as described above, 50 μl of serum diluted in PBS/BSA (1% w/v) was added to the wells and incubated for 1.5 h at 37° C. Sera added to the wells included that from the seven cohort members (D36, C98, C18, C54, C49, C64 and C124 [see Learmont et al, 1992]) and the control groups described above. The wells were again washed with PBS/Tween and subsequently incubated with 50 μl of biotinylated sheep anti-human Ig (diluted 1:1000 in 1% w/v BSA/PBS; Amersham) for 1 h at 37° C. Following further washing, 50 μl of Streptavidin-HRP (diluted 1:1000 in 1% w/v BSA/

PBS; Dakopatts) was added to the wells and the plate incubated at 37° C. for 30 min. An aliquot of 100 μl of substrate (O-phenylenediamine, Sigma) was finally added after washing and the plate allowed to incubate at room temperature for 15 min. The reaction was stopped by the addition of 1N $H_2SO_4$ and the plate read at 450/630 nm using a Titertek plate reader.

EXAMPLE 20

Recognition of full length recombinant Nef protein by patient sera

The prevalence of a Nef-specific antibody response in the cohort members (referred to herein as (LTNP1), long term progressors (LTP) HIV-1+ve individuals and another group of long term non-progressors (LTNP2) patients who were infected by different donors was assessed by EIA. Sera obtained from 14 normal individuals (HIV-1-ve) and 14 individuals with autoimmune disease (A/HIV-1-ve) were used as controls.

Figure 12B:
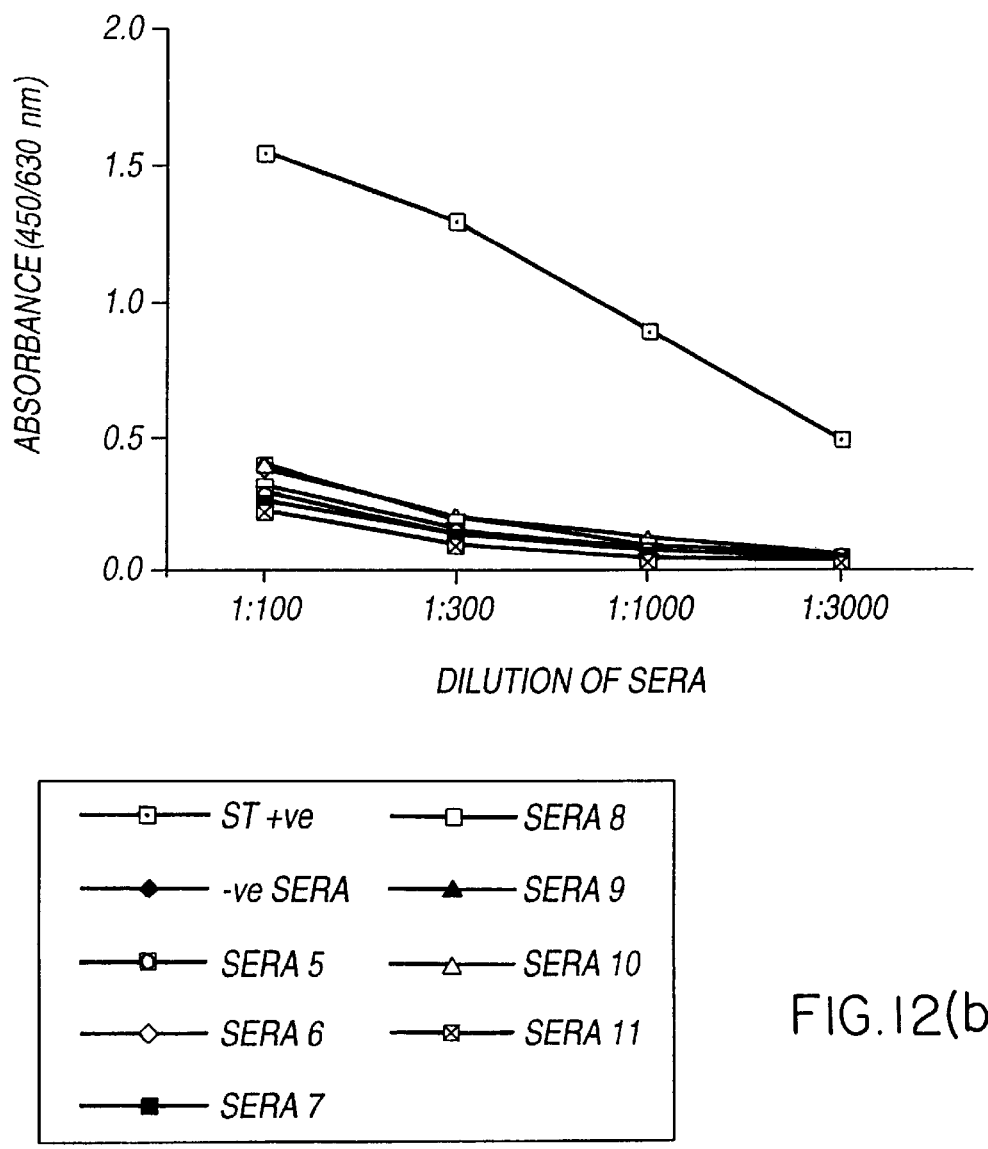
Figure 12C:
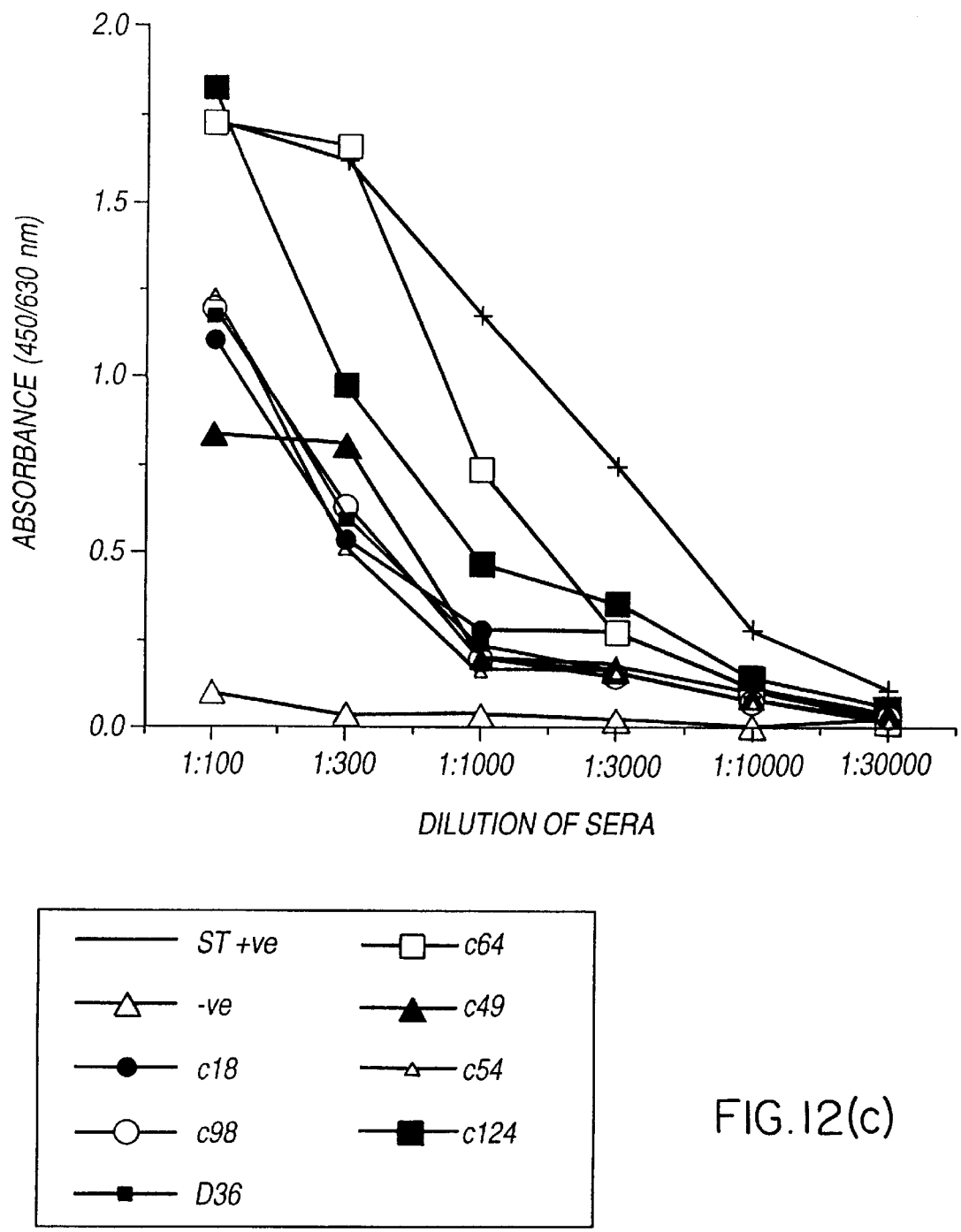
Figure 12D:
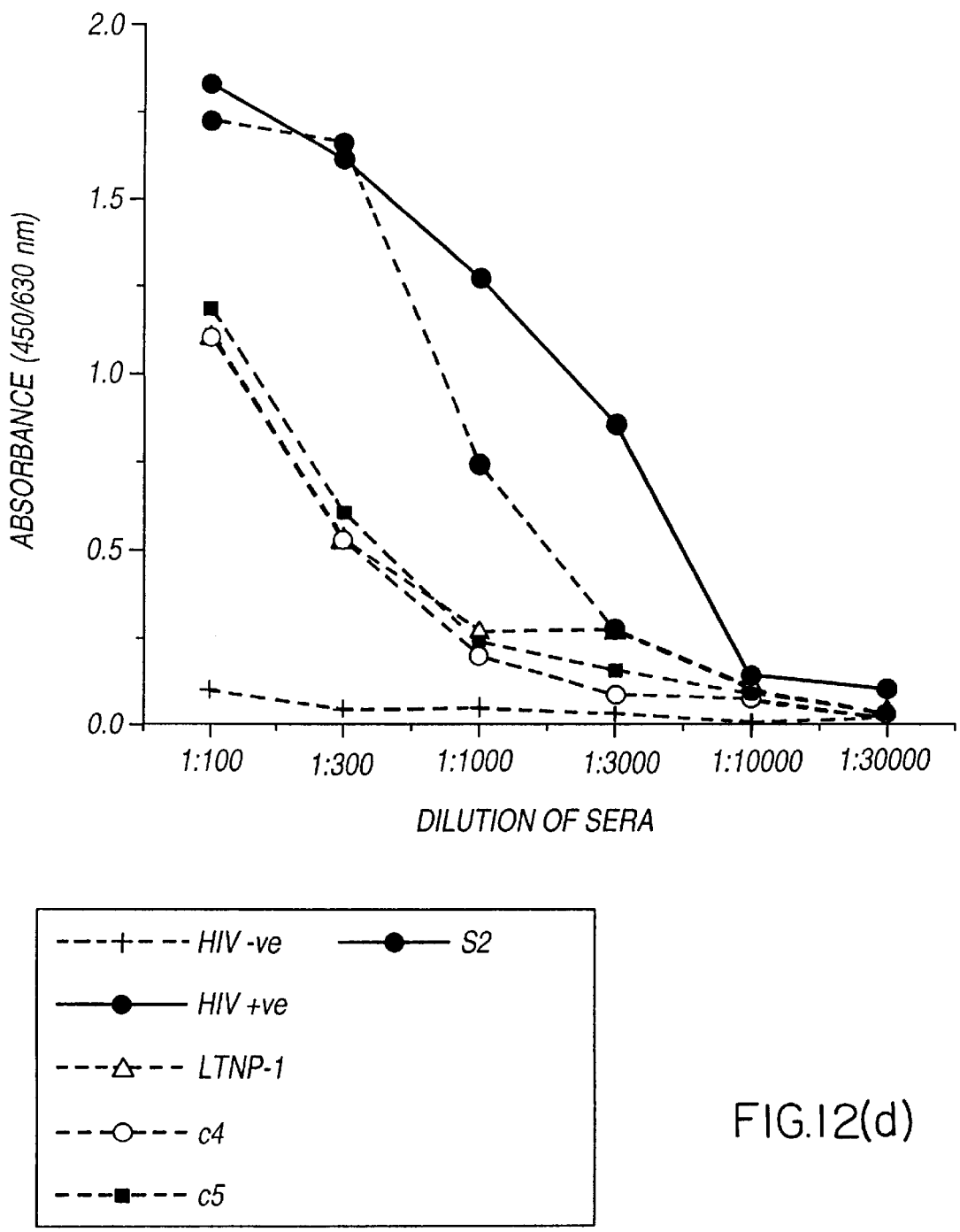

All individuals who were classified as LTP patients demonstrated high levels of antibodies that recognised full length Nef protein (FIG. 12a). Sera obtained from HIV-1-ve or the A/HIV-1-ve groups showed only low level recognition, which was considered at background levels, towards Nef protein (FIGS. 12b(i)–(iii)). In contrast to normal individuals, sera obtained from the LTNP1 cohort showed high recognition of Nef (FIG. 12c), indicating the presence of significant levels of Nef antibodies in the sera of these individuals. The sera titered out to approximately 1:3000. Similar levels of Nef antibodies were observed in the LW group (FIG. 12a). Nef-positive antibodies were also detected in the LTNP2 group and again titered at 1:3000 dilution (FIG. 12d).

EXAMPLE 21

Recognition of Nef-derived peptides by sera

Figure 13A:
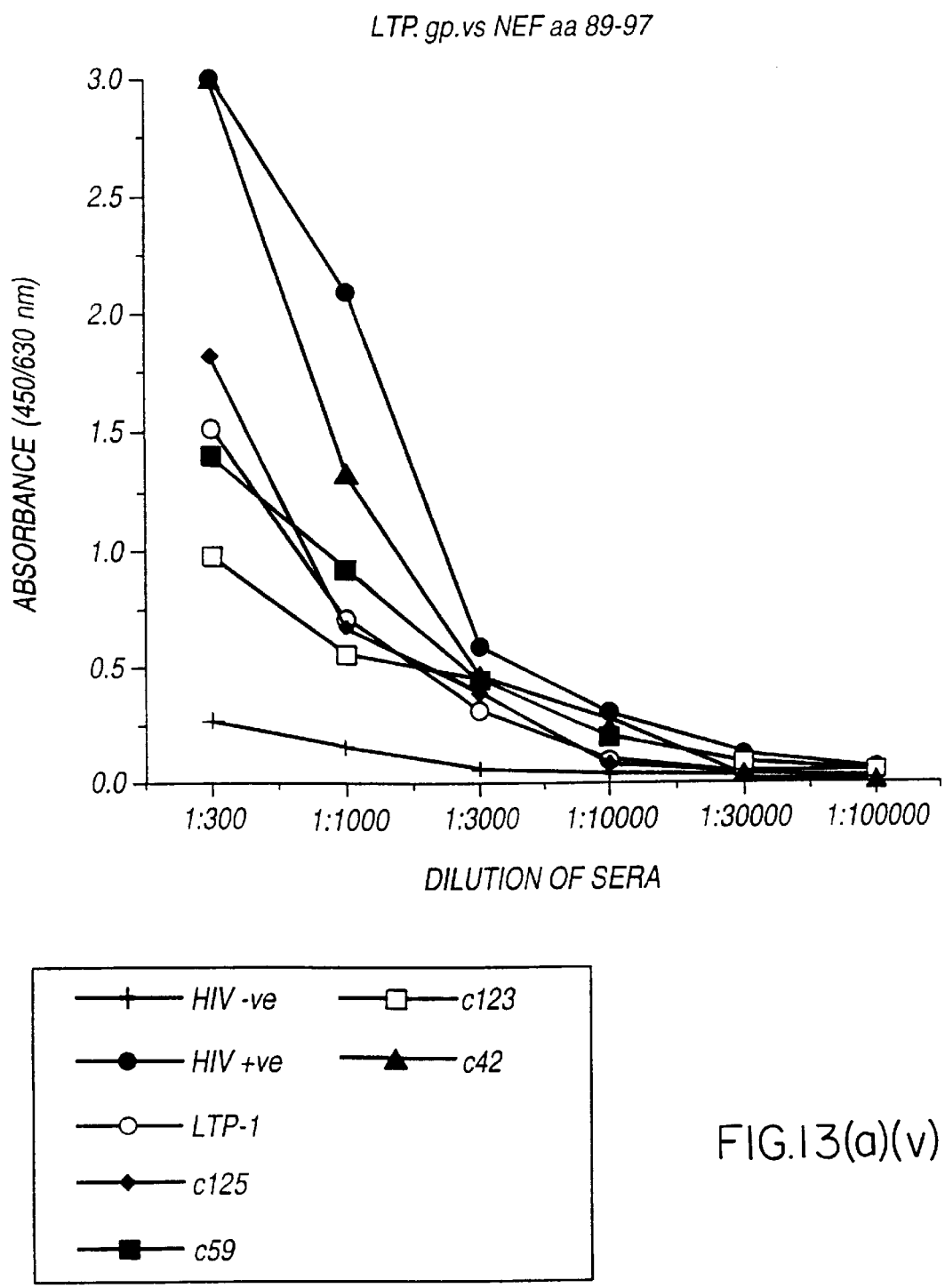
Figure 13C:
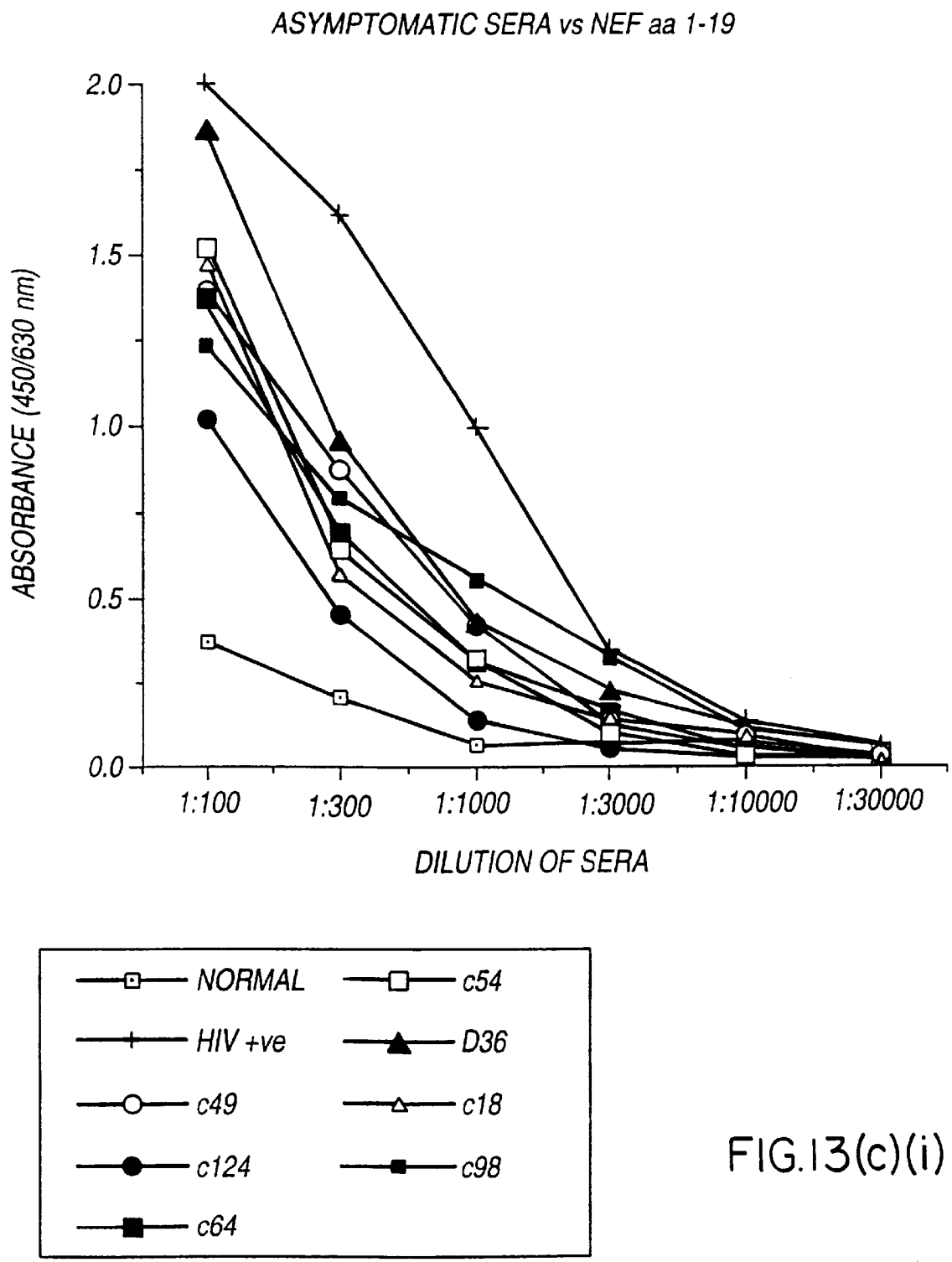
Figure 13C:
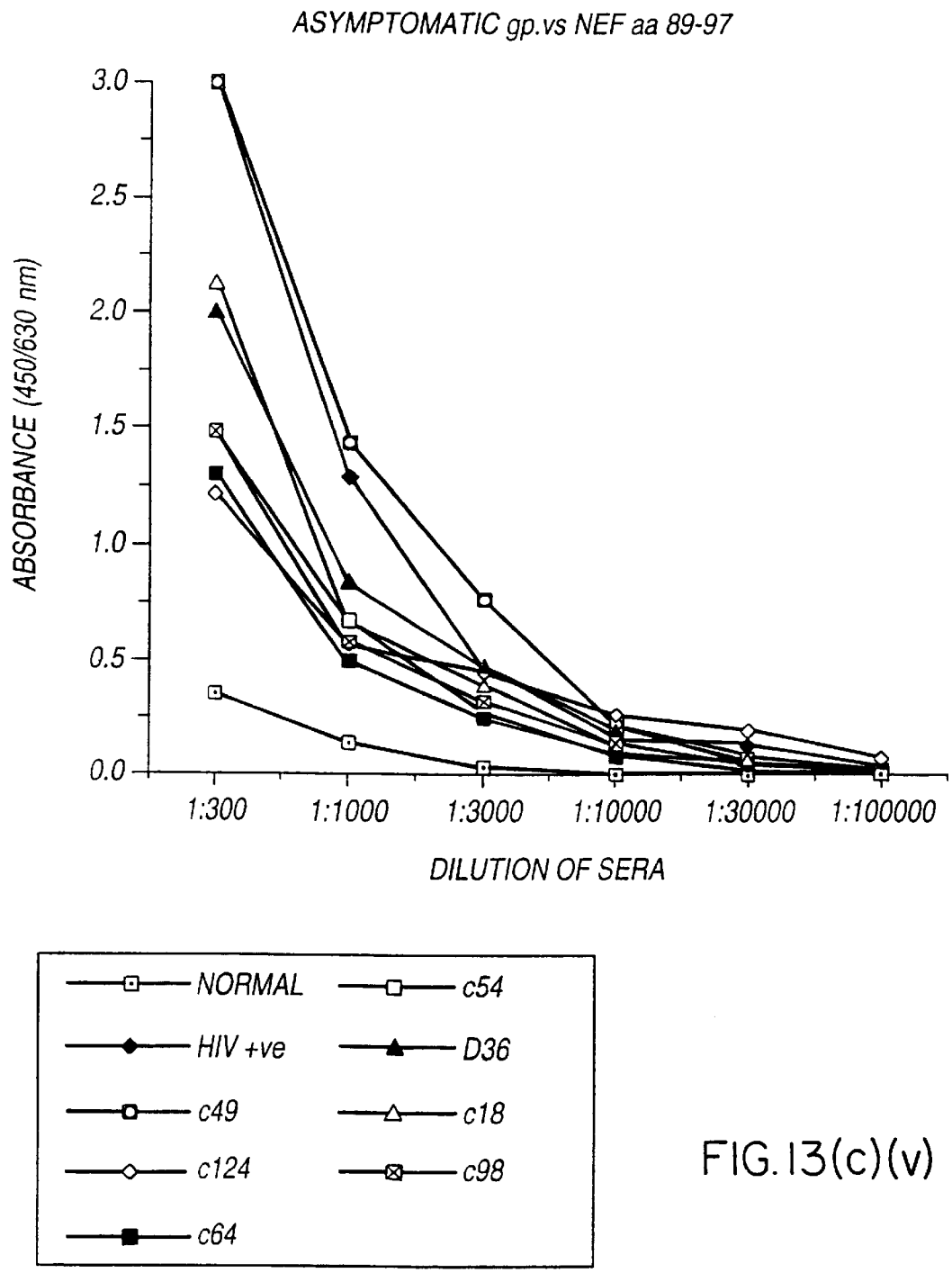
Figure 13D:
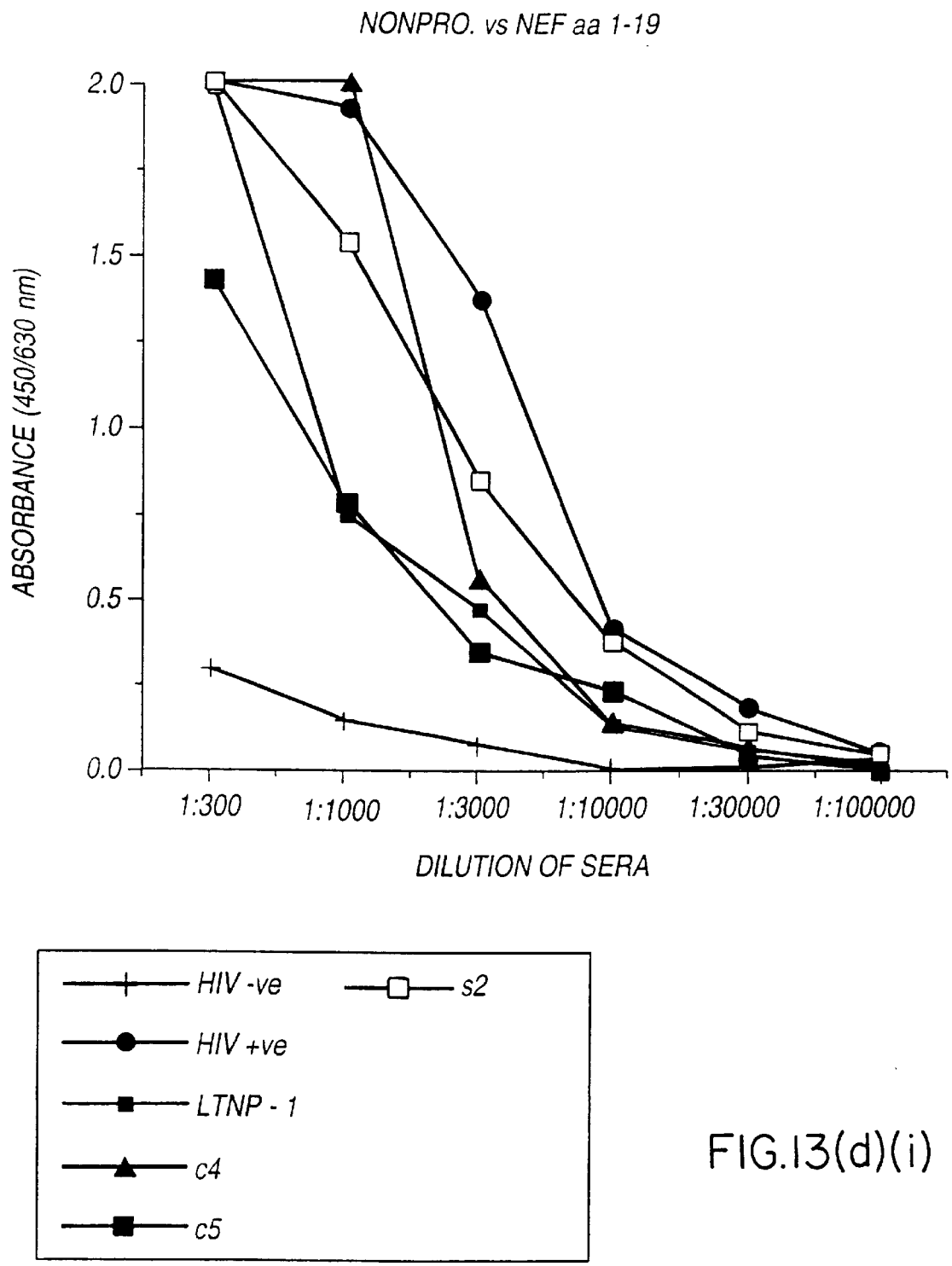
Figure 13D:
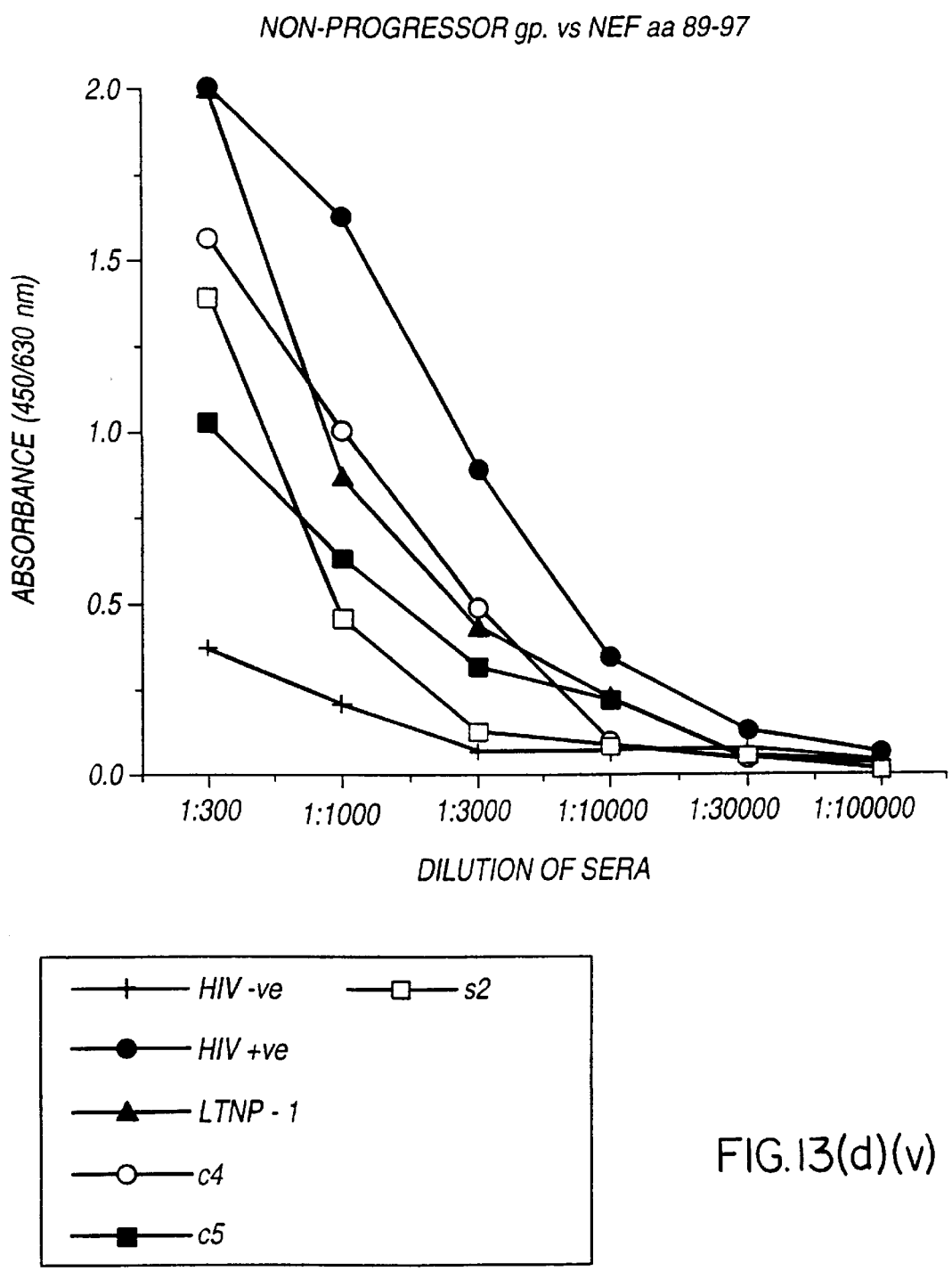

Recognition of synthetic peptides, which correspond to amino acid sequences of Nef, by the LTNP1 cohort was assessed. Various peptides were assessed to detect those antigenic epitopes of Nef protein recognised by these individuals. Peptides corresponding to amino acid sequences 1 to 19; 20 to 36; 44 to 65; 72 to 83; 89 to 97; 109 to 114; 164 to 186; 187 to 206; 121 to 135 and162 to 177 of HIV-$1_{NL43}$ Nef protein were used to screen sera for the presence of specific antibodies. All sera from the LTP group recognised all Nef-derived peptides tested (FIGS. 13a(i)–(x)). Sera titered between 1:1000 and 1:10,000. Sera from patients with autoimmune disease displayed only low background non-specific recognition. Normal sera from HIV-1-ve individuals tested to date also displayed only background activity (FIG. 13b). Sera from the LTNP1 and LTNP2 groups also showed significant reactivity against Nef peptides corresponding to Nef amino acid sequences 1–19, 20–36, 44–65, 72–83, 89–97, 109–114, 121–135, 164–86 and 187–206 (FIGS. 13c(i)–(x) and d(i)–(x)). Sera from the LTNP2 group also showed significant reactivity against Nef peptide 162–177 (FIGS. 13d(i)–(x)), similar to that showed by the LTP group, indicating that this region of Nef was immunogenic. However, sera from the LTNP1 cohort showed no significant reactivity towards peptide 162–177 above background levels obtained with normal HIV-1-ve sera FIGS. 13c(i)–(x)), indicating that this group of individuals were exposed to cells expressing a Nef protein which did not contain this region. While sera from the LTNP1 cohort did not react with the peptide corresponding to amino acid residues 162–177 of Nef, the sera from all patients did recognise a longer peptide, 164 to 186, which encompassed most of Nef 162–177. This clearly indicates that the sera recognised antigenic epitopes between 177–186.

These results clearly indicate that all individuals from the LNTP1 cohort were exposed at some time to HIV-1 infected cells expressing a Nef protein that only had a small deletion encompassing amino acids 162 to 177.

The antibody testing has identified an antigenic region in the Nef protein which if deleted gives rise to attenuated HIV-1 viral strains. Hence, testing of the HIV-1 positive population may identify further examples of individuals infected with attenuated viral quasispecies. Additionally, lack of recognition of this antigenic epitope offers an antibody assay for testing animals experimentally infected with an HIV-1 nef attenuated viral strain, in particular deleted in the region covering Nef amino acids 162 to 177 (relative to HIV-$1_{NL43}$ Nef).

Those skilled in the art will appreciate that the invention describe herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

AZAD et al (1994) *J. Gen Virol.* 75: 651–655.
BACHMANN B. LÜKE W AND HUNSMANN G (1990). *Nucl Acids Res* 18:1309.
BARRE-SINOUSSI F, CHERMANN J C, REY F, et al (1983) *Science* 220: 868–871.
BUSCH MP, EL AMAD Z. SHEPPARD HW, ASCHER MS. LANG W (1991) *N Engl J Med* 325: 733–735.
CHENG-MAYER C, SHIODA T, LEVY J A (1991) *J Virol* 65: 6931–6941.
CLERICI M, STOCKS NI, ZAJAC R A, et al (1989) *J Clin Invest* 84: 1892–1899.
COX and OAKES (1989) *Survival Analysis*, Chapman & Hall.
DANIEL M D, KIRCHHOFF F, CZAJAK S C, SEHGAL P AND DESROSIERS R C (1992). *Science* 258: 1938–1941.
DELWART E L, et al (1993) *Science* 262: 1257–1261.
FECONDO et al (1993) *AIDS Res. Hum. Retro.* 9: 733–740.
FOUCHER RAM, et al (1992) i J Virol. 66: 3183–3187.
GAYNOR R (1992). *AIDS 6m* 347–363.
GOU L-H and WU R. (1982) *Nucleic Acids Research* 10: 2065–2084.
GREENWAY et al (1994) *Virology* 198: 245–256.
GROENINK M, FOUCHIER RAM, BROERSEN S, et al (1993) *Science* 260: 1513–1515.
HAMMES S R, DIXON E P, MALIM M H, CULLEN B R and GREENE W C, (1989) *Proc Natl Acad Sci USA* 86: 9549–9553.
HIRT B. (1967) *J Mol Biol* 26: 365–369.
HWANG S S, BOYLE T J, LYERLY HK, CULLEN B R (1991) *Scince* 253: 71–74.
KASLOW R A, DUQUESNOY R. VAN RADEN M, KINGSLEY L, MARRARI M. (1990) *Lancet* 335: 927–930.
KEMP B E, RYLATT D B, BUNDESEN P G, DOHERTY R R, MCPHEE D A, STAPLETON D, COTTIS L E, WILSON K, JOHN M A, KHAN J M, DINH D P, MILES S & HILLYARD C J (1988). *Science* 241: 1352–1354.

KESTLER H W, RINGLER D J, MORI K, PANICALI D L, SEHGAL P K, DANIEL M D & DESROSIERS R C (1991). *Cell* 65: 651–662.

KIERNAN R. et al (1990) *AIDS Res. Hum. Retroviruses* 6: 743–752.

KIM S. IKEUCHI K, BYRN R, GROOPMAN J and BALTIMORE D (1989) *Proc Natl Acad Sci USA* 86: 9544–9548.

LANG W. PERKINS H. ANDERSON R E, ROYCE R, JEWELL N. WILKELSTEIN W. (1989) *J Acquir Immnue Defic Syndr* 2: 63–69.

LEARMONT J, TINDALL B, EVANS L, CUNNINGHAM A, CUNNINGHAM P, WELLS J, PENNY R, KALDOR J AND COOPER D A. (1992). *Lancet* 340: 863–867.

LEARMONT J et al (1995) *AIDS Res. Hum Retro.* 11: 1.

LEGUERN M, SHIODA T, LEVY J A, CHENG-MAYER C. (1993) *Virology* 195; 441–447.

LEVY J A, (1993) *AIDS* 7; 1401–1410.

LIFSON A R, BUCHBINDER S P, SHEPPARD H W, et al (1991) *J infect Dis* 163: 959–965.

LUCIW P A, CHENG-MAYER C and LEVY J A (1987) *Proc Natl Acad Sci USA* 84: 1434–1438.

MANIATIS T et al (1982). Molecular cloning. A Laboratory Manual, 1st edition Pub. Cold Spring Harbor Laboratory Press.

MOSIER D E, GULIZIA R J, MACISAAC P D, TORBETT B E, LEVY J A (1993) *Science* 260: 689–692.

MYERS A, KORBAR B, BERZOFSKY J A, SMITH R F & PAVLAKIS S A eds (1992; 1993; 1994). Human retroviruses and AIDS. A compilation and analysis of nucleic acid and amino acid sequences. Pub Theoretical Biology and Biophysics Group. Los Alamos National Laborary, Los Alamos NM USA.

NEATE E V, HEALY D S, PRINGLE R C, GUST I D, AND JOWLETT J M B (1987). *Aust NZ J Med* 17: 4614–466.

NIEDERMAN T M J, THIELAN B J, and RATNER L. (1989) *Proc Natl Acad Sci USA* 86–1128–1132.

PEPER R J, TINA W Z, & MICHELSON M M (1968). *J Lab Clin Med* 72: 842–846.

SAMBROOK et al (1989) Molecular Cloning. A Laboratory Manual. Cold Spring Harbor Laboratory, Cold Spring Harbor, N.Y.

SANGER F, NICKLEN SAND COULSON A R (1977). *Proc Natl Acad Sci USA* 4: 5463–67.

SHEPPARD H W, LANG W, ASCHER M S, VITTINGHOF E and WINKELSTEIN W. (1993) *AIDS* 7: 1159–1166.

SHIODA T, LEVY J A, CHENG-MAYER C (1992) *Proc Natl Acad Sci USA* 89: 9434–9438.

SHUGARS D C, SMITH M S, GLUECK D H, NANTERMET P V, SEILLIER-MOISEIWITSCH F AND SWANSTROM R (1993). *J Virol* 67: 4639–4650.

SMITH J, AZAD A A, and DEACON N J (1992) *J Gen Virol* 73: 1825–1828.

SULLIVAN N, THALI M, FURMAN C, HO D D, SODROSKI J (1993) *J Virol* 67: 3674–3679.

TEEUWSEN V J P, SIEBELINK K H J, DE WOLF F. GOUDSMIT J, UYTDEHAAG F G C M, OSTERHAUS ADME (1990) *AIDS* 4: 77–81.

TERSMETTE M, D E GOEDE REY, BERT J M, et al (1988) *J Virol* 62: 2026–2032.

TERWILLIGER E, SODROSKI J G, ROSEN C A, and HASELTINE W A, (1986) *J Virol* 60: 754–760.

YAMANOTO K MORI S, OKAMOTO T, SINOTOHNO K AND KYOGOKU Y (1991). *Nucl Acids Res* 22: 6107–6112.

YANISCH-PERRON C, VIEIRA J. and MESSING J *Gene* 13: 103–119.

---

We claim:

1. A method for detecting a non-pathogenic HIV-1 strain in the body fluids of an HIV infected individual comprising:

(a) obtaining and preparing a biological sample from said HIV infected individual;

(b) admixing an aliquot of said sample with an HIV-$1_{NL43}$ Nef peptide consisting of amino acids 166–206;

(c) admixing an aliquot of said sample with an HIV-$1_{NL43}$ Nef peptide wherein said peptide contains a known HIV-1 antigenic determinant but excludes amino acids 166–206 of Nef;

(d) detecting the formation of antigen/antibody complexes of the samples of steps (a) and (b);

wherein the absence of immune complex formation in step (b) and the presence of immune complex formation in step (c) is indicative of said individual being infected with a non-pathogenic HIV-1 strain.

2. A method according to claim 1 wherein the peptide of step (c) comprises amino acids 15–27 of Nef.

3. A method for detecting a non-pathogenic HIV-1 strain in the body fluids of an HIV infected individual comprising:

(a) obtaining and preparing a biological sample from said HIV infected individual;

(b) determining the nucleotide sequence of a portion of the nef gene and U3 region of the long terminal repeat comprising nucleotides 9281–9437;

wherein the nucleotide numbering scheme employed is based upon isolate HIV-$1_{NL43}$ and the presence of a deletion of nucleotides 9281–9437 in the nef gene and U3 region of the long terminal repeat is indicative of a non-pathogenic HIV-1 strain.

4. A method for detecting a non-pathogenic HIV-1 strain in the body fluids of an HIV infected individual comprising:

(a) obtaining and preparing a biological sample from said HIV infected individual;

(b) admixing an aliquot of said sample with an antibody specific for an epitope contained within amino acids 166–206 of an HIV-$1_{NL43}$ Nef peptide;

(c) admixing an aliquot of said sample with an antibody specific for an HIV-$1_{NL43}$ Nef peptide, excluding amino acids 166–206;

(d) detecting the formation of antigen/antibody complexes in steps (b) and (c);

wherein the absence of immune complex formation in step (b) and the presence of immune complex formation in step (c) is indicative of said individual being infected with a non-pathogenic HIV-1 strain.

5. A method according to claim 4 wherein the antibody of step (c) is specific for an epitope contained within amino acids 15–27 of said Nef peptide.

* * * * *

SEQUENCE LISTING (1) GENERAL INFORMATION:

(iii) NUMBER OF SEQUENCES: 841

(2) INFORMATION FOR SEQ ID NO:1:

(i) SEQUENCE CHARACTERISTICS:
      (A) LENGTH: 9709 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

```
TGGAAGGGCT AATTTGGTCC CAAAAAAGAC AAGAGATCCT TGATCTGTGG ATCTACCACA      60

CACAAGGCTA CTTCCCTGAT TGGCAGAACT ACACACCAGG GCCAGGGATC AGATATCCAC     120

TGACCTTTGG ATGGTGCTTC AAGTTAGTAC CAGTTGAACC AGAGCAAGTA GAAGAGGCCA     180

AATAAGGAGA GAAGAACAGC TTGTTACACC CTATGAGCCA GCATGGGATG GAGGACCCGG     240

AGGGAGAAGT ATTAGTGTGG AAGTTTGACA GCCTCCTAGC ATTTCGTCAC ATGGCCCGAG     300

AGCTGCATCC GGAGTACTAC AAAGACTGCT GACATCGAGC TTTCTACAAG GGACTTTCCG     360

CTGGGGACTT TCCAGGGAGG TGTGGCCTGG GCGGGACTGG GGAGTGGCGA GCCCTCAGAT     420

GCTACATATA AGCAGCTGCT TTTTGCCTGT ACTGGGTCTC TCTGGTTAGA CCAGATCTGA     480
```

```
GCCTGGGAGC TCTCTGGCTA ACTAGGGAAC CCACTGCTTA AGCCTCAATA AAGCTTGCCT      540

TGAGTGCTCA AAGTAGTGTG TGCCCGTCTG TTGTGTGACT CTGGTAACTA GAGATCCCTC      600

AGACCCTTTT AGTCAGTGTG GAAAATCTCT AGCAGTGGCG CCCGAACAGG GACTTGAAAG      660

CGAAAGTAAA GCCAGAGGAG ATCTCTCGAC GCAGGACTCG GCTTGCTGAA GCGCGCACGG      720

CAAGAGGCGA GGGGCGGCGA CTGGTGAGTA CGCCAAAAAT TTTGACTAGC GGAGGCTAGA      780

AGGAGAGAGA TGGGTGCGAG AGCGTCGGTA TTAAGCGGGG GAGAATTAGA TAAATGGGAA      840

AAAATTCGGT TAAGGCCAGG GGGAAAGAAA CAATATAAAC TAAAACATAT AGTATGGGCA      900

AGCAGGGAGC TAGAACGATT CGCAGTTAAT CCTGGCCTTT TAGAGACATC AGAAGGCTGT      960

AGACAAATAC TGGGACAGCT ACAACCATCC CTTCAGACAG GATCAGAAGA ACTTAGATCA     1020

TTATATAATA CAATAGCAGT CCTCTATTGT GTGCATCAAA GGATAGATGT AAAAGACACC     1080

AAGGAAGCCT TAGATAAGAT AGAGGAAGAG CAAAACAAAA GTAAGAAAAA GGCACAGCAA     1140

GCAGCAGCTG ACACAGGAAA CAACAGCCAG GTCAGCCAAA ATTACCCTAT AGTGCAGAAC     1200

CTCCAGGGGC AAATGGTACA TCAGGCCATA TCACCTAGAC CTTTAAATGC ATGGGTAAAA     1260

GTAGTAGAAG AGAAGGCTTT CAGCCCAGAA GTAATACCCA TGTTTTCAGC ATTATCAGAA     1320

GGAGCCACCC CACAAGATTT AAATACCATG CTAAACACAG TGGGGGGACA TCAAGCAGCC     1380

ATGCAAATGT TAAAAGAGAC CATCAATGAG GAAGCTGCAG AATGGGATAG ATTGCATCCA     1440

GTGCATGCAG GGCCTATTGC ACCAGGCCAG ATGAGAGAAC CAAGGGGAAG TGACATAGCA     1500

GGAACTACTA GTACCCTTCA GGAACAAATA GGATGGATGA CACATAATCC ACCTATCCCA     1560

GTAGGAGAAA TCTATAAAAG ATGGATAATC CTGGGATTAA ATAAAATAGT AAGAATGTAT     1620

AGCCCTACCA GCATTCTGGA CATAAGACAA GGACCAAAGG AACCCTTTAG AGACTATGTA     1680

GACCGATTCT ATAAAACTCT AAGAGCCGAG CAAGCTTCAC AAGAGGTAAA AAATTGGATG     1740

ACAGAAACCT TGTTGGTCCA AAATGCGAAC CCAGATTGTA AGACTATTTT AAAAGCATTG     1800

GGACCAGGAG CGACACTAGA AGAAATGATG ACAGCATGTC AGGGAGTGGG GGACCCGGC      1860

CATAAAGCAA GAGTTTTGGC TGAAGCAATG AGCCAAGTAA CAAATCCAGC TACCATAATG     1920

ATACAGAAAG GCAATTTTAG GAACCAAAGA AAGACTGTTA AGTGTTTCAA TTGTGGCAAA     1980

GAAGGGCACA TAGCCAAAAA TTGCAGGGCC CCTAGGAAAA AGGGCTGTTG GAAATGTGGA     2040

AAGGAAGGAC ACCAAATGAA AGATTGTACT GAGAGACAGG CTAATTTTTT AGGGAAGATC     2100

TGGCCTTCCC ACAAGGGAAG GCCAGGGAAT TTTCTTCAGA GCAGACCAGA GCCAACAGCC     2160

CCACCAGAAG AGAGCTTCAG GTTTGGGAA GAGACAACAA CTCCCTCTCA GAAGCAGGAG     2220

CCGATAGACA AGGAACTGTA TCCTTTAGCT TCCCTCAGAT CACTCTTTGG CAGCGACCCC     2280

TCGTCACAAT AAAGATAGGG GGGCAATTAA AGGAAGCTCT ATTAGATACA GGAGCAGATG     2340

ATACAGTATT AGAAGAAATG AATTTGCCAG GAAGATGGAA ACCAAAAATG ATAGGGGGAA     2400

TTGGAGGTTT TATCAAAGTA GGACAGTATG ATCAGATACT CATAGAAATC TGCGGACATA     2460

AAGCTATAGG TACAGTATTA GTAGGACCTA CACCTGTCAA CATAATTGGA AGAAATCTGT     2520

TGACTCAGAT TGGCTGCACT TTAAATTTTC CCATTAGTCC TATTGAGACT GTACCAGTAA     2580

AATTAAAGCC AGGAATGGAT GGCCCAAAAG TTAAACAATG GCCATTGACA GAAGAAAAAA     2640

TAAAAGCATT AGTAGAAATT TGTACAGAAA TGGAAAAGGA AGGAAAAATT TCAAAAATTG     2700

GGCCTGAAAA TCCATACAAT ACTCCAGTAT TTGCCATAAA GAAAAAGAC AGTACTAAAT      2760

GGAGAAAATT AGTAGATTTC AGAGAACTTA ATAAGAGAAC TCAAGATTTC TGGGAAGTTC     2820

AATTAGGAAT ACCACATCCT GCAGGGTTAA AACAGAAAAA ATCAGTAACA GTACTGGATG     2880
```

-continued

```
TGGGCGATGC ATATTTTTCA GTTCCCTTAG ATAAAGACTT CAGGAAGTAT ACTGCATTTA    2940

CCATACCTAG TATAAACAAT GAGACACCAG GGATTAGATA TCAGTACAAT GTGCTTCCAC    3000

AGGGATGGAA AGGATCACCA GCAATATTCC AGTGTAGCAT GACAAAAATC TTAGAGCCTT    3060

TTAGAAAACA AAATCCAGAC ATAGTCATCT ATCAATACAT GGATGATTTG TATGTAGGAT    3120

CTGACTTAGA AATAGGGCAG CATAGAACAA AAATAGAGGA ACTGAGACAA CATCTGTTGA    3180

GGTGGGGATT TACCACACCA GACAAAAAAC ATCAGAAAGA ACCTCCATTC CTTTGGATGG    3240

GTTATGAACT CCATCCTGAT AAATGGACAG TACAGCCTAT AGTGCTGCCA GAAAAGGACA    3300

GCTGGACTGT CAATGACATA CAGAAATTAG TGGGAAAATT GAATTGGGCA AGTCAGATTT    3360

ATGCAGGGAT TAAAGTAAGG CAATTATGTA AACTTCTTAG GGGAACCAAA GCACTAACAG    3420

AAGTAGTACC ACTAACAGAA GAAGCAGAGC TAGAACTGGC AGAAAACAGG GAGATTCTAA    3480

AAGAACCGGT ACATGGAGTG TATTATGACC CATCAAAAGA CTTAATAGCA GAAATACAGA    3540

AGCAGGGGCA AGGCCAATGG ACATATCAAA TTTATCAAGA GCCATTTAAA AATCTGAAAA    3600

CAGGAAAATA TGCAAGAATG AAGGGTGCCC ACACTAATGA TGTGAAACAA TTAACAGAGG    3660

CAGTACAAAA AATAGCCACA GAAAGCATAG TAATATGGGG AAAGACTCCT AAATTTAAAT    3720

TACCCATACA AAAGGAAACA TGGGAAGCAT GGTGGACAGA GTATTGGCAA GCCACCTGGA    3780

TTCCTGAGTG GGAGTTTGTC AATACCCCTC CCTTAGTGAA GTTATGGTAC CAGTTAGAGA    3840

AAGAACCCAT AATAGGAGCA GAAACTTTCT ATGTAGATGG GGCAGCCAAT AGGGAAACTA    3900

AATTAGGAAA AGCAGGATAT GTAACTGACA GAGGAAGACA AAAAGTTGTC CCCCTAACGG    3960

ACACAACAAA TCAGAAGACT GAGTTACAAG CAATTCATCT AGCTTTGCAG GATTCGGGAT    4020

TAGAAGTAAA CATAGTGACA GACTCACAAT ATGCATTGGG AATCATTCAA GCACAACCAG    4080

ATAAGAGTGA ATCAGAGTTA GTCAGTCAAA TAATAGAGCA GTTAATAAAA AAGGAAAAAG    4140

TCTACCTGGC ATGGGTACCA GCACACAAAG GAATTGGAGG AAATGAACAA GTAGATGGGT    4200

TGGTCAGTGC TGGAATCAGG AAAGTACTAT TTTTAGATGG AATAGATAAG GCCCAAGAAG    4260

AACATGAGAA ATATCACAGT AATTGGAGAG CAATGGCTAG TGATTTTAAC CTACCACCTG    4320

TAGTAGCAAA AGAAATAGTA GCCAGCTGTG ATAAATGTCA GCTAAAAGGG GAAGCCATGC    4380

ATGGACAAGT AGACTGTAGC CCAGGAATAT GGCAGCTAGA TTGTACACAT TTAGAAGGAA    4440

AAGTTATCTT GGTAGCAGTT CATGTAGCCA GTGGATATAT AGAAGCAGAA GTAATTCCAG    4500

CAGAGACAGG GCAAGAAACA GCATACTTCC TCTTAAAATT AGCAGGAAGA TGGCCAGTAA    4560

AAACAGTACA TACAGACAAT GGCAGCAATT TCACCAGTAC TACAGTTAAG GCCGCCTGTT    4620

GGTGGGCGGG GATCAAGCAG GAATTTGGCA TTCCCTACAA TCCCCAAAGT CAAGGAGTAA    4680

TAGAATCTAT GAATAAAGAA TTAAAGAAAA TTATAGGACA GGTAAGAGAT CAGGCTGAAC    4740

ATCTTAAGAC AGCAGTACAA ATGGCAGTAT TCATCCACAA TTTTAAAAGA AAAGGGGGGA    4800

TTGGGGGGTA CAGTGCAGGG GAAAGAATAG TAGACATAAT AGCAACAGAC ATACAAACTA    4860

AAGAATTACA AAAACAAATT ACAAAAATTC AAAATTTTCG GGTTTATTAC AGGGACAGCA    4920

GAGATCCAGT TTGGAAAGGA CCAGCAAAGC TCCTCTGGAA AGGTGAAGGG GCAGTAGTAA    4980

TACAAGATAA TAGTGACATA AAAGTAGTGC CAAGAAGAAA AGCAAAGATC ATCAGGGATT    5040

ATGGAAAACA GATGGCAGGT GATGATTGTG TGGCAAGTAG ACAGGATGAG GATTAACACA    5100

TGGAAAAGAT TAGTAAAACA CCATATGTAT ATTTCAAGGA AAGCTAAGGA CTGGTTTTAT    5160

AGACATCACT ATGAAAGTAC TAATCCAAAA ATAAGTTCAG AAGTACACAT CCCACTAGGG    5220

GATGCTAAAT TAGTAATAAC AACATATTGG GGTCTGCATA CAGGAGAAAG AGACTGGCAT    5280
```

-continued

```
TTGGGTCAGG GAGTCTCCAT AGAATGGAGG AAAAAGAGAT ATAGCACACA AGTAGACCCT    5340
GACCTAGCAG ACCAACTAAT TCATCTGCAC TATTTTGATT GTTTTTCAGA ATCTGCTATA    5400
AGAAATACCA TATTAGGACG TATAGTTAGT CCTAGGTGTG AATATCAAGC AGGACATAAC    5460
AAGGTAGGAT CTCTACAGTA CTTGGCACTA GCAGCATTAA TAAAACCAAA ACAGATAAAG    5520
CCACCTTTGC CTAGTGTTAG GAAACTGACA GAGGACAGAT GGAACAAGCC CCAGAAGACC    5580
AAGGGCCACA GAGGGAGCCA TACAATGAAT GGACACTAGA GCTTTTAGAG GAACTTAAGA    5640
GTGAAGCTGT TAGACATTTT CCTAGGATAT GGCTCCATAA CTTAGGACAA CATATCTATG    5700
AAACTTACGG GGATACTTGG GCAGGAGTGG AAGCCATAAT AAGAATTCTG CAACAACTGC    5760
TGTTTATCCA TTTCAGAATT GGGTGTCGAC ATAGCAGAAT AGGCGTTACT CGACAGAGGA    5820
GAGCAAGAAA TGGAGCCAGT AGATCCTAGA CTAGAGCCCT GGAAGCATCC AGGAAGTCAG    5880
CCTAAAACTG CTTGTACCAA TTGCTATTGT AAAAAGTGTT GCTTTCATTG CCAAGTTTGT    5940
TTCATGACAA AAGCCTTAGG CATCTCCTAT GGCAGGAAGA AGCGGAGACA GCGACGAAGA    6000
GCTCATCAGA ACAGTCAGAC TCATCAAGCT TCTCTATCAA AGCAGTAAGT AGTACATGTA    6060
ATGCAACCTA TAATAGTAGC AATAGTAGCA TTAGTAGTAG CAATAATAAT AGCAATAGTT    6120
GTGTGGTCCA TAGTAATCAT AGAATATAGG AAAATATTAA GACAAAGAAA AATAGACAGG    6180
TTAATTGATA GACTAATAGA AAGAGCAGAA GACAGTGGCA ATGAGAGTGA AGGAGAAGTA    6240
TCAGCACTTG TGGAGATGGG GGTGGAAATG GGGCACCATG CTCCTTGGGA TATTGATGAT    6300
CTGTAGTGCT ACAGAAAAAT TGTGGGTCAC AGTCTATTAT GGGGTACCTG TGTGGAAGGA    6360
AGCAACCACC ACTCTATTTT GTGCATCAGA TGCTAAAGCA TATGATACAG AGGTACATAA    6420
TGTTTGGGCC ACACATGCCT GTGTACCCAC AGACCCCAAC CCACAAGAAG TAGTATTGGT    6480
AAATGTGACA GAAAATTTTA ACATGTGGAA AAATGACATG GTAGAACAGA TGCATGAGGA    6540
TATAATCAGT TTATGGGATC AAAGCCTAAA GCCATGTGTA AAATTAACCC CACTCTGTGT    6600
TAGTTTAAAG TGCACTGATT TGAAGAATGA TACTAATACC AATAGTAGTA GCGGGAGAAT    6660
GATAATGGAG AAAGGAGAGA TAAAAAACTG CTCTTTCAAT ATCAGCACAA GCATAAGAGA    6720
TAAGGTGCAG AAAGAATATG CATTCTTTTA TAAACTTGAT ATAGTACCAA TAGATAATAC    6780
CAGCTATAGG TTGATAAGTT GTAACACCTC AGTCATTACA CAGGCCTGTC CAAAGGTATC    6840
CTTTGAGCCA ATTCCCATAC ATTATTGTGC CCCGGCTGGT TTTGCGATTC TAAAATGTAA    6900
TAATAAGACG TTCAATGGAA CAGGACCATG TACAAATGTC AGCACAGTAC AATGTACACA    6960
TGGAATCAGG CCAGTAGTAT CAACTCAACT GCTGTTAAAT GGCAGTCTAG CAGAAGAAGA    7020
TGTAGTAATT AGATCTGCCA ATTTCACAGA CAATGCTAAA ACCATAATAG TACAGCTGAA    7080
CACATCTGTA GAAATTAATT GTACAAGACC CAACAACAAT ACAAGAAAAA GTATCCGTAT    7140
CCAGAGGGGA CCAGGGAGAG CATTTGTTAC AATAGGAAAA ATAGGAAATA TGAGACAAGC    7200
ACATTGTAAC ATTAGTAGAG CAAAATGGAA TGCCACTTTA AAACAGATAG CTAGCAAATT    7260
AAGAGAACAA TTTGGAAATA ATAAAACAAT AATCTTTAAG CAATCCTCAG GAGGGGACCC    7320
AGAAATTGTA ACGCACAGTT TTAATTGTGG AGGGGAATTT TTCTACTGTA ATTCAACACA    7380
ACTGTTTAAT AGTACTTGGT TTAATAGTAC TTGGAGTACT GAAGGGTCAA ATAACACTGA    7440
AGGAAGTGAC ACAATCACAC TCCCATGCAG AATAAAACAA TTTATAAACA TGTGGCAGGA    7500
AGTAGGAAAA GCAATGTATG CCCCTCCCAT CAGTGGACAA ATTAGATGTT CATCAAATAT    7560
TACTGGGCTG CTATTAACAA GAGATGGTGG TAATAACAAC AATGGGTCCG AGATCTTCAG    7620
ACCTGGAGGA GGCGATATGA GGGACAATTG GAGAAGTGAA TTATATAAAT ATAAAGTAGT    7680
```

```
AAAAATTGAA CCATTAGGAG TAGCACCCAC CAAGGCAAAG AGAAGAGTGG TGCAGAGAGA    7740

AAAAAGAGCA GTGGGAATAG GAGCTTTGTT CCTTGGGTTC TTGGGAGCAG CAGGAAGCAC    7800

TATGGGCTGC ACGTCAATGA CGCTGACGGT ACAGGCCAGA CAATTATTGT CTGATATAGT    7860

GCAGCAGCAG AACAATTTGC TGAGGGCTAT TGAGGCGCAA CAGCATCTGT TGCAACTCAC    7920

AGTCTGGGGC ATCAAACAGC TCCAGGCAAG AATCCTGGCT GTGGAAAGAT ACCTAAAGGA    7980

TCAACAGCTC CTGGGGATTT GGGGTTGCTC TGGAAAACTC ATTTGCACCA CTGCTGTGCC    8040

TTGGAATGCT AGTTGGAGTA ATAAATCTCT GGAACAGATT TGGAATAACA TGACCTGGAT    8100

GGAGTGGGAC AGAGAAATTA ACAATTACAC AAGCTTAATA CACTCCTTAA TTGAAGAATC    8160

GCAAAACCAG CAAGAAAAGA ATGAACAAGA ATTATTGGAA TTAGATAAAT GGGCAAGTTT    8220

GTGGAATTGG TTTAACATAA CAAATTGGCT GTGGTATATA AAATTATTCA TAATGATAGT    8280

AGGAGGCTTG GTAGGTTTAA GAATAGTTTT TGCTGTACTT TCTATAGTGA ATAGAGTTAG    8340

GCAGGGATAT TCACCATTAT CGTTTCAGAC CCACCTCCCA ATCCCGAGGG GACCCGACAG    8400

GCCCGAAGGA ATAGAAGAAG AAGGTGGAGA GAGAGACAGA GACAGATCCA TTCGATTAGT    8460

GAACGGATCC TTAGCACTTA TCTGGGACGA TCTGCGGAGC CTGTGCCTCT TCAGCTACCA    8520

CCGCTTGAGA GACTTACTCT TGATTGTAAC GAGGATTGTG GAACTTCTGG GACGCAGGGG    8580

GTGGGAAGCC CTCAAATATT GGTGGAATCT CCTACAGTAT TGGAGTCAGG AACTAAAGAA    8640

TAGTGCTGTT AACTTGCTCA ATGCCACAGC CATAGCAGTA GCTGAGGGGA CAGATAGGGT    8700

TATAGAAGTA TTACAAGCAG CTTATAGAGC TATTCGCCAC ATACCTAGAA GAATAAGACA    8760

GGGCTTGGAA AGGATTTTGC TATAAGATGG GTGGCAAGTG GTCAAAAAGT AGTGTGATTG    8820

GATGGCCTGC TGTAAGGGAA AGAATGAGAC GAGCTGAGCC AGCAGCAGAT GGGGTGGGAG    8880

CAGTATCTCG AGACCTAGAA AAACATGGAG CAATACACAAG TAGCAATACA GCAGCTAACA    8940

ATGCTGCTTG TGCCTGGCTA GAAGCACAAG AGGAGGAAGA GGTGGGTTTT CCAGTCACAC    9000

CTCAGGTACC TTTAAGACCA ATGACTTACA AGGCAGCTGT AGATCTTAGC CACTTTTTAA    9060

AAGAAAAGGG GGGACTGGAA GGGCTAATTC ACTCCCAAAG AAGACAAGAT ATCCTTGATC    9120

TGTGGATCTA CCACACACAA GGCTACTTCC CTGATTGGCA GAACTACACA CCAGGGCCAG    9180

GGGTCAGATA TCCACTGACC TTTGGATGGT GCTACAAGCT AGTACCAGTT GAGCCAGATA    9240

AGGTAGAAGA GGCCAATAAA GGAGAGAACA CCAGCTTGTT ACACCCTGTG AGCCTGCATG    9300

GAATGGATGA CCCTGAGAGA GAAGTGTTAG AGTGGAGGTT TGACAGCCGC CTAGCATTTC    9360

ATCACGTGGC CCGAGAGCTG CATCCGGAGT ACTTCAAGAA CTGCTGACAT CGAGCTTGCT    9420

ACAAGGGACT TTCCGCTGGG GACTTTCCAG GGAGGCGTGG CCTGGGCGGG ACTGGGGAGT    9480

GGCGAGCCCT CAGATGCTGC ATATAAGCAG CTGCTTTTTG CCTGTACTGG GTCTCTCTGG    9540

TTAGACCAGA TCTGAGCCTG GGAGCTCTCT GGCTAACTAG GGAACCCACT GCTTAAGCCT    9600

CAATAAAGCT TGCCTTGAGT GCTTCAAGTA GTGTGTGCCC GTCTGTTGTG TGACTCTGGT    9660

AACTAGAGAT CCCTCAGACC CTTTTAGTCA GTGTGGAAAA TCTCTAGCA               9709
```

(2) INFORMATION FOR SEQ ID NO:2:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA

```
        (xi) SEQUENCE DESCRIPTION: SEQ ID NO:2:

ATGGGTGGCA                                                              10

(2) INFORMATION FOR SEQ ID NO:3:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:3:

TGGGTGGCAA                                                              10

(2) INFORMATION FOR SEQ ID NO:4:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:4:

GGGTGGCAAG                                                              10

(2) INFORMATION FOR SEQ ID NO:5:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:5:

GGTGGCAAGT                                                              10

(2) INFORMATION FOR SEQ ID NO:6:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:6:

GTGGCAAGTG                                                              10

(2) INFORMATION FOR SEQ ID NO:7:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:7:

TGGCAAGTGG                                                              10
```

(2) INFORMATION FOR SEQ ID NO:8:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

GGCAAGTGGT                                            10

(2) INFORMATION FOR SEQ ID NO:9:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

GCAAGTGGTC                                            10

(2) INFORMATION FOR SEQ ID NO:10:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

CAAGTGGTCA                                            10

(2) INFORMATION FOR SEQ ID NO:11:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

AAGTGGTCAA                                            10

(2) INFORMATION FOR SEQ ID NO:12:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

AGTGGTCAAA                                            10

(2) INFORMATION FOR SEQ ID NO:13:

(i) SEQUENCE CHARACTERISTICS:
        (A) LENGTH: 10 base pairs
        (B) TYPE: nucleic acid

```
            (C) STRANDEDNESS: single
            (D) TOPOLOGY: linear (ii) MOLECULE TYPE: DNA (xi) SEQUENCE DESCRIPTION: SEQ ID NO:13:

GTGGTCAAAA                                                              10

(2) INFORMATION FOR SEQ ID NO:14:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:14:

TGGTCAAAAA                                                              10

(2) INFORMATION FOR SEQ ID NO:15:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:15:

GGTCAAAAAG                                                              10

(2) INFORMATION FOR SEQ ID NO:16:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:16:

GTCAAAAAGT                                                              10

(2) INFORMATION FOR SEQ ID NO:17:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:17:

TCAAAAAGTA                                                              10

(2) INFORMATION FOR SEQ ID NO:18:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA
```

(xi) SEQUENCE DESCRIPTION: SEQ ID NO:18:

CAAAAAGTAG                                                          10

(2) INFORMATION FOR SEQ ID NO:19:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

AAAAAGTAGT                                                          10

(2) INFORMATION FOR SEQ ID NO:20:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

AAAAGTAGTG                                                          10

(2) INFORMATION FOR SEQ ID NO:21:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

AAAGTAGTGT                                                          10

(2) INFORMATION FOR SEQ ID NO:22:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

AAGTAGTGTG                                                          10

(2) INFORMATION FOR SEQ ID NO:23:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

AGTAGTGTGA                                                          10

(2) INFORMATION FOR SEQ ID NO:24:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

GTAGTGTGAT                                    10

(2) INFORMATION FOR SEQ ID NO:25:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

TAGTGTGATT                                    10

(2) INFORMATION FOR SEQ ID NO:26:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

AGTGTGATTG                                    10

(2) INFORMATION FOR SEQ ID NO:27:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

GTGTGATTGG                                    10

(2) INFORMATION FOR SEQ ID NO:28:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

TGTGATTGGA                                    10

(2) INFORMATION FOR SEQ ID NO:29:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO:29:

GTGATTGGAT                                                                  10

(2) INFORMATION FOR SEQ ID NO:30:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

TGATTGGATG                                                                  10

(2) INFORMATION FOR SEQ ID NO:31:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

GATTGGATGG                                                                  10

(2) INFORMATION FOR SEQ ID NO:32:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

ATTGGATGGC                                                                  10

(2) INFORMATION FOR SEQ ID NO:33:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

TTGGATGGCC                                                                  10

(2) INFORMATION FOR SEQ ID NO:34:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:34:

TGGATGGCCT                                                                                      10

(2) INFORMATION FOR SEQ ID NO:35:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

GGATGGCCTG                                                                                      10

(2) INFORMATION FOR SEQ ID NO:36:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

GATGGCCTGC                                                                                      10

(2) INFORMATION FOR SEQ ID NO:37:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

ATGGCCTGCT                                                                                      10

(2) INFORMATION FOR SEQ ID NO:38:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

TGGCCTGCTG                                                                                      10

(2) INFORMATION FOR SEQ ID NO:39:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

GGCCTGCTGT                                                                                      10

(2) INFORMATION FOR SEQ ID NO:40:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

GCCTGCTGTA          10

(2) INFORMATION FOR SEQ ID NO:41:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

CCTGCTGTAA          10

(2) INFORMATION FOR SEQ ID NO:42:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:42:

CTGCTGTAAG          10

(2) INFORMATION FOR SEQ ID NO:43:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:43:

TGCTGTAAGG          10

(2) INFORMATION FOR SEQ ID NO:44:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:44:

GCTGTAAGGG          10

(2) INFORMATION FOR SEQ ID NO:45:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO:45:

CTGTAAGGGA                                                              10

(2) INFORMATION FOR SEQ ID NO:46:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:46:

TGTAAGGGAA                                                              10

(2) INFORMATION FOR SEQ ID NO:47:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:47:

GTAAGGGAAA                                                              10

(2) INFORMATION FOR SEQ ID NO:48:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:48:

TAAGGGAAAG                                                              10

(2) INFORMATION FOR SEQ ID NO:49:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:49:

AAGGGAAAGA                                                              10

(2) INFORMATION FOR SEQ ID NO:50:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:50:

AGGGAAAGAA                                                                              10

(2) INFORMATION FOR SEQ ID NO:51:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:51:

GGGAAAGAAT                                                                              10

(2) INFORMATION FOR SEQ ID NO:52:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:52:

GGAAAGAATG                                                                              10

(2) INFORMATION FOR SEQ ID NO:53:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:53:

GAAAGAATGA                                                                              10

(2) INFORMATION FOR SEQ ID NO:54:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:54:

AAAGAATGAG                                                                              10

(2) INFORMATION FOR SEQ ID NO:55:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:55:

AAGAATGAGA                                                                              10

(2) INFORMATION FOR SEQ ID NO:56:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:56:

AGAATGAGAC    10

(2) INFORMATION FOR SEQ ID NO:57:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:57:

GAATGAGACG    10

(2) INFORMATION FOR SEQ ID NO:58:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:58:

AATGAGACGA    10

(2) INFORMATION FOR SEQ ID NO:59:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:59:

ATGAGACGAG    10

(2) INFORMATION FOR SEQ ID NO:60:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:60:

TGAGACGAGC    10

(2) INFORMATION FOR SEQ ID NO:61:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO:61:

GAGACGAGCT                                                              10

(2) INFORMATION FOR SEQ ID NO:62:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:62:

AGACGAGCTG                                                              10

(2) INFORMATION FOR SEQ ID NO:63:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:63:

GACGAGCTGA                                                              10

(2) INFORMATION FOR SEQ ID NO:64:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:64:

ACGAGCTGAG                                                              10

(2) INFORMATION FOR SEQ ID NO:65:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:65:

CGAGCTGAGC                                                              10

(2) INFORMATION FOR SEQ ID NO:66:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:66:

GAGCTGAGCC					10

(2) INFORMATION FOR SEQ ID NO:67:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:67:

AGCTGAGCCA					10

(2) INFORMATION FOR SEQ ID NO:68:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:68:

GCTGAGCCAG					10

(2) INFORMATION FOR SEQ ID NO:69:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:69:

CTGAGCCAGC					10

(2) INFORMATION FOR SEQ ID NO:70:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:70:

TGAGCCAGCA					10

(2) INFORMATION FOR SEQ ID NO:71:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:71:

GAGCCAGCAG					10

(2) INFORMATION FOR SEQ ID NO:72:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:72:

AGCCAGCAGC    10

(2) INFORMATION FOR SEQ ID NO:73:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:73:

GCCAGCAGCA    10

(2) INFORMATION FOR SEQ ID NO:74:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:74:

CCAGCAGCAG    10

(2) INFORMATION FOR SEQ ID NO:75:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:75:

CAGCAGCAGA    10

(2) INFORMATION FOR SEQ ID NO:76:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:76:

AGCAGCAGAT    10

(2) INFORMATION FOR SEQ ID NO:77:

(i) SEQUENCE CHARACTERISTICS:
        (A) LENGTH: 10 base pairs
        (B) TYPE: nucleic acid (C) STRANDEDNESS: single
        (D) TOPOLOGY: linear (ii) MOLECULE TYPE: DNA (xi) SEQUENCE DESCRIPTION: SEQ ID NO:77:

GCAGCAGATG                                                                 10

(2) INFORMATION FOR SEQ ID NO:78:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:78:

CAGCAGATGG                                                                 10

(2) INFORMATION FOR SEQ ID NO:79:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:79:

AGCAGATGGG                                                                 10

(2) INFORMATION FOR SEQ ID NO:80:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:80:

GCAGATGGGG                                                                 10

(2) INFORMATION FOR SEQ ID NO:81:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:81:

CAGATGGGGT                                                                 10

(2) INFORMATION FOR SEQ ID NO:82:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:82:

AGATGGGGTG                                                                       10

(2) INFORMATION FOR SEQ ID NO:83:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:83:

GATGGGGTGG                                                                       10

(2) INFORMATION FOR SEQ ID NO:84:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:84:

ATGGGGTGGG                                                                       10

(2) INFORMATION FOR SEQ ID NO:85:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:85:

TGGGGTGGGA                                                                       10

(2) INFORMATION FOR SEQ ID NO:86:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:86:

GGGGTGGGAG                                                                       10

(2) INFORMATION FOR SEQ ID NO:87:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:87:

GGGTGGGAGC                                                                       10

(2) INFORMATION FOR SEQ ID NO:88:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:88:

GGTGGGAGCA          10

(2) INFORMATION FOR SEQ ID NO:89:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:89:

GTGGGAGCAG          10

(2) INFORMATION FOR SEQ ID NO:90:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:90:

TGGGAGCAGT          10

(2) INFORMATION FOR SEQ ID NO:91:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:91:

GGGAGCAGTA          10

(2) INFORMATION FOR SEQ ID NO:92:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:92:

GGAGCAGTAT          10

(2) INFORMATION FOR SEQ ID NO:93:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO:93:

GAGCAGTATC                                                                        10

(2) INFORMATION FOR SEQ ID NO:94:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:94:

AGCAGTATCT                                                                        10

(2) INFORMATION FOR SEQ ID NO:95:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:95:

GCAGTATCTC                                                                        10

(2) INFORMATION FOR SEQ ID NO:96:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:96:

CAGTATCTCG                                                                        10

(2) INFORMATION FOR SEQ ID NO:97:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:97:

AGTATCTCGA                                                                        10

(2) INFORMATION FOR SEQ ID NO:98:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:98:

GTATCTCGAG                                                          10

(2) INFORMATION FOR SEQ ID NO:99:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:99:

TATCTCGAGA                                                          10

(2) INFORMATION FOR SEQ ID NO:100:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:100:

ATCTCGAGAC                                                          10

(2) INFORMATION FOR SEQ ID NO:101:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:101:

TCTCGAGACC                                                          10

(2) INFORMATION FOR SEQ ID NO:102:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:102:

CTCGAGACCT                                                          10

(2) INFORMATION FOR SEQ ID NO:103:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:103:

TCGAGACCTA                                                          10

(2) INFORMATION FOR SEQ ID NO:104:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:104:

CGAGACCTAG    10

(2) INFORMATION FOR SEQ ID NO:105:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:105:

GAGACCTAGA    10

(2) INFORMATION FOR SEQ ID NO:106:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:106:

AGACCTAGAA    10

(2) INFORMATION FOR SEQ ID NO:107:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:107:

GACCTAGAAA    10

(2) INFORMATION FOR SEQ ID NO:108:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:108:

ACCTAGAAAA    10

(2) INFORMATION FOR SEQ ID NO:109:

(i) SEQUENCE CHARACTERISTICS:
        (A) LENGTH: 10 base pairs
        (B) TYPE: nucleic acid (C) STRANDEDNESS: single
        (D) TOPOLOGY: linear (ii) MOLECULE TYPE: DNA (xi) SEQUENCE DESCRIPTION: SEQ ID NO:109:

CCTAGAAAAA                                                                  10

(2) INFORMATION FOR SEQ ID NO:110:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:110:

CTAGAAAAAC                                                                  10

(2) INFORMATION FOR SEQ ID NO:111:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:111:

TAGAAAAACA                                                                  10

(2) INFORMATION FOR SEQ ID NO:112:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:112:

AGAAAAACAT                                                                  10

(2) INFORMATION FOR SEQ ID NO:113:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:113:

GAAAACATG                                                                   10

(2) INFORMATION FOR SEQ ID NO:114:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:114:

AAAAACATGG                                                                  10

(2) INFORMATION FOR SEQ ID NO:115:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:115:

AAAACATGGA                                                                  10

(2) INFORMATION FOR SEQ ID NO:116:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:116:

AAACATGGAG                                                                  10

(2) INFORMATION FOR SEQ ID NO:117:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:117:

AACATGGAGC                                                                  10

(2) INFORMATION FOR SEQ ID NO:118:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:118:

ACATGGAGCA                                                                  10

(2) INFORMATION FOR SEQ ID NO:119:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:119:

CATGGAGCAA                                                                  10

(2) INFORMATION FOR SEQ ID NO:120:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:120:

ATGGAGCAAT      10

(2) INFORMATION FOR SEQ ID NO:121:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:121:

TGGAGCAATC      10

(2) INFORMATION FOR SEQ ID NO:122:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:122:

GGAGCAATCA      10

(2) INFORMATION FOR SEQ ID NO:123:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:123:

GAGCAATCAC      10

(2) INFORMATION FOR SEQ ID NO:124:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:124:

AGCAATCACA      10

(2) INFORMATION FOR SEQ ID NO:125:

(i) SEQUENCE CHARACTERISTICS:
        (A) LENGTH: 10 base pairs
        (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO:125:

GCAATCACAA                                                                      10

(2) INFORMATION FOR SEQ ID NO:126:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:126:

CAATCACAAG                                                                      10

(2) INFORMATION FOR SEQ ID NO:127:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:127:

AATCACAAGT                                                                      10

(2) INFORMATION FOR SEQ ID NO:128:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:128:

ATCACAAGTA                                                                      10

(2) INFORMATION FOR SEQ ID NO:129:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:129:

TCACAAGTAG                                                                      10

(2) INFORMATION FOR SEQ ID NO:130:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA

```
    (xi) SEQUENCE DESCRIPTION: SEQ ID NO:130:

CACAAGTAGC                                                                    10

(2) INFORMATION FOR SEQ ID NO:131:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:131:

ACAAGTAGCA                                                                    10

(2) INFORMATION FOR SEQ ID NO:132:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:132:

CAAGTAGCAA                                                                    10

(2) INFORMATION FOR SEQ ID NO:133:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:133:

AAGTAGCAAT                                                                    10

(2) INFORMATION FOR SEQ ID NO:134:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:134:

AGTAGCAATA                                                                    10

(2) INFORMATION FOR SEQ ID NO:135:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:135:

GTAGCAATAC                                                                    10
```

(2) INFORMATION FOR SEQ ID NO:136:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:136:

TAGCAATACA    10

(2) INFORMATION FOR SEQ ID NO:137:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:137:

AGCAATACAG    10

(2) INFORMATION FOR SEQ ID NO:138:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:138:

GCAATACAGC    10

(2) INFORMATION FOR SEQ ID NO:139:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:139:

CAATACAGCA    10

(2) INFORMATION FOR SEQ ID NO:140:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:140:

AATACAGCAG    10

(2) INFORMATION FOR SEQ ID NO:141:

(i) SEQUENCE CHARACTERISTICS:
        (A) LENGTH: 10 base pairs
        (B) TYPE: nucleic acid

```
          (C) STRANDEDNESS: single
          (D) TOPOLOGY: linear (ii) MOLECULE TYPE: DNA (xi) SEQUENCE DESCRIPTION: SEQ ID NO:141:

ATACAGCAGC                                                                10

(2) INFORMATION FOR SEQ ID NO:142:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:142:

TACAGCAGCT                                                                10

(2) INFORMATION FOR SEQ ID NO:143:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:143:

ACAGCAGCTA                                                                10

(2) INFORMATION FOR SEQ ID NO:144:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:144:

CAGCAGCTAA                                                                10

(2) INFORMATION FOR SEQ ID NO:145:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:145:

AGCAGCTAAC                                                                10

(2) INFORMATION FOR SEQ ID NO:146:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA
```

-continued (xi) SEQUENCE DESCRIPTION: SEQ ID NO:146:

GCAGCTAACA                                                          10

(2) INFORMATION FOR SEQ ID NO:147:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:147:

CAGCTAACAA                                                          10

(2) INFORMATION FOR SEQ ID NO:148:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:148:

AGCTAACAAT                                                          10

(2) INFORMATION FOR SEQ ID NO:149:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:149:

GCTAACAATG                                                          10

(2) INFORMATION FOR SEQ ID NO:150:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:150:

CTAACAATGC                                                          10

(2) INFORMATION FOR SEQ ID NO:151:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:151:

TAACAATGCT                                                          10

(2) INFORMATION FOR SEQ ID NO:152:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:152:

AACAATGCTG                                                          10

(2) INFORMATION FOR SEQ ID NO:153:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:153:

ACAATGCTGC                                                          10

(2) INFORMATION FOR SEQ ID NO:154:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:154:

CAATGCTGCT                                                          10

(2) INFORMATION FOR SEQ ID NO:155:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:155:

AATGCTGCTT                                                          10

(2) INFORMATION FOR SEQ ID NO:156:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:156:

ATGCTGCTTG                                                          10

(2) INFORMATION FOR SEQ ID NO:157:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO:157:

TGCTGCTTGT                                                              10

(2) INFORMATION FOR SEQ ID NO:158:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:158:

GCTGCTTGTG                                                              10

(2) INFORMATION FOR SEQ ID NO:159:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:159:

CTGCTTGTGC                                                              10

(2) INFORMATION FOR SEQ ID NO:160:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:160:

TGCTTGTGCC                                                              10

(2) INFORMATION FOR SEQ ID NO:161:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:161:

GCTTGTGCCT                                                              10

(2) INFORMATION FOR SEQ ID NO:162:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA
```

```
    (xi) SEQUENCE DESCRIPTION: SEQ ID NO:162:

CTTGTGCCTG                                                              10

(2) INFORMATION FOR SEQ ID NO:163:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:163:

TTGTGCCTGG                                                              10

(2) INFORMATION FOR SEQ ID NO:164:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:164:

TGTGCCTGGC                                                              10

(2) INFORMATION FOR SEQ ID NO:165:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:165:

GTGCCTGGCT                                                              10

(2) INFORMATION FOR SEQ ID NO:166:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:166:

TGCCTGGCTA                                                              10

(2) INFORMATION FOR SEQ ID NO:167:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:167:

GCCTGGCTAG                                                              10
```

(2) INFORMATION FOR SEQ ID NO:168:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:168:

CCTGGCTAGA                                              10

(2) INFORMATION FOR SEQ ID NO:169:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:169:

CTGGCTAGAA                                              10

(2) INFORMATION FOR SEQ ID NO:170:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:170:

TGGCTAGAAG                                              10

(2) INFORMATION FOR SEQ ID NO:171:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:171:

GGCTAGAAGC                                              10

(2) INFORMATION FOR SEQ ID NO:172:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:172:

GCTAGAAGCA                                              10

(2) INFORMATION FOR SEQ ID NO:173:

(i) SEQUENCE CHARACTERISTICS:
        (A) LENGTH: 10 base pairs
        (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO:173:

CTAGAAGCAC                                                                    10

(2) INFORMATION FOR SEQ ID NO:174:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:174:

TAGAAGCACA                                                                    10

(2) INFORMATION FOR SEQ ID NO:175:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:175:

AGAAGCACAA                                                                    10

(2) INFORMATION FOR SEQ ID NO:176:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:176:

GAAGCACAAG                                                                    10

(2) INFORMATION FOR SEQ ID NO:177:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:177:

AAGCACAAGA                                                                    10

(2) INFORMATION FOR SEQ ID NO:178:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA

```
    (xi) SEQUENCE DESCRIPTION: SEQ ID NO:178:

AGCACAAGAG                                                              10

(2) INFORMATION FOR SEQ ID NO:179:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:179:

GCACAAGAGG                                                              10

(2) INFORMATION FOR SEQ ID NO:180:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:180:

CACAAGAGGA                                                              10

(2) INFORMATION FOR SEQ ID NO:181:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:181:

ACAAGAGGAG                                                              10

(2) INFORMATION FOR SEQ ID NO:182:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:182:

CAAGAGGAGG                                                              10

(2) INFORMATION FOR SEQ ID NO:183:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:183:

AAGAGGAGGA                                                              10
```

(2) INFORMATION FOR SEQ ID NO:184:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:184:

AGAGGAGGAA                                                              10

(2) INFORMATION FOR SEQ ID NO:185:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:185:

GAGGAGGAAG                                                              10

(2) INFORMATION FOR SEQ ID NO:186:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:186:

AGGAGGAAGA                                                              10

(2) INFORMATION FOR SEQ ID NO:187:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:187:

GGAGGAAGAG                                                              10

(2) INFORMATION FOR SEQ ID NO:188:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:188:

GAGGAAGAGG                                                              10

(2) INFORMATION FOR SEQ ID NO:189:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO:189:

AGGAAGAGGT                                                                    10

(2) INFORMATION FOR SEQ ID NO:190:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:190:

GGAAGAGGTG                                                                    10

(2) INFORMATION FOR SEQ ID NO:191:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:191:

GAAGAGGTGG                                                                    10

(2) INFORMATION FOR SEQ ID NO:192:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:192:

AAGAGGTGGG                                                                    10

(2) INFORMATION FOR SEQ ID NO:193:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:193:

AGAGGTGGGT                                                                    10

(2) INFORMATION FOR SEQ ID NO:194:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:194:

GAGGTGGGTT                                                          10

(2) INFORMATION FOR SEQ ID NO:195:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:195:

AGGTGGGTTT                                                          10

(2) INFORMATION FOR SEQ ID NO:196:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:196:

GGTGGGTTTT                                                          10

(2) INFORMATION FOR SEQ ID NO:197:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:197:

GTGGGTTTTC                                                          10

(2) INFORMATION FOR SEQ ID NO:198:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:198:

TGGGTTTTCC                                                          10

(2) INFORMATION FOR SEQ ID NO:199:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:199:

GGGTTTTCCA                                                          10

(2) INFORMATION FOR SEQ ID NO:200:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:200:

GGTTTTCCAG                                                                    10

(2) INFORMATION FOR SEQ ID NO:201:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:201:

GTTTTCCAGT                                                                    10

(2) INFORMATION FOR SEQ ID NO:202:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:202:

TTTTCCAGTC                                                                    10

(2) INFORMATION FOR SEQ ID NO:203:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:203:

TTTCCAGTCA                                                                    10

(2) INFORMATION FOR SEQ ID NO:204:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:204:

TTCCAGTCAC                                                                    10

(2) INFORMATION FOR SEQ ID NO:205:

(i) SEQUENCE CHARACTERISTICS:
        (A) LENGTH: 10 base pairs
        (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO:205:

TCCAGTCACA                                                              10

(2) INFORMATION FOR SEQ ID NO:206:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:206:

CCAGTCACAC                                                              10

(2) INFORMATION FOR SEQ ID NO:207:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:207:

CAGTCACACC                                                              10

(2) INFORMATION FOR SEQ ID NO:208:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:208:

AGTCACACCT                                                              10

(2) INFORMATION FOR SEQ ID NO:209:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:209:

GTCACACCTC                                                              10

(2) INFORMATION FOR SEQ ID NO:210:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:210:

TCACACCTCA                                                          10

(2) INFORMATION FOR SEQ ID NO:211:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:211:

CACACCTCAG                                                          10

(2) INFORMATION FOR SEQ ID NO:212:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:212:

ACACCTCAGG                                                          10

(2) INFORMATION FOR SEQ ID NO:213:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:213:

CACCTCAGGT                                                          10

(2) INFORMATION FOR SEQ ID NO:214:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:214:

ACCTCAGGTA                                                          10

(2) INFORMATION FOR SEQ ID NO:215:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:215:

CCTCAGGTAC                                                          10

(2) INFORMATION FOR SEQ ID NO:216:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:216:

CTCAGGTACC                                                              10

(2) INFORMATION FOR SEQ ID NO:217:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:217:

TCAGGTACCT                                                              10

(2) INFORMATION FOR SEQ ID NO:218:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:218:

CAGGTACCTT                                                              10

(2) INFORMATION FOR SEQ ID NO:219:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:219:

AGGTACCTTT                                                              10

(2) INFORMATION FOR SEQ ID NO:220:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:220:

GGTACCTTTA                                                              10

(2) INFORMATION FOR SEQ ID NO:221:

(i) SEQUENCE CHARACTERISTICS:
        (A) LENGTH: 10 base pairs
        (B) TYPE: nucleic acid (C) STRANDEDNESS: single
        (D) TOPOLOGY: linear (ii) MOLECULE TYPE: DNA (xi) SEQUENCE DESCRIPTION: SEQ ID NO:221:

GTACCTTTAA                                                                10

(2) INFORMATION FOR SEQ ID NO:222:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:222:

TACCTTTAAG                                                                10

(2) INFORMATION FOR SEQ ID NO:223:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:223:

ACCTTTAAGA                                                                10

(2) INFORMATION FOR SEQ ID NO:224:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:224:

CCTTTAAGAC                                                                10

(2) INFORMATION FOR SEQ ID NO:225:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:225:

CTTTAAGACC                                                                10

(2) INFORMATION FOR SEQ ID NO:226:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:226:

TTTAAGACCA                                                                                          10

(2) INFORMATION FOR SEQ ID NO:227:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:227:

TTAAGACCAA                                                                                          10

(2) INFORMATION FOR SEQ ID NO:228:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:228:

TAAGACCAAT                                                                                          10

(2) INFORMATION FOR SEQ ID NO:229:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:229:

AAGACCAATG                                                                                          10

(2) INFORMATION FOR SEQ ID NO:230:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:230:

AGACCAATGA                                                                                          10

(2) INFORMATION FOR SEQ ID NO:231:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:231:

GACCAATGAC                                                                                          10

(2) INFORMATION FOR SEQ ID NO:232:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:232:

ACCAATGACT      10

(2) INFORMATION FOR SEQ ID NO:233:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:233:

CCAATGACTT      10

(2) INFORMATION FOR SEQ ID NO:234:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:234:

CAATGACTTA      10

(2) INFORMATION FOR SEQ ID NO:235:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:235:

AATGACTTAC      10

(2) INFORMATION FOR SEQ ID NO:236:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:236:

ATGACTTACA      10

(2) INFORMATION FOR SEQ ID NO:237:

(i) SEQUENCE CHARACTERISTICS:
        (A) LENGTH: 10 base pairs
        (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO:237:

TGACTTACAA                                                              10

(2) INFORMATION FOR SEQ ID NO:238:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:238:

GACTTACAAG                                                              10

(2) INFORMATION FOR SEQ ID NO:239:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:239:

ACTTACAAGG                                                              10

(2) INFORMATION FOR SEQ ID NO:240:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:240:

CTTACAAGGC                                                              10

(2) INFORMATION FOR SEQ ID NO:241:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:241:

TTACAAGGCA                                                              10

(2) INFORMATION FOR SEQ ID NO:242:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA

```
          (xi) SEQUENCE DESCRIPTION: SEQ ID NO:242:

TACAAGGCAG                                                                10

(2) INFORMATION FOR SEQ ID NO:243:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:243:

ACAAGGCAGC                                                                10

(2) INFORMATION FOR SEQ ID NO:244:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:244:

CAAGGCAGCT                                                                10

(2) INFORMATION FOR SEQ ID NO:245:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:245:

AAGGCAGCTG                                                                10

(2) INFORMATION FOR SEQ ID NO:246:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:246:

AGGCAGCTGT                                                                10

(2) INFORMATION FOR SEQ ID NO:247:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:247:

GGCAGCTGTA                                                                10
```

(2) INFORMATION FOR SEQ ID NO:248:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:248:

GCAGCTGTAG    10

(2) INFORMATION FOR SEQ ID NO:249:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:249:

CAGCTGTAGA    10

(2) INFORMATION FOR SEQ ID NO:250:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:250:

AGCTGTAGAT    10

(2) INFORMATION FOR SEQ ID NO:251:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:251:

GCTGTAGATC    10

(2) INFORMATION FOR SEQ ID NO:252:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:252:

CTGTAGATCT    10

(2) INFORMATION FOR SEQ ID NO:253:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO:253:

TGTAGATCTT                                                              10

(2) INFORMATION FOR SEQ ID NO:254:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:254:

GTAGATCTTA                                                              10

(2) INFORMATION FOR SEQ ID NO:255:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:255:

TAGATCTTAG                                                              10

(2) INFORMATION FOR SEQ ID NO:256:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:256:

AGATCTTAGC                                                              10

(2) INFORMATION FOR SEQ ID NO:257:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:257:

GATCTTAGCC                                                              10

(2) INFORMATION FOR SEQ ID NO:258:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA
```

```
    (xi) SEQUENCE DESCRIPTION: SEQ ID NO:258:

ATCTTAGCCA                                                              10

(2) INFORMATION FOR SEQ ID NO:259:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:259:

TCTTAGCCAC                                                              10

(2) INFORMATION FOR SEQ ID NO:260:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:260:

CTTAGCCACT                                                              10

(2) INFORMATION FOR SEQ ID NO:261:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:261:

TTAGCCACTT                                                              10

(2) INFORMATION FOR SEQ ID NO:262:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:262:

TAGCCACTTT                                                              10

(2) INFORMATION FOR SEQ ID NO:263:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:263:

AGCCACTTTT                                                              10
```

(2) INFORMATION FOR SEQ ID NO:264:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:264:

GCCACTTTTT    10

(2) INFORMATION FOR SEQ ID NO:265:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:265:

CCACTTTTTA    10

(2) INFORMATION FOR SEQ ID NO:266:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:266:

CACTTTTTAA    10

(2) INFORMATION FOR SEQ ID NO:267:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:267:

ACTTTTTAAA    10

(2) INFORMATION FOR SEQ ID NO:268:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:268:

CTTTTTAAAA    10

(2) INFORMATION FOR SEQ ID NO:269:

(i) SEQUENCE CHARACTERISTICS:
        (A) LENGTH: 10 base pairs
        (B) TYPE: nucleic acid

```
            (C) STRANDEDNESS: single
            (D) TOPOLOGY: linear (ii) MOLECULE TYPE: DNA (xi) SEQUENCE DESCRIPTION: SEQ ID NO:269:

TTTTTAAAAG                                                              10

(2) INFORMATION FOR SEQ ID NO:270:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:270:

TTTTAAAAGA                                                              10

(2) INFORMATION FOR SEQ ID NO:271:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:271:

TTTAAAAGAA                                                              10

(2) INFORMATION FOR SEQ ID NO:272:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:272:

TTAAAAGAAA                                                              10

(2) INFORMATION FOR SEQ ID NO:273:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:273:

TAAAAGAAAA                                                              10

(2) INFORMATION FOR SEQ ID NO:274:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA
```

(xi) SEQUENCE DESCRIPTION: SEQ ID NO:274:

AAAAGAAAAG                                                              10

(2) INFORMATION FOR SEQ ID NO:275:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:275:

AAAGAAAAGG                                                              10

(2) INFORMATION FOR SEQ ID NO:276:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:276:

AAGAAAAGGG                                                              10

(2) INFORMATION FOR SEQ ID NO:277:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:277:

AGAAAAGGGG                                                              10

(2) INFORMATION FOR SEQ ID NO:278:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:278:

GAAAAGGGGG                                                              10

(2) INFORMATION FOR SEQ ID NO:279:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:279:

AAAAGGGGGG                                                              10

-continued (2) INFORMATION FOR SEQ ID NO:280:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:280:

AAAGGGGGGA                                            10

(2) INFORMATION FOR SEQ ID NO:281:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:281:

AAGGGGGGAC                                            10

(2) INFORMATION FOR SEQ ID NO:282:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:282:

AGGGGGGACT                                            10

(2) INFORMATION FOR SEQ ID NO:283:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:283:

GGGGGGACTG                                            10

(2) INFORMATION FOR SEQ ID NO:284:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:284:

GGGGGACTGG                                            10

(2) INFORMATION FOR SEQ ID NO:285:

(i) SEQUENCE CHARACTERISTICS:
        (A) LENGTH: 10 base pairs
        (B) TYPE: nucleic acid -continued

```
          (C) STRANDEDNESS: single
          (D) TOPOLOGY: linear (ii) MOLECULE TYPE: DNA (xi) SEQUENCE DESCRIPTION: SEQ ID NO:285:

GGGGACTGGA                                                                    10

(2) INFORMATION FOR SEQ ID NO:286:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:286:

GGGACTGGAA                                                                    10

(2) INFORMATION FOR SEQ ID NO:287:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:287:

GGACTGGAAG                                                                    10

(2) INFORMATION FOR SEQ ID NO:288:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:288:

GACTGGAAGG                                                                    10

(2) INFORMATION FOR SEQ ID NO:289:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:289:

ACTGGAAGGG                                                                    10

(2) INFORMATION FOR SEQ ID NO:290:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA
```

(xi) SEQUENCE DESCRIPTION: SEQ ID NO:290:

CTGGAAGGGC                                                                10

(2) INFORMATION FOR SEQ ID NO:291:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:291:

TGGAAGGGCT                                                                10

(2) INFORMATION FOR SEQ ID NO:292:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:292:

GGAAGGGCTA                                                                10

(2) INFORMATION FOR SEQ ID NO:293:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:293:

GAAGGGCTAA                                                                10

(2) INFORMATION FOR SEQ ID NO:294:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:294:

AAGGGCTAAT                                                                10

(2) INFORMATION FOR SEQ ID NO:295:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:295:

AGGGCTAATT                                                                10

(2) INFORMATION FOR SEQ ID NO:296:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:296:

GGGCTAATTC           10

(2) INFORMATION FOR SEQ ID NO:297:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:297:

GGCTAATTCA           10

(2) INFORMATION FOR SEQ ID NO:298:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:298:

GCTAATTCAC           10

(2) INFORMATION FOR SEQ ID NO:299:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:299:

CTAATTCACT           10

(2) INFORMATION FOR SEQ ID NO:300:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:300:

TAATTCACTC           10

(2) INFORMATION FOR SEQ ID NO:301:

(i) SEQUENCE CHARACTERISTICS:
        (A) LENGTH: 10 base pairs
        (B) TYPE: nucleic acid

```
            (C) STRANDEDNESS: single
            (D) TOPOLOGY: linear (ii) MOLECULE TYPE: DNA (xi) SEQUENCE DESCRIPTION: SEQ ID NO:301:

AATTCACTCC                                                              10

(2) INFORMATION FOR SEQ ID NO:302:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:302:

ATTCACTCCC                                                              10

(2) INFORMATION FOR SEQ ID NO:303:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:303:

TTCACTCCCA                                                              10

(2) INFORMATION FOR SEQ ID NO:304:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:304:

TCACTCCCAA                                                              10

(2) INFORMATION FOR SEQ ID NO:305:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:305:

CACTCCCAAA                                                              10

(2) INFORMATION FOR SEQ ID NO:306:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA
```

```
        (xi) SEQUENCE DESCRIPTION: SEQ ID NO:306:

ACTCCCAAAG                                                          10

(2) INFORMATION FOR SEQ ID NO:307:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:307:

CTCCCAAAGA                                                          10

(2) INFORMATION FOR SEQ ID NO:308:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:308:

TCCCAAAGAA                                                          10

(2) INFORMATION FOR SEQ ID NO:309:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:309:

CCCAAAGAAG                                                          10

(2) INFORMATION FOR SEQ ID NO:310:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:310:

CCAAAGAAGA                                                          10

(2) INFORMATION FOR SEQ ID NO:311:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:311:

CAAAGAAGAC                                                          10
```

(2) INFORMATION FOR SEQ ID NO:312:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:312:

AAAGAAGACA          10

(2) INFORMATION FOR SEQ ID NO:313:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:313:

AAGAAGACAA          10

(2) INFORMATION FOR SEQ ID NO:314:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:314:

AGAAGACAAG          10

(2) INFORMATION FOR SEQ ID NO:315:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:315:

GAAGACAAGA          10

(2) INFORMATION FOR SEQ ID NO:316:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:316:

AAGACAAGAT          10

(2) INFORMATION FOR SEQ ID NO:317:

(i) SEQUENCE CHARACTERISTICS:
        (A) LENGTH: 10 base pairs
        (B) TYPE: nucleic acid

```
          (C) STRANDEDNESS: single
          (D) TOPOLOGY: linear (ii) MOLECULE TYPE: DNA (xi) SEQUENCE DESCRIPTION: SEQ ID NO:317:

AGACAAGATA                                                            10

(2) INFORMATION FOR SEQ ID NO:318:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:318:

GACAAGATAT                                                            10

(2) INFORMATION FOR SEQ ID NO:319:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:319:

ACAAGATATC                                                            10

(2) INFORMATION FOR SEQ ID NO:320:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:320:

CAAGATATCC                                                            10

(2) INFORMATION FOR SEQ ID NO:321:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:321:

AAGATATCCT                                                            10

(2) INFORMATION FOR SEQ ID NO:322:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA
```

(xi) SEQUENCE DESCRIPTION: SEQ ID NO:322:

AGATATCCTT                                                                         10

(2) INFORMATION FOR SEQ ID NO:323:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:323:

GATATCCTTG                                                                         10

(2) INFORMATION FOR SEQ ID NO:324:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:324:

ATATCCTTGA                                                                         10

(2) INFORMATION FOR SEQ ID NO:325:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:325:

TATCCTTGAT                                                                         10

(2) INFORMATION FOR SEQ ID NO:326:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:326:

ATCCTTGATC                                                                         10

(2) INFORMATION FOR SEQ ID NO:327:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:327:

TCCTTGATCT                                                                         10

(2) INFORMATION FOR SEQ ID NO:328:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:328:

CCTTGATCTG                                                            10

(2) INFORMATION FOR SEQ ID NO:329:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:329:

CTTGATCTGT                                                            10

(2) INFORMATION FOR SEQ ID NO:330:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:330:

TTGATCTGTG                                                            10

(2) INFORMATION FOR SEQ ID NO:331:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:331:

TGATCTGTGG                                                            10

(2) INFORMATION FOR SEQ ID NO:332:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:332:

GATCTGTGGA                                                            10

(2) INFORMATION FOR SEQ ID NO:333:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO:333:

ATCTGTGGAT                                                              10

(2) INFORMATION FOR SEQ ID NO:334:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:334:

TCTGTGGATC                                                              10

(2) INFORMATION FOR SEQ ID NO:335:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:335:

CTGTGGATCT                                                              10

(2) INFORMATION FOR SEQ ID NO:336:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:336:

TGTGGATCTA                                                              10

(2) INFORMATION FOR SEQ ID NO:337:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:337:

GTGGATCTAC                                                              10

(2) INFORMATION FOR SEQ ID NO:338:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:338:

TGGATCTACC                                                            10

(2) INFORMATION FOR SEQ ID NO:339:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:339:

GGATCTACCA                                                            10

(2) INFORMATION FOR SEQ ID NO:340:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:340:

GATCTACCAC                                                            10

(2) INFORMATION FOR SEQ ID NO:341:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:341:

ATCTACCACA                                                            10

(2) INFORMATION FOR SEQ ID NO:342:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:342:

TCTACCACAC                                                            10

(2) INFORMATION FOR SEQ ID NO:343:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:343:

CTACCACACA                                                            10

(2) INFORMATION FOR SEQ ID NO:344:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:344:

TACCACACAC    10

(2) INFORMATION FOR SEQ ID NO:345:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:345:

ACCACACACA    10

(2) INFORMATION FOR SEQ ID NO:346:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:346:

CCACACACAA    10

(2) INFORMATION FOR SEQ ID NO:347:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:347:

CACACACAAG    10

(2) INFORMATION FOR SEQ ID NO:348:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:348:

ACACACAAGG    10

(2) INFORMATION FOR SEQ ID NO:349:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO:349:

CACACAAGGC                                                              10

(2) INFORMATION FOR SEQ ID NO:350:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:350:

ACACAAGGCT                                                              10

(2) INFORMATION FOR SEQ ID NO:351:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:351:

CACAAGGCTA                                                              10

(2) INFORMATION FOR SEQ ID NO:352:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:352:

ACAAGGCTAC                                                              10

(2) INFORMATION FOR SEQ ID NO:353:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:353:

CAAGGCTACT                                                              10

(2) INFORMATION FOR SEQ ID NO:354:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:354:

AAGGCTACTT                                                                            10

(2) INFORMATION FOR SEQ ID NO:355:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:355:

AGGCTACTTC                                                                            10

(2) INFORMATION FOR SEQ ID NO:356:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:356:

GGCTACTTCC                                                                            10

(2) INFORMATION FOR SEQ ID NO:357:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:357:

GCTACTTCCC                                                                            10

(2) INFORMATION FOR SEQ ID NO:358:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:358:

CTACTTCCCT                                                                            10

(2) INFORMATION FOR SEQ ID NO:359:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:359:

TACTTCCCTG                                                                            10

(2) INFORMATION FOR SEQ ID NO:360:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:360:

ACTTCCCTGA                                                            10

(2) INFORMATION FOR SEQ ID NO:361:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:361:

CTTCCCTGAT                                                            10

(2) INFORMATION FOR SEQ ID NO:362:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:362:

TTCCCTGATT                                                            10

(2) INFORMATION FOR SEQ ID NO:363:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:363:

TCCCTGATTG                                                            10

(2) INFORMATION FOR SEQ ID NO:364:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:364:

CCCTGATTGG                                                           10

(2) INFORMATION FOR SEQ ID NO:365:

(i) SEQUENCE CHARACTERISTICS:
        (A) LENGTH: 10 base pairs
        (B) TYPE: nucleic acid -continued

```
            (C) STRANDEDNESS: single
            (D) TOPOLOGY: linear (ii) MOLECULE TYPE: DNA (xi) SEQUENCE DESCRIPTION: SEQ ID NO:365:

CCTGATTGGC                                                          10

(2) INFORMATION FOR SEQ ID NO:366:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:366:

CTGATTGGCA                                                          10

(2) INFORMATION FOR SEQ ID NO:367:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:367:

TGATTGGCAG                                                          10

(2) INFORMATION FOR SEQ ID NO:368:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:368:

GATTGGCAGA                                                          10

(2) INFORMATION FOR SEQ ID NO:369:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:369:

ATTGGCAGAA                                                          10

(2) INFORMATION FOR SEQ ID NO:370:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA
```

(xi) SEQUENCE DESCRIPTION: SEQ ID NO:370:

TTGGCAGAAC                                                          10

(2) INFORMATION FOR SEQ ID NO:371:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:371:

TGGCAGAACT                                                          10

(2) INFORMATION FOR SEQ ID NO:372:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:372:

GGCAGAACTA                                                          10

(2) INFORMATION FOR SEQ ID NO:373:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:373:

GCAGAACTAC                                                          10

(2) INFORMATION FOR SEQ ID NO:374:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:374:

CAGAACTACA                                                          10

(2) INFORMATION FOR SEQ ID NO:375:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:375:

AGAACTACAC                                                          10

(2) INFORMATION FOR SEQ ID NO:376:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:376:

GAACTACACA                                                          10

(2) INFORMATION FOR SEQ ID NO:377:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:377:

AACTACACAC                                                          10

(2) INFORMATION FOR SEQ ID NO:378:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:378:

ACTACACACC                                                          10

(2) INFORMATION FOR SEQ ID NO:379:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:379:

CTACACACCA                                                          10

(2) INFORMATION FOR SEQ ID NO:380:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:380:

TACACACCAG                                                          10

(2) INFORMATION FOR SEQ ID NO:381:

(i) SEQUENCE CHARACTERISTICS:
        (A) LENGTH: 10 base pairs
        (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO:381:

ACACACCAGG                                                              10

(2) INFORMATION FOR SEQ ID NO:382:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:382:

CACACCAGGG                                                              10

(2) INFORMATION FOR SEQ ID NO:383:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:383:

ACACCAGGGC                                                              10

(2) INFORMATION FOR SEQ ID NO:384:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:384:

CACCAGGGCC                                                              10

(2) INFORMATION FOR SEQ ID NO:385:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:385:

ACCAGGGCCA                                                              10

(2) INFORMATION FOR SEQ ID NO:386:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA -continued (xi) SEQUENCE DESCRIPTION: SEQ ID NO:386:

CCAGGGCCAG                                                          10

(2) INFORMATION FOR SEQ ID NO:387:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:387:

CAGGGCCAGG                                                          10

(2) INFORMATION FOR SEQ ID NO:388:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:388:

AGGGCCAGGG                                                          10

(2) INFORMATION FOR SEQ ID NO:389:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:389:

GGGCCAGGGG                                                          10

(2) INFORMATION FOR SEQ ID NO:390:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:390:

GGCCAGGGGT                                                          10

(2) INFORMATION FOR SEQ ID NO:391:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:391:

GCCAGGGGTC                                                          10

(2) INFORMATION FOR SEQ ID NO:392:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:392:

CCAGGGGTCA                                                            10

(2) INFORMATION FOR SEQ ID NO:393:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:393:

CAGGGGTCAG                                                            10

(2) INFORMATION FOR SEQ ID NO:394:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:394:

AGGGGTCAGA                                                            10

(2) INFORMATION FOR SEQ ID NO:395:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:395:

GGGGTCAGAT                                                            10

(2) INFORMATION FOR SEQ ID NO:396:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:396:

GGGTCAGATA                                                            10

(2) INFORMATION FOR SEQ ID NO:397:

(i) SEQUENCE CHARACTERISTICS:
           (A) LENGTH: 10 base pairs
           (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO:397:

GGTCAGATAT                                                                    10

(2) INFORMATION FOR SEQ ID NO:398:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:398:

GTCAGATATC                                                                    10

(2) INFORMATION FOR SEQ ID NO:399:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:399:

TCAGATATCC                                                                    10

(2) INFORMATION FOR SEQ ID NO:400:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:400:

CAGATATCCA                                                                    10

(2) INFORMATION FOR SEQ ID NO:401:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:401:

AGATATCCAC                                                                    10

(2) INFORMATION FOR SEQ ID NO:402:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:402:

GATATCCACT                                                              10

(2) INFORMATION FOR SEQ ID NO:403:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:403:

ATATCCACTG                                                              10

(2) INFORMATION FOR SEQ ID NO:404:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:404:

TATCCACTGA                                                              10

(2) INFORMATION FOR SEQ ID NO:405:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:405:

ATCCACTGAC                                                              10

(2) INFORMATION FOR SEQ ID NO:406:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:406:

TCCACTGACC                                                              10

(2) INFORMATION FOR SEQ ID NO:407:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:407:

CCACTGACCT                                                              10

(2) INFORMATION FOR SEQ ID NO:408:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:408:

CACTGACCTT    10

(2) INFORMATION FOR SEQ ID NO:409:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:409:

ACTGACCTTT    10

(2) INFORMATION FOR SEQ ID NO:410:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:410:

CTGACCTTTG    10

(2) INFORMATION FOR SEQ ID NO:411:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:411:

TGACCTTTGG    10

(2) INFORMATION FOR SEQ ID NO:412:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:412:

GACCTTTGGA    10

(2) INFORMATION FOR SEQ ID NO:413:

(i) SEQUENCE CHARACTERISTICS:
        (A) LENGTH: 10 base pairs
        (B) TYPE: nucleic acid (C) STRANDEDNESS: single
       (D) TOPOLOGY: linear (ii) MOLECULE TYPE: DNA (xi) SEQUENCE DESCRIPTION: SEQ ID NO:413:

ACCTTTGGAT                                                              10

(2) INFORMATION FOR SEQ ID NO:414:

(i) SEQUENCE CHARACTERISTICS:
       (A) LENGTH: 10 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:414:

CCTTTGGATG                                                              10

(2) INFORMATION FOR SEQ ID NO:415:

(i) SEQUENCE CHARACTERISTICS:
       (A) LENGTH: 10 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:415:

CTTTGGATGG                                                              10

(2) INFORMATION FOR SEQ ID NO:416:

(i) SEQUENCE CHARACTERISTICS:
       (A) LENGTH: 10 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:416:

TTTGGATGGT                                                              10

(2) INFORMATION FOR SEQ ID NO:417:

(i) SEQUENCE CHARACTERISTICS:
       (A) LENGTH: 10 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:417:

TTGGATGGTG                                                              10

(2) INFORMATION FOR SEQ ID NO:418:

(i) SEQUENCE CHARACTERISTICS:
       (A) LENGTH: 10 base pairs
       (B) TYPE: nucleic acid
       (C) STRANDEDNESS: single
       (D) TOPOLOGY: linear (ii) MOLECULE TYPE: DNA

```
    (xi) SEQUENCE DESCRIPTION: SEQ ID NO:418:

TGGATGGTGC                                                              10

(2) INFORMATION FOR SEQ ID NO:419:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:419:

GGATGGTGCT                                                              10

(2) INFORMATION FOR SEQ ID NO:420:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:420:

GATGGTGCTA                                                              10

(2) INFORMATION FOR SEQ ID NO:421:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:421:

ATGGTGCTAC                                                              10

(2) INFORMATION FOR SEQ ID NO:422:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:422:

TGGTGCTACA                                                              10

(2) INFORMATION FOR SEQ ID NO:423:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:423:

GGTGCTACAA                                                              10
```

(2) INFORMATION FOR SEQ ID NO:424:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:424:

GTGCTACAAG                                           10

(2) INFORMATION FOR SEQ ID NO:425:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:425:

TGCTACAAGC                                           10

(2) INFORMATION FOR SEQ ID NO:426:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:426:

GCTACAAGCT                                           10

(2) INFORMATION FOR SEQ ID NO:427:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:427:

CTACAAGCTA                                           10

(2) INFORMATION FOR SEQ ID NO:428:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:428:

TACAAGCTAG                                           10

(2) INFORMATION FOR SEQ ID NO:429:

(i) SEQUENCE CHARACTERISTICS:
        (A) LENGTH: 10 base pairs
        (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO:429:

ACAAGCTAGT                                                              10

(2) INFORMATION FOR SEQ ID NO:430:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:430:

CAAGCTAGTA                                                              10

(2) INFORMATION FOR SEQ ID NO:431:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:431:

AAGCTAGTAC                                                              10

(2) INFORMATION FOR SEQ ID NO:432:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:432:

AGCTAGTACC                                                              10

(2) INFORMATION FOR SEQ ID NO:433:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:433:

GCTAGTACCA                                                              10

(2) INFORMATION FOR SEQ ID NO:434:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:434:

CTAGTACCAG                                                              10

(2) INFORMATION FOR SEQ ID NO:435:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:435:

TAGTACCAGT                                                              10

(2) INFORMATION FOR SEQ ID NO:436:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:436:

AGTACCAGTT                                                              10

(2) INFORMATION FOR SEQ ID NO:437:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:437:

GTACCAGTTG                                                              10

(2) INFORMATION FOR SEQ ID NO:438:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:438:

TACCAGTTGA                                                              10

(2) INFORMATION FOR SEQ ID NO:439:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:439:

ACCAGTTGAG                                                              10

(2) INFORMATION FOR SEQ ID NO:440:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:440:

CCAGTTGAGC      10

(2) INFORMATION FOR SEQ ID NO:441:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:441:

CAGTTGAGCC      10

(2) INFORMATION FOR SEQ ID NO:442:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:442:

AGTTGAGCCA      10

(2) INFORMATION FOR SEQ ID NO:443:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:443:

GTTGAGCCAG      10

(2) INFORMATION FOR SEQ ID NO:444:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:444:

TTGAGCCAGA      10

(2) INFORMATION FOR SEQ ID NO:445:

(i) SEQUENCE CHARACTERISTICS:
        (A) LENGTH: 10 base pairs
        (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO:445:

TGAGCCAGAT                                                                10

(2) INFORMATION FOR SEQ ID NO:446:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:446:

GAGCCAGATA                                                                10

(2) INFORMATION FOR SEQ ID NO:447:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:447:

AGCCAGATAA                                                                10

(2) INFORMATION FOR SEQ ID NO:448:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:448:

GCCAGATAAG                                                                10

(2) INFORMATION FOR SEQ ID NO:449:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:449:

CCAGATAAGG                                                                10

(2) INFORMATION FOR SEQ ID NO:450:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:450:

CAGATAAGGT                                                                10

(2) INFORMATION FOR SEQ ID NO:451:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:451:

AGATAAGGTA                                                                10

(2) INFORMATION FOR SEQ ID NO:452:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:452:

GATAAGGTAG                                                                10

(2) INFORMATION FOR SEQ ID NO:453:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:453:

ATAAGGTAGA                                                                10

(2) INFORMATION FOR SEQ ID NO:454:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:454:

TAAGGTAGAA                                                                10

(2) INFORMATION FOR SEQ ID NO:455:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:455:

AAGGTAGAAG                                                                10

(2) INFORMATION FOR SEQ ID NO:456:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:456:

AGGTAGAAGA          10

(2) INFORMATION FOR SEQ ID NO:457:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:457:

GGTAGAAGAG          10

(2) INFORMATION FOR SEQ ID NO:458:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:458:

GTAGAAGAGG          10

(2) INFORMATION FOR SEQ ID NO:459:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:459:

TAGAAGAGGC          10

(2) INFORMATION FOR SEQ ID NO:460:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:460:

AGAAGAGGCC          10

(2) INFORMATION FOR SEQ ID NO:461:

(i) SEQUENCE CHARACTERISTICS:
        (A) LENGTH: 10 base pairs
        (B) TYPE: nucleic acid -continued

```
        (C) STRANDEDNESS: single
        (D) TOPOLOGY: linear (ii) MOLECULE TYPE: DNA (xi) SEQUENCE DESCRIPTION: SEQ ID NO:461:

GAAGAGGCCA                                                             10

(2) INFORMATION FOR SEQ ID NO:462:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:462:

AAGAGGCCAA                                                             10

(2) INFORMATION FOR SEQ ID NO:463:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:463:

AGAGGCCAAT                                                             10

(2) INFORMATION FOR SEQ ID NO:464:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:464:

GAGGCCAATA                                                             10

(2) INFORMATION FOR SEQ ID NO:465:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:465:

AGGCCAATAA                                                             10

(2) INFORMATION FOR SEQ ID NO:466:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:466:

GGCCAATAAA                                                              10

(2) INFORMATION FOR SEQ ID NO:467:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:467:

GCCAATAAAG                                                              10

(2) INFORMATION FOR SEQ ID NO:468:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:468:

CCAATAAAGG                                                              10

(2) INFORMATION FOR SEQ ID NO:469:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:469:

CAATAAAGGA                                                              10

(2) INFORMATION FOR SEQ ID NO:470:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:470:

AATAAAGGAG                                                              10

(2) INFORMATION FOR SEQ ID NO:471:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:471:

ATAAAGGAGA                                                              10

(2) INFORMATION FOR SEQ ID NO:472:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:472:

TAAAGGAGAG                                                             10

(2) INFORMATION FOR SEQ ID NO:473:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:473:

AAAGGAGAGA                                                             10

(2) INFORMATION FOR SEQ ID NO:474:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:474:

AAGGAGAGAA                                                             10

(2) INFORMATION FOR SEQ ID NO:475:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:475:

AGGAGAGAAC                                                             10

(2) INFORMATION FOR SEQ ID NO:476:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:476:

GGAGAGAACA                                                             10

(2) INFORMATION FOR SEQ ID NO:477:

(i) SEQUENCE CHARACTERISTICS:
        (A) LENGTH: 10 base pairs
        (B) TYPE: nucleic acid (C) STRANDEDNESS: single
        (D) TOPOLOGY: linear (ii) MOLECULE TYPE: DNA (xi) SEQUENCE DESCRIPTION: SEQ ID NO:477:

GAGAGAACAC                                                                    10

(2) INFORMATION FOR SEQ ID NO:478:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:478:

AGAGAACACC                                                                    10

(2) INFORMATION FOR SEQ ID NO:479:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:479:

GAGAACACCA                                                                    10

(2) INFORMATION FOR SEQ ID NO:480:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:480:

AGAACACCAG                                                                    10

(2) INFORMATION FOR SEQ ID NO:481:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:481:

GAACACCAGC                                                                    10

(2) INFORMATION FOR SEQ ID NO:482:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:482:

AACACCAGCT                                                                      10

(2) INFORMATION FOR SEQ ID NO:483:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:483:

ACACCAGCTT                                                                      10

(2) INFORMATION FOR SEQ ID NO:484:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:484:

CACCAGCTTG                                                                      10

(2) INFORMATION FOR SEQ ID NO:485:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:485:

ACCAGCTTGT                                                                      10

(2) INFORMATION FOR SEQ ID NO:486:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:486:

CCAGCTTGTT                                                                      10

(2) INFORMATION FOR SEQ ID NO:487:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:487:

CAGCTTGTTA                                                                      10

(2) INFORMATION FOR SEQ ID NO:488:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:488:

AGCTTGTTAC                                                                 10

(2) INFORMATION FOR SEQ ID NO:489:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:489:

GCTTGTTACA                                                                 10

(2) INFORMATION FOR SEQ ID NO:490:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:490:

CTTGTTACAC                                                                 10

(2) INFORMATION FOR SEQ ID NO:491:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:491:

TTGTTACACC                                                                 10

(2) INFORMATION FOR SEQ ID NO:492:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:492:

TGTTACACCC                                                                 10

(2) INFORMATION FOR SEQ ID NO:493:

(i) SEQUENCE CHARACTERISTICS:
        (A) LENGTH: 10 base pairs
        (B) TYPE: nucleic acid -continued

```
            (C) STRANDEDNESS: single
            (D) TOPOLOGY: linear (ii) MOLECULE TYPE: DNA (xi) SEQUENCE DESCRIPTION: SEQ ID NO:493:

GTTACACCCT                                                          10

(2) INFORMATION FOR SEQ ID NO:494:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:494:

TTACACCCTG                                                          10

(2) INFORMATION FOR SEQ ID NO:495:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:495:

TACACCCTGT                                                          10

(2) INFORMATION FOR SEQ ID NO:496:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:496:

ACACCCTGTG                                                          10

(2) INFORMATION FOR SEQ ID NO:497:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:497:

CACCCTGTGA                                                          10

(2) INFORMATION FOR SEQ ID NO:498:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA
```

```
        (xi) SEQUENCE DESCRIPTION: SEQ ID NO:498:

ACCCTGTGAG                                                              10

(2) INFORMATION FOR SEQ ID NO:499:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:499:

CCCTGTGAGC                                                              10

(2) INFORMATION FOR SEQ ID NO:500:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:500:

CCTGTGAGCC                                                              10

(2) INFORMATION FOR SEQ ID NO:501:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:501:

CTGTGAGCCT                                                              10

(2) INFORMATION FOR SEQ ID NO:502:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:502:

TGTGAGCCTG                                                              10

(2) INFORMATION FOR SEQ ID NO:503:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:503:

GTGAGCCTGC                                                              10
```

(2) INFORMATION FOR SEQ ID NO:504:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:504:

TGAGCCTGCA          10

(2) INFORMATION FOR SEQ ID NO:505:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:505:

GAGCCTGCAT          10

(2) INFORMATION FOR SEQ ID NO:506:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:506:

AGCCTGCATG          10

(2) INFORMATION FOR SEQ ID NO:507:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:507:

GCCTGCATGG          10

(2) INFORMATION FOR SEQ ID NO:508:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:508:

CCTGCATGGA          10

(2) INFORMATION FOR SEQ ID NO:509:

(i) SEQUENCE CHARACTERISTICS:
        (A) LENGTH: 10 base pairs
        (B) TYPE: nucleic acid

```
      (C) STRANDEDNESS: single
      (D) TOPOLOGY: linear (ii) MOLECULE TYPE: DNA (xi) SEQUENCE DESCRIPTION: SEQ ID NO:509:

CTGCATGGAA                                                              10

(2) INFORMATION FOR SEQ ID NO:510:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:510:

TGCATGGAAT                                                              10

(2) INFORMATION FOR SEQ ID NO:511:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:511:

GCATGGAATG                                                              10

(2) INFORMATION FOR SEQ ID NO:512:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:512:

CATGGAATGG                                                              10

(2) INFORMATION FOR SEQ ID NO:513:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:513:

ATGGAATGGA                                                              10

(2) INFORMATION FOR SEQ ID NO:514:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA
```

(xi) SEQUENCE DESCRIPTION: SEQ ID NO:514:

TGGAATGGAT                                                                    10

(2) INFORMATION FOR SEQ ID NO:515:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:515:

GGAATGGATG                                                                    10

(2) INFORMATION FOR SEQ ID NO:516:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:516:

GAATGGATGA                                                                    10

(2) INFORMATION FOR SEQ ID NO:517:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:517:

AATGGATGAC                                                                    10

(2) INFORMATION FOR SEQ ID NO:518:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:518:

ATGGATGACC                                                                    10

(2) INFORMATION FOR SEQ ID NO:519:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:519:

TGGATGACCC                                                                    10

(2) INFORMATION FOR SEQ ID NO:520:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:520:

GGATGACCCT                                                              10

(2) INFORMATION FOR SEQ ID NO:521:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:521:

GATGACCCTG                                                              10

(2) INFORMATION FOR SEQ ID NO:522:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:522:

ATGACCCTGA                                                              10

(2) INFORMATION FOR SEQ ID NO:523:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:523:

TGACCCTGAG                                                              10

(2) INFORMATION FOR SEQ ID NO:524:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:524:

GACCCTGAGA                                                              10

(2) INFORMATION FOR SEQ ID NO:525:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO:525:

ACCCTGAGAG                                                              10

(2) INFORMATION FOR SEQ ID NO:526:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:526:

CCCTGAGAGA                                                              10

(2) INFORMATION FOR SEQ ID NO:527:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:527:

CCTGAGAGAG                                                              10

(2) INFORMATION FOR SEQ ID NO:528:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:528:

CTGAGAGAGA                                                              10

(2) INFORMATION FOR SEQ ID NO:529:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:529:

TGAGAGAGAA                                                              10

(2) INFORMATION FOR SEQ ID NO:530:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:530:

GAGAGAGAAG 10

(2) INFORMATION FOR SEQ ID NO:531:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:531:

AGAGAGAAGT 10

(2) INFORMATION FOR SEQ ID NO:532:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:532:

GAGAGAAGTG 10

(2) INFORMATION FOR SEQ ID NO:533:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:533:

AGAGAAGTGT 10

(2) INFORMATION FOR SEQ ID NO:534:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:534:

GAGAAGTGTT 10

(2) INFORMATION FOR SEQ ID NO:535:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:535:

AGAAGTGTTA 10

(2) INFORMATION FOR SEQ ID NO:536:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:536:

GAAGTGTTAG       10

(2) INFORMATION FOR SEQ ID NO:537:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:537:

AAGTGTTAGA       10

(2) INFORMATION FOR SEQ ID NO:538:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:538:

AGTGTTAGAG       10

(2) INFORMATION FOR SEQ ID NO:539:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:539:

GTGTTAGAGT       10

(2) INFORMATION FOR SEQ ID NO:540:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:540:

TGTTAGAGTG       10

(2) INFORMATION FOR SEQ ID NO:541:

(i) SEQUENCE CHARACTERISTICS:
        (A) LENGTH: 10 base pairs
        (B) TYPE: nucleic acid

```
            (C) STRANDEDNESS: single
            (D) TOPOLOGY: linear (ii) MOLECULE TYPE: DNA (xi) SEQUENCE DESCRIPTION: SEQ ID NO:541:

GTTAGAGTGG                                                              10

(2) INFORMATION FOR SEQ ID NO:542:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:542:

TTAGAGTGGA                                                              10

(2) INFORMATION FOR SEQ ID NO:543:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:543:

TAGAGTGGAG                                                              10

(2) INFORMATION FOR SEQ ID NO:544:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:544:

AGAGTGGAGG                                                              10

(2) INFORMATION FOR SEQ ID NO:545:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:545:

GAGTGGAGGT                                                              10

(2) INFORMATION FOR SEQ ID NO:546:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA
```

(xi) SEQUENCE DESCRIPTION: SEQ ID NO:546:

AGTGGAGGTT                                                                 10

(2) INFORMATION FOR SEQ ID NO:547:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:547:

GTGGAGGTTT                                                                 10

(2) INFORMATION FOR SEQ ID NO:548:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:548:

TGGAGGTTTG                                                                 10

(2) INFORMATION FOR SEQ ID NO:549:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:549:

GGAGGTTTGA                                                                 10

(2) INFORMATION FOR SEQ ID NO:550:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:550:

GAGGTTTGAC                                                                 10

(2) INFORMATION FOR SEQ ID NO:551:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:551:

AGGTTTGACA                                                                 10

(2) INFORMATION FOR SEQ ID NO:552:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:552:

GGTTTGACAG                                                          10

(2) INFORMATION FOR SEQ ID NO:553:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:553:

GTTTGACAGC                                                          10

(2) INFORMATION FOR SEQ ID NO:554:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:554:

TTTGACAGCC                                                          10

(2) INFORMATION FOR SEQ ID NO:555:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:555:

TTGACAGCCG                                                          10

(2) INFORMATION FOR SEQ ID NO:556:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:556:

TGACAGCCGC                                                          10

(2) INFORMATION FOR SEQ ID NO:557:

(i) SEQUENCE CHARACTERISTICS:
      (A) LENGTH: 10 base pairs
      (B) TYPE: nucleic acid -continued (C) STRANDEDNESS: single
            (D) TOPOLOGY: linear (ii) MOLECULE TYPE: DNA (xi) SEQUENCE DESCRIPTION: SEQ ID NO:557:

GACAGCCGCC                                                                    10

(2) INFORMATION FOR SEQ ID NO:558:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:558:

ACAGCCGCCT                                                                    10

(2) INFORMATION FOR SEQ ID NO:559:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:559:

CAGCCGCCTA                                                                    10

(2) INFORMATION FOR SEQ ID NO:560:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:560:

AGCCGCCTAG                                                                    10

(2) INFORMATION FOR SEQ ID NO:561:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:561:

GCCGCCTAGC                                                                    10

(2) INFORMATION FOR SEQ ID NO:562:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA

```
        (xi) SEQUENCE DESCRIPTION: SEQ ID NO:562:

CCGCCTAGCA                                                              10

(2) INFORMATION FOR SEQ ID NO:563:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:563:

CGCCTAGCAT                                                              10

(2) INFORMATION FOR SEQ ID NO:564:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:564:

GCCTAGCATT                                                              10

(2) INFORMATION FOR SEQ ID NO:565:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:565:

CCTAGCATTT                                                              10

(2) INFORMATION FOR SEQ ID NO:566:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:566:

CTAGCATTTC                                                              10

(2) INFORMATION FOR SEQ ID NO:567:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:567:

TAGCATTTCA                                                              10
```

(2) INFORMATION FOR SEQ ID NO:568:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:568:

AGCATTTCAT                                                               10

(2) INFORMATION FOR SEQ ID NO:569:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:569:

GCATTTCATC                                                               10

(2) INFORMATION FOR SEQ ID NO:570:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:570:

CATTTCATCA                                                               10

(2) INFORMATION FOR SEQ ID NO:571:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:571:

ATTTCATCAC                                                               10

(2) INFORMATION FOR SEQ ID NO:572:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:572:

TTTCATCACG                                                               10

(2) INFORMATION FOR SEQ ID NO:573:

(i) SEQUENCE CHARACTERISTICS:
        (A) LENGTH: 10 base pairs
        (B) TYPE: nucleic acid (C) STRANDEDNESS: single
        (D) TOPOLOGY: linear (ii) MOLECULE TYPE: DNA (xi) SEQUENCE DESCRIPTION: SEQ ID NO:573:

TTCATCACGT                                                                    10

(2) INFORMATION FOR SEQ ID NO:574:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:574:

TCATCACGTG                                                                    10

(2) INFORMATION FOR SEQ ID NO:575:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:575:

CATCACGTGG                                                                    10

(2) INFORMATION FOR SEQ ID NO:576:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:576:

ATCACGTGGC                                                                    10

(2) INFORMATION FOR SEQ ID NO:577:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:577:

TCACGTGGCC                                                                    10

(2) INFORMATION FOR SEQ ID NO:578:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:578:

CACGTGGCCC                                                    10

(2) INFORMATION FOR SEQ ID NO:579:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:579:

ACGTGGCCCG                                                    10

(2) INFORMATION FOR SEQ ID NO:580:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:580:

CGTGGCCCGA                                                    10

(2) INFORMATION FOR SEQ ID NO:581:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:581:

GTGGCCCGAG                                                    10

(2) INFORMATION FOR SEQ ID NO:582:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:582:

TGGCCCGAGA                                                    10

(2) INFORMATION FOR SEQ ID NO:583:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:583:

GGCCCGAGAG                                                    10

(2) INFORMATION FOR SEQ ID NO:584:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:584:

GCCCGAGAGC                                                              10

(2) INFORMATION FOR SEQ ID NO:585:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:585:

CCCGAGAGCT                                                              10

(2) INFORMATION FOR SEQ ID NO:586:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:586:

CCGAGAGCTG                                                              10

(2) INFORMATION FOR SEQ ID NO:587:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:587:

CGAGAGCTGC                                                              10

(2) INFORMATION FOR SEQ ID NO:588:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:588:

GAGAGCTGCA                                                              10

(2) INFORMATION FOR SEQ ID NO:589:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO:589:

AGAGCTGCAT                                                              10

(2) INFORMATION FOR SEQ ID NO:590:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:590:

GAGCTGCATC                                                              10

(2) INFORMATION FOR SEQ ID NO:591:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:591:

AGCTGCATCC                                                              10

(2) INFORMATION FOR SEQ ID NO:592:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:592:

GCTGCATCCG                                                              10

(2) INFORMATION FOR SEQ ID NO:593:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:593:

CTGCATCCGG                                                              10

(2) INFORMATION FOR SEQ ID NO:594:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:594:

TGCATCCGGA                                                                    10

(2) INFORMATION FOR SEQ ID NO:595:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:595:

GCATCCGGAG                                                                    10

(2) INFORMATION FOR SEQ ID NO:596:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:596:

CATCCGGAGT                                                                    10

(2) INFORMATION FOR SEQ ID NO:597:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:597:

ATCCGGAGTA                                                                    10

(2) INFORMATION FOR SEQ ID NO:598:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:598:

TCCGGAGTAC                                                                    10

(2) INFORMATION FOR SEQ ID NO:599:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:599:

CCGGAGTACT                                                                    10

(2) INFORMATION FOR SEQ ID NO:600:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:600:

CGGAGTACTT                                              10

(2) INFORMATION FOR SEQ ID NO:601:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:601:

GGAGTACTTC                                              10

(2) INFORMATION FOR SEQ ID NO:602:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:602:

GAGTACTTCA                                              10

(2) INFORMATION FOR SEQ ID NO:603:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:603:

AGTACTTCAA                                              10

(2) INFORMATION FOR SEQ ID NO:604:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:604:

GTACTTCAAG                                              10

(2) INFORMATION FOR SEQ ID NO:605:

(i) SEQUENCE CHARACTERISTICS:
        (A) LENGTH: 10 base pairs
        (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO:605:

TACTTCAAGA                                                              10

(2) INFORMATION FOR SEQ ID NO:606:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:606:

ACTTCAAGAA                                                              10

(2) INFORMATION FOR SEQ ID NO:607:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:607:

CTTCAAGAAC                                                              10

(2) INFORMATION FOR SEQ ID NO:608:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:608:

TTCAAGAACT                                                              10

(2) INFORMATION FOR SEQ ID NO:609:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:609:

TCAAGAACTG                                                              10

(2) INFORMATION FOR SEQ ID NO:610:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:610:

CAAGAACTGC                                                           10

(2) INFORMATION FOR SEQ ID NO:611:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:611:

AAGAACTGCT                                                           10

(2) INFORMATION FOR SEQ ID NO:612:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:612:

AGAACTGCTG                                                           10

(2) INFORMATION FOR SEQ ID NO:613:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:613:

GAACTGCTGA                                                           10

(2) INFORMATION FOR SEQ ID NO:614:

(i) SEQUENCE CHARACTERISTICS:
        (A) LENGTH: 1305 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:614:

GAAGAGATTT GGGAGAACAT GACCTGGATG CAGTGGGAAA AAGAAATTCA CAATCACACA      60

AAATACATAT ACTCCTTACT TGAAAAATCG CAGAACCAAC AAGAAAAGAA TGAACAAGAA     120

CTATTGGAAT TGGATCAATG GGCAAGTTTG TGGAATTGGT TTGACATAAC AAAATGGCTG     180

TGGTATATAA AAATATTCAT AATGGTAGTA GGAGGCTTGA TAGGTTTAAG AATAGTTTTT     240

GCTGTACTTT CTATAGTGAA TAGAGTTAGG CAGGGATACT CACCATTGTC GTTTCAGACC     300

CTCCTCCCAA CCCCGAGGGG ACCCGACAGG CCCGAAGGAA TCGAAGAAGA AGGTGGAGAG     360

AGAGACAGAG ACAGATCCAC TCGATTAGTA CACGGATTCT TAGCACTTTT CTGGGACGAC     420

CTGAGGAGCC TGTGCCTCTT CCTCTACCAC CACTTGAGAG ACTTACTCTT GATTGTAACA     480

AGGATTGTGG AACTTCTGGG ACGCAGGGGA TGGGAAGCCC TCAAATATTG GTGGAACCTC     540

| CTAAAGTATT | GGAGCCAGGA | ACTGCAGAAG | AGTGCTGTTA | TCTTGCTCAA | TGCCACCGCC | 600 |
| ATAGCAGTAG | CTGAGGGGAC | AGATAGAGTT | TTAGAAGTAT | TACAAAGAGC | TTATAGAGCT | 660 |
| ATCCTCCACA | TACCTAGAAG | AATAAGACAG | GGCCTCGAAA | TGGCTTTGCT | ATAAAATGGG | 720 |
| TGGCAAGTGA | GCAAAAAGTA | GTGTAGTCAG | ATAGCATGCA | TCATAAGGGG | TGGGGGCCAA | 780 |
| CAACTAACAA | TGCTGATCGT | GCCTGGCTAG | AAGCACAAGA | GAAGGAAGAA | GCGGGTTTTC | 840 |
| CAGTCAAACC | TCAGGTAGCT | GTAGATCTTA | GCCACTTTTT | AAAAGAAAAG | GGGGGACTGG | 900 |
| AAGGGCTAAT | TCACTCCCAA | AGAAGACAAG | ATACACAGTG | CTGCAAACTA | TTACCAGTGG | 960 |
| AGTCAGCGAA | GATAGAAGAG | GCCAATGGAG | GAGAAAACCA | CAGATTGTTC | TGTTGGGGAC | 1020 |
| TTTCCATCCG | TTGGGGACTT | TCCAAGGCGG | CGTGGCCTGG | GTGACTAGTT | CCGGTGGGGA | 1080 |
| CTTTCCAAGA | AGGCGCGGCC | TGGGCGGGAC | TGGGGAGTGG | CGAGCCCTCA | GATGCTGCAT | 1140 |
| ATAAGCAGCT | GCTTTCTGCT | GTTACTGGGT | CTCTCGGGTT | AGACCAGATC | TGAGCCTGGG | 1200 |
| AGCTCTCTGG | CTAACTAGGG | AACCCACTGC | TTAAGCCTCA | ATAAAGCTTG | CCTTGAGTGC | 1260 |
| TTCAAGTAGT | GTGTGCCCGT | CTGTTGTGTG | ACTCTGGTAT | CTAGA | | 1305 |

(2) INFORMATION FOR SEQ ID NO:615:

(i) SEQUENCE CHARACTERISTICS:
        (A) LENGTH: 1208 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:615:

| GAAACAATTT | GGGATAACAT | GACCTGGATG | CAGTGGGAAA | GAGAAATTGA | CAATTACACA | 60 |
| AACATAATAT | ACACCTTAAT | TGAAGAATCG | CAGAACCAAC | AAGAAAAAAA | TGAACTAGAA | 120 |
| TTATTGGAAT | TGGATAAATG | GCAAATTTG | TGGAATTGGT | TTAGTATATC | AAACTGGCTA | 180 |
| TGGTATATAA | AATTATTCAT | AATGGTAGTA | GGAGGCTTGG | TAGGTTTAAG | AATAGTTTTT | 240 |
| ACTGTACTTT | CTATAGTGAA | TAGAGTTAGG | CAGGGATACT | CACCATTGTC | GTTTCAGACC | 300 |
| CACCTCCCAA | CCCCGAAGGG | ACCCGACAGG | CCAGAAGGAA | TCGAAGAAGA | AGGTGGAGAG | 360 |
| AGAGACAGAG | GCAGCTCCAC | TCGATTAGTG | CACGGATTCT | TAGCACTTTT | CTGGGACGAC | 420 |
| CTGAGGAGTC | TGTGCCTCTT | CAGCTACCAC | CACTTGAGAG | ACTTACTCTT | GATTGTAACG | 480 |
| AGGATTGTGG | AACTTCTGGG | ACGCAGGGGA | TGGGAAGCCC | TCAAATACTG | GTGGAATCTC | 540 |
| CTGCAGTATT | GGAGGCAGGA | ACTACAGAAG | AGTGCTGTTA | GCTTGTTCAA | TGGCACGGCC | 600 |
| ATAGCAGTAG | CTGAGGGGAC | AGATAGAGTT | ATAGAAGCTT | TACGAAGGGC | TTATAGAGCT | 660 |
| ATTCTCCACA | TACCTAGAAG | AATAAGACAG | GGCTTAGAAA | GGGCTTTGCT | ATAAAATGGG | 720 |
| TGGCAAGTGG | TCAGAAAGTA | GTGTGGTTAG | AAGGCATGTA | CCTTTAAGAC | AAGGCAGCTA | 780 |
| TAGATCTTAG | CCGCTTTTTA | AAAGAAAAGG | GGGGACTGGA | AGGGCTAATT | CACTCACAGA | 840 |
| GAAGATCAGT | TGAACCAGAA | GAAGATAGAA | GAGGCCATGA | AGAAGAAAAC | AACAGATTGT | 900 |
| TCCGTTTGTT | CCGTTGGGGA | CTTTCCAGGA | GACGTGGCCT | GAGTGATAAG | CCGCTGGGGA | 960 |
| CTTTCCGAAG | AGGCGTGACG | GGACTTTCCA | AGGCGACGTG | GCCTGGGCGG | GACTGGGGAG | 1020 |
| TGGCGAGCCC | TCAGATGCTG | CATATAAGCA | GCTGCTTTCT | GCCTGTACTG | GGTCTCTCTG | 1080 |
| GTTAGACCAG | ATCTGAGCCT | GGGAGCTCTC | TGGCTAACTA | GGGAACCCAC | TGCTTAAGCC | 1140 |
| TCAATAAAGC | TTGCCTTGAG | TGCTTCAAGT | AGTGTGTGCC | CGTCTGTTGT | GTGACTCTGG | 1200 |
| TATCTAGA | | | | | | 1208 |

(2) INFORMATION FOR SEQ ID NO:616:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:616:

TGGAAGGGCT AATTTGGT                                  18

(2) INFORMATION FOR SEQ ID NO:617:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:617:

ATCTTCCCTA AAAAATTAGC CTGTC                            25

(2) INFORMATION FOR SEQ ID NO:618:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:618:

AGGCTCAGAT CTGGTCTAAC                                20

(2) INFORMATION FOR SEQ ID NO:619:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:619:

AGCAGCAGGA AGCACTATGG                                20

(2) INFORMATION FOR SEQ ID NO:620:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:620:

TGCTAGAGAT TTTCCACAC                                 19

(2) INFORMATION FOR SEQ ID NO:621:

(i) SEQUENCE CHARACTERISTICS:

(A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:621:

AGTGAATAGA GTTAGGCAGG                                           20

(2) INFORMATION FOR SEQ ID NO:622:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:622:

GTAAGACAGT ATGATCAGAT A                                         21

(2) INFORMATION FOR SEQ ID NO:623:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:623:

TTGTAGGGAA TTCCAAATTC C                                         21

(2) INFORMATION FOR SEQ ID NO:624:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:624:

CAGGATCCTA CACCTGTCAA CATAAT                                    26

(2) INFORMATION FOR SEQ ID NO:625:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:625:

GGGAATTCCT TATTCCTGCT TG                                        22

(2) INFORMATION FOR SEQ ID NO:626:

(i) SEQUENCE CHARACTERISTICS:
            (A) LENGTH: 18 base pairs
            (B) TYPE: nucleic acid
            (C) STRANDEDNESS: single
            (D) TOPOLOGY: linear -continued (ii) MOLECULE TYPE: DNA (xi) SEQUENCE DESCRIPTION: SEQ ID NO:626:

CCAGAAGTTC CACAATCC                                          18

(2) INFORMATION FOR SEQ ID NO:627:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:627:

TTCTTCTAGG TATGTGGAG                                       19

(2) INFORMATION FOR SEQ ID NO:628:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:628:

AGTGAATTAG CCCTTCCAG                                       19

(2) INFORMATION FOR SEQ ID NO:629:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:629:

TGCTAGAGAT TTTCCACAC                                       19

(2) INFORMATION FOR SEQ ID NO:630:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:630:

TGCTCTGGAA AACTCAT                                             17

(2) INFORMATION FOR SEQ ID NO:631:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:631:

CTTTCTATAG TGAATAGAG                                       19

(2) INFORMATION FOR SEQ ID NO:632:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:632:

TATTGGAGTC AGGAACT                                                  17

(2) INFORMATION FOR SEQ ID NO:633:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:633:

GGTCTAACCA GAGAGAC                                                  17

(2) INFORMATION FOR SEQ ID NO:634:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:634:

Ala Val Arg Glu Arg Met Arg Arg Ala Glu Pro Ala Ala
1               5                   10

(2) INFORMATION FOR SEQ ID NO:635:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:635:

Pro Thr Ser Gln Ser Arg Gly Asp Pro Thr Gly Pro Lys Glu
1               5                   10

(2) INFORMATION FOR SEQ ID NO:636:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:636:

Pro Ser Ser Gln Pro Arg Gly Asp Pro Thr Gly Pro Lys Glu Ser Lys
1               5                   10                  15

Lys Lys Val Glu Arg Glu Thr Glu Thr Asp Pro Leu Asp (2) INFORMATION FOR SEQ ID NO:637:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:637:

```
Pro Thr Ser Gln Pro Arg Arg Asp Pro Thr Gly Gln Lys Glu Ser Lys
1               5                   10                  15
Lys Lys Val Glu Arg Glu Thr Glu Ala Ala Pro Leu Asp
            20                  25
```

(2) INFORMATION FOR SEQ ID NO:638:

(i) SEQUENCE CHARACTERISTICS:
        (A) LENGTH: 91 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:638:

```
Asp Pro Pro Pro Asn Pro Glu Gly Thr Arg Gln Ala Arg Arg Asn Arg
1               5                   10                  15
Arg Arg Arg Trp Arg Glu Arg Gln Arg Gln Ile His Ser Ile Ser Glu
            20                  25                  30
Arg Ile Leu Ser Thr Tyr Leu Gly Arg Ser Ala Glu Pro Val Pro Leu
        35                  40                  45
Gln Leu Pro Pro Leu Glu Arg Leu Thr Leu Asp Cys Asn Glu Asp Cys
    50                  55                  60
Gly Thr Ser Gly Thr Gln Gly Val Gly Ser Pro Gln Ile Leu Val Glu
65                  70                  75                  80
Ser Pro Thr Val Leu Glu Ser Gly Thr Lys Glu
            85                  90
```

(2) INFORMATION FOR SEQ ID NO:639:

(i) SEQUENCE CHARACTERISTICS:
        (A) LENGTH: 105 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:639:

```
Asp Pro Pro Pro Asn Pro Glu Gly Thr Arg Gln Ala Arg Arg Asn Arg
1               5                   10                  15
Arg Arg Arg Trp Arg Glu Arg Gln Arg Gln Ile His Ser Ile Ser Thr
            20                  25                  30
Arg Ile Leu Ser Thr Phe Leu Gly Arg Pro Glu Glu Pro Val Pro Leu
        35                  40                  45
Pro Leu Pro Pro Leu Glu Arg Leu Thr Leu Asp Cys Asn Lys Asp Cys
    50                  55                  60
Gly Thr Ser Gly Thr Gln Gly Met Gly Ser Pro Gln Ile Leu Val Glu
65                  70                  75                  80
```

```
Pro Pro Lys Val Leu Glu Pro Gly Thr Ala Glu Glu Cys Cys Tyr Leu
                85                  90                  95

Ala Gln Cys His Arg His Ser Ser Ser
            100             105
```

(2) INFORMATION FOR SEQ ID NO:640:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:640:

```
Asp Pro Pro Pro Asn Pro Glu Gly Thr Arg Gln Ala Arg Arg Asn Arg
1               5                   10                  15

Arg Arg Arg Trp Arg Glu Arg Gln Arg Gln Leu His Ser Ile Ser Ala
                20                  25                  30

Arg Ile Leu Ser Thr Phe Leu Gly Arg Pro Glu Glu Ser Val Pro Leu
                35                  40                  45

Gln Leu Pro Pro Leu Glu Arg Leu Thr Leu Asp Cys Asn Glu Asp Cys
50                  55                  60

Gly Thr Ser Gly Thr Gln Gly Met Gly Ser Pro Gln Ile Leu Val Glu
65                  70                  75                  80

Ser Pro Ala Val Leu Glu Ala Gly Thr Thr Glu Glu Cys Cys
                85                  90
```

(2) INFORMATION FOR SEQ ID NO:641:

(i) SEQUENCE CHARACTERISTICS:
        (A) LENGTH: 237 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:641:

```
Glu Gln Ile Trp Asn Asn Met Thr Trp Met Glu Trp Asp Arg Glu Ile
1               5                   10                  15

Asn Asn Tyr Thr Ser Leu Ile His Ser Leu Ile Glu Glu Ser Gln Asn
                20                  25                  30

Gln Gln Glu Lys Asn Glu Gln Glu Leu Leu Glu Leu Asp Lys Trp Ala
                35                  40                  45

Ser Leu Trp Asn Trp Phe Asn Ile Thr Asn Trp Leu Trp Tyr Ile Lys
                50                  55                  60

Leu Phe Ile Met Ile Val Gly Gly Leu Val Gly Leu Arg Ile Val Phe
65                  70                  75                  80

Ala Val Leu Ser Ile Val Asn Arg Val Arg Gln Gly Tyr Ser Pro Leu
                85                  90                  95

Ser Phe Gln Thr His Leu Pro Ile Pro Arg Gly Pro Asp Arg Pro Glu
                100                 105                 110

Gly Ile Glu Glu Glu Gly Gly Glu Arg Asp Arg Asp Arg Ser Ile Arg
                115                 120                 125

Leu Val Asn Gly Ser Leu Ala Leu Ile Trp Asp Asp Leu Arg Ser Leu
                130                 135                 140

Cys Leu Phe Ser Tyr His Arg Leu Arg Asp Leu Leu Leu Ile Val Thr
145                 150                 155                 160
```

Arg Ile Val Glu Leu Leu Gly Arg Arg Gly Trp Glu Ala Leu Lys Tyr
            165                 170                 175

Trp Trp Asn Leu Leu Gln Tyr Trp Ser Gln Glu Leu Lys Asn Ser Ala
            180                 185                 190

Val Asn Leu Asn Ala Thr Ala Ile Ala Val Ala Glu Gly Thr Asp
            195                 200                 205

Arg Val Ile Glu Val Leu Gln Ala Ala Tyr Arg Ala Ile Arg His Ile
            210                 215                 220

Pro Arg Arg Ile Arg Gln Gly Leu Glu Arg Ile Leu Leu
225                 230                 235

(2) INFORMATION FOR SEQ ID NO:642:

(i) SEQUENCE CHARACTERISTICS:
        (A) LENGTH: 237 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:642:

Glu Glu Ile Trp Glu Asn Met Thr Trp Met Gln Trp Glu Lys Glu Ile
1               5                   10                  15

His Asn His Thr Lys Tyr Ile Tyr Ser Leu Leu Glu Lys Ser Gln Asn
            20                  25                  30

Gln Gln Glu Lys Asn Glu Gln Glu Leu Leu Glu Leu Asp Gln Trp Ala
            35                  40                  45

Ser Leu Trp Asn Trp Phe Asp Ile Thr Lys Trp Leu Trp Tyr Ile Lys
        50                  55                  60

Ile Phe Ile Met Val Val Gly Gly Leu Ile Gly Leu Arg Ile Val Phe
65              70                  75                  80

Ala Val Leu Ser Ile Val Asn Arg Val Arg Gln Gly Tyr Ser Pro Leu
            85                  90                  95

Ser Phe Gln Thr Leu Leu Pro Thr Pro Arg Gly Pro Asp Arg Pro Glu
            100                 105                 110

Gly Ile Glu Glu Met Gly Gly Glu Arg Asp Arg Asp Arg Ser Thr Arg
            115                 120                 125

Leu Val His Gly Phe Leu Ala Leu Phe Trp Asp Asp Leu Arg Ser Leu
130                 135                 140

Cys Leu Phe Leu Tyr His His Leu Arg Asp Leu Leu Leu Ile Val Thr
145                 150                 155                 160

Arg Ile Val Glu Leu Leu Gly Arg Arg Gly Trp Glu Ala Leu Lys Tyr
            165                 170                 175

Trp Trp Asn Leu Leu Lys Tyr Trp Ser Gln Glu Leu Gln Lys Ser Ala
            180                 185                 190

Val Ile Leu Leu Asn Ala Thr Ala Ile Ala Val Ala Glu Gly Thr Asp
            195                 200                 205

Arg Val Leu Glu Val Leu Gln Arg Ala Tyr Arg Ala Ile Leu His Ile
            210                 215                 220

Pro Arg Arg Ile Arg Gln Gly Leu Glu Met Ala Leu Leu
225                 230                 235

(2) INFORMATION FOR SEQ ID NO:643:

(i) SEQUENCE CHARACTERISTICS:
        (A) LENGTH: 237 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO:643:

Glu Thr Ile Trp Asp Asn Met Thr Trp Met Gln Trp Glu Arg Glu Ile
1               5                   10                  15

Asp Asn Tyr Thr Asn Ile Ile Tyr Thr Leu Ile Glu Glu Ser Gln Asn
            20                  25                  30

Gln Gln Glu Lys Asn Glu Leu Glu Leu Leu Glu Leu Asp Lys Trp Ala
        35                  40                  45

Asn Leu Trp Asn Trp Phe Ser Ile Ser Asn Trp Leu Trp Tyr Ile Lys
50                  55                  60

Leu Phe Ile Met Val Val Gly Leu Val Gly Leu Arg Ile Val Phe
65                  70                  75                  80

Thr Val Leu Ser Ile Val Asn Arg Val Arg Gln Gly Tyr Ser Pro Leu
                85                  90                  95

Ser Phe Gln Thr His Leu Pro Thr Pro Lys Gly Pro Asp Arg Pro Glu
            100                 105                 110

Gly Ile Glu Glu Glu Gly Gly Glu Arg Asp Arg Gly Ser Ser Thr Arg
        115                 120                 125

Leu Val His Gly Phe Leu Ala Leu Phe Trp Asp Asp Leu Arg Ser Leu
    130                 135                 140

Cys Leu Phe Ser Tyr His His Leu Arg Asp Leu Leu Leu Ile Val Thr
145                 150                 155                 160

Arg Ile Val Glu Leu Leu Gly Arg Arg Gly Trp Glu Ala Leu Lys Tyr
                165                 170                 175

Trp Trp Asn Leu Leu Gln Tyr Trp Arg Gln Glu Leu Gln Lys Ser Ala
            180                 185                 190

Val Ser Leu Phe Asn Gly Thr Ala Ile Ala Val Ala Glu Gly Thr Asp
        195                 200                 205

Arg Val Ile Glu Ala Leu Arg Arg Ala Tyr Arg Ala Ile Leu His Ile
    210                 215                 220

Pro Arg Arg Ile Arg Gln Gly Leu Glu Arg Ala Leu Leu
225                 230                 235

(2) INFORMATION FOR SEQ ID NO:644:

(i) SEQUENCE CHARACTERISTICS:
        (A) LENGTH: 206 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:644:

Met Gly Gly Lys Trp Ser Lys Ser Ser Val Ile Gly Trp Pro Ala Val
1               5                   10                  15

Arg Glu Arg Met Arg Arg Ala Glu Pro Ala Ala Asp Gly Val Gly Ala
            20                  25                  30

Val Ser Arg Asp Leu Glu Lys His Gly Ala Ile Thr Ser Ser Asn Thr
        35                  40                  45

Ala Ala Asn Asn Ala Ala Cys Ala Trp Leu Glu Ala Gln Glu Glu Glu
    50                  55                  60

Glu Val Gly Phe Pro Val Thr Pro Gln Val Pro Leu Arg Pro Met Thr
65                  70                  75                  80

Tyr Lys Ala Ala Val Asp Leu Ser His Phe Leu Lys Glu Lys Gly Gly

```
            85                  90                  95
Leu Glu Gly Leu Ile His Ser Gln Arg Arg Gln Asp Ile Leu Asp Leu
            100                 105                 110

Trp Ile Tyr His Thr Gln Gly Tyr Phe Pro Asp Trp Gln Asn Tyr Thr
            115                 120                 125

Pro Gly Pro Gly Val Arg Tyr Pro Leu Thr Phe Gly Trp Cys Tyr Lys
            130                 135                 140

Leu Val Pro Val Glu Pro Asp Lys Val Glu Glu Ala Asn Lys Gly Glu
145                 150                 155                 160

Asn Thr Ser Leu Leu His Pro Val Ser Leu His Gly Met Asp Asp Pro
                165                 170                 175

Glu Arg Glu Val Leu Glu Trp Arg Phe Asp Ser Arg Leu Ala Phe His
            180                 185                 190

His Val Ala Arg Glu Leu His Pro Glu Tyr Phe Lys Asn Cys
            195                 200                 205
```

(2) INFORMATION FOR SEQ ID NO:645:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:645:

```
Met Gly Gly Lys
1
```

(2) INFORMATION FOR SEQ ID NO:646:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:646:

```
Met Gly Gly Lys Trp Ser Glu Ser Ser Val Val Arg Arg His Val Pro
1               5                   10                  15

Leu Arg Gln Gly Ser Tyr Arg Ser
                20
```

(2) INFORMATION FOR SEQ ID NO:647:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:647:

```
CGAGCTTGCT ACAAGGGACT TTCCGCTGGG GACTTTCCAG GGAGGCGTGG CCTGGGCGGG      60

ACTGGGGAGT GGCGAGCCCT CA                                              82
```

(2) INFORMATION FOR SEQ ID NO:648:

(i) SEQUENCE CHARACTERISTICS:
        (A) LENGTH: 78 base pairs (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:648:

CTGTTGGGGA CTTTCCATCC GTTGGGGACT TTCCAAGGCG GCGTGGCCTG GGTGACTAGT      60

TCCGGTGGGG ACTTTCCA                                                   78

(2) INFORMATION FOR SEQ ID NO:649:

(i) SEQUENCE CHARACTERISTICS:
          (A) LENGTH: 67 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:649:

CCGTTTGTTC CGTTGGGGAC TTTCCAGGAG ACGTGGCCTG AGTGACTAAG CCGCTGGGGA      60

CTTTCCG                                                               67

(2) INFORMATION FOR SEQ ID NO:650:

(i) SEQUENCE CHARACTERISTICS:
          (A) LENGTH: 621 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:650:

ATGGGTGGCA AGTGGTCAAA AAGTAGTGTG ATTGGATGGC CTGCTGTAAG GGAAAGAATG      60

AGACGAGCTG AGCCAGCAGC AGATGGGGTG GGAGCAGTAT CTCGAGACCT AGAAAAACAT     120

GGAGCAATCA CAAGTAGCAA TACAGCAGCT AACAATGCTG CTTGTGCCTG GCTAGAAGCA     180

CAAGAGGAGG AAGAGGTGGG TTTTCCAGTC ACACCTCAGG TACCTTTAAG ACCAATGACT     240

TACAAGGCAG CTGTAGATCT TAGCCACTTT TTAAAAGAAA AGGGGGGACT GGAAGGGCTA     300

ATTCACTCCC AAAGAAGACA AGATATCCTT GATCTGTGGA TCTACCACAC ACAAGGCTAC     360

TTCCCTGATT GGCAGAACTA CACACCAGGG CCAGGGGTCA GATATCCACT GACCTTTGGA     420

TGGTGCTACA AGCTAGTACC AGTTGAGCCA GATAAGGTAG AAGAGGCCAA TAAAGGAGAG     480

AACACCAGCT TGTTACACCC TGTGAGCCTG CATGGAATGG ATGACCCTGA GAGAGAAGTG     540

TTAGAGTGGA GGTTTGACAG CCGCCTAGCA TTTCATCACG TGGCCCGAGA GCTGCATCCG     600

GAGTACTTCA AGAACTGCTG A                                              621

(2) INFORMATION FOR SEQ ID NO:651:

(i) SEQUENCE CHARACTERISTICS:
          (A) LENGTH: 1596 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:651:

GAACAGATTT GGAATAACAT GACCTGGATG GAGTGGGACA GAGAAATTAA CAATTACACA      60

AGCTTAATAC ACTCCTTAAT TGAAGAATCG CAAAACCAGC AAGAAAAGAA TGAACAAGAA     120

```
TTATTGGAAT TAGATAAATG GGCAAGTTTG TGGAATTGGT TTAACATAAC AAATTGGCTG      180

TGGTATATAA AATTATTCAT AATGATAGTA GGAGGCTTGG TAGGTTTAAG AATAGTTTTT      240

GCTGTACTTT CTATAGTGAA TAGAGTTAGG CAGGGATATT CACCATTATC GTTTCAGACC      300

CACCTCCCAA TCCCGAGGGG ACCCGACAGG CCCGAAGGAA TAGAAGAAGA AGGTGGAGAG      360

AGAGACAGAG ACAGATCCAT TCGATTAGTG AACGGATCCT TAGCACTTAT CTGGGACGAT      420

CTGCGGAGCC TGTGCCTCTT CAGCTACCAC CGCTTGAGAG ACTTACTCTT GATTGTAACG      480

AGGATTGTGG AACTTCTGGG ACGCAGGGGG TGGGAAGCCC TCAAATATTG GTGGAATCTC      540

CTACAGTATT GGAGTCAGGA ACTAAAGAAT AGTGCTGTTA ACTTGCTCAA TGCCACAGCC      600

ATAGCAGTAG CTGAGGGGAC AGATAGGGTT ATAGAAGTAT TACAAGCAGC TTATAGAGCT      660

ATTCGCCACA TACCTAGAAG AATAAGACAG GGCTTGGAAA GGATTTTGCT ATAAGATGGG      720

TGGCAAGTGG TCAAAAAGTA GTGTGATTGG ATGGCCTGCT GTAAGGGAAA GAATGAGACG      780

AGCTGAGCCA GCAGCAGATG GGGTGGGAGC AGTATCTCGA GACCTAGAAA AACATGGAGC      840

AATCACAAGT AGCAATACAG CAGCTAACAA TGCTGCTTGT GCCTGGCTAG AAGCACAAGA      900

GGAGGAAGAG GTGGGTTTTC CAGTCACACC TCAGGTACCT TTAAGACCAA TGACTTACAA      960

GGCAGCTGTA GATCTTAGCC ACTTTTTAAA AGAAAAGGGG GGACTGGAAG GGCTAATTCA     1020

CTCCCAAAGA AGACAAGATA TCCTTGATCT GTGGATCTAC CACACACAAG GCTACTTCCC     1080

TGATTGGCAG AACTACACAC CAGGGCCAGG GGTCAGATAT CCACTGACCT TTGGATGGTG     1140

CTACAAGCTA GTACCAGTTG AGCCAGATAA GGTAGAAGAG GCCAATAAAG GAGAGAACAC     1200

CAGCTTGTTA CACCCTGTGA GCCTGCATGG AATGGATGAC CCTGAGAGAG AAGTGTTAGA     1260

GTGGAGGTTT GACAGCCGCC TAGCATTTCA TCACGTGGCC CGAGAGCTGC ATCCGGAGTA     1320

CTTCAAGAAC TGCTGACATC GAGCTTGCTA CAAGGGACTT TCCGCTGGGG ACTTTCCAGG     1380

GAGGCGTGGC CTGGGCGGGA CTGGGGAGTG GCGAGCCCTC AGATGCTGCA TATAAGCAGC     1440

TGCTTTTTGC CTGTACTGGG TCTCTCTGGT TAGACCAGAT CTGAGCCTGG GAGCTCTCTG     1500

GCTAACTAGG GAACCCACTG CTTAAGCCTC AATAAAGCTT GCCTTGAGTG CTTCAAGTAG     1560

TGTGTGCCCG TCTGTTGTGT GACTCTGGTA ACTAGA                              1596

(2) INFORMATION FOR SEQ ID NO:652:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:652:

GCTTTTTGCC                                                             10

(2) INFORMATION FOR SEQ ID NO:653:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:653:

CTTTTTGCCT                                                             10
```

(2) INFORMATION FOR SEQ ID NO:654:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:654:

TTTTTGCCTG    10

(2) INFORMATION FOR SEQ ID NO:655:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:655:

TTTTGCCTGT    10

(2) INFORMATION FOR SEQ ID NO:656:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:656:

TTTGCCTGTA    10

(2) INFORMATION FOR SEQ ID NO:657:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:657:

TTGCCTGTAC    10

(2) INFORMATION FOR SEQ ID NO:658:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:658:

TGCCTGTACT    10

(2) INFORMATION FOR SEQ ID NO:659:

(i) SEQUENCE CHARACTERISTICS:

(A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:659:

GCCTGTACTG                                                                    10

(2) INFORMATION FOR SEQ ID NO:660:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:660:

CCTGTACTGG                                                                    10

(2) INFORMATION FOR SEQ ID NO:661:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:661:

CTGTACTGGG                                                                    10

(2) INFORMATION FOR SEQ ID NO:662:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:662:

TGTACTGGGT                                                                    10

(2) INFORMATION FOR SEQ ID NO:663:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:663:

GTACTGGGTC                                                                    10

(2) INFORMATION FOR SEQ ID NO:664:

(i) SEQUENCE CHARACTERISTICS:
            (A) LENGTH: 10 base pairs
            (B) TYPE: nucleic acid
            (C) STRANDEDNESS: single
            (D) TOPOLOGY: linear

```
        (ii) MOLECULE TYPE: DNA (xi) SEQUENCE DESCRIPTION: SEQ ID NO:664:

TACTGGGTCT                                                              10

(2) INFORMATION FOR SEQ ID NO:665:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:665:

ACTGGGTCTC                                                              10

(2) INFORMATION FOR SEQ ID NO:666:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:666:

CTGGGTCTCT                                                              10

(2) INFORMATION FOR SEQ ID NO:667:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:667:

TGGGTCTCTC                                                              10

(2) INFORMATION FOR SEQ ID NO:668:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:668:

GGGTCTCTCT                                                              10

(2) INFORMATION FOR SEQ ID NO:669:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:669:

GGTCTCTCTG                                                              10
```

(2) INFORMATION FOR SEQ ID NO:670:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:670:

GTCTCTCTGG      10

(2) INFORMATION FOR SEQ ID NO:671:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:671:

TCTCTCTGGT      10

(2) INFORMATION FOR SEQ ID NO:672:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:672:

CTCTCTGGTT      10

(2) INFORMATION FOR SEQ ID NO:673:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:673:

TCTCTGGTTA      10

(2) INFORMATION FOR SEQ ID NO:674:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:674:

CTCTGGTTAG      10

(2) INFORMATION FOR SEQ ID NO:675:

(i) SEQUENCE CHARACTERISTICS:

(A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:675:

TCTCTGGTTA                                                                10

(2) INFORMATION FOR SEQ ID NO:676:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:676:

CTGGTTAGAC                                                                10

(2) INFORMATION FOR SEQ ID NO:677:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:677:

TGGTTAGACC                                                                10

(2) INFORMATION FOR SEQ ID NO:678:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:678:

GGTTAGACCA                                                                10

(2) INFORMATION FOR SEQ ID NO:679:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:679:

GTTAGACCAG                                                                10

(2) INFORMATION FOR SEQ ID NO:680:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:680:

TTAGACCAGA                                                                      10

(2) INFORMATION FOR SEQ ID NO:681:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:681:

TAGACCAGAT                                                                      10

(2) INFORMATION FOR SEQ ID NO:682:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:682:

AGACCAGATC                                                                      10

(2) INFORMATION FOR SEQ ID NO:683:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:683:

GACCAGATCT                                                                      10

(2) INFORMATION FOR SEQ ID NO:684:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:684:

ACCAGATCTG                                                                      10

(2) INFORMATION FOR SEQ ID NO:685:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:685:

CCAGATCTGA                                                                      10

(2) INFORMATION FOR SEQ ID NO:686:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:686:

CAGATCTGAG    10

(2) INFORMATION FOR SEQ ID NO:687:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:687:

AGATCTGAGC    10

(2) INFORMATION FOR SEQ ID NO:688:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:688:

GATCTGAGCC    10

(2) INFORMATION FOR SEQ ID NO:689:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:689:

ATCTGAGCCT    10

(2) INFORMATION FOR SEQ ID NO:690:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:690:

TCTGAGCCTG    10

(2) INFORMATION FOR SEQ ID NO:691:

(i) SEQUENCE CHARACTERISTICS:

(A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:691:

CTGAGCCTGG                                                                10

(2) INFORMATION FOR SEQ ID NO:692:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:692:

TGAGCCTGGG                                                                10

(2) INFORMATION FOR SEQ ID NO:693:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:693:

GAGCCTGGGA                                                                10

(2) INFORMATION FOR SEQ ID NO:694:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:694:

AGCCTGGGAG                                                                10

(2) INFORMATION FOR SEQ ID NO:695:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:695:

GCCTGGGAGC                                                                10

(2) INFORMATION FOR SEQ ID NO:696:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:696:

CCTGGGAGCT                                                              10

(2) INFORMATION FOR SEQ ID NO:697:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:697:

CTGGGAGCTC                                                              10

(2) INFORMATION FOR SEQ ID NO:698:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:698:

TGGGAGCTCT                                                              10

(2) INFORMATION FOR SEQ ID NO:699:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:699:

GGGAGCTCTC                                                              10

(2) INFORMATION FOR SEQ ID NO:700:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:700:

GGAGCTCTCT                                                              10

(2) INFORMATION FOR SEQ ID NO:701:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:701:

GAGCTCTCTG                                                              10

(2) INFORMATION FOR SEQ ID NO:702:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:702:

AGCTCTCTGG          10

(2) INFORMATION FOR SEQ ID NO:703:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:703:

GCTCTCTGGC          10

(2) INFORMATION FOR SEQ ID NO:704:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:704:

CTCTCTGGCT          10

(2) INFORMATION FOR SEQ ID NO:705:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:705:

TCTCTGGCTA          10

(2) INFORMATION FOR SEQ ID NO:706:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:706:

CTCTGGCTAA          10

(2) INFORMATION FOR SEQ ID NO:707:

(i) SEQUENCE CHARACTERISTICS:

(A) LENGTH: 10 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:707:

TCTGGCTAAC                                                                  10

(2) INFORMATION FOR SEQ ID NO:708:

(i) SEQUENCE CHARACTERISTICS:
                (A) LENGTH: 10 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:708:

CTGGCTAACT                                                                  10

(2) INFORMATION FOR SEQ ID NO:709:

(i) SEQUENCE CHARACTERISTICS:
                (A) LENGTH: 10 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:709:

TGGCTAACTA                                                                  10

(2) INFORMATION FOR SEQ ID NO:710:

(i) SEQUENCE CHARACTERISTICS:
                (A) LENGTH: 10 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:710:

GGCTAACTAG                                                                  10

(2) INFORMATION FOR SEQ ID NO:711:

(i) SEQUENCE CHARACTERISTICS:
                (A) LENGTH: 10 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:711:

GCTAACTAGG                                                                  10

(2) INFORMATION FOR SEQ ID NO:712:

(i) SEQUENCE CHARACTERISTICS:
                (A) LENGTH: 10 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:712:

CTAACTAGGG                                                               10

(2) INFORMATION FOR SEQ ID NO:713:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:713:

TAACTAGGGA                                                               10

(2) INFORMATION FOR SEQ ID NO:714:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:714:

AACTAGGGAA                                                               10

(2) INFORMATION FOR SEQ ID NO:715:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:715:

ACTAGGGAAC                                                               10

(2) INFORMATION FOR SEQ ID NO:716:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:716:

CTAGGGAACC                                                               10

(2) INFORMATION FOR SEQ ID NO:717:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:717:

TAGGGAACCC                                                               10

(2) INFORMATION FOR SEQ ID NO:718:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:718:

AGGGAACCCA                                                                10

(2) INFORMATION FOR SEQ ID NO:719:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:719:

GGGAACCCAC                                                                10

(2) INFORMATION FOR SEQ ID NO:720:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:720:

GGAACCCACT                                                                10

(2) INFORMATION FOR SEQ ID NO:721:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:721:

GAACCCACTG                                                                10

(2) INFORMATION FOR SEQ ID NO:722:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:722:

AACCCACTGC                                                                10

(2) INFORMATION FOR SEQ ID NO:723:

(i) SEQUENCE CHARACTERISTICS:

(A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:723:

ACCCACTGCT                                                              10

(2) INFORMATION FOR SEQ ID NO:724:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:724:

CCCACTGCTT                                                              10

(2) INFORMATION FOR SEQ ID NO:725:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:725:

CCACTGCTTA                                                              10

(2) INFORMATION FOR SEQ ID NO:726:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:726:

CACTGCTTAA                                                              10

(2) INFORMATION FOR SEQ ID NO:727:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:727:

ACTGCTTAAG                                                              10

(2) INFORMATION FOR SEQ ID NO:728:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:728:

CTGCTTAAGC                                                              10

(2) INFORMATION FOR SEQ ID NO:729:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:729:

TGCTTAAGCC                                                              10

(2) INFORMATION FOR SEQ ID NO:730:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:730:

GCTTAAGCCT                                                              10

(2) INFORMATION FOR SEQ ID NO:731:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:731:

CTTAAGCCTC                                                              10

(2) INFORMATION FOR SEQ ID NO:732:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:732:

TTAAGCCTCA                                                              10

(2) INFORMATION FOR SEQ ID NO:733:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:733:

TAAGCCTCAA                                                              10

(2) INFORMATION FOR SEQ ID NO:734:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:734:

AAGCCTCAAT                                                          10

(2) INFORMATION FOR SEQ ID NO:735:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:735:

AGCCTCAATA                                                          10

(2) INFORMATION FOR SEQ ID NO:736:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:736:

GCCTCAATAA                                                          10

(2) INFORMATION FOR SEQ ID NO:737:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:737:

CCTCAATAAA                                                          10

(2) INFORMATION FOR SEQ ID NO:738:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:738:

CTCAATAAAG                                                          10

(2) INFORMATION FOR SEQ ID NO:739:

(i) SEQUENCE CHARACTERISTICS:

(A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:739:

TCAATAAAGC                                                                10

(2) INFORMATION FOR SEQ ID NO:740:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:740:

CAATAAAGCT                                                                10

(2) INFORMATION FOR SEQ ID NO:741:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:741:

AATAAAGCTT                                                                10

(2) INFORMATION FOR SEQ ID NO:742:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:742:

ATAAAGCTTG                                                                10

(2) INFORMATION FOR SEQ ID NO:743:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:743:

TAAAGCTTGC                                                                10

(2) INFORMATION FOR SEQ ID NO:744:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:744:

AAAGCTTGCC                                                            10

(2) INFORMATION FOR SEQ ID NO:745:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:745:

AAGCTTGCCT                                                            10

(2) INFORMATION FOR SEQ ID NO:746:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:746:

AGCTTGCCTT                                                            10

(2) INFORMATION FOR SEQ ID NO:747:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:747:

GCTTGCCTTG                                                            10

(2) INFORMATION FOR SEQ ID NO:748:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:748:

CTTGCCTTGA                                                            10

(2) INFORMATION FOR SEQ ID NO:749:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:749:

TTGCCTTGAG                                                            10

(2) INFORMATION FOR SEQ ID NO:750:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:750:

TGCCTTGAGT    10

(2) INFORMATION FOR SEQ ID NO:751:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:751:

GCCTTGAGTG    10

(2) INFORMATION FOR SEQ ID NO:752:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:752:

CCTTGAGTGC    10

(2) INFORMATION FOR SEQ ID NO:753:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:753:

CTTGAGTGCT    10

(2) INFORMATION FOR SEQ ID NO:754:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:754:

TTGAGTGCTT    10

(2) INFORMATION FOR SEQ ID NO:755:

(i) SEQUENCE CHARACTERISTICS:

(A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:755:

TGAGTGCTTC                                                                      10

(2) INFORMATION FOR SEQ ID NO:756:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:756:

GAGTGCTTCA                                                                      10

(2) INFORMATION FOR SEQ ID NO:757:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:757:

AGTGCTTCAA                                                                      10

(2) INFORMATION FOR SEQ ID NO:758:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:758:

GTGCTTCAAG                                                                      10

(2) INFORMATION FOR SEQ ID NO:759:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:759:

TGCTTCAAGT                                                                      10

(2) INFORMATION FOR SEQ ID NO:760:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:760:

GCTTCAAGTA                                                                      10

(2) INFORMATION FOR SEQ ID NO:761:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:761:

CTTCAAGTAG                                                                      10

(2) INFORMATION FOR SEQ ID NO:762:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:762:

TTCAAGTAGT                                                                      10

(2) INFORMATION FOR SEQ ID NO:763:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:763:

TCAAGTAGTG                                                                      10

(2) INFORMATION FOR SEQ ID NO:764:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:764:

CAAGTAGTGT                                                                      10

(2) INFORMATION FOR SEQ ID NO:765:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:765:

AAGTAGTGTG                                                                      10

(2) INFORMATION FOR SEQ ID NO:766:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:766:

AGTAGTGTGT                                                                  10

(2) INFORMATION FOR SEQ ID NO:767:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:767:

GTAGTGTGTG                                                                  10

(2) INFORMATION FOR SEQ ID NO:768:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:768:

TAGTGTGTGC                                                                  10

(2) INFORMATION FOR SEQ ID NO:769:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:769:

AGTGTGTGCC                                                                  10

(2) INFORMATION FOR SEQ ID NO:770:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:770:

GTGTGTGCCC                                                                  10

(2) INFORMATION FOR SEQ ID NO:771:

(i) SEQUENCE CHARACTERISTICS:

(A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:771:

TGTGTGCCCG                                                            10

(2) INFORMATION FOR SEQ ID NO:772:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:772:

GTGTGCCCGT                                                            10

(2) INFORMATION FOR SEQ ID NO:773:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:773:

TGTGCCCGTC                                                            10

(2) INFORMATION FOR SEQ ID NO:774:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:774:

GTGCCCGTCT                                                            10

(2) INFORMATION FOR SEQ ID NO:775:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:775:

TGCCCGTCTG                                                            10

(2) INFORMATION FOR SEQ ID NO:776:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:776:

GCCCGTCTGT                                                                          10

(2) INFORMATION FOR SEQ ID NO:777:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:777:

CCCGTCTGTT                                                                          10

(2) INFORMATION FOR SEQ ID NO:778:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:778:

CCGTCTGTTG                                                                          10

(2) INFORMATION FOR SEQ ID NO:779:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:779:

CGTCTGTTGT                                                                          10

(2) INFORMATION FOR SEQ ID NO:780:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:780:

GTCTGTTGTG                                                                          10

(2) INFORMATION FOR SEQ ID NO:781:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:781:

TCTGTTGTGT                                                                          10

(2) INFORMATION FOR SEQ ID NO:782:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:782:

CTGTTGTGTG    10

(2) INFORMATION FOR SEQ ID NO:783:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:783:

TGTTGTGTGA    10

(2) INFORMATION FOR SEQ ID NO:784:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:784:

GTTGTGTGAC    10

(2) INFORMATION FOR SEQ ID NO:785:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:785:

TTGTGTGACT    10

(2) INFORMATION FOR SEQ ID NO:786:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:786:

TGTGTGACTC    10

(2) INFORMATION FOR SEQ ID NO:787:

(i) SEQUENCE CHARACTERISTICS:

(A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:787:

GTGTGACTCT                                                                  10

(2) INFORMATION FOR SEQ ID NO:788:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:788:

TGTGTGACTC                                                                  10

(2) INFORMATION FOR SEQ ID NO:789:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:789:

GTGTGACTCT                                                                  10

(2) INFORMATION FOR SEQ ID NO:790:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:790:

TGTGACTCTG                                                                  10

(2) INFORMATION FOR SEQ ID NO:791:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:791:

GTGACTCTGG                                                                  10

(2) INFORMATION FOR SEQ ID NO:792:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:792:

TGACTCTGGT                                                              10

(2) INFORMATION FOR SEQ ID NO:793:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:793:

GACTCTGGTA                                                              10

(2) INFORMATION FOR SEQ ID NO:794:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:794:

ACTCTGGTAA                                                              10

(2) INFORMATION FOR SEQ ID NO:795:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:795:

CTCTGGTAAC                                                              10

(2) INFORMATION FOR SEQ ID NO:796:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:796:

TCTGGTAACT                                                              10

(2) INFORMATION FOR SEQ ID NO:797:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:797:

CTGGTAACTA                                                              10

(2) INFORMATION FOR SEQ ID NO:798:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:798:

```
TGGTAACTAG                                                              10
```

(2) INFORMATION FOR SEQ ID NO:799:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:799:

```
GGTAACTAGA                                                              10
```

(2) INFORMATION FOR SEQ ID NO:800:

(i) SEQUENCE CHARACTERISTICS:
        (A) LENGTH: 9207 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:800:

```
TGGAAGGGCT AATTCACTCA CGGAAAAGAC CAGTTGAACC AGAAGAAGAT AGAAGAGGCC          60
ATGAAGAAGA AAACAACAGA TTGTTCTGCT TGCTCAGCTG GGGACTTTCC AGAAGGCGCG         120
GCCTGAGTGA CTAAGCCCCG TTGGGGACTT TCCGAAGAGG CATGAAGGGA CTTTCCAAGG         180
CAGGCGTGGC CTGGGCGGGA CTGGGAGTG GCGAGCCCTC AGATGCTGCA TATAAGCAGC          240
TGCTTTCTGC CTGTACTGGG TCTCTCTGGT TAGACCAGAT CTGAGCCTGG GAGCTCTCTG         300
GCTAGCTAGG GAACCCACTG CTTAAGCCTC AATAAAGCTT GCCTTGAGTG CTTCAAGTAG         360
TGTGTGCCCG TCTGTTGTGT GACTCTGGTA TCTAGAGATC CCTCAGACCA TTTTAGTCCG         420
TGTGGAAAAT CTCTAGCAGT GGCGCCCGAA CAGGGACTTG AAAGCGAAAG GAAAACCAGA         480
GGAGCTCTCT CGACGCAGGA CTCGGCTTGC TGAAGCGCGC ACGGCAAGAG GCGAGGGGCG         540
GCGACTGGTG AGTACGCCGA AAATTTTGAC TAGCGGAGGC TAGAAGGAGA GAGATGGGTG         600
CGAGAGCGTC AATATTAAGC GGGGGAAAAT TAGATAGATG GGAGAAAATT CGGTTAAGGC         660
CAGGAGGAAA GAAAAAGTAT AAATTAAAAC ATATAGTATG GGCAAGCAGG GAGCTAGAAC         720
GATTCGCAGT CAATCCTGGC CTGTTGGAAA CATCAGAAGG CTGTAGACAA ATACTGGGAC         780
AGTTACACCC GTCCCTTCAG ACAGGATCAG AAGAACTTAA ATCAGTATAT AATGCAGTAG         840
CAGTCCTCTA TTGTGTGCAT CAAAACATAG ACATAAAGGA CACCAAGGAA GCTTTAGAAA         900
AGATAGAGGA AGAGCAAAAC AAATGTAAGA AAAAAGCACA GCAAGCAGCA GCACAGCAAG         960
CAGCAGCTGG CACAGGAAAC AGCAACCCGG TCAGCCAAAA TTACCCTATA GTACAGAACA        1020
TGCAGGGGCA AATGGTACAT CAGGCCATAT CACCTAGAAC TTTAAATGCA TGGGTAAAAG        1080
```

```
TAATAGAAGA GAAGGCTTTC AGCCCAGAGG TAATACCCAT GTTTTCAGCA TTATCAGAAG    1140

GAGCCACCCC ACAAGATTTA AACACCATGC TAAACACAGT GGGGGACAT CAAGCAGCTA     1200

TGCAAATGTT AAAAGAGACC ATCAATGAGG AAGCTGCAGA ATGGGATAGA TTACATCCAG    1260

CGCAGGCAGG GCCTGTTGCA CCAGGCCAGA TGAGAGACCC AAGGGGAAGT GACATAGCAG    1320

GAACTACTAG TACCCTTCAG GAACAAATAG GATGGATGAC AGGTAATCCA GCTATCCCAG    1380

TAGGAGAAAT CTATAAAAGA TGGATAATCC TGGGATTAAA TAAAATAGTA AGGATGTATA    1440

GCCCTATCAG CATTCTGGAC ATAAAACAAG GACCAAAGGA ACCCTTTAGA GACTATGTAG    1500

ACCGGTTCTA TAAAACTCTA AGAGCCGAGC AAGCTACACA GGAGGTAAAA AATTGGATGA    1560

CAGAAACCTT GTTGGTCCAA AATGCAAACC CAGATTGTAA GACTATTTTA AAAGCATTGG    1620

GACCAGCAGC TACACTAGAA GAAATGATGA CAGCATGTCA GGGAGTGGGA GGACCCAGCC    1680

ATAAAGCAAG AGTTTTGGCA GAAGCAATGA GCCAAGCAAC AAATGCAGCT ACTGTAATGA    1740

TGCAGAGAAG CAATTTTAGA AACCAAAGAA AGAATGTTAA GTGTTTCAAT TGTGGCAAAG    1800

AAGGGCACAT AGCCAGAAAT TGCAGGGCTC CTAGGAAAAG GGCTGTTGG AAATGTGGAA     1860

AGGAAGGACA CCAAATGAAA GATTGTACTG AGAGACAGGC TAATTTTTTA GGGAAAATCT    1920

GGCCTTCCCA CAAGGGGAGG CCAGGGAACT TCTTCAGAG CAGGCCAGAA CCAACAGCCC     1980

CTCTCCAGGG CAGGCCGGAG CCATCAGCCC CGCCAGAAGA GAGCTTCAGG TTTGGGGAGG    2040

AGACAACAAC TCCCTCTCAG AAGCAGGAGC CGATAGACAG GGACAGGGAT CTGTATCCTT    2100

TAGCTTCCCT CAGATCACTC TTTGGCAACG ACCCCTCGTC ACAATAAAGA TAGGGGGGCA    2160

GCTGAAGGAA GCTCTATTAG ATACAGGAGC AGATGATACA GTATTAGAAG ACATGCATTT    2220

GCCAGGAAAA TGGAAACCAA AAATGATAGG GGGAATTGGA GGTTTTATCA AAGTAAAACA    2280

ATATGATGAA ATTCTTGTAG AAATCTGTGG ACATAAAGCT ATAGGTACAG TATTAGTAGG    2340

ACCTACACCT GTCAACATAA TTGGAAGAAA TCTGTTGACT CAGATTGGTT GCACTTTAAA    2400

TTTTCCCATT AGTCCTATTG AAACTGTACC AGTACAATTA AAGCCAGGAA TGGATGGCCC    2460

AAAGGTTAAA CAATGGCCAT TGACAGAAGA GAAAATAAAA GCATTAGTAG AAATTTGTAC    2520

AGAAATGGAA AAGGAAGGAA AGATTTCAAA AATTGGGCCT GAAAATCCAT ACAATACTCC    2580

AGTATTTGCC ATAAAGAAAA AAGATGGTAC TAAATGGAGA AAATTAGTAG ATTTCAGAGA    2640

CCTTAATAAG AGAACTCAAG ACTTCTGGGA AGTTCAATTA GGAATACCAC ATCCCTCAGG    2700

ATTAAAAAAG AAAAAATCAG TAACAGTACT GGATGTGGGT GATGCATACT TTTCAGTTCC    2760

CTTAGATGAA AACTTCAGGA AGTATACTGC ATTTACCATA CCTAGTATAA ATAATGAGAC    2820

ACCAGGGATT AGATATCAGT ACAATGTGCT TCCACAGGGA TGGAAAGGAT CACCAGCAAT    2880

ATTCCAAAGT AGCATGACAA GAATCTTAGA GCCTTTTAGA AGACAAAATC CAGACATAGT    2940

TATCTATCAA TACATGGATG ACTTGTATGT AGGATCTGAT TTAGAAATAG GACAGCATAG    3000

AATAAAAATA GAGGAACTGA GACAACATCT GTTGAAGTGG GGATTTACCA CACCAGACAA    3060

AAAGCATCAG AAAGAACCCC CATTCCTTTG GATGGGTTAT GAACTCCATC CTGATAAATG    3120

GACAGTGCAA CCTATAGTAC TGCCAGAAAA AGACAGCTGG ACTGTCAATG ACATACAGAA    3180

GTTAGTGGGT AAATTAAATT GGGCAAGTCA GATTTACCCA GGAATTAAAG TAAGGCAATT    3240

ATGTAAACTC CTTAGGGGAA CCAAAGCACT AACAGAAGTA ATACCACTAA CAGAAGAAGC    3300

AGAGCTAGAA CTGGCAGAAA ACAGGGAAAT TCTAAGAGAA CCAGTACATG GAGTGTATTA    3360

TGACCCATCA AAAGACTTAA TAGCAGAAAT ACAGAAGCAG GAGCAAGGCC AATGGACATA    3420

TCAAATTTAT CAAGATCAAT TTAAAAATCT AAAAACAGGA AAGTATGCAA GATTGAGGGG    3480
```

-continued

| | |
|---|---|
| TGCCCACACT AATGATGTAA AACAATTTCC AGAGGCAGTG CAAAAAATAG CCACAGAAAG | 3540 |
| CATAGTAATA TGGGGAAAGA CTCCTAAATT TAGACTACCC ATACAAAAG AAACATGGGA | 3600 |
| CGCATGGTGG ACAGAGTATT GGCAAGCCAC CTGGATTCCT GAGTGGGAGT TTGTCAATAC | 3660 |
| CCCTCCCCTA GTAAAATTAT GGTACCAGTT AGAAAAAGAA CCCATAATAG GAGCAGAAAC | 3720 |
| TTTCTATGTA GATGGGCAG CTAACAGAGA GACTAAATTA GGAAAAGCAG GATATGTTAC | 3780 |
| TGACAGAGGA AGACAAAAAG TTGTCTCCCT AACTGACACA ACAAATCAGA AGACTGAGTT | 3840 |
| ACAAGCAATT CATCTAGCTT TGCAGGATTC AGGATTAGAA GTAAACATAG TAACAGACTC | 3900 |
| ACAGTATGCA TTAGGAATCA TTCAAGCACA ACCAGATAAA AGTGAATCAG AAATAGTCAA | 3960 |
| TCAAATAATA GAGCAATTAA TAAAAAGGA AAAGGTCTAC CTGGCATGGG TACCAGCACA | 4020 |
| CAAAGGAATT GGAGGGAATG AACAAGTAGA TAAATTAGTC AGTGCTGGAA TCAGGAAAAT | 4080 |
| ACTATTTTTA GATGGAATAG ATAAGGCACA AGAAGGCCAT GAGAAATATC ACAGTAATTG | 4140 |
| GAGAGCAATG GCTAGTGGTT TTAACCTGCC ACCTATAGTA GCAAAAGAAA TAGTAGCCAG | 4200 |
| CTGTGATAAA TGTCAGCTAA AAGGAGAAGC CATGCATGGA CAAGTAGACT GTAGTCCAGG | 4260 |
| AATATGGCAA CTAGATTGTA CACATCTAGA AGGAAAAATT ATCCTGGTAG CAGTTCATGT | 4320 |
| AGCCAGTGGA TATATAGAAG CAGAAGTTAT TCCAGCAGAG ACAGGGCAGG AAACAGCATA | 4380 |
| CTTTATCTTA AAATTAGCAG GAAGGTGGCC AGTAAACACA ATACATACAG ACAATGGCGG | 4440 |
| CAATTTCATC AGTACCACGG TTAAGGCCGC CTGTTGGTGG GCAGGGATCA AGCAGGAATT | 4500 |
| TGGCATTCCC TACAATCCCC AAAGCCAAGG AGTAGTGGAA TCTATGAATA GAGAATTAAA | 4560 |
| GAAAATTATA GGACAGGTAA GAGATCAGGC TGAACATCTT AAGACAGCAG TACAAATGGC | 4620 |
| AGTATTCATC CACAATTTTA AAAGAAAAGG GGGGATTGGG GGATACAGTG CAGGGGAAAG | 4680 |
| AATAGTAGAC ATAATAGCAA CAGACATACA AACTAAAGAA TTACAAAAGC AAATTACAAA | 4740 |
| AATTCAAAAT TTTCGGGTTT ATTACAGGGA CAGCAGAGAT CCACTTTGGA AAGGACCAGC | 4800 |
| AAAACTTCTC TGGAAAGGCG AAGGGGCAGT AGTAATACAA GATAATAGTG ACATAAAAGT | 4860 |
| AGTGCCAAGA AGAAAAGTAA AGATCATTAG GGATTATGGA AAACAGATGG CAGGTGATGA | 4920 |
| TTGTGTGGCA AGTAGACAGG ATGAGGATTA GAACATGGAA CAGTTTAGTG AAACACCATA | 4980 |
| TGTATGTTTC AAAGAAAGCT AAGGGATGGA TTTATAGACA TCACTATGAA AACACTCATC | 5040 |
| CAAAAATAAG CTCAGAAGTA CACATCCCAC TAGGGGAAGC TAGATTGGTA ATAACAACAT | 5100 |
| ATTGGGGTCT ACATACAGGA GAAAGAGACT GGCATTTGGG TCAGGGAGTC TCCATAGAAT | 5160 |
| GGAGGGAAAG GACATATAGA ACACAAGTAG ACCCCGAACT AGCAGACCAA CTAATTCATA | 5220 |
| TACATTACTT TGATTGTTTT TCAGAATCTG CCATAAGAAG TGCCATATTA GGATATAGAG | 5280 |
| TTAGGCATAG GTGTGAATAT CAAGCAGGAC ATAACAAGGT AGGATCTCTA CAGTACTTGG | 5340 |
| CACTAACAGC ATTAATAACA CCAAAGAAGA TAAAGCCACC TTTGCCTAGT GTTGCGAAAC | 5400 |
| TGACAGAGGA TAGATGGAAC AAGCCCCAGA AGACCAAGGG CCACAGAGGC AGCCATACAA | 5460 |
| TGAATGGACA CTAGAACTTT TAGAGGAGCT TAAGAATGAA GCTGTTAGGC ATTTTCCTAG | 5520 |
| GGTATGGCTC CATGGCTTAG GGCAACATAT CTATGAAACT TATGGGGATA CTTGGGAAGG | 5580 |
| AGTGGAGGCC ATAACAAGAA CTCTGCAACA ACTGCTGTTT ATTCATTTCA GAATTGGGTG | 5640 |
| TCAACATAGC AGAATAGGCA TTATTCGACA GAGGAGAGCA AGAAATGGAG CCAGTAGATC | 5700 |
| CTAGACTAGA GCCCTGGAAG CATCCAGGAA GTCAGCCTAA GACTGCGTGT ACCACTTGCT | 5760 |
| ATTGTAAAAA GTGCTGCTTT CATTGCCAAG TTTGTTTTAT GACAAAAGGC TTAGGCATCT | 5820 |
| CCTATGGCAG GAAGAAGCGG AGACAGCGAC GAAGAGCTCC TCAAGACAGT CAGACTCATC | 5880 |

```
AAGCTTATCT ATCAAAGCAG TAAGTAATAT ATGTAATGCA ACCTTTACAA ATAGTAGCAA    5940

TAGTAGCATT AGTAGTAGCA GGAATAATAG CAATAGTTGT GTGGACCATA GTATTCATAG    6000

AATATAAGAA AATATTAAGA CAAAGAAAAA TAGACAGGTT GATTGATAGA ATAAGAGAAA    6060

GAGCAGAAGA CAGTGGCAAT GACAGTGAAG GGGATCAGGA AGAATTATCG GCACTTGTGG    6120

ACATGGGGCA CCATGATCCT TGGGATATTA ATGATCTGTA GAGCTGCAAA CAATTTGTGG    6180

GTCACAGTCT ATTATGGGGT ACCTGTGTGG AGAGAAGCAA CCACCACTCT ATTTTGTGCA    6240

TCAGATGCCA AGGCATATGA TGCAGAGGTA CATAATGTTT GGGCCACACA TGCCTGTGTA    6300

CCCACAGACC CTAACCCACA AGAAGTAGAA TTGAAAAATG TGACAGAAAA TTTTAACATG    6360

TGGAAAAATA ACATGGTAGA ACAGATGCAT GAGGATATAA TCAGTTTATG GGATCAAAGC    6420

CTGAAGCCAT GTGTAAAATT AACCCCACTC TGTGTTTCTT TAAATTGCAC TGATGCTACT    6480

AATACCACTA ATAGTAATAC CACTAGCAGC AGCGAGAAAC CGAAGGGGAC AGGGGAAATA    6540

AAAAACTGCT CTTTCAATAT CACCCACAAGC ATAAGAGATA AGGTGCAGAA ACAATATGCA    6600

CTTTTTTATA GCCTTGATGT AGTACCAATG GATGATAATG ATAATAGTAC AAGCTATAGG    6660

TTAATAAGTT GTAACACCTC AATCATTACA CAGGCCTGTC CAAAGATATC CTTTGAGCCA    6720

ATTCCCATAC ATTATTGTGC CCCGGCTGGT TTTGCGATTC TAAAGTGTAA AGATAAAAGG    6780

TTCAATGGAA AAGGACCATG TACAAGTGTC AGCACAGTAC AGTGTACACA TGGAATTAGG    6840

CCAGTAGTAT CAACTCAACT GTTGTTAAAT GGCAGTCTAG CAGAAGAAGA GGTAGTAATT    6900

AGATCTGACA ATTTTACGAA CAATGCTAAA ACCATAATAG TACAGCTGAG CAAATCTGTA    6960

GAAATTACTT GTGTAAGACC CAACAACAAT ACAAGAAAAA GTATAAGTAT GGGACCAGGG    7020

AGAGCATTTT ATACAACAGA AATAATAGGA GATATAAGAC AAGCATATTG TAACATTAGT    7080

AAAGCAAACT GGACTGACAC TTTAGAACAG ATAGCTAGAA AATTAAGAGA ACAATTTGAG    7140

AATAAAACAA TAGTCTTTAA GCCATCCTCA GGAGGGGACC CAGAAATTGT AACACAGTTT    7200

TACAGTTTTA ATTGTGGAGG GGAATTTTTC TACTGTAATT CAACACAACT GTTTAATGGT    7260

ACTTGGAATG GTACTTGGGT TAATGGTACT TGGAGTAGTA ATAATACGAC TGATACTGCA    7320

AATATCACAC TCCCATGCAG AATAAAACAA TTTATAAACA TGTGGCAGGA AGTAGGAAAA    7380

GCAATGTATG CCCCTCCCAT CAAAGGACAA ATTAAATGTA CATCAAATAT TACAGGGCTG    7440

ATATTAACAA GAGATGGTGG TAACAATAAC ACCACGAACG ACAACGAGAC CGAGACCTTC    7500

AGACCTGGAG GAGGAGATAT GAGGGACAAT TGGAGAAGTG AATTATATAA ATATAAAGTA    7560

GTACAAGTTG AACCATTAGG AGTAGCACCC ACCAAGGCAA AGAGAAGAGT GGTGCAAAGA    7620

GAAAAAAGAG CAGTGGGAAT AGGAGCTATG TTCCTTGGGT TCTTAGGAGC AGCAGGAAGC    7680

ACTATGGGCG CAGCGTCAGT GACGCTGACG GTACAAGCCA GACAATTATT GTCTGGTATA    7740

GTGCAGCAGC AGAACAATCT GCTGAGGGCT ATTGAGGCGC AACAGCATCT GTTGCAACTC    7800

ACAGTCTGGG GCATCAAACA GCTCCAGGCA AGAGTCCTGG CTGTGGAAAG ATACCTAAGG    7860

GATCAACAGC TCCTGGGACT TTGGGGTTGC TCTGGAAAAC TCATTTGCAC CACTACTGTG    7920

CCTTGGAACA ATAGCTGGAG TAATAAATCT CTGGAAACAA TTTGGGATAA CATGACCTGG    7980

ATGCAGTGGG AAAGAGAAAT TGACAATTAC ACAAACATAA TATACACCTT AATTGAAGAA    8040

TCGCAGAACC AACAAGAAAA AAATGAACTA GAATTATTGG AATTGGATAA ATGGGCAAAT    8100

TTGTGGAATT GGTTTAGTAT ATCAAACTGG CTATGGTATA TAAAATTATT CATAATGGTA    8160

GTAGGAGGCT TGGTAGGTTT AAGAATAGTT TTTACTGTAC TTTCTATAGT TAATAGAGTT    8220

AGGCAGGGAT ACTCACCATT ATCGTTTCAG ACCCACCTCC CAACCCCGAA GGGACCCGAC    8280
```

```
AGGCCAGAAG GAATCGAAGA AGAAGGTGGA GAGAGAGACA GAGGCAGCTC CACTCGATTA    8340

GTGCACGGAT TCTTAGCACT TTTCTGGGAC GACCTGAGGA GTCTGTGCCT CTTCAGCTAC    8400

CACCACTTGA GAGACTTACT CTTGATTGTA ACGAGGATTG TGGAACTTCT GGGACGCAGG    8460

GGATGGGAAG CCCTCAAATA CTGGTGGAAT CTCCTGCAGT ATTGGAGGCA GGAACTACAG    8520

AAGAGTGCTG TTAGCTTGTT CAATGGCACG GCCATAGCAG TAGCTGAGGG GACAGATAGA    8580

GTTATAGAAG CTTTACGAAG GGCTTATAGA GCTATTCTCC ACATACCTAG AAGAATAAGA    8640

CAGGGCTTAG AAAGGGCTTT GCTATAAAAT GGGTGGCAAG TGGTCAGAAA GTAGTGTGGT    8700

TAGAAGGCAT GTACCTTTAA GACAAGGCAG CTATAGATCT TAGCCGCTTT TTAAAAGAAA    8760

AGGGGGGACT GGAAGGGCTA ATTCACTCAC GGAAAAGACC AGTTGAACCA GAAGAAGATA    8820

GAAGAGGCCA TGAAGAAGAA AACAACAGAT TGTTCTGCTT GCTCAGCTGG GGACTTTCCA    8880

GAAGGCGCGG CCTGAGTGAC TAAGCCCCGT TGGGGACTTT CCGAAGAGGC ATGAAGGGAC    8940

TTTCCAAGGC AGGCGTGGCC TGGGCGGGAC TGGGGAGTGG CGAGCCCTCA GATGCTGCAT    9000

ATAAGCAGCT GCTTTCTGCC TGTACTGGGT CTCTCTGGTT AGACCAGATC TGAGCCTGGG    9060

AGCTCTCTGG CTAGCTAGGG AACCCACTGC TTAAGCCTCA ATAAAGCTTG CCTTGAGTGC    9120

TTCAAGTAGT GTGTGCCCGT CTGTTGTGTG ACTCTGGTAT CTAGAGATCC CTCAGACCAT    9180

TTTAGTCCGT GTGGAAAATC TCTAGCA                                       9207

(2) INFORMATION FOR SEQ ID NO:801:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:801:

Asn Thr Ser Leu Leu His Pro Val Ser Leu His Gly Met Asp Asp Pro Glu
 1               5                  10                  15

(2) INFORMATION FOR SEQ ID NO:802:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:802:

ACCAGCTTGT TACACCCTGT GAGCCTGCAT GGAATGGATG ACCCTGAG                   48

(2) INFORMATION FOR SEQ ID NO:803:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:803:

ACCAGCTTGT                                                            10

(2) INFORMATION FOR SEQ ID NO:804:
```

(i) SEQUENCE CHARACTERISTICS:
    (A) LENGTH: 10 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:804:

CCAGCTTGTT                                                            10

(2) INFORMATION FOR SEQ ID NO:805:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:805:

CAGCTTGTTA                                                            10

(2) INFORMATION FOR SEQ ID NO:806:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:806:

AGCTTGTTAC                                                            10

(2) INFORMATION FOR SEQ ID NO:807:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:807:

GCTTGTTACA                                                            10

(2) INFORMATION FOR SEQ ID NO:808:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:808:

CTTGTTACAC                                                            10

(2) INFORMATION FOR SEQ ID NO:809:

(i) SEQUENCE CHARACTERISTICS:
        (A) LENGTH: 10 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO:809:

TTGTTACACC                                                                10

(2) INFORMATION FOR SEQ ID NO:810:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:810:

TGTTACACCC                                                                10

(2) INFORMATION FOR SEQ ID NO:811:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:811:

GTTACACCCT                                                                10

(2) INFORMATION FOR SEQ ID NO:812:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:812:

TTACACCCTG                                                                10

(2) INFORMATION FOR SEQ ID NO:813:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:813:

TACACCCTGT                                                                10

(2) INFORMATION FOR SEQ ID NO:814:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:814:

ACACCCTGTG                                                               10

(2) INFORMATION FOR SEQ ID NO:815:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:815:

CACCCTGTGA                                                               10

(2) INFORMATION FOR SEQ ID NO:816:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:816:

ACCCTGTGAG                                                               10

(2) INFORMATION FOR SEQ ID NO:817:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:817:

CCCTGTGAGC                                                               10

(2) INFORMATION FOR SEQ ID NO:818:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:818:

CCTGTGAGCC                                                               10

(2) INFORMATION FOR SEQ ID NO:819:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:819:

CTGTGAGCCT                                                               10

(2) INFORMATION FOR SEQ ID NO:820:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:820:

TGTGAGCCTG                                                                10

(2) INFORMATION FOR SEQ ID NO:821:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:821:

GTGAGCCTGC                                                                10

(2) INFORMATION FOR SEQ ID NO:822:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:822:

TGAGCCTGCA                                                                10

(2) INFORMATION FOR SEQ ID NO:823:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:823:

GAGCCTGCAT                                                                10

(2) INFORMATION FOR SEQ ID NO:824:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:824:

AGCCTGCATG                                                                10

(2) INFORMATION FOR SEQ ID NO:825:

(i) SEQUENCE CHARACTERISTICS:
        (A) LENGTH: 10 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO:825:

GCCTGCATGG                                                                 10

(2) INFORMATION FOR SEQ ID NO:826:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:826:

CCTGCATGGA                                                                 10

(2) INFORMATION FOR SEQ ID NO:827:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:827:

CTGCATGGAA                                                                 10

(2) INFORMATION FOR SEQ ID NO:828:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:828:

TGCATGGAAT                                                                 10

(2) INFORMATION FOR SEQ ID NO:829:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:829:

GCATGGAATG                                                                 10

(2) INFORMATION FOR SEQ ID NO:830:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:830:

CATGGAATGG                                                              10

(2) INFORMATION FOR SEQ ID NO:831:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:831:

ATGGAATGGA                                                              10

(2) INFORMATION FOR SEQ ID NO:832:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:832:

TGGAATGGAT                                                              10

(2) INFORMATION FOR SEQ ID NO:833:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:833:

GGAATGGATG                                                              10

(2) INFORMATION FOR SEQ ID NO:834:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:834:

GAATGGATGA                                                              10

(2) INFORMATION FOR SEQ ID NO:835:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:835:

AATGGATGAC                                                              10

(2) INFORMATION FOR SEQ ID NO:836:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:836:

ATGGATGACC                                                                  10

(2) INFORMATION FOR SEQ ID NO:837:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:837:

TGGATGACCC                                                                  10

(2) INFORMATION FOR SEQ ID NO:838:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:838:

GGATGACCCT                                                                  10

(2) INFORMATION FOR SEQ ID NO:839:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:839:

GATGACCCTG                                                                  10

(2) INFORMATION FOR SEQ ID NO:840:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:840:

ATGACCCTGA                                                                  10

(2) INFORMATION FOR SEQ ID NO:841:

(i) SEQUENCE CHARACTERISTICS:
        (A) LENGTH: 10 base pairs
        (B) TYPE: nucleic acid
        (C) STRANDEDNESS: single -continued

```
        (D) TOPOLOGY: linear (ii) MOLECULE TYPE: DNA (xi) SEQUENCE DESCRIPTION: SEQ ID NO:841:

TGACCCTGAG                                                              10
```